United States Patent
Bakardjiev et al.

(10) Patent No.: US 12,404,318 B2
(45) Date of Patent: Sep. 2, 2025

(54) COMBINATION HBV THERAPY

(71) Applicants: Vir Biotechnology, Inc., San Francisco, CA (US); Humabs Biomed SA, Bellinzona (CH)

(72) Inventors: Anna Bakardjiev, San Francisco, CA (US); Phillip S. Pang, Menlo Park, CA (US); Davide Corti, Bellinzona (CH)

(73) Assignees: Vir Biotechnology, Inc., San Francisco, CA (US); Humabs BioMed SA, Bellinzona (CH)

( * ) Notice: Subject to any disclaimer, the term of this patent is extended or adjusted under 35 U.S.C. 154(b) by 1045 days.

(21) Appl. No.: 17/415,529

(22) PCT Filed: Dec. 19, 2019

(86) PCT No.: PCT/US2019/067643
§ 371 (c)(1),
(2) Date: Jun. 17, 2021

(87) PCT Pub. No.: WO2020/132346
PCT Pub. Date: Jun. 25, 2020

(65) Prior Publication Data
US 2022/0056110 A1    Feb. 24, 2022

Related U.S. Application Data

(60) Provisional application No. 62/782,896, filed on Dec. 20, 2018.

(51) Int. Cl.
| | | |
|---|---|---|
| *C07K 16/08* | (2006.01) |
| *A61K 31/7105* | (2006.01) |
| *A61K 39/00* | (2006.01) |
| *A61K 39/42* | (2006.01) |
| *A61K 47/54* | (2017.01) |
| *A61P 31/20* | (2006.01) |

(52) U.S. Cl.
CPC ........ *C07K 16/082* (2013.01); *A61K 31/7105* (2013.01); *A61K 39/42* (2013.01); *A61K 47/549* (2017.08); *A61P 31/20* (2018.01); *A61K 2039/505* (2013.01); *A61K 2039/545* (2013.01); *C07K 2317/24* (2013.01); *C07K 2317/76* (2013.01)

(58) Field of Classification Search
CPC .............. C07K 16/082; C07K 2317/24; C07K 2317/76; C07K 2317/52; C07K 2317/90; A61K 31/7105; A61K 39/42; A61K 47/549; A61K 2039/505; A61K 2039/545; A61K 31/522; A61K 31/675; A61K 45/06; A61K 31/713; A61K 2300/00; A61K 48/00; A61K 2039/54; A61P 31/20
See application file for complete search history.

(56) References Cited

U.S. PATENT DOCUMENTS

| | | |
|---|---|---|
| 8,802,820 B2 | 8/2014 | Chamberlain et al. |
| 9,683,029 B2 | 6/2017 | Kim et al. |
| 10,683,344 B2 | 6/2020 | Corti |
| 11,390,664 B2 | 7/2022 | Corti |
| 2015/0166637 A1 | 6/2015 | Kim et al. |
| 2015/0297745 A1 | 10/2015 | Cobbold et al. |
| 2015/0299289 A1 | 10/2015 | Urban et al. |
| 2017/0260527 A1 | 9/2017 | Fitzgerald et al. |
| 2018/0195073 A1 | 7/2018 | Fitzgerald et al. |
| 2018/0244756 A1 | 8/2018 | Graham et al. |
| 2021/0179693 A1 | 6/2021 | Lazar |
| 2021/0332365 A1* | 10/2021 | Jadhav ............... A61P 31/20 |
| 2022/0127336 A1 | 4/2022 | Corti |
| 2022/0380441 A1 | 12/2022 | Pang et al. |

FOREIGN PATENT DOCUMENTS

| | | |
|---|---|---|
| WO | WO 9739029 A2 | 10/1997 |
| WO | WO 9740164 A1 | 10/1997 |
| WO | WO 9829442 A1 | 7/1998 |
| WO | 0005266 A1 | 2/2000 |
| WO | WO 2006076640 A1 | 7/2006 |
| WO | WO 2008143954 A2 | 11/2008 |
| WO | WO 2009069917 A1 | 6/2009 |
| WO | 2010132659 A2 | 11/2010 |
| WO | 2011/047312 A1 | 4/2011 |
| WO | WO 2014032176 A1 | 3/2014 |
| WO | 2015112800 A1 | 7/2015 |
| WO | WO 2015107126 A1 | 7/2015 |
| WO | 2016/028649 A1 | 2/2016 |
| WO | 2016/077321 A1 | 5/2016 |
| WO | 2017/027350 A2 | 2/2017 |

(Continued)

OTHER PUBLICATIONS

Li G-Q et al. Combination of small interfering RNA and lamivudine on inhibition of human B virus replication in HepG2.2.15 cells. (World J Gastroenterol. Apr. 28, 2007;13(16):2324-2327.) (Year: 2007).*
Uniprot IgG1 human (https://www.uniprot.org/uniprotkb/P0DOX5/ entry sequence from 2018) (Year: 2018).*
Uniprot Immunoglobulin lambda constant 2 (https://www.uniprot.org/uniprotkb/P0DOY2/entry sequence from 2017) (Year: 2017).*
Saxena A et al. Advances in Therapeutic Fc Engineering—Modulation of IgG-Associated Effector Functions and Serum Half-life. (Front. Immunol. 7:580 1-11 doi: 10.3389/fimmu.2016.00580) (Year: 2016).*
Buchanan A et al. Engineering a therapeutic IgG molecule to address cysteinylation, aggregation and enhance thermal stability and expression. (MAbs. 2013 5(2):255-262.) (Year: 2013).*

(Continued)

*Primary Examiner* — Karen A. Canella
*Assistant Examiner* — John J Skoko, III
(74) *Attorney, Agent, or Firm* — Fox Rothschild LLP

(57) ABSTRACT

The present disclosure provides methods for treating HBV infection using combination therapies, and related kits and compositions for use. The components of the combination therapies include an inhibitor of HBV gene expression or an agent that reduces HBV antigenic load, and an anti-HBV antibody.

16 Claims, 18 Drawing Sheets

Specification includes a Sequence Listing.

(56) References Cited

FOREIGN PATENT DOCUMENTS

| WO | 2017/059878 A1 | 4/2017 |
|---|---|---|
| WO | 2017/060504 A1 | 4/2017 |
| WO | 2017/106346 A2 | 6/2017 |
| WO | WO 2017100542 A1 | 6/2017 |
| WO | 2018/027106 A2 | 2/2018 |
| WO | WO 2018098328 A1 | 5/2018 |
| WO | 2018/195165 A1 | 10/2018 |
| WO | 2018/207023 A2 | 11/2018 |
| WO | WO 2019125846 A1 | 6/2019 |
| WO | 2020/036862 A1 | 2/2020 |
| WO | WO 2020132091 A2 | 6/2020 |
| WO | WO 2020132346 A1 | 6/2020 |
| WO | 2021042000 A1 | 3/2021 |

OTHER PUBLICATIONS

Zhang et al., "N-acetylgalactosamine delivery systems for RNA therapeutics: a patent perspective," *Expert Opinion on Therapeutic Patents* 33(9):539-547, Nov. 7, 2023. (9 pages).

Huh et al., "The Identification of Free Cysteine Residues Within Antibodies and a Potential Role for Free Cysteine Residues in Covalent Aggregation Because of Agitation Stress," Journal of Pharmaceutical Sciences, 102 (6):1701-1711, Jun. 2013.

Mostafa, et al., "Immunoaffinity extraction using conformation-dependent antibodies coupled to SE-HPLC for the development of stability and potency-indicating assay for quadrivalent human papillomavirus vaccine," Journal of Chromatography B, 1032 (2016): 211-217.

Merriam-Webster, "Prevent," retrieved online from <URL: https://www.merriam-webster.com/dictionary/prevent>, Aug. 14, 2024.

Merriam-Webster, "Infect," retrieved online from <URL: https://www.merriam-webster.com/dictionary/infect>, Aug. 14, 2024.

Anonymous, "Conservative replacement," Wikipedia, Mar. 11, 2018, pp. 1-3, XP93121795, retrieved online from <URL: https://en.wikipedia.org/w/index.php?title=Conservative_replacement&oldid=829953914>, Jan. 19, 2024.

"A New Era: We are developing a broad portfolio of product candidates that are designed to combat serious, global infectious diseases in entirely new ways, creating medicines that will have a meaningful impact on people around the world," VIR Pipeline, Retrieved from https://www.vir.bio/pipeline/, Accessed Apr. 8, 2020, 5 pages.

"RNAi Roundtable: ALN-HBV in Development for the Treatment of Hepatitis B Virus (HBV) Infection," Alnylam Pharmaceuticals, Jul. 29, 2014, 56 pages.

"Vir Biotechnology and Alnylam Pharmaceuticals Initiate Phase 1/2 Study of VIR-2218," VIR, Businesswire, Nov. 26, 2018, 4 pages.

"Vir Biotechnology, Inc.," 40th Annual Cowen Healthcare Conference, Mar. 30, 2020, 25 pages.

ClinicalTrials.gov, "Study of VIR-2218 in Healthy Volunteers and Patients With Chronic Hepatitis B," *U.S. National Library of Medicine*, first posted Sep. 14, 2018, retrieved Apr. 8, 2020, 4 pages.

Dilillo et al., "Differential Fc-Receptor Engagement Drives an Anti-tumor Vaccinal Effect," *Cell* 161:1035-1045, May 21, 2015.

"EASL 2017 Clinical Practice Guidelines on the management of hepatitis B virus infection," *Journal of Hepatology* 67:370-398, 2017.

Flisiak et al., "siRNA drug development against hepatitis B virus infection," Expert Opinion on Biological Therapy 18(6):609-617, 2018.

Furman et al., "Early Engineering Approaches to Improve Peptide Developability and Manufacturability," *The AAPS Journal* 17(1):111-120, Jan. 2015.

Gao et al., "Antibody-mediated immunotherapy against chronic hepatitis B virus infection," *Human Vaccines & Immunotherapeutics* 13(8):1768-1773, 2017.

Hinton et al., "An Engineered Human IgG1 Antibody with Longer Serum Half-Life," *The Journal of Immunology* 176:346-356, 2006.

Ho et al., "Generation of monoclonal antibody-producing mammalian cell lines," *Pharm. Bioprocess.* 1(1):71-87, 2013.

Janas et al., "Selection of GalNAc-conjugated siRNAs with limited off-target-driven rat hepatotoxicity," *Nature Communications* 9(723):1-10, 2018.

Krebs et al., "T Cells Expressing a Chimeric Antigen Receptor That Binds Hepatitis B Virus Envelope Proteins Control Virus Replication in Mice," *Gastroenterology* 145:456-465, 2013.

Kuo et al., "Neonatal Fc receptor and IgG-based therapeutics," *mAbs* 3(5):422-430, Oct. 2011.

Li et al., "A potent human neutralizing antibody Fc-dependently reduces established HBV infections," *eLife* 6:e26738, Sep. 2017, 30 pages.

Nair et al., "Multivalent N-Acetylgalactosamine-Conjugated siRNA Localizes in Hepatocytes and Elicits Robust RNAi-Mediated Gene Silencing," *J. Am. Chem. Soc.* 136:16958-16961, 2014.

Nassal, "HBV cccDNA: viral persistence reservoir and key obstacle for a cure of chronic hepatitis B," *Gut* 64:1972-1984, 2015.

Neumann et al., "Novel Mechanism of Antibodies to Hepatitis B Virus in Blocking Viral Particle Release from Cells," *Hepatology* 52:875-885, 2010.

Schlegel et al., "Chirality Dependent Potency Enhancement and Structural Impact of Glycol Nucleic Acid Modification on siRNA," *J. Am. Chem. Soc.* 139(25): 8537-8546, 2017.

Abou-Jaoude et al., "Entry of Hepatitis Delta Virus Requires the Conserved Cysteine Residues of the Hepatitis B Virus Envelope Protein Antigenic Loop and Is Blocked by Inhibitors of Thiol-Disulfide Exchange," *Journal of Virology* 81(23):13057-13066, Dec. 2007.

Ahmed et al., "Structural Characterization of GASDALIE Fc Bound to the Activiating Fc receptor FcγRIIIa," *J. Struct. Biol.* 194(1):78-89, Apr. 2016.

Armour et al., "Recombinant human IgG molecules lacking Fcγ receptor I binding and monocyte triggering activities," *Eur. J. Immunol.* 29:2613-2624, 1999.

Banks et al., "Removal of Cysteinylation from an Upaired Sulfhydryl in the Variable Region of a Recombinant Monoclonal IgG1 Antibody Improves Homogeneity, Stability, and Biological Activity," *Journal of Pharmaceutical Sciences* 97(2):P775-790, Feb. 1, 2008. (abstract only).

Block et al., "Chronic hepatitis B: What should be the goal for new therapies?" *Antiviral Res.* 98(1):27-34, Apr. 2013.

Bruhns et al., "Specificity and affinity of human Fcγ receptors and their polymorphic variants for human IgG sunglasses," *Blood* 113(16):3716-3725, Apr. 16, 2009.

Bruns et al., "Enhancement of Hepatitis B Virus Infection by Noninfectious Subviral Particles," *J. of Virology* 72(2):1462-1468, Feb. 1998.

Brüggemann et al., "A repertoire of monoclonal antibodies with human heavy chains from transgenic mice," *PNAS* 86:6709-6713, Sep. 1989.

Cerino et al., "A Human Monoclonal Antibody against Hepatitis B Surface Antigen with Potent Neutralizing Activity," *Plos One* 10(4), Apr. 29, 2015. (10 pages).

Chu et al., "Inhibition of B cell receptor-mediated activation of primary human B cells by coengagement of CD19 and FcγRIIb with Fc-engineered antibodies," *Molecular Immunology* 45:3926-3933, 2008.

ClinicalTrials.gov, "A Phase 1 Study of GC1102 (Recombinant Hepatitis B Immunoglobulin) in Chronic Hepatitis B Patients," retrieved from URL=https://clinicaltrials.gov/study/NCT02569372, last updated Oct. 16, 2017, downloaded Oct. 31, 2023. (14 pages).

Dunbar et al., "ANARCI: antigen receptor numbering and receptor classification," *Bioinformatics* 32(2):298-300, Sep. 30, 2015.

Eren et al., "Preclinical Evaluation of Two Human Anti-Hepatitis B Virus (HBV) Monoclonal Antibodies in the HBV-Trimera Mouse Model and in HBV Chronic Carrier Chimpanzees," *Hepatology* 32(3):588-596, 2000.

Galun et al., "Clinical Evaluation (Phase I) of a Combination of Two Human Monoclonal Antibodies to HBV: Safety and Antiviral Properties," *Hepatology* 35(3):673-679, Mar. 2002.

(56) References Cited

OTHER PUBLICATIONS

International Search Report and Written Opinion, mailed Feb. 1, 2021, for International Application No. PCT/US2019/067216, 27 pages.
International Search Report and Written Opinion, mailed Feb. 8, 2017, for International Application No. PCT/EP2016/074114, 17 pages.
International Search Report and Written Opinion, mailed Jan. 25, 2021, for International Application No. PCT/US2020/048649, 12 pages.
Jaoudé et al., "Role of the Antigenic Loop of the Hepatitis B Virus Envelope Proteins in Infectivity of Hepatitis Delta Virus," *Journal of Virology* 79(16):10460-10466, Aug. 2005.
Martin et al., "Selection of Ig u Heavy Chains by Complementarity-Determining Region 3 Length and Amino Acid Composition," *Journal of Immunology* 171:4663-4671, 2003.
Miliotou et al., "CAR T-cell Therapy: A New Era in Cancer Immunotherapy," *Current Pharmaceutical Biotechnology* 19:5-18, 2018.
Mimoto et al., Engineered antibody Fc variant with selectively enhanced FcγRIIb binding over both FcγRIIaR131 and FcγRIIaH131, *Prot. Eng. Des. Sel.* 26(10):589-598, Jun. 5, 2013.
Moore et al., "Accelerated Clearance of IgE in Chimpanzees Is Mediated By Xmab7195, An Fc-Engineered Antibody With Enhanced Affinity for Inhibitory Receptor Fcγriib," *Am. J. Respir. Crit. Care Med.* 189:A4261, 2014.
Plath et al., "Characterization of mAb dimers reveals predominant dimer forms common in therapeutic mAbs," *MABS* 8(5):928-940, 2016.
Qiu et al., "Identification and Characterization of a C(K/R)TC Motif as a Common Epitope Present in All Subtypes of Hepatitis B Surface Antigen," *The Journal of Immunology* 156(9):3350-3356, 1996.
Salisse et al., "A Function Essential to Viral Entry Underlies the Hepatitis B Virus "a" Determinant," *Journal of Virology* 83(18):9321-9328, Sep. 2009.
Shields et al., "High Resolution Mapping of the Binding Site of Human IgG1 for FcγRI, FcγRII, FcγRIII, and FcRn and Design of IgG1 Variants with Improved Binding to the FcγR," *J. Biol. Chem.* 276(9):6591-6604, Mar. 2, 2001.
Shirazi et al., "Monoclonal antibodies to various epitopes of hepatitis B surface antigen inhibit hepatitis B virus infection," *Journal of Gastroenterology and Hepatology* 29(5):1083-1091, 2014.
Sureau et al., "Production of Infectious Hepatitis Delta Virus In Vitro and Neutralization with Antibodies Directed against Hepatitis B Virus Pre-S Antigens," *Journal of Virology* 66(2):1241-1245, 1992.
Takaki et al., "Molecular Mechanism to Control Post-Transplantation Hepatitis B Recurrence," *Int. J. Mol. Sci.* 16:17494-17513, 2015.
Thorpe et al., "The Preparation and Cytotoxic Properties of Antibody-Toxin Conjugates," *Immunol. Rev.* 62:119-158, 1982.
Traggiai et al., "An efficient method to make human monoclonal antibodies from memory B cells: potent neutralization of SARS coronavirus," *Nature Medicine* 10(8):871-875, 2004.
Tsuge et al., "Antiviral effects of anti-HBs immunoglobulin and vaccine on HBs antigen seroclearance for chronic hepatitis B infection," *Journal of Gastroenterology* 51:1073-1080, Mar. 2016. (9 pages).
Volz et al., "Impaired Intrahepatic Hepatitis B Virus Productivity Contributes to Low Viremia in Most HBeAg-Negative Patients," *Gastroenterology* 133:843-852, 2007.
Wang et al., "IgG Fc engineering to modulate antibody effector functions," *Protein Cell* 9(1):63-73, 2018.
Wedemeyer et al., "Update on the Management of HBV-HDV Coinfection," *Current Hepatitis Reports* 11(2):95-101, 2012.
Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A1 ," *J. Immunol.* 164:5313-5318, 2000.
Zhang et al., "Prolonged suppression of HBV in mice by a novel antibody that targets a unique epitope on hepatitis B surface antigen," *Gut* 0:1-14, 2015 [Published Online Sep. 2015] (16 pages).
Zubkin et al., "Strategy of Vaccination Against HBV-infection in Hemodialysis Patients with 'Isolated' HBcAb," *International Journal of Infectious Diseases* 10:S42-S43, 2006. (abstract only).
Hong et al., "In vivo neutralization of hepatitis B virus infection by an anti-preS1 humanized antibody in chimpanzees," *Virology* 318:134-141, Jan. 2004. (8 pages).
Hong et al., "Recent Progress on Neutralizing Antibodies against Hepatitis B Virus and its Implications," *Infectious Disorders—Drug Targets* 19(3):213-223, Sep. 2019. (11 pages).
Warne, "Development of high concentration protein biopharmaceuticals: The use of platform approaches in formulation development," European Journal of Pharmaceutics and Biopharmaceutics, 78(2), p. 208-212, Mar. 2011, (5 pages).
Record History [online], "Study of VIR-2218 in Healthy Subjects and Patients With Chronic Hepatitis B," ClinicalTrials. gov ID No. NCT03672188, study record submitted May 8, 2019 [retrieved from the Internet Feb. 26, 2025], https://clinicaltrials.gov/study/NCT03672188?tab=history&a=2#StudyPageTop, (13 pages).
"Hepatitis B," World Health Organization, Jul. 18, 2019, retrieved from https://web.archive.org/web/20191205031400/http://www.who.int/news-room/fact-sheets/detail/hepatitis-b, accessed Mar. 4, 2025, (8 pages).
Chen et al., "5'-Triphosphate-siRNA activates RIG-I-dependent type I interferon production and enhances inhibition of hepatitis B virus replication in HepG2.2.15 cells," European Journal of Pharmacology, vol. 721, Issues 1-3, pp. 86-95 (Dec. 2013), (10 pages).
Fanning et al., "Therapeutic strategies for hepatitis B virus infection: towards a cure," Nat Rev Drug Discov 18, 827-844, Nov. 2019, (18 pages).
Foster et al., "Advanced siRNA Designs Further Improve In Vivo Performance of GaINAc-siRNA Conjugates," Mol Ther. 26(3):708-717, Jan. 2018, (10 pages).
Hayashi et al., "Efficacy and safety of treatment with peginterferon alfa-2a for chronic hetatitis B patients," Kanzo, 2012, vol. 53(3), pp. 135-146, [with English abstract], (12 pages).
Javanbakht et al., "Liver-Targeted Anti-HBV Single-Stranded Oligonucleotides with Locked Nucleic Acid Potently Reduce HBV Gene Express In Vivo," Molecular Therapy: Nucleic Acids 11:441-454, Jun. 2018, (14 pages).
Qiao et al., "The Inhibition of IFN Induce SAMHD1 to the Replication of HBV in Huh7.0 Cells," J. China Biotechnology 39(3): 1-6, Mar. 2019, [with English abstract], (6 pages).
Tanaka, "Hepatitis B Virus Treatment: From "Clinical Healing" to "Functional Healing"," Journal of the Japanese Society of Internal Medicine, 2018, vol. 107(1), pp. 32-37, [with English translation, pp. 32-38], (13 pages).
Tsutsumi et al., "Recent advances in hepatitis B research and drug development," Kanzo, 2017, vol. 58(4), pp. 217-227, [with English translation, (15 pages) ], (26 pages).
Xu et al., "Addition of nucleoside analogues to peg-IFNα-2a enhances virological response in chronic hepatitis B patients without early response to peg-IFNα-2a: a randomized controlled trial," BMC Gastroenterology(2017) 17:102, (8 pages).
Zhang et al., "Consensus on Pegylated Interferon Alpha in Treatment of Chronic Hepatitis B," Journal of Clinical and Translational Hepatology 2018, 6(1):1-10, (10 pages).

\* cited by examiner

COMBINATION HBV THERAPY

STATEMENT REGARDING SEQUENCE LISTING

The Sequence Listing associated with this application is provided in text format in lieu of a paper copy, and is hereby incorporated by reference into the specification. The name of the text file containing the Sequence Listing is 930485_401USPC_SEQUENCE_LISTING.txt. The text file is 111 KB, was created on Jun. 17, 2021, and is being submitted electronically via EFS-Web.

BACKGROUND

Worldwide more than 400 million people have chronic HBV infection (CHB), and thus are at increased risk of developing serious liver disease, such as chronic hepatitis, cirrhosis, liver failure, and hepatocellular carcinoma (HCC), resulting in an estimated 600,000 deaths each year. Longitudinal studies of patients with CHB indicate that the 5-year cumulative incidence of developing cirrhosis ranges from 8 to 20%, and the 5-year cumulative incidence of hepatic decompensation is approximately 20%. The worldwide incidence of HCC has increased and presently constitutes the third leading cause of cancer-related deaths worldwide (El-Serag H. B., and Rudolph K. L., Gastroenterology 132: 2557-76 (2007)).

HBV is a DNA virus with a lipid envelope and an icosahedral nucleocapsid enclosing the viral DNA genome and DNA polymerase. The HBV capsid is formed in the cytosol of the infected cell during packaging of an RNA pregenome replication complex, and is made up of core protein, also known as HBcAg, and its cleavage variant, HBeAg. When the viral DNA dissociates from the capsid upon entry into a new cell, it can be converted to covalently closed circular DNA (cccDNA), which may remain in liver cells following HBV treatment and has the potential to reactivate infection. The lipid envelope includes the hepatitis B surface antigen (HBsAg), which refers to three separate proteins, S-HBsAg (small antigen), M-HBsAg (middle antigen), and L-HBsAg (large antigen) that are encoded by the same open reading frame but utilize distinct start codons. HBsAg is the antigen present in currently available hepatitis B vaccines. HBV also encodes the protein HBx, which inhibits tumor suppressor p53, promotes cell cycle progression, and increases production of reactive oxygen species.

In addition to producing virions, HBV also causes production of subviral particles (SVPs), which include the lipid envelope of an HBV virion, but are not replication competent and typically lack the nucleocapsid. SVPs can be produced up to 3-4 µlog in excess over replication competent virions. High levels of HBsAg preset on the SVPs can exhaust HBsAg-specific T-cell response, which is likely an important factor contributing to the inability of the immune system to clear HBV infection during chronic hepatitis B (Chisari, F. V., et al., Pathologie Biologie 58:258-66 (2010)).

The natural evolution of CHB infection includes four consecutive phases: (1) early 'immunotolerant' phase, which is associated with high levels of virus replication and minimal liver inflammation; (2) immune reactive phase, which is associated with significant hepatic inflammation and elevated serum aminotransferases; with some patients progressing to (3) 'non-replicative' or 'inactive' phase, which is associated with: seroconversion to anti-HBe; an undetectable or low level of viremia (below 2000 IU/ml by PCR-based assays); and resolution of hepatic inflammation; and for some individuals, (4) reactivation of the virus. Reactivation of HBV infection can be associated with the emergence of specific viral mutations that prevent the production of HBeAg but do not hamper virus replication, which is known as HBeAg-negative chronic hepatitis B. HBeAg-negative chronic hepatitis B (also known as anti-HBe-positive or precore mutant hepatitis) is characterized by fluctuating serum HBV DNA and serum aminotransferases (ALT and AST) levels, and progressive liver disease.

The primary goal of currently available treatments for HBV is to permanently suppress HBV replication and improve liver disease. Clinically important short-term goals include: achieving HBeAg-seroconversion, normalizing serum ALT and AST, resolving liver inflammation, and preventing hepatic decompensation. An ultimate long-term goal of HBV treatment is to achieve durable immune response to prevent development of cirrhosis and liver cancer, and therefore prolong survival. Currently available HBV treatments do not completely clear the virus due to persistence of cccHBV DNA in the nuclei of infected hepatocytes. However, treatment-induced clearance of serum HBsAg is a marker of termination of chronic HBV infection and has been associated with the best long-term outcome.

Although the three primary HBV proteins (HBsAg, HBeAg, and HBcAg) all have immunoinhibitory properties, HBsAg comprises the overwhelming majority of HBV protein in the circulation of HBV infected subjects. Additionally, while the removal (via seroconversion) of HBeAg or reductions in serum viremia are not correlated with the development of sustained control of HBV infection off treatment, the removal of serum HBsAg from the blood (and seroconversion) in HBV infection is a well-recognized prognostic indicator of antiviral response on treatment that will lead to control of HBV infection off treatment (although this only occurs in a small fraction of patients receiving immunotherapy). Thus, removal of HBsAg may be an important strategy for overcoming viral inhibition of immune function in subjects with HBV infection.

The current standard methods of treatment for HBV include interferon or thymosin a1-based immunotherapies and the suppression of viral production by inhibition of the HBV polymerase. HBV polymerase inhibitors are effective in reducing viral production but have little to no effect in rapidly reducing HBsAg or can slowly reduce HBsAg with long term treatment in a limited number of patients (as is the case with tenofovir disoproxil fumarate). Interferon-based immunotherapy can achieve a reduction of both viral production and early removal of HBsAg from the blood, but only in a small percentage of treated subjects. The generally accepted role of HBsAg in the blood is to sequester anti-HBsAg antibodies and allow infectious viral particles to escape immune detection, which is likely one of the reasons why HBV infection remains a chronic condition. In addition, HBsAg, HBeAg, and HBcAg all have immuno-inhibitory properties and the persistence of these viral proteins in the blood of patients following the administration of any of the currently available treatments for HBV likely has a significant impact in preventing patients from achieving immunological control of their HBV infection.

None of the currently available treatments restore immunological control of HBV in a large proportion of patients. Accordingly, there remains a need for an effective treatment against HBV infection that can inhibit viral replication as well as restore immunological control in the majority of patients.

SUMMARY

In some embodiments, the present disclosure provides an inhibitor of HBV gene expression for use in the treatment of a chronic HBV infection in a subject, wherein the subject is subsequently administered an anti-HBV antibody.

The present disclosure also provides an agent that reduces HBV antigenic load for use in the treatment of a chronic HBV infection in a subject, wherein the subject is subsequently administered an anti-HBV antibody.

The present disclosure also provides a composition for use in the treatment of a chronic HBV infection in a subject, wherein (a) the composition comprises an anti-HBV antibody and the subject has been previously administered an inhibitor of gene expression; or (b) composition comprises an anti-HBV antibody and the subject has been previously administered an agent that reduces HBV antigenic load.

In some embodiments, the present disclosure provides for the use of an inhibitor of HBV gene expression and an anti-HBV antibody in the manufacture of a medicament for the treatment of a chronic HBV infection. The present disclosure also provides for the use of agent that reduces HBV antigenic load and an anti-HBV antibody in the manufacture of a medicament for the treatment of a chronic HBV infection.

In some embodiments, the present disclosure provides a method of treating chronic HBV infection in a subject in need thereof, comprising: administering to the subject an agent that reduces HBV antigenic load; and administering to the subject an anti-HBV antibody. The present disclosure also provides a method of treating chronic HBV infection in a subject in need thereof, comprising: administering to the subject an inhibitor of HBV gene expression; and administering to the subject an anti-HBV antibody.

In some methods, compositions for use, or uses described herein, the anti-HBV antibody is HBC34 or a non-natural variant of HBC34.

In some methods, compositions for use, or uses described herein, the agent that reduces HBV antigenic load or the inhibitor of HBV gene expression is an RNAi agent (e.g., an siRNA, such as HBV02).

The present disclosure also provides, in some embodiments, kits comprising an RNAi agent and an anti-HBV antibody as disclosed herein, optionally with instructions for practicing a method described herein.

BRIEF DESCRIPTION OF THE DRAWINGS

FIG. 1 depicts the dosing schedule of a combination therapy study in a murine HBV model (an AAV-HBV model), as described in Example 1. Entecavir was administered orally once per day. An HBV-specific siRNA was administered subcutaneously once at the start of the study, and a mouse-chimeric anti-HBV antibody was administered intraperitoneally twice per week, during weeks three and four of the study. A subset of the mice were sacrificed at week four, and the other subset was sacrificed at week six of the study.

FIG. 2A depicts results of assaying for HBV viral load in mouse serum samples, measured as HBV DNA copy number, of mice treated with HBV02 siRNA (squares, solid line); a mouse-chimeric HBC34 antibody (HBC34v7; at 15 mg/kg) (circles, solid line); or saline (triangles, solid line).

FIG. 2B depicts results of assaying for HBV viral load in mouse serum samples, measured as HBV DNA copy number, of mice treated with a control siRNA and control antibody (squares, dashed line); entecavir alone ("ETV," diamonds, dashed line); HBV02 siRNA and the mouse-chimeric HBC34v7 antibody (at 15 mg/kg) (circles, dashed line); or HBV02 siRNA, HBC34v7 antibody (at 15 mg/kg), and entecavir (triangles, solid line).

FIG. 3A depicts HBsAg levels measured from mouse serum following treatment with HBV02 siRNA (squares, solid line); mouse-chimeric HBC34v7 antibody at 15 mg/kg (circles, solid line); or saline (triangles, solid line).

FIG. 3B depicts HBsAg levels measured from mouse serum following treatment with a control siRNA and control antibody (squares, dashed line); entecavir alone ("ETV," diamonds, dashed line); HBV02 siRNA and mouse-chimeric HBC34v7 antibody (at 15 mg/kg) (circles, dashed line); or HBV02 siRNA, mouse-chimeric HBC34v7 antibody (at 15 mg/kg), and entecavir (triangles, dashed line).

FIG. 4 depicts levels of free antibody measured from mouse serum between Day 14 and 42 post siRNA administration. The following treatment groups are depicted: mouse-chimeric HBC34v7 antibody alone (circles); HBV02 siRNA, mouse-chimeric HBC34v7 antibody, and entecavir (squares); and HBV02 siRNA and mouse-chimeric HBC34v7 antibody (triangles).

FIG. 5A depicts results of assaying for HBV viral load in mouse serum samples, measured as HBV DNA copy number, following siRNA, antibody, and/or control treatments. Mice were injected with AAV/HBV virus on day −28. AAV/HBV-infected C57Bl/6 mice were administered one of eleven different treatments on day 0: (1) an HBV-specific siRNA (HBV02, having an antisense strand of SEQ ID NO:8; see description in Example 1); (2)-(3) an anti-HBV antibody (a fully murinized HBC24), at one of two doses; (4)-(5) the HBV02 siRNA at one dose, and the fully murinized HBC24 at one of two doses; (6-9) the HBV02 siRNA at one of two doses, and a fully murinized anti-HBV antibody HBC34 (HBC34v35), at one of three antibody doses; (10) a control siRNA and a control antibody; or (11) PBS only, administered intraperitoneally. Results are shown for treatments 1-5, 10, and 11.

FIG. 5B depicts results of assaying for HBV viral load in mouse serum samples, measured as HBV DNA copy number, following siRNA, antibody, and/or control treatments. Mice were injected with AAV/HBV virus on day −28. AAV/HBV-infected C57Bl/6 mice were administered one of eleven different treatments on day 0: (1) an HBV-specific siRNA (HBV02, having an antisense strand of SEQ ID NO:8; see description in Example 1); (2)-(3) an anti-HBV antibody (a fully murinized HBC24), at one of two doses; (4)-(5) the HBV02 siRNA at one dose, and the fully murinized HBC24 at one of two doses; (6-9) the HBV02 siRNA at one of two doses, and a fully murinized anti-HBV antibody HBC34 (HBC34v35), at one of three antibody doses; (10) a control siRNA and a control antibody; or (11) PBS only, administered intraperitoneally. Results are shown for treatments 1 and 6-11.

FIG. 6A depicts HBsAg levels measured from mouse serum following siRNA, antibody, and/or control treatments, as described above for FIG. 5A.

FIG. 6B depicts HBsAg levels measured from mouse serum following siRNA, antibody, and/or control treatments, as described above for FIG. 5B.

FIG. 7A depicts HBeAg levels measured from mouse serum following siRNA, antibody, and/or control treatments, as described above for FIG. 5A.

FIG. 7B depicts HBeAg levels measured from mouse serum following siRNA, antibody, and/or control treatments, as described above for FIG. 5B.

FIG. 8 shows the experimental design for the study described in Example 3, including a dosage schedule for evaluating serum clearance of HBsAG and viral entry inhibition in a mouse model following treatment with an anti-HBV antibody and an HBV-specific siRNA. AAV/HBV-infected SCID mice with transplanted primary human hepatocytes (n=4 mice per treatment group) were administered one of seven different treatments: (1) PBS only; (2-4) an anti-HBV antibody (a fully murinized HBC34v35), at one of three doses, administered intraperitoneally twice per week during weeks two and three; or (5-7) an HBV-specific siRNA (HBV02, with having an antisense strand of SEQ ID NO:8; see description in Example 1) administered subcutaneously once at the beginning of the study, and the fully murinized HBC34v35, at one of three antibody doses, administered intraperitoneally twice per week during weeks two and three. Mice were sacrificed at week 6.

DETAILED DESCRIPTION

Figure 1:
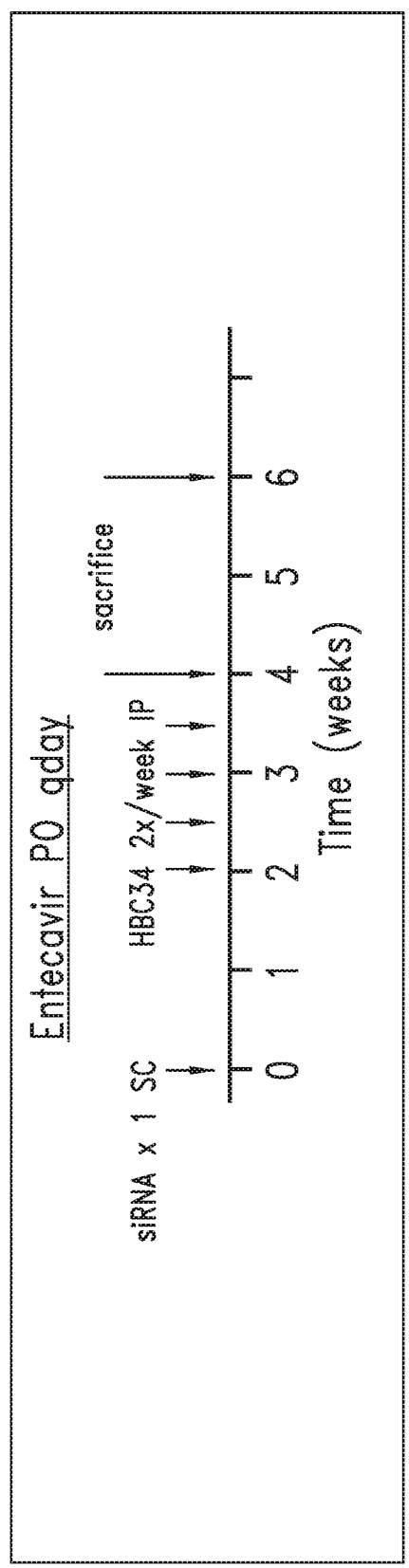

The instant disclosure provides methods and compositions for use in treating hepatitis B virus (HBV) infection with an inhibitor of HBV protein expression and an anti-HBV antibody, and related kits. The combination therapies may be used to treat chronic hepatitis B (CHB).

In some embodiments, the methods include treating chronic HBV infection in a subject in need thereof, by: (i) administering to the subject an inhibitor of HBV gene expression; and (ii) administering to the subject an anti-HBV antibody. In particular embodiments, expression of at least one HBV gene is reduced after administering the inhibitor of HBV gene expression, and the anti-HBV antibody is administered to the subject when expression of the at least one HBV gene is reduced.

In certain embodiments, the inhibitor of HBV gene expression is an RNAi agent that inhibits expression of an HBV transcript. In particular embodiments, the RNAi agent is an siRNA (also referred to herein as "double-stranded RNA" or "dsRNA") that targets and inhibits expression of an mRNA encoded by the X gene of HBV.

In certain embodiments, the anti-HBV antibody recognizes HBV genotypes A, B, C, D, E, F, G, H, I, and J; and/or is a human antibody. In particular embodiments, the anti-HBV antibody is selected from: an HBC34 wild-type antibody, a non-natural variant of an HBC34 antibody, and/or an HBC24 antibody.

In some embodiments described herein, the inhibitor of HBV gene expression and anti-HBV antibody work synergistically to reduce viral load and circulating HBsAg. This combination therapy may provide a functional cure for chronic HBV, and may allow for administration of lower doses of antibody, leading to a reduced potential for antibody-induced toxicity.

I. Glossary

The following sections provide a detailed description of an HBV combination therapy, including: inhibitors of HBV protein expression; anti-HBV antibodies; methods of treating a subject using an inhibitor of HBV protein expression in combination with an anti-HBV antibody; and kits related to combination therapies.

Prior to setting forth this disclosure in more detail, it may be helpful to an understanding thereof to provide definitions of certain terms to be used herein. Additional definitions are set forth throughout this disclosure.

In the present description, the term "about" means±20% of the indicated range, value, or structure, unless otherwise indicated.

The term "comprise" means the presence of the stated features, integers, steps, or components as referred to in the claims, but that it does not preclude the presence or addition of one or more other features, integers, steps, components, or groups thereof. The term "consisting essentially of" limits the scope of a claim to the specified materials or steps and those that do not materially affect the basic and novel characteristics of the claimed invention.

It should be understood that the terms "a" and "an" as used herein refer to "one or more" of the enumerated components. The use of the alternative (e.g., "or") should be understood to mean either one, both, or any combination thereof of the alternatives, and may be used synonymously with "and/or". As used herein, the terms "include" and "have" are used synonymously, which terms and variants thereof are intended to be construed as non-limiting.

The word "substantially" does not exclude "completely"; e.g., a composition which is "substantially free" from Y may be completely free from Y. Where necessary, the word "substantially" may be omitted from definitions provided herein.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, the terms "peptide", "polypeptide", and "protein" and variations of these terms refer to a molecule, in particular a peptide, oligopeptide, polypeptide, or protein including fusion protein, respectively, comprising at least two amino acids joined to each other by a normal peptide bond, or by a modified peptide bond, such as for example in the cases of isosteric peptides. For example, a peptide, polypeptide, or protein may be composed of amino acids selected from the 20 amino acids defined by the genetic code, linked to each other by a normal peptide bond ("classical" polypeptide). A peptide, polypeptide, or protein can be composed of L-amino acids and/or D-amino acids. In particular, the terms "peptide", "polypeptide", and "protein" also include "peptidomimetics," which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide, or protein may comprise amino acids other than the 20 amino acids defined by the genetic code in addition to these amino acids, or it can be composed of amino acids other than the 20 amino acids defined by the genetic code. In particular, a peptide, polypeptide, or protein in the context of the present disclosure can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain, or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", or "protein" in the context of the present disclosure in particular also include modified peptides, polypeptides, and proteins. For example, peptide, polypeptide, or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation, or ubiquitination. Such modifications are fully detailed in the literature (Proteins Structure and Molecular Properties, 2nd Ed., T. E. Creighton, New York (1993); Post-translational Covalent Modifications of Proteins, B. C. Johnson, Ed., Academic Press, New York (1983); Seifter, et al., Analysis for protein modifications and nonprotein cofactors, Meth. Enzymol. 182:626-46 (1990); and Rattan, et al., Protein Synthesis: Post-translational Modifications and Aging, Ann NY Acad Sci 663:48-62 (1992)). Accordingly, the terms "peptide", "polypeptide", and "protein" include for example lipopeptides, lipoproteins, glycopeptides, glycoproteins, and the like.

As used herein a "(poly)peptide" comprises a single chain of amino acid monomers linked by peptide bonds as explained above. A "protein", as used herein, comprises one or more, e.g., 1, 2, 3, 4, 5, 6, 7, 8, 9 or 10 (poly)peptides, i.e., one or more chains of amino acid monomers linked by peptide bonds as explained above. In particular embodiments, a protein according to the present disclosure comprises 1, 2, 3, or 4 polypeptides.

The term "recombinant", as used herein (e.g., a recombinant antibody, a recombinant protein, a recombinant nucleic acid, etc.), refers to any molecule (antibody, protein, nucleic acid, siRNA, etc.) that is prepared, expressed, created, or isolated by recombinant means, and which is not naturally occurring. As used herein, the terms "nucleic acid", "nucleic acid molecule," and "polynucleotide" are used interchangeably and are intended to include DNA molecules and RNA molecules. A nucleic acid molecule may be single-stranded or double-stranded. In particular embodiments, the nucleic acid molecule is double-stranded RNA.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

As used herein, the term "sequence variant" refers to any sequence having one or more alterations in comparison to a reference sequence, whereby a reference sequence is any of the sequences listed in the sequence listing, i.e., SEQ ID NO:1 to SEQ ID NO:104. Thus, the term "sequence variant" includes nucleotide sequence variants and amino acid sequence variants. For a sequence variant in the context of a nucleotide sequence, the reference sequence is also a nucleotide sequence, whereas for a sequence variant in the context of an amino acid sequence, the reference sequence is also an amino acid sequence. A "sequence variant" as used herein is at least 80%, at least 85%, at least 90%, at least 95%, at least 98%, or at least 99% identical to the reference sequence. Sequence identity is usually calculated with regard to the full length of the reference sequence (i.e., the sequence recited in the application), unless otherwise specified. Percentage identity, as referred to herein, can be determined, for example, using BLAST using the default parameters specified by the NCBI (the National Center for Biotechnology Information; http://www.ncbi.nlm.nih.gov/) [Blosum 62 matrix; gap open penalty=1 1 and gap extension penalty=1]. A "sequence variant" in the context of a nucleic acid (nucleotide) sequence has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "sequence variant" of a nucleotide sequence can either result in a change in the respective reference amino acid sequence, i.e., in an amino acid "sequence variant" or not. In certain embodiments, the nucleotide sequence variants are variants that do not result in amino acid sequence variants (i.e., silent mutations). However, nucleotide sequence variants leading to "non-silent" mutations are also within the scope, in particular such nucleotide sequence variants, which result in an amino acid sequence, which is at least 80%, at least 85%, at least 90%, at least 95%, at least 98%, or at least 99% identical to the reference amino acid sequence. A "sequence variant" in the context of an amino acid sequence has an altered sequence in which one or more of the amino acids is deleted, substituted or inserted in comparison to the reference amino acid sequence. As a result of the alterations, such a sequence variant has an amino acid sequence which is at least 80%, at least 85%, at least 90%, at least 95%, at least 98%, or at least 99% identical to the reference amino acid sequence. For example, per 100 amino acids of the reference sequence a variant sequence having no more than 10 alterations, i.e., any combination of deletions, insertions, or substitutions, is "at least 90% identical" to the reference sequence.

While it is possible to have non-conservative amino acid substitutions, in certain embodiments, the substitutions are conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine, and isoleucine, with another; substitution of one hydoxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine, and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Unless otherwise stated, alterations in the sequence variants do not abolish the functionality of the respective reference sequence, for example, in the present case, the functionality of a sequence of an anti-HBV antibody or an inhibitor of HBV gene expression (e.g., an siRNA) to sufficiently neutralize infection of HBV or reduce HBV protein expression, respectively. Guidance in determining which nucleotides and amino acid residues, respectively, may be substituted, inserted, or deleted without abolishing such functionality can be found by using computer programs well known in the art.

As used herein, a nucleic acid sequence or an amino acid sequence "derived from" a designated nucleic acid, peptide, polypeptide, or protein refers to the origin of the nucleic acid, peptide, polypeptide, or protein. In some embodiments, the nucleic acid sequence or amino acid sequence which is derived from a particular sequence has an amino acid sequence that is essentially identical to that sequence or a portion thereof, from which it is derived, whereby "essentially identical" includes sequence variants as defined above. In certain embodiments, the nucleic acid sequence or amino acid sequence which is derived from a particular peptide or protein is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins, and nucleic acids are thus identifiable to one of ordinary skill in the art. Likewise, sequences "derived from" other sequence are usually identifiable to one of ordinary skill in the art as having its origin in the sequence.

In some embodiments, a nucleic acid sequence or an amino acid sequence derived from another nucleic acid, peptide, polypeptide, or protein may be identical to the starting nucleic acid, peptide, polypeptide, or protein (from which it is derived). However, a nucleic acid sequence or an amino acid sequence derived from another nucleic acid, peptide, polypeptide, or protein may also have one or more mutations relative to the starting nucleic acid, peptide, polypeptide, or protein (from which it is derived), in particular a nucleic acid sequence or an amino acid sequence derived from another nucleic acid, peptide, polypeptide, or protein may be a functional sequence variant as described above of the starting nucleic acid, peptide, polypeptide, or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g., a corresponding genomic sequence. A mutation, e.g., in comparison to a genomic sequence, may be, for example, a (naturally occurring) somatic mutation, a spontaneous mutation, an induced mutation, e.g., induced by enzymes, chemicals, or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g., in a nucleic acid sequence or in an amino acid sequence. A mutation includes substitution, deletion, and insertion of one or more nucleotides or amino acids as well as inversion of several successive nucleotides or amino acids. To achieve a mutation in an amino acid sequence, a mutation may be introduced into the nucleotide sequence encoding said amino acid sequence in order to express a (recombinant) mutated polypeptide. A mutation may be achieved, e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

As used herein, the term "coding sequence" is intended to refer to a polynucleotide molecule, which encodes the amino acid sequence of a protein product. The boundaries of the coding sequence are generally determined by an open reading frame, which usually begins with an ATG start codon.

The term "expression" as used herein refers to any step involved in the production of the polypeptide, including transcription, post-transcriptional modification, translation, post-translational modification, secretion, or the like.

In some aspects, the present disclosure relates to the use of an inhibitor of HBV gene expression. As used herein, an "inhibitor of HBV gene expression" is any agent that results in at least partial reduction of the expression of an HBV gene, as manifested by a reduction of the amount of HBV mRNA which can be isolated from or detected in a first cell or group of cells in which an HBV gene is transcribed and which has or have been treated with an inhibitor of HBV gene expression, such that the expression of the HBV gene is inhibited, as compared to a second cell or group of cells substantially identical to the first cell or group of cells but which has or have not been so treated (control cells). In some embodiments, an inhibitor of HBV gene expression is an RNAi agent (e.g., an siRNA). HBV gene expression can be measured by methods known in the art. Unless otherwise stated, "HBV gene expression" as used herein is determined using rtPCR or by measuring protein expression using enzyme-linked immunosorbent assay (ELISA) or immunohistochemistry.

In some aspects, the present disclosure relates to the use of an agent that reduces HBV antigenic load. As used herein, an "agent that reduces HBV antigenic load" refers to any agent that results in a reduction in the amount of an HBV antigen that can be isolated from or detected in a first cell or group of cells that has or have been treated with the agent, as compared to a second cell or group of cells substantially identical to the first cell or group of cells but which has or have not been so treated (control cells). In some embodiments, an agent that reduces HBV antigenic load is an RNAi agent (e.g., an siRNA). Antigenic load can be measured by methods known in the art. Unless otherwise stated, "HBV antigenic load" as used herein is determined by measuring by the amount of antigen (e.g., HBsAg) using ELISA.

The present disclosure provides combination therapy to treat HBV, which includes an anti-HBV antibody. In certain embodiments, the anti-HBV antibody or an antigen binding fragment thereof binds to the antigenic loop region of HBsAg and neutralizes infection with hepatitis B virus.

As used herein, the term "antibody" encompasses various forms of antibodies including, without being limited to, whole antibodies, antibody fragments, antigen binding fragments, human antibodies, chimeric antibodies, humanized antibodies, recombinant antibodies, and genetically engineered antibodies (variant or mutant antibodies) as long as the characteristic properties of the antibody are retained. In some embodiments, the antibodies are human antibodies and/or monoclonal antibodies. In particular embodiments, the antibodies are human monoclonal antibodies. In certain particular embodiments, the antibodies are recombinant human monoclonal antibodies. As used herein, the terms "antigen binding fragment," "fragment," and "antibody fragment" are used interchangeably to refer to any fragment of an antibody of the combination therapy that retains the antigen-binding activity of the antibody. Examples of antibody fragments include, but are not limited to, a single chain antibody, Fab, Fab', F(ab')2, Fv, or scFv. Further, the term "antibody" as used herein includes both antibodies and antigen binding fragments thereof.

As used herein, a "neutralizing antibody" is one that can neutralize, i.e., prevent, inhibit, reduce, impede, or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

Human antibodies are well-known in the state of the art (van Dijk, M. A., and van de Winkel, J. C, Curr. Opin. Chem. Biol. 5:368-74 (2001)). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90:2551-55 (1993); Jakobovits, A., et al., Nature 362:255-258 (1993); Bruggemann, M., et al., Year Immunol. 7:3340 (1993)). Human antibodies can also be produced in phage display libraries (Hoogenboom, H. R., and Winter, G., Mol. Biol. 227:381-88 (1992); Marks, J. D., et al., Mol Biol. 222:581-97 (1991)). The techniques of Cole, et al. and Boerner, et al. are also available for the preparation of human monoclonal antibodies (Cole, et al., Monoclonal Antibodies and Cancer Therapy, Alan R. Liss, p. 77 (1985); Boerner, P., et al., Immunol. 147:86-95 (1991)). In some embodiments, human monoclonal antibodies are prepared by using improved EBV-B cell immortalization as described in Traggiai, E., et al. (Nat Med. 10(8): 871-5 (2004)). The term "human antibody" as used herein also comprises such antibodies which are modified, e.g., in the variable region, to generate properties as described herein.

Antibodies of the combination therapy can be of any isotype (e.g., IgA, IgG, IgM, i.e., a κ, γ, or μ heavy chain), but in certain particular embodiments, the antibodies are IgG. Within the IgG isotype, antibodies may be IgG1, IgG2, IgG3, or IgG4 subclass. In particular embodiments, the antibodies are IgG1. Antibodies of the combination therapy may have a κ or a λ light chain. HBsAg-specific antibodies of the IgG-type may advantageously also block the release of HBV and HBsAg from infected cells, based on antigen-independent uptake of IgG through FcRN-IgG receptors into hepatocytes. Therefore, HBsAg-specific antibodies of the IgG-type can bind intracellularly and thereby block the release of HBV virions and HBsAg.

As used herein, the term "variable region" (variable region of a light chain ($V_L$), variable region of a heavy chain ($V_H$)) denotes the portion of an antibody light chain (LC) or heavy chain (HC) (typically around the 105-120 amino-terminal amino acids of a mature antibody heavy chain or light chain) that comprises complementarity determining regions ("CDRs") and framework regions ("FRs"), and that is involved directly in binding the antibody to the antigen. The terms "complementarity determining region," and "CDR," are synonymous with "hypervariable region" or "HVR," and are known in the art to refer to non-contiguous sequences of amino acids within antibody variable regions, which confer antigen specificity and/or binding affinity. In general, there are three CDRs in each variable region of an immunoglobulin binding protein; e.g., for antibodies, the $V_H$ and $V_L$ regions generally comprise six CDRs (CDRH1, CDRH2, CDRH3; CDRL1, CDRL2, CDRL3). Immunoglobulin sequences can be aligned to a numbering scheme (e.g., Kabat, EU, International Immunogenetics Information System (IMGT) and Aho), which can allow equivalent residue positions to be annotated and for different molecules to be compared using Antigen receptor Numbering And Receptor Classification (ANARCI) software tool (Bioinformatics 15:298-300 (2016)). It will be understood that in certain embodiments, an antibody or antigen binding fragment of the present disclosure can comprise all or part of a heavy chain (HC), a light chain (LC), or both. For example, a full-length intact IgG antibody monomer typically includes a $V_H$, a CH1, a CH2, a CH3, a $V_L$, and a CL.

In certain embodiments, the anti-HBV antibodies of the combination therapy, according to the present disclosure, or the antigen binding fragment thereof, is a purified antibody, a single chain antibody, a Fab, a Fab', a F(ab')2, a Fv, or an scFv. The antibodies of the combination therapy may thus be human antibodies, monoclonal antibodies, human monoclonal antibodies, recombinant antibodies, and/or purified antibodies. The present disclosure also provides fragments of the antibodies, particularly fragments that retain the antigen-binding activity of the antibodies. Such fragments include, but are not limited to, single chain antibodies, Fab, Fab', F(ab')2, Fv, or scFv. Although in some places, the present disclosure may refer explicitly to antigen binding fragment(s), antibody fragment(s), variant(s) and/or derivative(s) of antibodies, as used herein the term "antibody" or "antibody of the combination therapy" includes all categories of antibodies, namely, antigen binding fragment(s), antibody fragment(s), variant(s), and derivative(s) of antibodies.

Fragments of the antibodies can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. The present disclosure also encompasses single-chain Fv fragments (scFv) derived from the heavy and light chains of an antibody of the disclosure. For example, the disclosure includes a scFv comprising the CDRs from an antibody of the disclosure. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the present disclosure may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the antibody/antibody fragment may be a component of a multispecific molecule in which the sequences target the epitopes as described herein, and other regions of the multispecific molecule bind to other targets. Exemplary multispecific molecules include, but are not limited to, bispecific Fab2, trispecific Fab3, bispecific scFv, and diabodies (Holliger and Hudson, Nature Biotechnology 9:1126-36 (2005)).

Antibodies according to the present disclosure may be provided in purified form. Typically, the antibody will be present in a composition that is substantially free of other polypeptides e.g., where less than 90% (by weight), usually less than 60% and more usually less than 50% of the composition is made up of other polypeptides.

Antibodies and antigen binding fragments of the present disclosure may, in embodiments, be multispecific (e.g., bispecific, trispecific, tetraspecific, or the like), and may be provided in any multispecific format, as disclosed herein. In certain embodiments, an antibody or antigen-binding fragment of the present disclosure is a multispecific antibody, such as a bispecific or trispecific antibody. Formats for bispecific antibodies are disclosed in, for example, Spiess, et al. (Mol. Immunol. 67(2):95 (2015)), and Brinkmann and Kontermann (mAbs 9(2):182-212 (2017)), which bispecific formats and methods of making the same are incorporated herein by reference and include, for example, Bispecific T cell Engagers (BiTEs), DARTs, Knobs-Into-Holes (KIH) assemblies, scFv-CH3-KIH assemblies, KIH Common Light-Chain antibodies, TandAbs, Triple Bodies, TriBi Minibodies, Fab-scFv, scFv-CH-CL-scFv, F(ab')2-scFv2, tetravalent HCabs, Intrabodies, CrossMabs, Dual Action Fabs (DAFs) (two-in-one or four-in-one), DutaMabs, DT-IgG, Charge Pairs, Fab-arm Exchange, SEEDbodies, Triomabs, LUZ-Y assemblies, Fcabs, KX-bodies, orthogonal Fabs, DVD-IgGs, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, Zybody, and DVI-IgG (four-in-one). A bispecific or multispecific antibody may comprise a HBV- and/or HDV-specific binding domain of the instant disclosure in combination with another such binding domain of the instant disclosure, or in combination with a different binding domain that specifically binds to HBV and/or HDV (e.g., at a same or a different epitope), or with a binding domain that specifically binds to a different antigen.

The term "vaccine" as used herein is typically understood to be a prophylactic or therapeutic material providing at least one antigen or immunogen. The antigen or immunogen may be derived from any material that is suitable for vaccination. For example, the antigen or immunogen may be derived from a pathogen, such as from bacteria or virus particles, etc., or from a tumor or cancerous tissue. The antigen or immunogen stimulates the body's adaptive immune system to provide an adaptive immune response. In particular, an "antigen" or an "immunogen" refers typically to a substance which may be recognized by the immune system (e.g., the adaptive immune system), and which is capable of triggering an antigen-specific immune response, e.g., by formation of antibodies and/or antigen-specific T cells as part of an adaptive immune response. Typically, an antigen may be or may comprise a peptide or protein which may be presented by the MHC to T-cells.

Doses are often expressed in relation to bodyweight. Thus, a dose which is expressed as [g, mg, or other unit]/kg (or g, mg, etc.) usually refers to [g, mg, or other unit]"per kg (or g, mg, etc.) bodyweight", even if the term "bodyweight" is not explicitly mentioned.

As used herein, "Hepatitis B virus," used interchangeably with the term "HBV" refers to the well-known non-cytopathic, liver-tropic DNA virus belonging to the Hepadnaviridae family. The HBV genome is partially double-stranded, circular DNA with four overlapping reading frames (that may be referred to herein as "genes," "open reading frames," or "transcripts"): C, X, P, and S. The core protein is coded for by gene C (HBcAg). Hepatitis B e antigen (HBeAg) is produced by proteolytic processing of the pre-core (pre-C) protein. The DNA polymerase is encoded by gene P. Gene S is the gene that codes for the surface antigens (HBsAg). The HBsAg gene is one long open reading frame which contains three in frame "start" (ATG) codons resulting in polypeptides of three different sizes called large, middle, and small S antigens, pre-S1+pre-S2+S, pre-S2+S, or S. Surface antigens in addition to decorating the envelope of HBV, are also part of subviral particles, which are produced at large excess as compared to virion particles, and play a role in immune tolerance and in sequestering anti-HBsAg antibodies, thereby allowing for infectious particles to escape immune detection. The function of the non-structural protein coded for by gene X is not fully understood, but it plays a role in transcriptional trans-activation and replication and is associated with the development of liver cancer. Eight genotypes of HBV, designated A to H, have been determined, and two additional genotypes I and J have been proposed, each having a distinct geographical distribution. The term "HBV" includes any of the genotypes of HBV (A to J). The complete coding sequence of the reference sequence of the HBV genome may be found in for example, GenBank Accession Nos. GI:21326584 and GI:3582357. Amino acid sequences for the C, X, P, and S proteins can be found at, for example, NCBI Accession numbers YP_009173857.1 (C protein); YP_009173867.1 and BAA32912.1 (X protein); YP_009173866.1 and BAA32913.1 (P protein); and YP_009173869.1, YP_009173870.1, YP_009173871.1, and BAA32914.1 (S protein). Additional examples of HBV mRNA sequences are readily available using publicly available databases, e.g., GenBank, UniProt, and OMIM. The International Repository for Hepatitis B Virus Strain Data can be accessed at http://www.hpa-bioinformatics.org.uk/HepSEQ/main.php. The term "HBV," as used herein, also refers to naturally occurring DNA sequence variations of the HBV genome, i.e., genotypes A-J and variants thereof.

II. Inhibitors of HBV Protein Expression and Delivery Systems

The present disclosure provides inhibitors of HBV protein expression for use in a combination therapy for treating HBV. In certain embodiments, the inhibitor of HBV gene expression is an RNAi agent. As used herein, the term "RNA interference agent" or "RNAi agent" refers to an agent that contains RNA as that term is defined herein, and which mediates the targeted cleavage of an RNA transcript via an RNA-induced silencing complex (RISC) pathway. In some embodiments, an RNAi agent as described herein effects inhibition of expression of an HBV gene.

In one aspect, an RNA interference agent includes a single-stranded RNA that interacts with a target RNA sequence to direct the cleavage of the target RNA. Without wishing to be bound to a particular theory, long double-stranded RNA (dsRNA) introduced into plants and invertebrate cells is broken down into siRNA by a Type III endonuclease known as Dicer (Sharp, et al., Genes Dev. 15:485 (2001)). Dicer, a ribonuclease-III-like enzyme, processes the dsRNA into 19-23 base pair short interfering RNAs (siRNAs) with characteristic two base 3' overhangs (Bernstein, et al., Nature 409:363 (2001)). The siRNAs are then incorporated into an RNA-induced silencing complex (RISC) where one or more helicases unwind the siRNA duplex, enabling the complementary antisense strand to guide target recognition (Nykanen, et al., Cell 107:309 (2001)). Upon binding to the appropriate target mRNA, one or more endonucleases within the RISC cleaves the target to induce silencing (Elbashir, et al, Genes Dev. 15:188 (2001)). Thus, in one aspect the technology described herein relates to a single stranded RNA that promotes the formation of a RISC complex to effect silencing of the target gene.

The terms "silence," "inhibit the expression of," "down-regulate the expression of," "suppress the expression of," and the like, in so far as they refer to an HBV gene, herein refer to the at least partial reduction of the expression of an HBV gene, as manifested by a reduction of the amount of HBV mRNA which can be isolated from or detected in a first cell or group of cells in which an HBV gene is transcribed and which has or have been treated with an inhibitor of HBV gene expression, such that the expression of the HBV gene is inhibited, as compared to a second cell or group of cells substantially identical to the first cell or group of cells but which has or have not been so treated (control cells). The degree of inhibition can be measured, by example, as the difference between the degree of mRNA expression in a control cell minus the degree of mRNA expression in a treated cell. Alternatively, the degree of inhibition can be given in terms of a reduction of a parameter that is functionally linked to HBV gene expression, e.g., the amount of protein encoded by an HBV gene, or the number of cells displaying a certain phenotype, e.g., an HBV infection phenotype such as HBV infection, HBV protein expression (such as hepatitis B surface antigen, HBsAg), or changes in cellular gene expression reflecting HBV gene expression (e.g., Smc5/6 expression and localization). The degree of inhibition may also be measured using a cell engineered to express a reporter gene reflecting HBV RNA expression. In principle, HBV gene silencing can be determined in any cell expressing the HBV gene, e.g., an HBV-infected cell or a cell engineered to express the HBV gene, and by any appropriate assay.

The level of HBV RNA that is expressed by a cell or group of cells, or the level of circulating HBV RNA, may be determined using any method known in the art for assessing mRNA expression, such as the rtPCR method provided in Example 2 of International Application Publication No. WO 2016/077321A1 and U.S. Patent Application No. US2017/0349900A1, which methods are incorporated herein by reference. In some embodiments, the level of expression of an HBV gene (e.g., total HBV RNA, an HBV transcript, e.g., HBV 3.5 kb transcript) in a sample is determined by detecting a transcribed polynucleotide, or portion thereof, e.g., RNA of the HBV gene. RNA may be extracted from cells using RNA extraction techniques including, for example, using acid phenol/guanidine isothiocyanate extraction (RNAzol B; Biogenesis), RNeasy RNA preparation kits (Qiagen®), or PAXgene (PreAnalytix, Switzerland). Typical assay formats utilizing ribonucleic acid hybridization include nuclear run-on assays, RT-PCR, RNase protection assays (Melton et al., Nuc. Acids Res. 12:7035), northern blotting, in situ hybridization, and microarray analysis. Circulating HBV mRNA may be detected using methods the described in International Application Publication No. WO 2012/177906A1 and U.S. Patent Application No. US2014/0275211A1, which methods are incorporated herein by reference.

As used herein, "target sequence" refers to a contiguous portion of the nucleotide sequence of an mRNA molecule formed during the transcription of an HBV gene, including mRNA that is a product of RNA processing of a primary transcription product. The target portion of the sequence will be at least long enough to serve as a substrate for RNAi-directed cleavage at or near that portion. For example, the target sequence will generally be from 9-36 nucleotides in length, e.g., 15-30 nucleotides in length, including all subranges there between. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an RNAi agent, e.g., within an siRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, an siRNA comprising one oligonucleotide 21 nucleotides in length, and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary," and "substantially complementary" herein can be used with respect to the base matching between the sense strand and the antisense strand of an siRNA, or between the antisense strand of an RNAi agent and a target sequence, as will be understood from the context of their use.

As used herein, a polynucleotide that is "substantially complementary" to at least part of a messenger RNA (mRNA) refers to a polynucleotide that is substantially complementary to a contiguous portion of the mRNA of interest (e.g., an mRNA encoding an HBV protein). For example, a polynucleotide is complementary to at least a part of an HBV mRNA if the sequence is substantially complementary to a non-interrupted portion of the HBV mRNA.

a. siRNAs

In some embodiments, the RNAi agent comprises an siRNA. The term "siRNA," as used herein, refers to an RNAi that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range there between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, and 21-22 base pairs. siRNAs generated in the cell by processing with Dicer and similar enzymes are generally in the range of 19-22 base pairs in length. The term "double-stranded RNA" or "dsRNA," is also used herein synonymously to refer to an siRNA as described above.

One strand of the duplex region of an siRNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of an siRNA are comprised by separate RNA molecules, those molecules need not, but can be covalently connected. Where the two strands are connected covalently by means other than a hairpin loop, the connecting structure is referred to as a "linker."

The term "antisense strand" or "guide strand" refers to the strand of an RNAi agent, e.g., an siRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches can be in the internal or terminal regions of the molecule.

Generally, the most tolerated mismatches are in the terminal regions, e.g., within 5, 4, 3, or 2 nucleotides of the 5' and/or 3' terminus.

The term "sense strand" or "passenger strand" as used herein, refers to the strand of an RNAi that includes a region that is substantially complementary to a region of the antisense strand as that term is defined herein.

In another aspect, the agent is a single-stranded antisense RNA molecule. The antisense RNA molecule can have 15-30 nucleotides complementary to the target. For example, the antisense RNA molecule may have a sequence of at least 15, 16, 17, 18, 19, 20, 21, or more contiguous nucleotides from one of the antisense sequences disclosed herein.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described in greater detail below. However, siRNA molecules comprising ribonucleoside analogs or derivatives retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate, or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20, or more, up to the entire length of the siRNA molecule. The modifications need not be the same for each of such a plurality of modified ribonucleosides in an RNA molecule. In some embodiments, modified RNAs contemplated for use in methods and compositions described herein are peptide nucleic acids (PNAs) that have the ability to form the required duplex structure and that permit or mediate the specific degradation of a target RNA via a RISC pathway.

In some embodiments, a modified ribonucleoside includes a deoxyribonucleoside. For example, an RNAi agent can comprise one or more deoxynucleosides, including, for example, a deoxynucleoside overhang(s), or one or more deoxynucleosides within the double-stranded portion of an siRNA. However, the term "RNAi agent" as used herein does not include a fully DNA molecule.

As used herein, the term "nucleotide overhang" refers to at least one unpaired nucleotide that protrudes from the duplex structure of an RNAi agent, e.g., an siRNA. For example, when a 3'-end of one strand of an siRNA extends beyond the 5'-end of the other strand, or vice versa, there is a nucleotide overhang. An siRNA can comprise an overhang of at least one nucleotide; alternatively the overhang can comprise at least two nucleotides, at least three nucleotides, at least four nucleotides, at least five nucleotides, or more. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5' end, 3' end, or both ends of either an antisense or sense strand of an siRNA.

In some embodiments, the antisense strand of an siRNA has a 1-10 nucleotide overhang at the 3' end and/or the 5' end. In some embodiments, the sense strand of an siRNA has a 1-10 nucleotide overhang at the 3' end and/or the 5' end. In some other embodiments, one or more of the nucleotides in the overhang is replaced with a nucleoside thiophosphate.

In some embodiments, at least one end of an siRNA has a single-stranded nucleotide overhang of 1 to 4, generally 1 or 2 nucleotides. siRNAs having at least one nucleotide overhang can have unexpectedly superior inhibitory properties relative to their blunt-ended counterparts.

The terms "blunt" or "blunt ended" as used herein in reference to an siRNA mean that there are no unpaired nucleotides or nucleotide analogs at a given terminal end of an siRNA, i.e., no nucleotide overhang. One or both ends of an siRNA can be blunt. Where both ends of an siRNA are blunt, the siRNA is said to be "blunt ended." A "blunt ended" siRNA is an siRNA that is blunt at both ends, i.e., has no nucleotide overhang at either end of the molecule. Most often such a molecule will be double-stranded over its entire length.

In certain embodiments, the combination therapy described herein includes one or more RNAi agents that inhibit the expression of the HBV gene. In some embodiments, the RNAi agent includes short interfering ribonucleic acid (siRNA) molecules for inhibiting the expression of an HBV gene in a mammal, e.g., in an HBV-infected human, where the siRNA includes an antisense strand having a region of complementarity which is complementary to at least a part of an mRNA formed in the expression of an HBV gene, and where the region of complementarity is 30 nucleotides or less in length, generally 19-24 nucleotides in length, and where the siRNA, upon contact with a cell expressing the HBV gene, inhibits the expression of the HBV gene by at least 10% as assayed by, for example, a PCR or branched DNA (bDNA)-based method, or by a protein-based method, such as by Western blot. Expression of an HBV gene in cell culture or expression of a cellular gene as a surrogate for HBV gene expression (e.g., Smc5/6), such as in COS cells, HeLa cells, primary hepatocytes, HepG2 cells, primary cultured cells or in a biological sample from a subject, can be assayed by measuring HBV mRNA levels, such as by bDNA or TaqMan assay, or by measuring protein levels, such as by immunofluorescence analysis, using, for example, Western Blotting or flow cytometric techniques.

An siRNA includes two RNA strands that are complementary and hybridize to form a duplex structure under conditions in which the siRNA will be used. One strand of an siRNA (the antisense strand) includes a region of complementarity that is substantially complementary, and generally fully complementary, to a target sequence. The target sequence can be derived from the sequence of an mRNA formed during the expression of an HBV gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the siRNA is between 15 and 20 nucleotides in length, inclusive, and in other embodiments, the siRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). siRNAs having duplexes as short as 9 base pairs can, under some circumstances, mediate RNAi-directed RNA cleavage. Most often a target will be at least 15 nucleotides in length. In certain embodiments, the target is 15-30 nucleotides in length.

One of skill in the art will also recognize that the duplex region is a primary functional portion of an siRNA, e.g., a duplex region of 9 to 36, e.g., 15-30 base pairs. Thus, in some embodiments, to the extent that it becomes processed to a functional duplex of e.g., 15-30 base pairs that targets a desired RNA for cleavage, an RNA molecule or complex of RNA molecules having a duplex region greater than 30 base pairs is an siRNA. Thus, an ordinarily skilled artisan will recognize that in some embodiments, then, a miRNA is an siRNA. In some other embodiments, an siRNA is not a naturally occurring miRNA. In some embodiments, an RNAi agent useful to target expression of an HBV gene is not generated in the target cell by cleavage of a larger double-stranded RNA.

An siRNA as described herein can be synthesized by standard methods known in the art, e.g., by use of an automated DNA synthesizer, such as are commercially available from, for example, Biosearch, Applied Biosystems, Inc.

In some embodiments, the RNAi agent comprises an siRNA that targets and inhibits expression of an HBV mRNA. In some embodiments, the RNAi agent comprises an siRNA that targets and inhibits expression of an mRNA encoded by an HBV genome according to NCBI Reference Sequence NC_003977.2 (GenBank Accession No. GI:21326584) (SEQ ID NO:1). Transcription of the HBV genome results in polycistronic, overlapping RNAs, and therefore, in some embodiments, an siRNA of the combination therapy targeting a single HBV gene may result in significant inhibition of expression of most or all HBV transcripts. In some embodiments the mRNA target of the siRNA may be an mRNA encoded by: P gene, nucleotides 2309-3182 and 1-1625 of NC_003977.1; S gene (encoding L, M, and S proteins), nucleotides 2850-3182 and 1-837 of NC_003977; X protein, nucleotides 1376-1840 of NC_003977; and/or C gene, nucleotides 1816-2454 of NC_003977.

In some embodiments, the siRNA targets and inhibits expression of an mRNA encoded by the X gene of HBV. In some embodiments, the RNAi agent or siRNA targets an mRNA encoded by a portion of the HBV genome comprising the sequence GTGTGCACTTCGCTTCAC (SEQ ID NO:2), which corresponds to nucleotides 1579-1597 of NC_003977.2 (GenBank Accession No. GI:21326584) (SEQ ID NO:1).

In still further embodiments, the siRNA has a sense strand comprising 5'-GUGUGCACUUCGCUUCACA-3' (SEQ ID NO:3) and an antisense strand comprising 5'-UGUGAAGCGAAGUGCACACUU-3' (SEQ ID NO:4).

In certain embodiments, the inhibitor of HBV gene expression comprises an siRNA comprising a sense strand and an antisense strand, wherein the sense strand comprises SEQ ID NO:3, or a sequence that differs by not more than 4, not more than 3, not more than 2, or not more than 1 nucleotides from SEQ ID NO:3; and wherein the antisense strand comprises SEQ ID NO:4, or a sequence that differs by not more than 4, not more than 3, not more than 2, or not more than 1 nucleotides from SEQ ID NO:4.

In one aspect, an siRNA will include at least two nucleotide sequences, a sense and an antisense sequence, whereby: the sense sequence comprises SEQ ID NO:3, and the corresponding antisense sequence comprises SEQ ID NO:4. In this aspect, one of the two sequences is complementary to the other of the two sequences, with one of the sequences being substantially complementary to a sequence of an mRNA generated in the expression of an HBV gene. As such, in this aspect, an siRNA will include two oligonucleotides, where one oligonucleotide is described as the sense strand, and the second oligonucleotide is described as the corresponding antisense strand of the sense strand. As described elsewhere herein and as known in the art, the complementary sequences of an siRNA can also be contained as self-complementary regions of a single nucleic acid molecule, as opposed to being on separate oligonucleotides.

In still further embodiments, the siRNA has a sense strand comprising 5'-GGUGGACUUCUCUCAAUUUUA-3' (SEQ ID NO:106) and an antisense strand comprising 5'-UAAAAUUGAGAGAAGUCCACCAC-3' (SEQ ID NO:107).

In certain embodiments, the inhibitor of HBV gene expression comprises an siRNA comprising a sense strand and an antisense strand, wherein the sense strand comprises SEQ ID NO:106, or a sequence that differs by not more than 4, not more than 3, not more than 2, or not more than 1 nucleotides from SEQ ID NO:106; and wherein the antisense strand comprises SEQ ID NO:107, or a sequence that differs by not more than 4, not more than 3, not more than 2, or not more than 1 nucleotides from SEQ ID NO:107.

In one aspect, an siRNA will include at least two nucleotide sequences, a sense and an antisense sequence, whereby: the sense sequence comprises SEQ ID NO:106, and the corresponding antisense sequence comprises SEQ ID NO:107. In this aspect, one of the two sequences is complementary to the other of the two sequences, with one of the sequences being substantially complementary to a sequence of an mRNA generated in the expression of an HBV gene. As such, in this aspect, an siRNA will include two oligonucleotides, where one oligonucleotide is described as the sense strand, and the second oligonucleotide is described as the corresponding antisense strand of the sense strand. As described elsewhere herein and as known in the art, the complementary sequences of an siRNA can also be contained as self-complementary regions of a single nucleic acid molecule, as opposed to being on separate oligonucleotides.

The skilled person is well aware that siRNAs having a duplex structure of between 20 and 23, but specifically 21, base pairs have been hailed as particularly effective in inducing RNA interference (Elbashir, et al., EMBO 20:6877-88 (2001)). However, others have found that shorter or longer RNA duplex structures can be effective as well. In the embodiments described above, siRNAs described herein can include at least one strand of a length of minimally 21 nucleotides. In some embodiments, shorter duplexes having one of the sequences of SEQ ID NO:3, SEQ ID NO:4, SEQ ID NO:106, or SEQ ID NO:107 minus only a few nucleotides on one or both ends are similarly effective as compared to the siRNAs described above. Hence, siRNAs having a partial sequence of at least 15, 16, 17, 18, 19, 20, or more contiguous nucleotides from one or both of SEQ ID NO:3 and SEQ ID NO:4, and differing in their ability to inhibit the expression of an HBV gene by not more than 5, 10, 15, 20, 25, or 30% inhibition from an siRNA comprising the full sequence, are contemplated according to the technology described herein. Also within the present disclosure are siRNAs having a partial sequence of at least 15, 16, 17, 18, 19, 20, or more contiguous nucleotides from one or both of SEQ ID NO:106 and SEQ ID NO:107, and differing in their ability to inhibit the expression of an HBV gene by not more than 5, 10, 15, 20, 25, or 30% inhibition from an siRNA comprising the full sequence, are contemplated according to the technology described herein.

In addition, the siRNAs provided in herein identify a site in an HBV gene transcript that is susceptible to RISC-mediated cleavage. As such, the technology described herein further features RNAi agents that target within one of such sequences. As used herein, an RNAi agent is said to target within a particular site of an RNA transcript if the RNAi agent promotes cleavage of the transcript anywhere within that particular site. In some embodiments, the RNAi agent includes at least 15 contiguous nucleotides from one or both of the sequences of SEQ ID NO:3 and SEQ ID NO:4, coupled to additional nucleotide sequences taken from the region contiguous to the selected sequence in the HBV gene. In some embodiments, the RNAi agent includes at least 15 contiguous nucleotides from one or both of the sequences of SEQ ID NO:106 and SEQ ID NO:107, coupled to additional nucleotide sequences taken from the region contiguous to the selected sequence in the HBV gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an RNAi agent, mediate the best inhibition of target gene expression. It is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., SEQ ID NO:3, SEQ ID NO:4, SEQ ID NO:106, or SEQ ID NO:107, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of RNAi agents based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An RNAi agent as described herein can contain one or more mismatches to the target sequence. In some embodiments, an RNAi agent as described herein contains no more than 3 mismatches. In some embodiments, if the antisense strand of the RNAi agent contains mismatches to a target sequence, the area of mismatch is not located in the center of the region of complementarity. In particular embodiments, if the antisense strand of the RNAi agent contains mismatches to the target sequence, the mismatch is restricted to within the last 5 nucleotides from either the 5' or 3' end of the region of complementarity. For example, for a 23 nucleotide RNAi agent RNA strand which is complementary to a region of an HBV gene, the RNA strand may not contain any mismatch within the central 13 nucleotides. The methods described herein or methods known in the art can be used to determine whether an RNAi agent containing a mismatch to a target sequence is effective in inhibiting the expression of an HBV gene. Consideration of the efficacy of RNAi agents with mismatches in inhibiting expression of an HBV gene is important, especially if the particular region of complementarity in the HBV gene is known to have polymorphic sequence variation.

b. Chemically Modified RNAi Agents

In some embodiments, the RNA of an RNAi agent, e.g., an siRNA, is chemically modified to enhance stability or other beneficial characteristics. The nucleic acids featured in the technology described herein can be synthesized and/or modified by methods well established in the art, such as those described in "Current protocols in nucleic acid chemistry," Beaucage, S. L., et al. (Edrs.), John Wiley & Sons, Inc., New York, NY, USA, which methods are incorporated herein by reference.

Modifications include, for example, (a) end modifications, e.g., 5' end modifications (phosphorylation, conjugation, inverted linkages, etc.), 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

It is not necessary for all positions in a given compound to be uniformly modified, and in fact more than one of the aforementioned modifications can be incorporated in a single compound or even at a single nucleoside within an RNAi agent. The technology described herein also includes RNAi agent compounds that are chimeric compounds. "Chimeric" RNAi agent compounds or "chimeras," in the context of this disclosure, are RNAi agent compounds, such as siRNAs, which contain two or more chemically distinct regions, each made up of at least one monomer unit, i.e., a nucleotide in the case of an siRNA compound. These RNAi agents typically contain at least one region wherein the RNA is modified so as to confer upon the RNAi agent increased resistance to nuclease degradation, increased cellular uptake, and/or increased binding affinity for the target nucleic acid. An additional region of the RNAi agent can serve as a substrate for enzymes capable of cleaving RNA: DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of RNAi agent inhibition of gene expression. Consequently, comparable results can often be obtained with shorter RNAi agents when chimeric siRNAs are used, compared to phosphorothioate deoxy siRNAs hybridizing to the same target region. Cleavage of the RNA target can be routinely detected by gel electrophoresis and, if necessary, associated nucleic acid hybridization techniques known in the art.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts, and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6, 239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464; each of which is herein incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439; each of which is herein incorporated by reference for teachings relevant to such methods of preparation.

In other embodiments, suitable RNA mimetics suitable are contemplated for use in RNAi agents, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262; each of which is incorporated herein by reference for teachings relevant to such methods of preparation. Further teaching of PNA compounds can be found, for example, in Nielsen, et al. (Science, 254:1497-1500 (1991)).

Some embodiments featured in the technology described herein include RNAs with phosphorothioate backbones and oligonucleosides with heteroatom backbones, and in particular —$CH_2$—NH—$CH_2$—, —$CH_2$—N($CH_3$)—O—$CH_2$- [known as a methylene (methylimino) or MMI backbone], —$CH_2$—O—N($CH_3$)—$CH_2$—, —$CH_2$—N($CH_3$)—N($CH_3$)—$CH_2$—, and —N($CH_3$)—$CH_2$—$CH_2$— [wherein the native phosphodiester backbone is represented as —O—P—O—$CH_2$-] of U.S. Pat. No. 5,489,677, and the amide backbones of U.S. Pat. No. 5,602,240. In some embodiments, the RNAs featured herein have morpholino backbone structures of U.S. Pat. No. 5,034,506.

Modified RNAs can also contain one or more substituted sugar moieties. The RNAi agents, e.g., siRNAs, featured herein can include one of the following at the 2' position: OH; F; O—, S—, or N-alkyl; O—, S—, or N-alkenyl; O-, S- or N-alkynyl; or O-alkyl-O-alkyl; wherein the alkyl, alkenyl, and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)·$_n$O$CH_3$, O($CH_2$)$_n$$NH_2$, O($CH_2$)$_n$$CH_3$, O($CH_2$)$_n$ONH2, and O($CH_2$)$_n$ON[($CH_2$)$_n$$CH_3$)]$_2$, where n and m are from 1 to about 10. In some embodiments, siRNAs include one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an RNAi agent, or a group for improving the pharmacodynamic properties of an RNAi agent, and other substituents having similar properties. In some embodiments, the modification includes a 2'-methoxyethoxy (2'-O—$CH_2$$CH_2$O$CH_3$, also known as 2'-O-(2-methoxyethyl) or 2'-MOE) (Martin, et al., Helv. Chim. Acta 78:486-504 (1995)), i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, and 2'-dimethylaminoethoxyethoxy (also known in the art as 2*-O-dimethylaminoethoxyethyl or 2*-DMAEOE), i.e., 2*—O—$CH_2$—O—$CH_2$—N($CH_3$)$_2$.

Other exemplary modifications include 2'-methoxy (2'-O$CH_3$), 2'-aminopropoxy (2-O$CH_2$$CH_2$$CH_2$$NH_2$), and 2'-fluoro (2'-F). Similar modifications can also be made at other positions on the RNA of an RNAi agent, particularly the 3' position of the sugar on the 3' terminal nucleotide or in 2'-5' linked siRNAs and the 5' position of the 5' terminal nucleotide. RNAi agents can also have sugar mimetics such as cyclobutyl moieties in place of the pentofuranosyl sugar.

Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920; each of which is incorporated herein by reference for teachings relevant to such methods of preparation.

An RNAi agent can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo, particularly 5-bromo, 5-trifluoromethyl, and other 5-substituted uracils and cytosines, 7-methylguanine and 7-methyladenine, 8-azaguanine and 8-azaadenine, 7-deazaguanine and 7-daazaadenine, and 3-deazaguanine and 3-deazaadenine. Further nucleobases include those disclosed in U.S. Pat. No. 3,687,808, those disclosed in Modified Nucleosides in Biochemistry, Biotechnology and Medicine (Herdewijn, P. ed. Wiley-VCH, (2008)); those disclosed in The Concise Encyclopedia Of Polymer Science And Engineering (pages 858-859, Kroschwitz, J. L, ed. John Wiley & Sons (1990)), those disclosed by Englisch et al. (Angewandte Chemie, International Edition, 30, 613 (1991)), and those disclosed by Sanghvi, Y S. (Chapter 15, dsRNA Research and Applications, pages 289-302, Crooke, S. T. and Lebleu, B., Ed., CRC Press (1993)). Certain of these nucleobases are particularly useful for increasing the binding affinity of the oligomeric compounds featured in the technology described herein. These include 5-substituted pyrimidines, 6-azapyrimidines and N-2, N-6, and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, pp. 276-278 (1993)) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, U.S. Pat. Nos. 3,687,808; 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088; each of which is incorporated herein by reference for teachings relevant to such methods of preparation.

The RNA of an RNAi agent can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J., et al., Nucleic Acids Research 33(1):439-47 (2005); Mook, OR., et al., Mol Cane Ther 6(3):833-43 (2007); Grunweller, A., et al, Nucleic Acids Research 31(12):3185-93 (2003)).

Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845; each of which is incorporated herein by reference for teachings relevant to such methods of preparation.

In certain embodiments, the combination therapy includes an siRNA that is modified to include one or more adenosine-glycol nucleic acid ("GNA"). A description of adenosine-GNA can be found, for example, in Zhang, et al. (JACS 127(12):4174-75 (2005)).

In some embodiments, the present disclosure provides methods and related compositions, wherein the RNAi is an siRNA comprising an oligonucleotide sequence having one or more modified nucleotides. Abbreviations for nucleotide monomers in modified nucleic acid sequences as used herein are provided in Table 1.

TABLE 1

Abbreviations of nucleotide monomers used in modified nucleic acid sequence representation. It will be understood that, unless otherwise indicated, these monomers, when present in an oligonucleotide, are mutually linked by 5'-3'-phosphodiester bonds.

| Abbreviation | Nucleotide(s) |
|---|---|
| A | adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | uridine-3'-phosphate |
| Uf | 2'-fluorouridine-3'-phosphate |
| Ufs | 2'-fluorouridine-3'-phosphorothioate |
| Us | uridine-3'-phosphorothioate |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol (also referred to as "Hyp-(GalNAc-alkyl)3") |
| (Agn) | adenosine-glycol nucleic acid (GNA) |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |

In some embodiments, the inhibitor of HBV gene expression comprises an siRNA, wherein the siRNA has a sense strand comprising 5'-gsusguGfcAfCfUfucgcuucacaL96-3' (SEQ ID NO: 5) and an antisense strand comprising 5'-usGfsugaAfgCfGfaaguGfcAfcacsusu-3' (SEQ TD NO: 6).

In still further embodiments, the siRNA has a sense strand comprising 5'-gsusguGfcAfCfUfucgcuucacaL96-3' (SEQ TD NO:7) and an antisense strand comprising 5'-usGfsuga(Agn)gCfGfaaguGfcAfcacsusu-3' (SEQ TD NO: 8).

In certain embodiments, the inhibitor of HBV gene expression comprises an siRNA comprising a sense strand and an antisense strand, wherein the sense strand comprises SEQ ID NO:5 or SEQ ID NO: 7, or a sequence that differs by not more than 4, not more than 3, not more than 2, or not more than 1 nucleotide from SEQ ID NO:5 or SEQ ID NO:7, respectively.

In certain embodiments, the inhibitor of HBV gene expression comprises an siRNA comprising a sense strand and an antisense strand, wherein the antisense strand comprises SEQ ID NO:6 or SEQ ID NO:8, or a sequence that differs by not more than 4, not more than 3, not more than 2, or not more than 1 nucleotide from SEQ ID NO:6 or SEQ ID NO:8, respectively.

In some embodiments, the inhibitor of HBV gene expression comprises an siRNA, wherein the siRNA has a sense strand comprising 5'-gsgsuggaCfuUfCfUfcucaAfU-fuuuaL96-3' (SEQ ID NO:108) and an antisense strand comprising 5'-usAfsaaaUfuGfAfgagaAfgUfccaccsasc-3' (SEQ ID NO:109).

In certain embodiments, the inhibitor of HBV gene expression comprises an siRNA comprising a sense strand and an antisense strand, wherein the sense strand comprises SEQ ID NO:108, or a sequence that differs by not more than 4, not more than 3, not more than 2, or not more than 1 nucleotide from SEQ ID NO:108.

c. Ligand-Conjugated RNAi Agents

In some embodiments, the RNAi agent includes modifications involving chemically linking to the RNA one or more ligands, moieties, or conjugates that enhance the activity, cellular distribution, or cellular uptake of the RNAi agent. Such moieties include but are not limited to lipid moieties such as a cholesterol moiety (Letsinger, et al., Proc. Natl. Acid. Sci. USA 86:6553-56 (1989)), cholic acid (Manoharan, et al., Biorg. Med. Chem. Let. 4:1053-60 (1994)), a thioether, e.g., beryl-S-tritylthiol (Manoharan, et al., Ann. N.Y. Acad. Sci. 660:306-9 (1992); Manoharan, et al., Biorg. Med. Chem. Let. 3:2765-70 (1993)), a thiocholesterol (Oberhauser, et al., Nucl. Acids Res. 20:533-38 (1992)), an aliphatic chain, e.g., dodecandiol or undecyl residues (Saison-Behmoaras, et al., EMBO J 10:1111-18 (1991); Kabanov, et al., FEBS Lett. 259:327-30 (1990); Svinarchuk, et al., Biochimie 75:49-54 (1993)), a phospholipid, e.g., di-hexadecyl-rac-glycerol or triethyl-ammonium 1,2-di-O-hexadecyl-rac-glycero-3-phosphonate (Manoharan, et al., Tetrahedron Lett. 36:3651-54 (1995); Shea, et al., Nucl. Acids Res. 18:3777-83 (1990)), a polyamine or a polyethylene glycol chain (Manoharan, et al., Nucleosides & Nucleotides 14:969-73 (1995)), or adamantane acetic acid (Manoharan, et al., Tetrahedron Lett. 36:3651-54 (1995)), a palmityl moiety (Mishra, et al., Biochim. Biophys. Acta 1264:229-37 (1995)), or an octadecylamine or hexylaminocarbonyloxycholesterol moiety (Crooke, et al., J. Pharmacol. Exp. Ther. 277:923-37 (1996)).

In some embodiments, a ligand alters the distribution, targeting, or lifetime of an RNAi agent into which it is incorporated. In some embodiments, a ligand provides an enhanced affinity for a selected target, e.g., molecule, cell, or cell type, compartment, e.g., a cellular or organ compartment, tissue, organ, or region of the body, as, e.g., compared to a species absent such a ligand. In such embodiments, the ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a liver cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. Other examples of ligands include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic molecules (e.g., cholesterol, cholic acid, adamantane acetic acid, 1-pyrene butyric acid, dihydrotestosterone, 1,3-Bis-0(hexadecyl)glycerol, geranyloxyhexyl group, hexadecylglycerol, borneol, menthol, 1,3-propanediol, heptadecyl group, palmitic acid, myristic acid,03-(oleoyl)lithocholic acid, 03-(oleoyl)cholenic acid, dimethoxytrityl, or phenoxazine), peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, and AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, and multivalent fucose. The ligand can be, for example, a lipopolysaccharide, an activator of p38 MAP kinase, or an activator of NF-KB.

The ligand can be a substance, e.g., a drug, which can increase the uptake of the RNAi agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In another aspect, the ligand is a moiety, e.g., a vitamin, which is taken up by a target cell, e.g., a liver cell. Exemplary vitamins include vitamin A, E, and K. Other exemplary vitamins include are B vitamin, e.g., folic acid, B12, riboflavin, biotin, pyridoxal, or other vitamins or nutrients taken up by target cells such as liver cells. Also included are HSA and low density lipoprotein (LDL).

In some embodiments, a ligand attached to an RNAi agent as described herein acts as a pharmacokinetic (PK) modulator. As used herein, a "PK modulator" refers to a pharmacokinetic modulator. PK modulators include lipophiles, bile acids, steroids, phospholipid analogues, peptides, protein binding agents, PEG, vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin, etc. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable to the technology described herein as ligands (e.g., as PK modulating ligands). In addition, aptamers that bind serum components (e.g., serum proteins) are also suitable for use as PK modulating ligands in the embodiments described herein.

(i) Lipid conjugates. In some embodiments, the ligand or conjugate is a lipid or lipid-based molecule. A lipid or lipid-based ligand can (a) increase resistance to degradation of the conjugate, (b) increase targeting or transport into a target cell or cell membrane, and/or (c) can be used to adjust binding to a serum protein, e.g., HSA. Such a lipid or lipid-based molecule may bind a serum protein, e.g., human serum albumin (HSA). An HSA-binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In some embodiments, the lipid based ligand binds HSA. The lipid based ligand may bind to HSA with a sufficient affinity such that the conjugate will be distributed to a non-kidney tissue. In certain particular embodiments, the HSA-ligand binding is reversible.

In some other embodiments, the lipid based ligand binds HSA weakly or not at all, such that the conjugate will be distributed to the kidney. Other moieties that target to kidney cells can also be used in place of or in addition to the lipid based ligand.

(ii) Cell Permeation Peptide and Agents. In another aspect, the ligand is a cell-permeation agent, such as a helical cell-permeation agent. In some embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. In some embodiments, the helical agent is an alpha-helical agent. In certain particular embodiments, the helical agent has a lipophilic and a lipophobic phase.

A "cell permeation peptide" is capable of permeating a cell, e.g., a microbial cell, such as a bacterial or fungal cell, or a mammalian cell, such as a human cell. A microbial cell-permeating peptide can be, for example, an alpha-helical linear peptide (e.g., LL-37 or Ceropin PI), a disulfide bond-containing peptide (e.g., a-defensin, 0-defensin, or bactenecin), or a peptide containing only one or two dominating amino acids (e.g., PR-39 or indolicidin).

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to RNAi agents can affect pharmacokinetic distribution of the RNAi, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:9). An RFGF analogue (e.g., amino acid sequence AALLPVL-LAAP (SEQ ID NO:10) containing a hydrophobic MTS can also be a targeting moiety. The peptide moiety can be a "delivery" peptide, which can carry large polar molecules including peptides, oligonucleotides, and proteins across cell membranes. For example, sequences from the HIV Tat protein (GRKKRRQRRRPPQ (SEQ ID NO:11) and the *Drosophila* Antennapedia protein (RQIKIWFQNR-RMKWK (SEQ ID NO:12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam, et al., Nature 354:82-84 (1991)).

A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 µlarge T antigen (Simeoni, et al., Nucl. Acids Res. 31:2717-24 (2003)).

(iii) Carbohydrate Conjugates. In some embodiments, the RNAi agent oligonucleotides described herein further comprise carbohydrate conjugates. The carbohydrate conjugates may be advantageous for the in vivo delivery of nucleic acids, as well as compositions suitable for in vivo therapeutic use. As used herein, "carbohydrate" refers to a compound which is either a carbohydrate per se made up of one or more monosaccharide units having at least 6 carbon atoms (which can be linear, branched, or cyclic) with an oxygen, nitrogen, or sulfur atom bonded to each carbon atom; or a compound having as a part thereof a carbohydrate moiety made up of one or more monosaccharide units each having at least six carbon atoms (which can be linear, branched, or cyclic), with an oxygen, nitrogen, or sulfur atom bonded to each carbon atom. Representative carbohydrates include the sugars (mono-, di-, tri-, and oligosaccharides containing from about 4-9 monosaccharide units), and polysaccharides such as starches, glycogen, cellulose, and polysaccharide gums. Specific monosaccharides include C5 and above (in some embodiments, C5-C8) sugars; and di- and trisaccharides include sugars having two or three monosaccharide units (in some embodiments, C5-C8).

In some embodiments, the carbohydrate conjugate is selected from the group consisting of:
Formula I
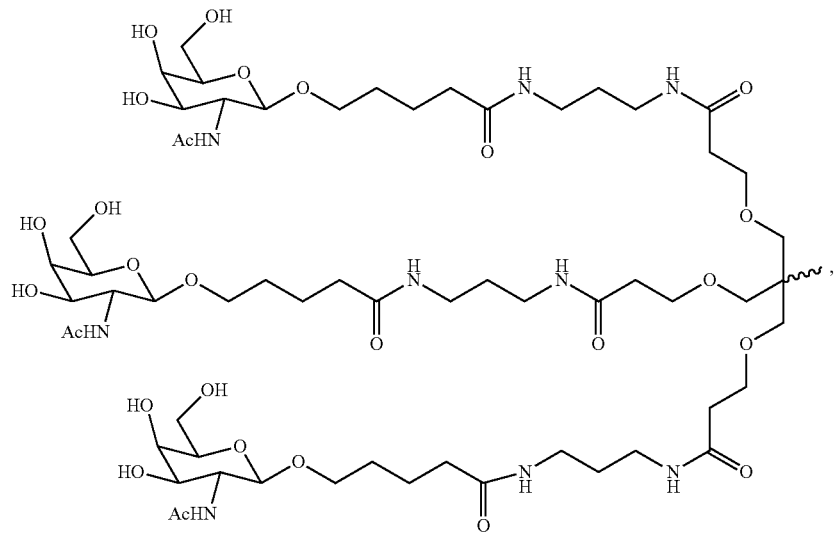
Formula II
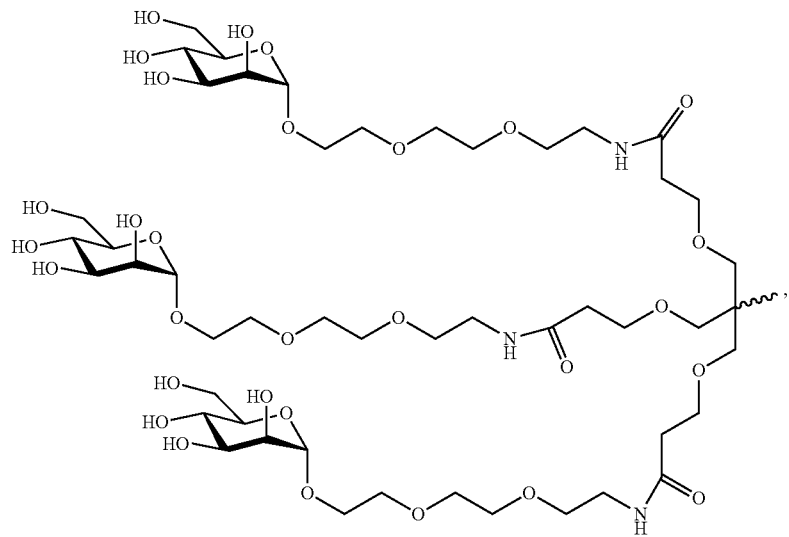
Formula III
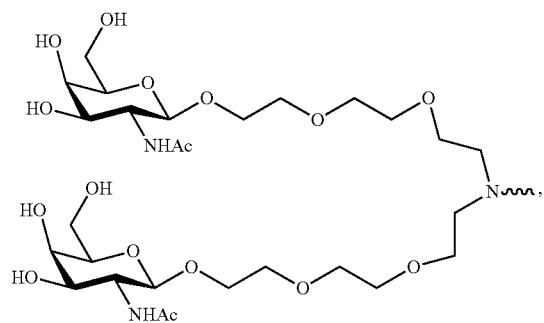
Formula IV
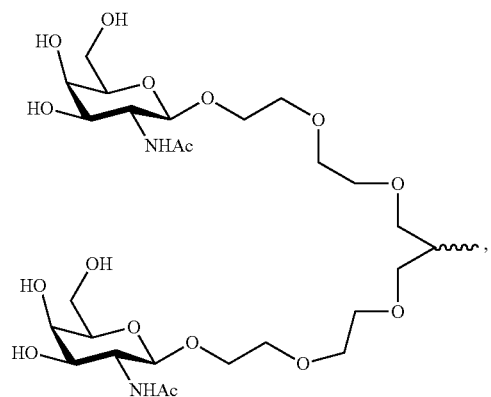

Formula V
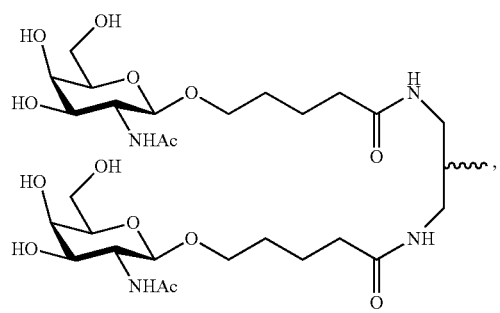
Formula VI
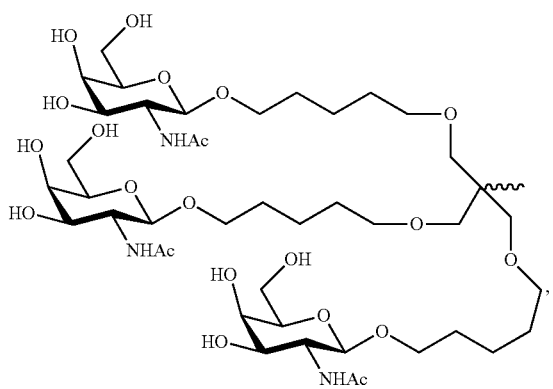
Formula VII
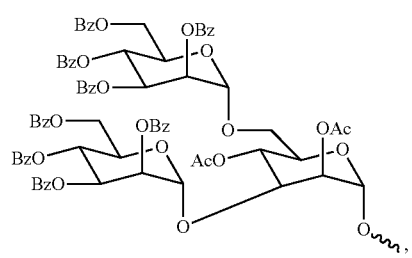
Formula VIII
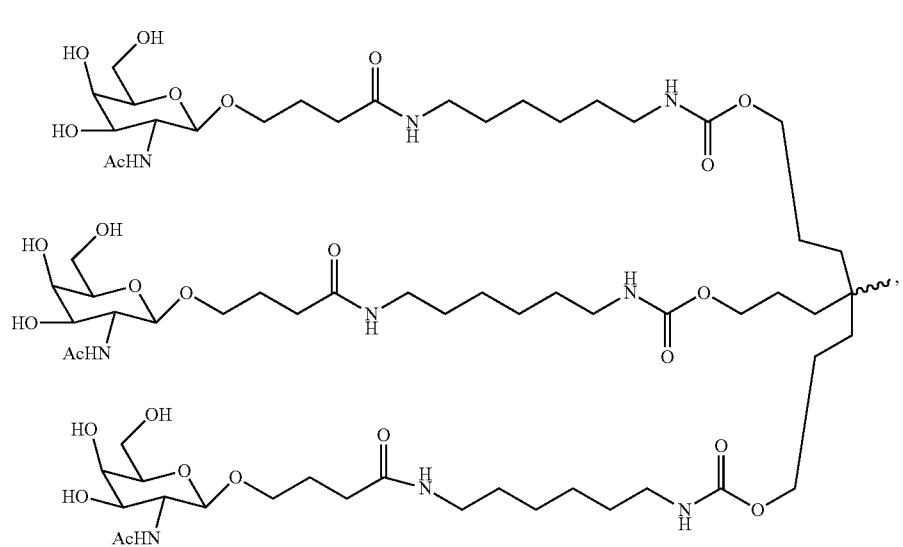

Formula IX
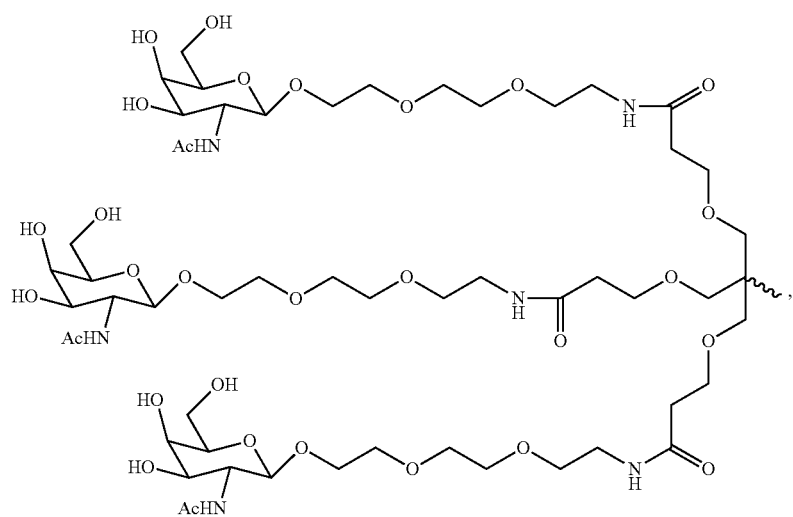
Formula X
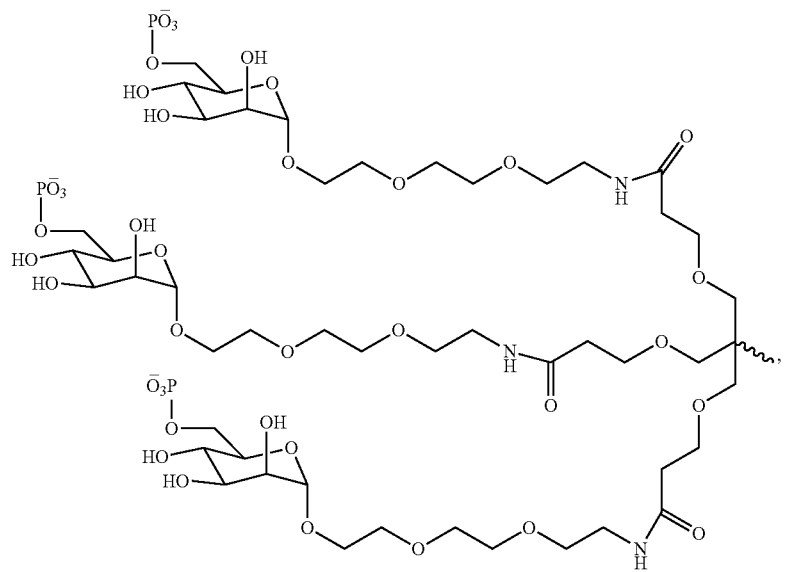

-continued
Formula XI
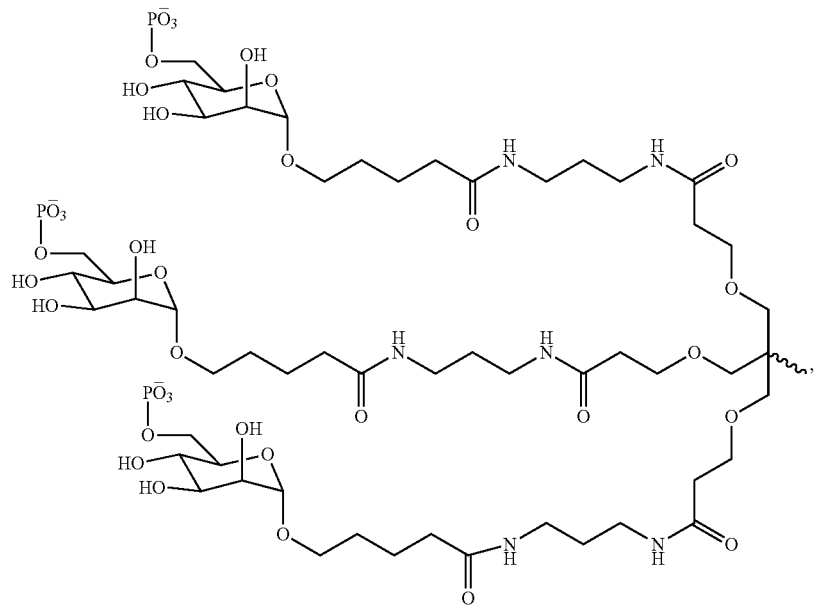
Formula XII
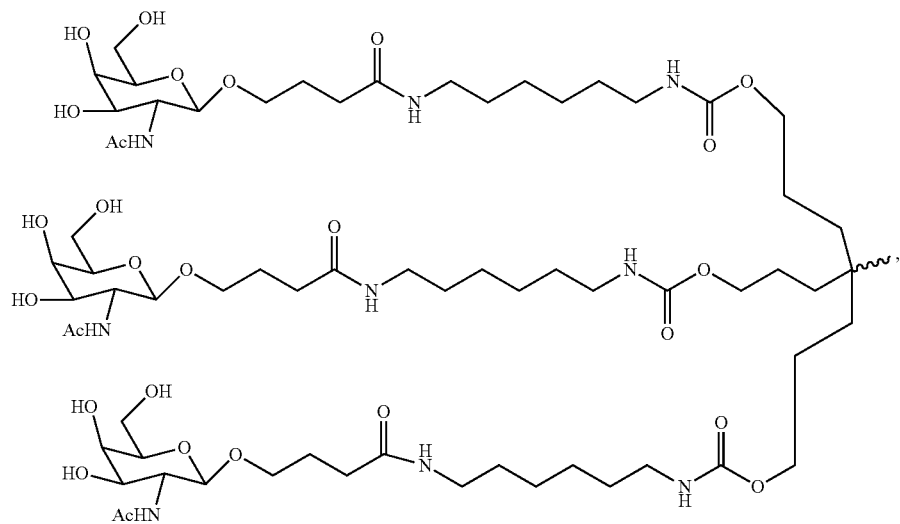
Formula XIII
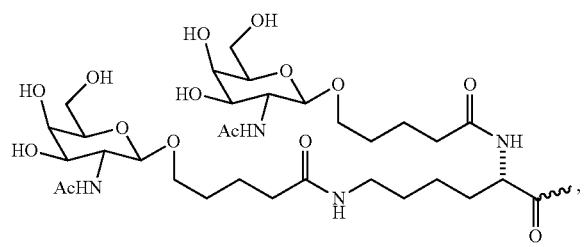
Formula XIV
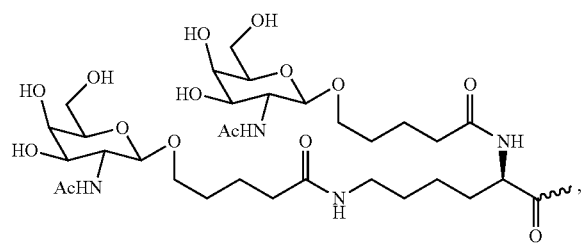

Formula XV
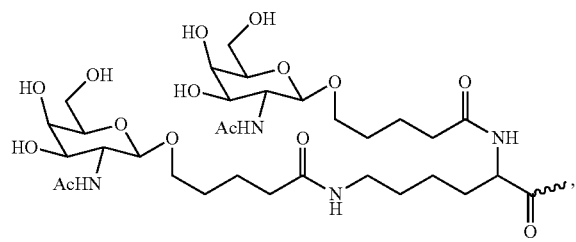
Formula XVI
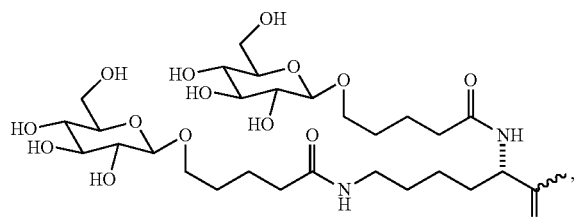
Formula XVII
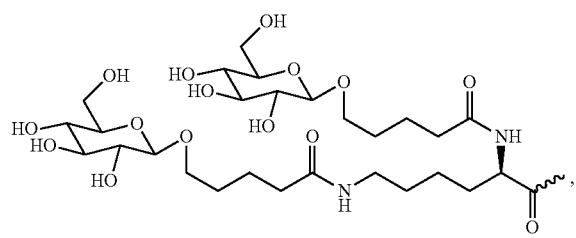
Formula XVIII
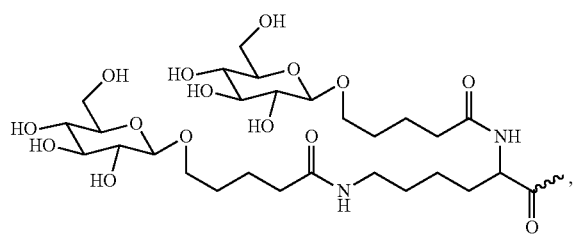
Formula XIX
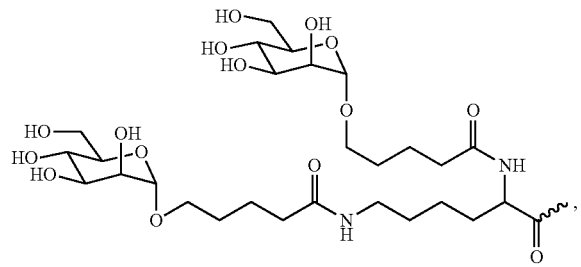
Formula XX
, and
Formula XXI
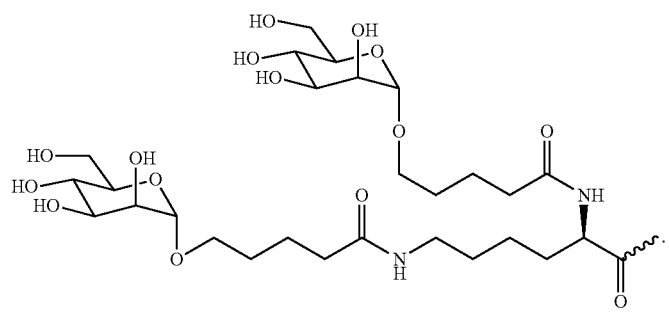
Another representative carbohydrate conjugate for use in the embodiments described herein includes, but is not limited to,

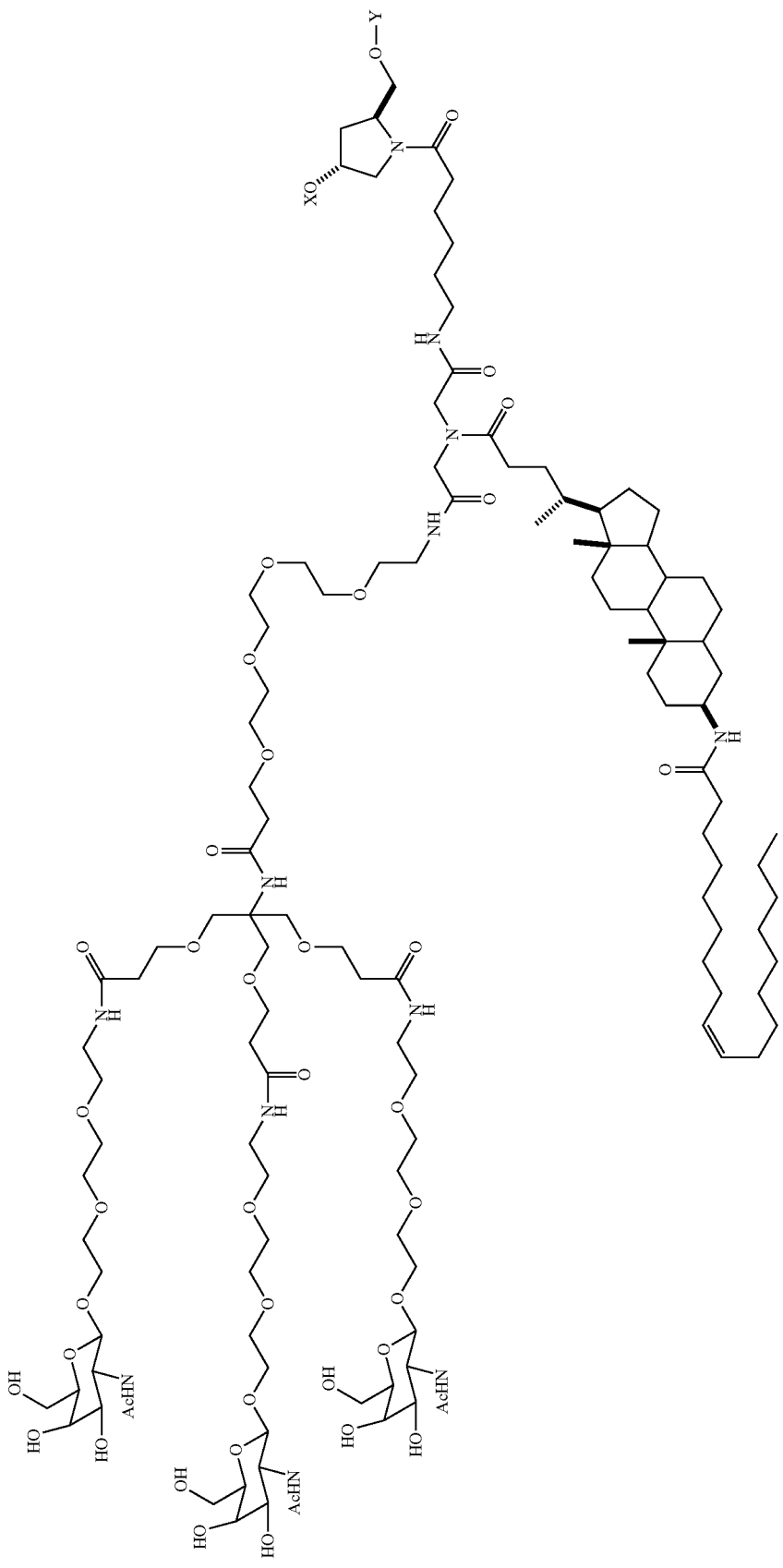

(Formula XXII), wherein when one of X or Y is an oligonucleotide, the other is a hydrogen.

In some embodiments, the carbohydrate conjugate further comprises another ligand such as, but not limited to, a PK modulator, an endosomolytic ligand, or a cell permeation peptide.

(iv) Linkers. In some embodiments, the conjugates described herein can be attached to the RNAi agent oligonucleotide with various linkers that can be cleavable or non-cleavable.

The term "linker" or "linking group" means an organic moiety that connects two parts of a compound. Linkers typically comprise a direct bond or an atom such as oxygen or sulfur, a unit such as NR8, C(O), C(O)NH, SO, SO2, SO2NH, or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, and alkynylhereroaryl, which one or more methylenes can be interrupted or terminated by O, S, S(O), SO2, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In certain embodiments, the linker is between 1-24 atoms, between 4-24 atoms, between 6-18 atoms, between 8-18 atoms, or between 8-16 atoms.

A cleavable linking group is one which is sufficiently stable outside the cell, but which upon entry into a target cell is cleaved to release the two parts the linker is holding together. In certain embodiments, the cleavable linking group is cleaved at least 10 times, or at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases. A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a particular pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver-targeting ligands can be linked to the cationic lipids through a linker that includes an ester group. Liver cells are rich in esterases, and therefore the linker will be cleaved more efficiently in liver cells than in cell types that are not esterase-rich. Other cell types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It can be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell-free systems, in cells, in cell culture, in organ or tissue culture, or in whole animals. It can be useful to make initial evaluations in cell-free or culture conditions and to confirm by further evaluations in whole animals. In certain embodiments, useful candidate compounds are cleaved at least 2, at least 4, at least 10 or at least 100 times faster in the cell (or under in vitro conditions selected to mimic intracellular conditions) as compared to blood or serum (or under in vitro conditions selected to mimic extracellular conditions).

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular RNAi moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In some embodiments, candidate compounds are cleaved by at most 10% in the blood. In certain embodiments, useful candidate compounds are degraded at least 2, at least 4, at least 10, or at least 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O— P(O)(ORk)-S—, —S—P(O)(ORk)-S—, —O—P(S)(ORk)-S—, —S—P(S)(ORk)-O—, —O—P(O)(Rk)-O—, —O— P(S)(Rk)-O—, —S—P(O)(Rk)-O—, —S—P(S)(Rk)-O—, —S—P(O)(Rk)-S—, —O—P(S)(Rk)-S—. In certain embodiments, the phosphate-based linking groups are selected from: —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—. In particular embodiments, the phosphate-linking group is —O—P(O)(OH)—O—. These candidates can be evaluated using methods analogous to those described above.

Acid cleavable linking groups are linking groups that are cleaved under acidic conditions. In some embodiments, acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes, can provide a cleaving environment for acid cleavable linking groups. Examples of acid cleavable linking groups include but are not limited to hydrazones, esters, and esters of amino acids. Acid cleavable groups can have the general formula —C=N—, C(O)O, or —OC(O). In some embodiments, the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-based cleavable linking groups are cleaved by enzymes such as esterases and amidases in cells. Examples of ester-based cleavable linking groups include but are not limited to esters of alkylene, alkenylene, and alkynylene groups. Ester cleavable linking groups have the general formula —C(O)O—, or —OC(O)—. These candidates can be evaluated using methods analogous to those described above.

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides, etc.) and polypeptides. Peptide-based cleavable groups do not include the amide group (—C(O)NH—). The amide group can be formed between any alkylene, alkenylene, or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula -NHCHRAC(O)NHCHRBC(O)—, where RA and RB are the R groups of the two adjacent amino acids. These candidates can be evaluated using methods analogous to those described above.

Representative carbohydrate conjugates with linkers include, but are not limited to, (Formula XXIII)

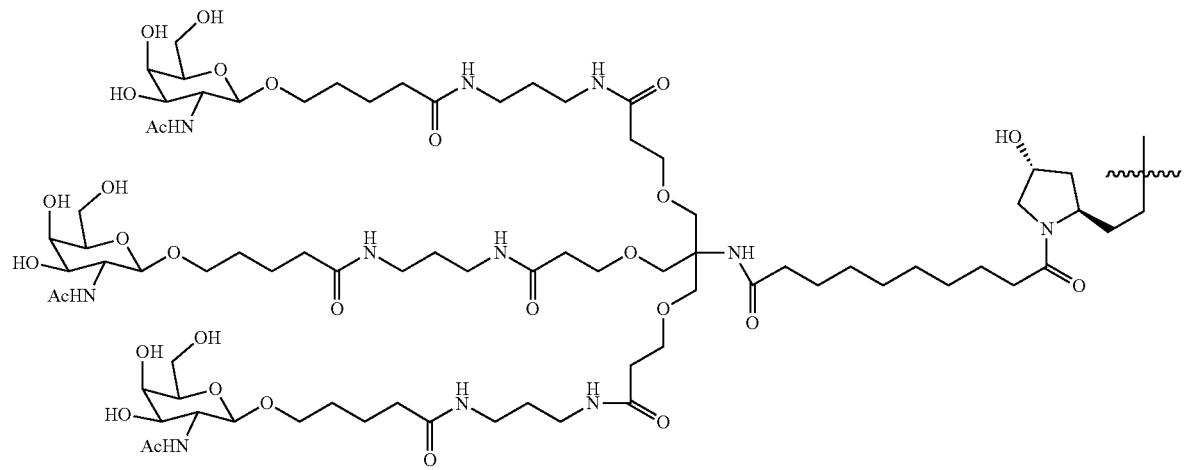

, (Formula XXIV)
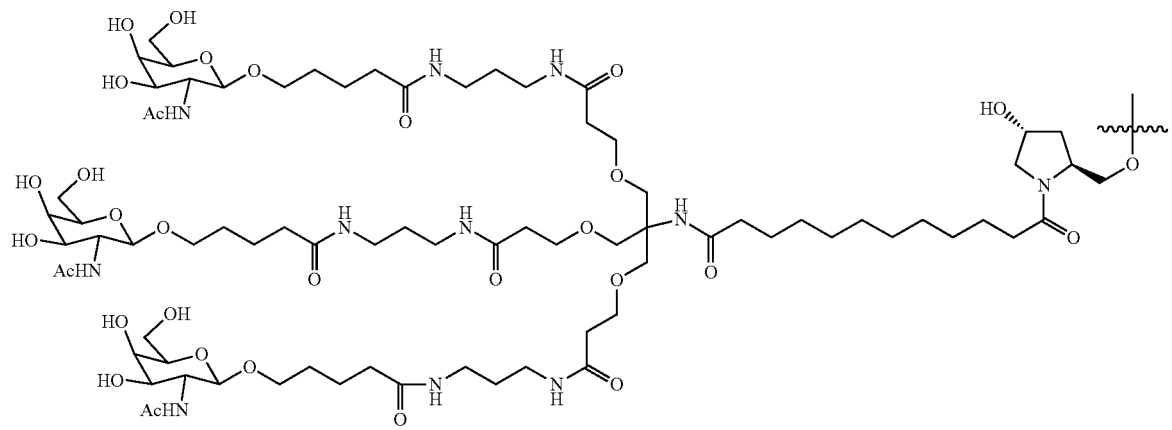
(Formula XXV)
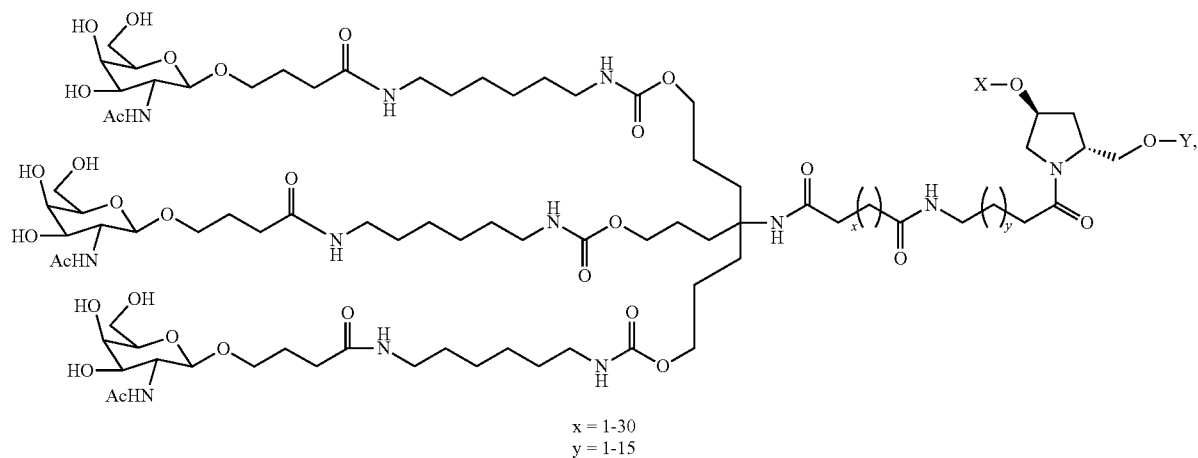
x = 1-30
y = 1-15
(Formula XXVI)
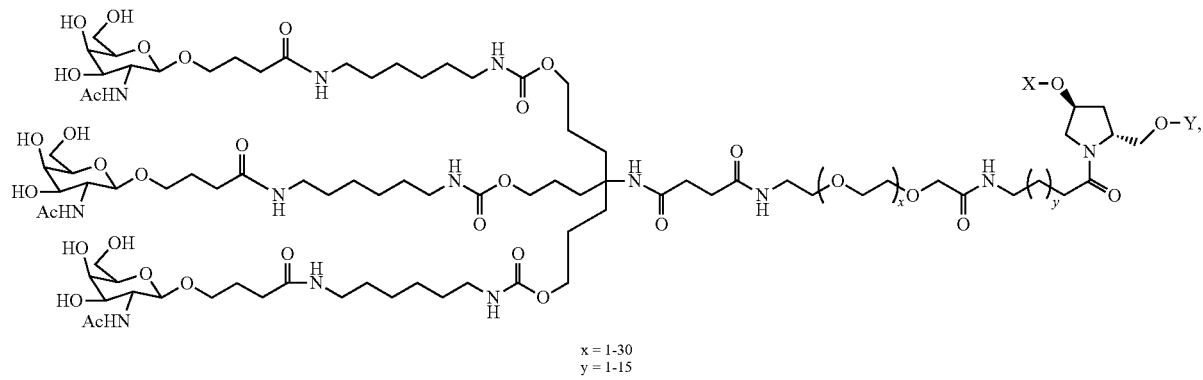
x = 1-30
y = 1-15

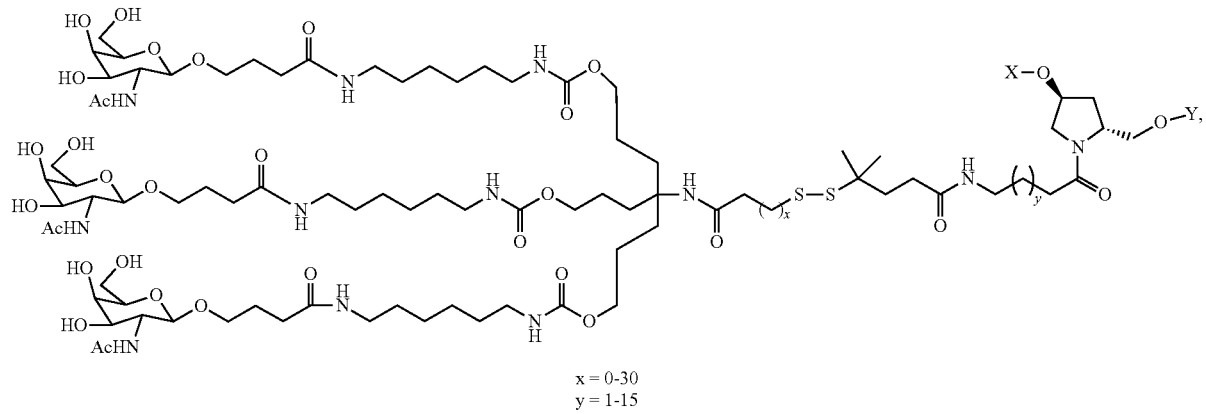
(Formula XXVII)
x = 0-30
y = 1-15
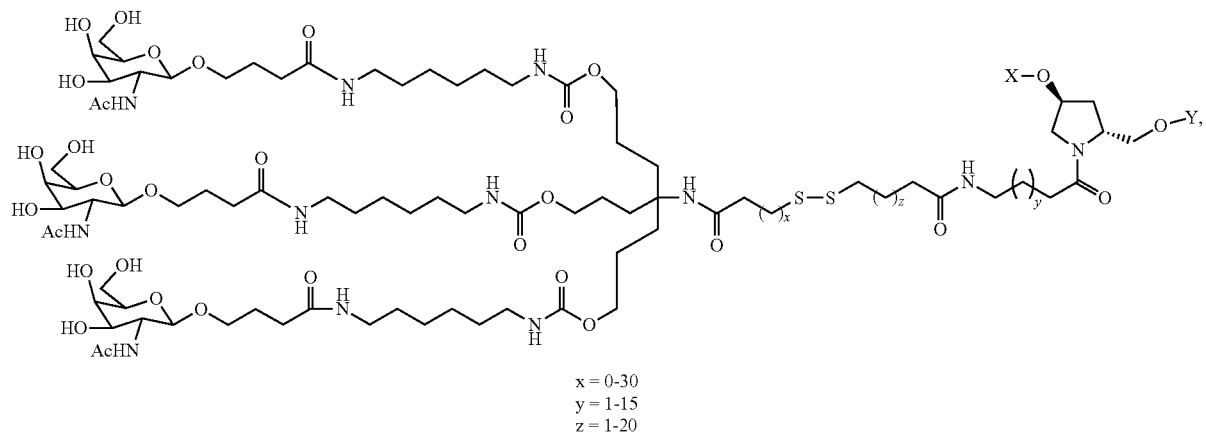
(Formula XXXVIII)
x = 0-30
y = 1-15
z = 1-20
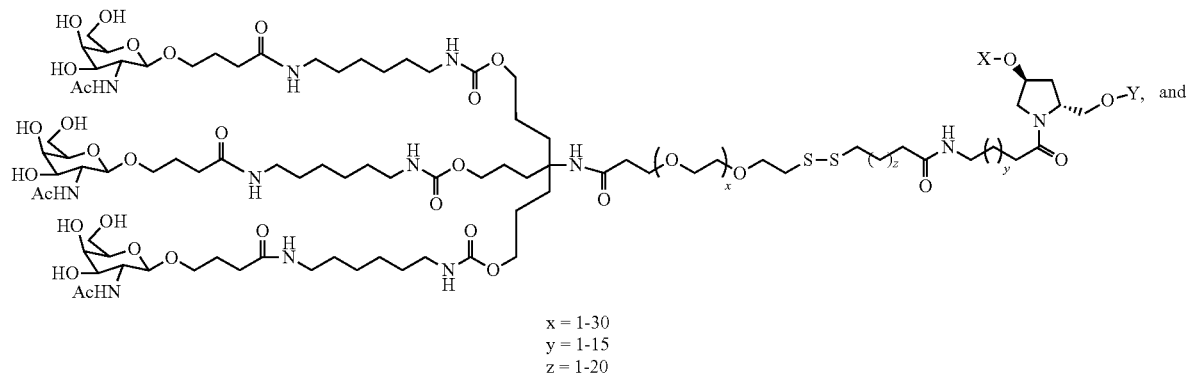
(Formula XXIX)
x = 1-30
y = 1-15
z = 1-20

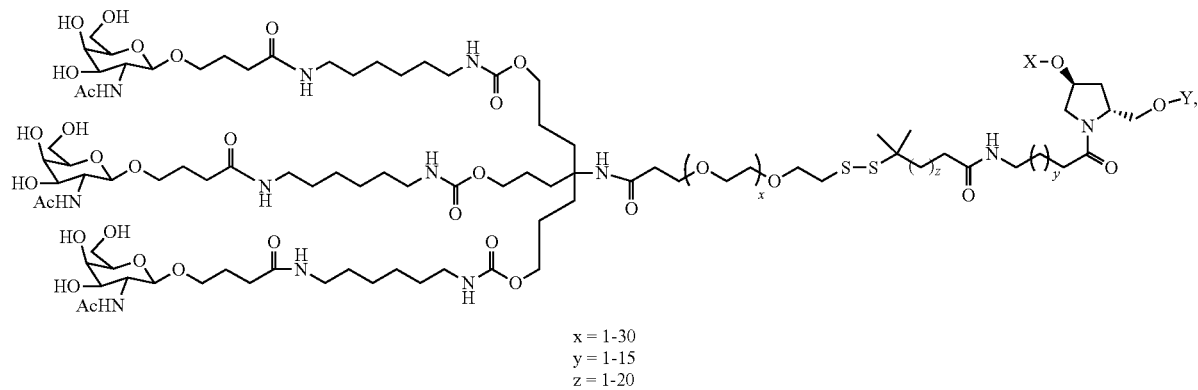

(Formula XXX)

x = 1-30
y = 1-15
z = 1-20 wherein when one of X or Y is an oligonucleotide, the other is a hydrogen.

In certain embodiments of the compositions and methods, a ligand is one or more "GalNAc" (N-acetylgalactosamine) derivatives attached through a bivalent or trivalent branched linker. For example, in some embodiments the siRNA is conjugated to a GalNAc ligand as shown in the following structure:

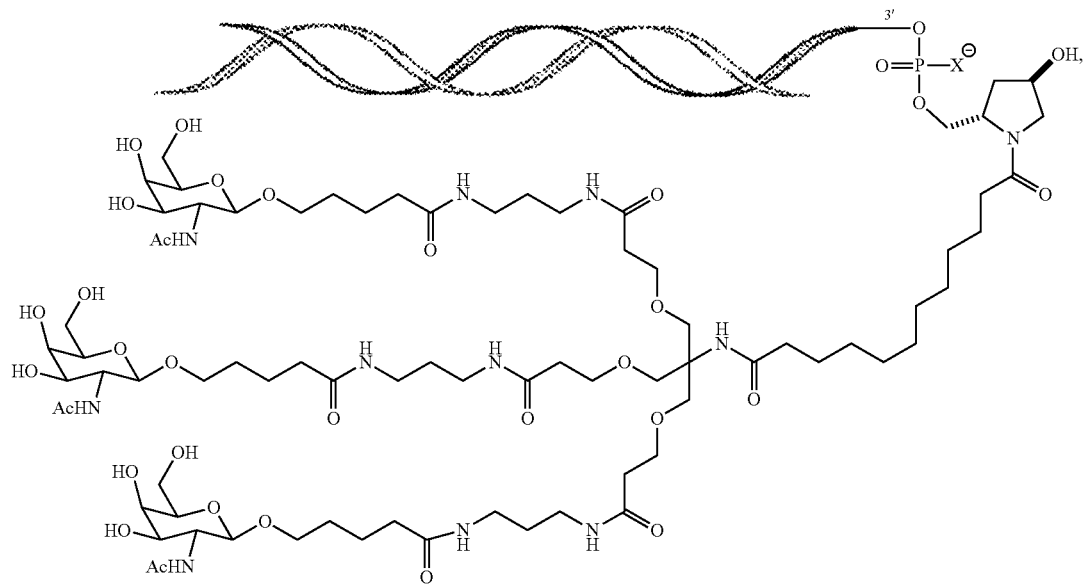

wherein X is O or S.

In some embodiments, the sense strand of the siRNA is conjugated to a ligand attached at the 3' terminus of the sense strand through a linker as shown in the following structure:

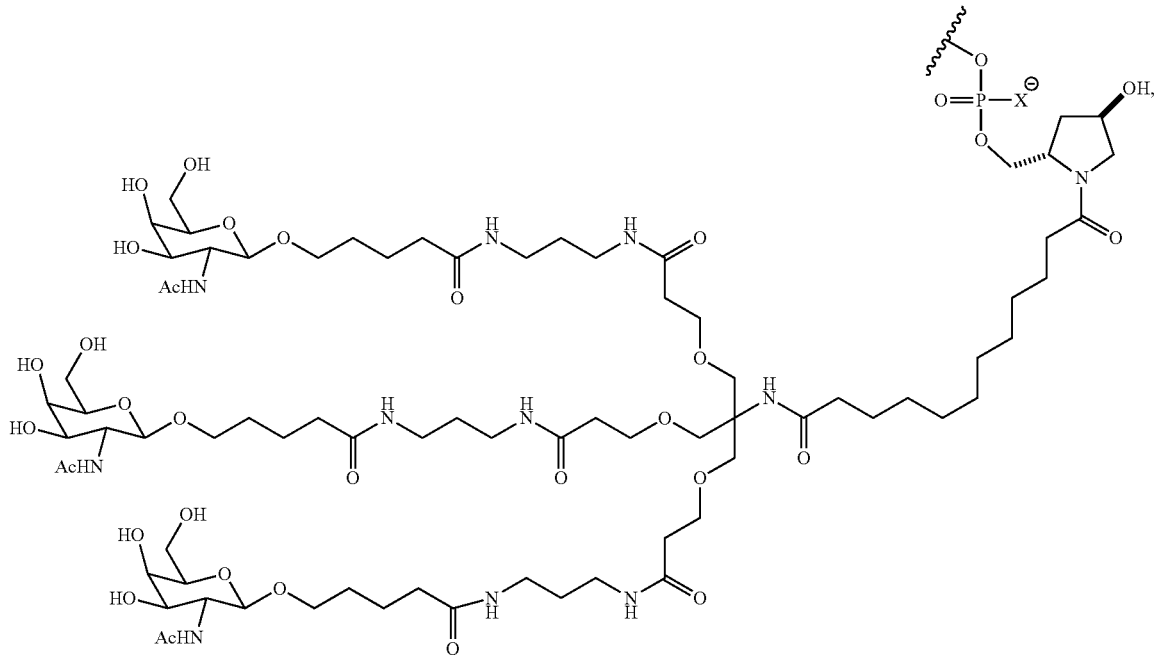

wherein X is O or S.

In some embodiments, the combination therapy includes an siRNA that is conjugated to a bivalent or trivalent branched linker selected from the group of structures shown in any of formula (XXXI)-(XXXIV):

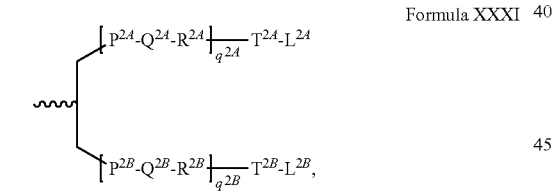
Formula XXXI

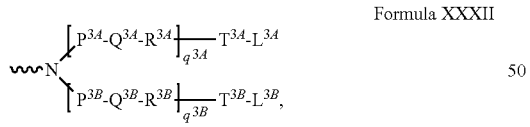
Formula XXXII

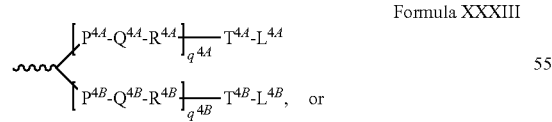
Formula XXXIII

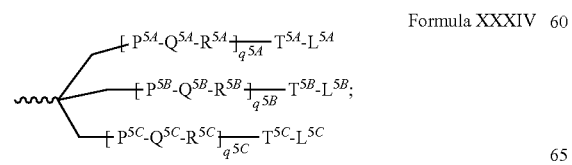
Formula XXXIV wherein:

q2A, q2B, q3A, q3B, q4A, q4B, q5A, q5B, and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$ and $T^{5C}$ are each independently for each occurrence absent, CO, NH, O, S, OC(O), NHC(O), CH$_2$, CH$_2$NH, or CH$_2$O;

$Q^{2A}$, $Q^{2B}$, $Q^{3A}$, $Q^{3B}$, $Q^{4A}$, $Q^{4B}$, $Q^{5A}$, $Q^{5B}$ and $Q^{5C}$ are independently for each occurrence absent, alkylene, or substituted alkylene wherein one or more methylenes can be interrupted or terminated by one or more of O, S, S(O), SO2, N($R^N$), C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, and $R^{5C}$ are each independently for each occurrence absent, NH, O, S, CH$_2$, C(O)O, C(O)NH, NHCH($R^a$)C(O), —C(O)—CH($R^a$)—NH—, CO, CH=N—O,

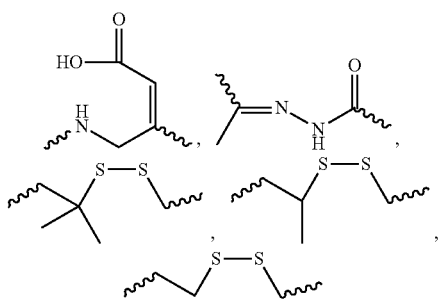

or heterocyclyl;

$L^{2A}$, $L^{2B}$, $L^{3A}$, $L^{3B}$, $L^{4A}$, $L^{4B}$, $L^{5A}$, $L^{5B}$, and $L^5C$ represent the ligand; i.e., each independently for each occurrence a monosaccharide (such as GalNAc), disaccharide, trisaccharide, tetrasaccharide, oligosaccharide, or polysaccharide;

and $R^a$ is H or amino acid side chain. Trivalent conjugating GalNAc derivatives are particularly useful for use with RNAi agents for inhibiting the expression of a target gene, such as those of formula (XXXIV):

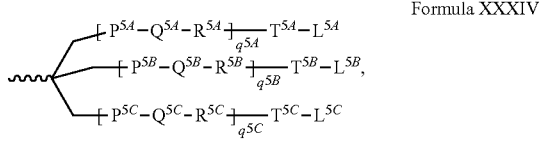

Formula XXXIV wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas I, VI, X, IX, and XII.

Representative U.S. patents that teach the preparation of RNA conjugates include U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; and 7,037,646; each of which is incorporated herein by reference for teachings relevant to such methods of preparation.

In certain instances, the RNA of an RNAi agent can be modified by a non-ligand group. A number of non-ligand molecules have been conjugated to RNAi agents in order to enhance the activity, cellular distribution or cellular uptake of the RNAi agents, and procedures for performing such conjugations are available in the scientific literature. Such non-ligand moieties have included lipid moieties, such as cholesterol (Kubo, T., et al., Biochem. Biophys. Res. Comm. 365(1):54-61 (2007); Letsinger, et al., Proc. Natl. Acad. Sci. USA 86:6553 (1989)), cholic acid (Manoharan, et al., Bioorg. Med. Chem. Lett. 4:1053 (1994)), a thioether, e.g., hexyl-S-tritylthiol (Manoharan, et al., Ann. N.Y. Acad. Sci. 660:306 (1992); Manoharan, et al., Bioorg. Med. Chem. Let. 3:2765 (1993)), a thiocholesterol (Oberhauser, et al., Nucl. Acids Res. 20:533 (1992)), an aliphatic chain, e.g., dodecandiol or undecyl residues (Saison-Behmoaras, et al., EMBO J. 10:111 (1991); Kabanov, et al., FEBS Lett. 259: 327 (1990); Svinarchuk, et al., Biochimie 75:49 (1993)), a phospholipid, e.g., di-hexadecyl-rac-glycerol or triethylammonium 1,2-di-O-hexadecyl-rac-glycero-3-H-phosphonate (Manoharan, et al., Tetrahedron Lett. 36:3651 (1995); Shea, et al., Nucl. Acids Res. 18:3777 (1990)), a polyamine or a polyethylene glycol chain (Manoharan, et al., Nucleosides & Nucleotides 14:969 (1995)), or adamantane acetic acid (Manoharan, et al., Tetrahedron Lett. 36:3651 (1195)), a palmityl moiety (Mishra, et al., Biochim. Biophys. Acta 1264:229 (1995)), or an octadecylamine or hexylaminocarbonyl-oxycholesterol moiety (Crooke, et al., J. Pharmacol. Exp. Ther. 277:923 (1996)).

Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

d. RNAi Agent Delivery

"Introducing into a cell," when referring to an RNAi agent, means facilitating or effecting uptake or absorption into the cell, as is understood by those skilled in the art.

Absorption or uptake of an RNAi agent can occur through unaided diffusive or active cellular processes, or by auxiliary agents or devices. The meaning of this term is not limited to cells in vitro; an RNAi agent can also be "introduced into a cell," wherein the cell is part of a living organism. In such an instance, introduction into the cell will include the delivery to the organism. For example, for in vivo delivery, an RNAi agent can be injected into a tissue site or administered systemically. In vivo delivery can also be by a beta-glucan delivery system, such as those described in U.S. Pat. Nos. 5,032,401 and 5,607,677, and U.S. Publication No. 2005/0281781, which are incorporated herein by reference for teachings relevant to such delivery systems. In vitro introduction into a cell includes methods known in the art such as electroporation and lipofection. Further approaches are described herein below or are known in the art.

The delivery of an RNAi agent to a subject in need thereof can be achieved in a number of different ways. In vivo delivery can be performed directly by administering a composition comprising an RNAi agent, e.g., an siRNA, to a subject. Alternatively, delivery can be performed indirectly by administering one or more vectors that encode and direct the expression of the RNAi agent. These alternatives are discussed further below.

In general, any method of delivering a nucleic acid molecule can be adapted for use with an RNAi agent (see, e.g., Akhtar S. and Julian R L., Trends Cell. Biol. 2(5):139-44 (1992) and WO94/02595, which are incorporated herein by reference for teachings relevant to such methods of delivery). Three factors that are particularly important in successfully delivering an RNAi agent in vivo: (a) biological stability of the delivered molecule, (2) preventing nonspecific effects, and (3) accumulation of the delivered molecule in the target tissue. The nonspecific effects of an RNAi agent can be minimized by local administration, for example, by direct injection or implantation into a tissue (as a non-limiting example, a tumor) or topically administering the preparation. Local administration to a treatment site maximizes local concentration of the agent, limits the exposure of the agent to systemic tissues that can otherwise be harmed by the agent or that can degrade the agent, and permits a lower total dose of the RNAi agent to be administered. Several studies have shown successful knockdown of gene products when an RNAi agent is administered locally. For example, intraocular delivery of a VEGF siRNA by intravitreal injection in cynomolgus monkeys (Tolentino, M. J., et al., Retina 24:132-38 (2004)) and subretinal injections in mice (Reich, S. J., et al., Mol. Vis. 9:210-16 (2003)) were both shown to prevent neovascularization in an experimental model of age-related macular degeneration. In addition, direct intratumoral injection of an siRNA in mice reduces tumor volume (Pille, J., et al., Mol. Ther. 11:267-74 (2005)) and can prolong survival of tumor-bearing mice (Kim, W. J., et al., Mol. Ther. 14:343-50 (2006); Li, S., et al., Mol. Ther.

15:515-23 (2007)). RNA interference has also shown success with local delivery to the CNS by direct injection (Dorn, G., et al., Nucleic Acids 32:e49 (2004); Tan, P. H., et al., Gene Ther. 12:59-66 (2005); Makimura, H., et al., BMC Neurosci. 3:18 (2002); Shishkina, G. T., et al., Neuroscience 129:521-28 (2004); Thakker, E. R., et al. Proc. Natl. Acad. Sci. U.S.A. 101:17270-75 (2004); Akaneya, Y., et al., J. Neurophysiol. 93:594-602 (2005)) and to the lungs by intranasal administration (Howard, K. A., et al., Mol. Ther. 14:476-84 (2006); Zhang, X., et al., J. Biol. Chem. 279: 10677-84 (2004); Bitko, V., et al., Nat. Med. 11:50-55 (2005)). For administering an RNAi agent systemically for the treatment of a disease, the RNA can be modified or alternatively delivered using a drug delivery system; both methods act to prevent the rapid degradation of the siRNA by endo- and exo-nucleases in vivo. Modification of the RNA or the pharmaceutical carrier can also permit targeting of the RNAi agent composition to the target tissue and avoid undesirable off-target effects. RNAi agents can be modified by chemical conjugation to lipophilic groups such as cholesterol to enhance cellular uptake and prevent degradation. For example, an RNAi agent directed against ApoB conjugated to a lipophilic cholesterol moiety was injected systemically into mice and resulted in knockdown of apoB mRNA in both the liver and jejunum (Soutschek, J., et al., Nature 432:173-78 (2004)). In some other embodiments, the RNAi agent can be delivered using drug delivery systems such as a nanoparticle, a dendrimer, a polymer, liposomes, or a cationic delivery system. Positively charged cationic delivery systems typically facilitate binding of an RNAi agent (negatively charged) and enhance interactions at the negatively charged cell membrane to permit efficient uptake of an RNAi agent by the cell. Cationic lipids, dendrimers, or polymers can either be bound to an RNAi, or induced to form a vesicle or micelle (see, e.g., Kim, S. H., et al., Journal of Controlled Release 129(2):107-16 (2008)) that encases an RNAi agent. The formation of vesicles or micelles further prevents degradation of the RNAi agent when administered systemically. Methods for making and administering cationic-RNAi agent complexes are well within the abilities of one skilled in the art (see, e.g., Sorensen, D. R., et al., J. Mol. Biol 327:761-66 (2003); Verma, U. N., et al., Clin. Cancer Res. 9:1291-1300 (2003); Arnold, A. S. et al., J. Hypertens. 25:197-205 (2007); which methods are incorporated herein by reference). Some non-limiting examples of drug delivery systems useful for systemic delivery of RNAi agents include DOTAP (Sorensen, D. R., et al. (2003), supra; Verma, U. N., et al., (2003), supra), Oligofectamine, "solid nucleic acid lipid particles" (Zimmermann, T. S., et al., Nature 441:111-14 (2006)), cardiolipin (Chien, P. Y., et al., Cancer Gene Ther. 12:321-28 (2005); Pal, A., et al., Int J. Oncol. 26: 1087-91 (2005)), polyethylenimine (Bonnet, M. E., et al., Pharm. Res. 25(12):2972-82; Aigner, A., J. Biomed. Biotechnol. 2006(4):71659 (2006)), Arg-Gly-Asp (RGD) peptides (Liu, S., Mol. Pharm. 3:472-487 (2006)), and polyamidoamines (Tomalia, D. A., et al., Biochem. Soc. Trans. 35:61-7 (2007); Yoo, H., et al., Pharm. Res. 16:1799-1804 (1999)).

As used herein, the term "SNALP" refers to a stable nucleic acid-lipid particle. A SNALP represents a vesicle of lipids coating a reduced aqueous interior comprising a nucleic acid such as an RNAi agent or a plasmid from which an RNAi agent is transcribed. SNALPs are described, e.g., in U.S. Patent Application Publication Nos. US2006/ 0240093 and US2007/0135372, and in International Application Publication No. WO 2009/082817. These applications are incorporated herein by reference for teachings relevant to SNALPs.

In some embodiments, an RNAi forms a complex with cyclodextrin for systemic administration. Methods for administration and pharmaceutical compositions of RNAis and cyclodextrins can be found in U.S. Pat. No. 7,427,605, which is incorporated herein by reference for teachings relevant to such compositions and methods. In some embodiments, a gene encoding an RNAi is encoded and expressed from an expression vector. Examples of vectors and their use in delivering RNAis are described in U.S. Patent Application No. US2017/0349900A1, which examples are incorporated herein by reference.

e. Pharmaceutical Compositions and Formulation of RNAi Agents

In some embodiments, provided herein are pharmaceutical compositions containing an RNAi agent, as described herein, and a pharmaceutically acceptable carrier or excipient. The pharmaceutical composition containing the RNAi agent is useful in a combination therapy to treat HBV infection or reduce HBV viral load in a subject. Such pharmaceutical compositions are formulated based on the mode of delivery. For example, compositions may be formulated for systemic administration via parenteral delivery, e.g., by intravenous (IV) delivery, or for direct delivery into the brain parenchyma, e.g., by infusion into the brain, such as by continuous pump infusion.

A "pharmaceutically acceptable carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutically acceptable carriers or excipients include, but are not limited to, binding agents (e.g., pregelatinized maize starch, polyvinylpyrrolidone, hydroxypropyl methylcellulose); fillers (e.g., lactose and other sugars, microcrystalline cellulose, pectin, gelatin, calcium sulfate, ethyl cellulose, polyacrylates, calcium hydrogen phosphate); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate); disintegrants (e.g., starch, sodium starch glycolate); and wetting agents (e.g., sodium lauryl sulphate).

Pharmaceutically acceptable organic or inorganic excipients suitable for non-parenteral administration which do not deleteriously react with nucleic acids can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone, and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents, and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone, and the like.

In some embodiments, the pharmaceutical compositions containing an RNAi agent described herein are administered in dosages sufficient to inhibit expression of an HBV gene. In general, a suitable dose of an RNAi agent will be in the range of 0.001 to 200.0 milligrams per kilogram body weight of the recipient per day, and more typically in the range of 1 to 50 mg per kilogram body weight per day. For example, an siRNA can be administered at 0.01 mg/kg, 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition can be administered once daily, or the RNAi agent can be administered as two, three, or more sub-doses at appropriate intervals throughout the day or even using continuous infusion or delivery through a controlled release formulation. In that case, the RNAi agent contained in each sub-dose must be correspondingly smaller in order to achieve the total daily dosage. The dosage unit can also be compounded for delivery over several days, e.g., using a conventional sustained release formulation which provides sustained release of the RNAi over a several day period. Sustained release formulations are well known in the art and are particularly useful for delivery of agents at a particular site, such as could be used with the agents of the technology described herein. In this embodiment, the dosage unit contains a corresponding multiple of the daily dose.

The effect of a single dose on the level of expression of an HBV gene can be long-lasting, such that subsequent doses are administered at not more than 3, 4, or 5 day intervals, or at not more than 1, 2, 3, or 4 week intervals.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual RNAi agents encompassed by the technology described herein can be made using conventional methodologies or on the basis of in vivo testing using an appropriate animal model, as described elsewhere herein.

Mouse models are available for the study of HBV infection, and such models can be used for in vivo testing of RNAi, as well as for determining a dose that is effective at reducing HBV gene expression.

In some embodiments, administration of pharmaceutical compositions and formulations described herein can be topical (e.g., by a transdermal patch), pulmonary (e.g., by inhalation or insufflation of powders or aerosols, including by nebulizer); intratracheal; intranasal; epidermal and transdermal; oral; or parenteral. Parenteral administration includes intravenous, intraarterial, subcutaneous, intraperitoneal, and intramuscular injection or infusion; subdermal administration (e.g., via an implanted device); or intracranial administration (e.g., by intraparenchymal, intrathecal, or intraventricular, administration).

In certain embodiments, an RNAi agent used in a combination therapy for treating HBV as disclosed herein is delivered subcutaneously.

In some embodiments, RNAi agents can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids, and powders. Conventional pharmaceutical carriers, aqueous, powder, or oily bases, thickeners, and the like can be necessary or desirable. Coated condoms, gloves, and the like can also be useful. Suitable topical formulations include those in which the RNAis featured in the technology described herein are in admixture with a topical delivery agent such as lipids, liposomes, fatty acids, fatty acid esters, steroids, chelating agents, and surfactants. Suitable lipids and liposomes include neutral (e.g., dioleoylphosphatidyl DOPE ethanolamine, dimyristoylphosphatidyl choline DMPC, distearolyphosphatidyl choline), negative (e.g., dimyristoylphosphatidyl glycerol DMPG), and cationic (e.g., dioleoyltetramethylaminopropyl DOTAP and dioleoylphosphatidyl ethanolamine DOTMA). RNAi agents can be encapsulated within liposomes or can form complexes thereto, in particular to cationic liposomes. Alternatively, RNAi agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride, or pharmaceutically acceptable salt thereof. Examples of topical formulations are described in detail in U.S. Pat. No. 6,747,014, which is incorporated herein by reference for teachings relevant to such topical formulations.

Vesicles, such as liposomes, may be used in formulations for delivering RNAi agents disclosed herein; such formulation may have desirable properties such as specificity and the duration of action. As used herein, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes can possess the advantage of being able to fuse to the cell wall. Non-cationic liposomes, although not able to fuse as efficiently with the cell wall, may be taken up by macrophages in vivo. Important considerations in the preparation of liposome formulations are lipid surface charge, vesicle size, and the aqueous volume of the liposomes.

In some embodiments, liposomal delivery may have the following advantageous properties: being highly deformable and able to pass through fine pores in the skin; biocompatibility and biodegradabilty; ability to incorporate a wide range of water- and lipid-soluble drugs; ability to protect encapsulated drugs in their internal compartments from metabolism and degradation (Rosoff, in Pharmaceutical Dosage Forms, Lieberman, Rieger and Banker (Eds.), Marcel Dekker, Inc., New York, N.Y., volume 1, p. 245 (1998)); for topical delivery, reduced side-effects related to high systemic absorption of the administered drug, increased accumulation of the administered drug at the desired target, and the ability to administer a wide variety of drugs, both hydrophilic and hydrophobic, into the skin; and ability to deliver agents including high-molecular weight nucleic acids, analgesics, antibodies, and hormones to the skin.

Liposomes fall into two broad classes. Cationic liposomes are positively charged liposomes which interact with the negatively charged nucleic acid molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang, et al., Biochem. Biophys. Res. Commun. 147, 980-985 (1987)).

Liposomes that are pH-sensitive or negatively-charged, entrap nucleic acids rather than complex with them. Since both the DNA and the lipid are similarly charged, repulsion rather than complex formation occurs. Nevertheless, some DNA is entrapped within the aqueous interior of these liposomes. pH-sensitive liposomes have been used to deliver nucleic acids to cell monolayers in culture (e.g., Zhou, et al., Journal of Controlled Release 19, 269-74 (1992)).

In some embodiments, a liposomal composition is formed from phosphatidylcholine (PC), such as, for example, soybean PC and egg PC. In some embodiments, liposomal compositions include phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions can be formed from dimyristoyl phosphatidylglycerol, while anionic fusogenic liposomes can be formed from dioleoyl phosphatidylethanolamine (DOPE). In still other embodiments, a liposomal composition is formed from mixtures of phospholipid and/or phosphatidylcholine and/or cholesterol.

In some embodiments, liposomal drug formulations are delivered topically to the skin.

In some embodiments, an RNAi agent used in a combination therapy described herein is fully encapsulated in a lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs may be used for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in International Application Publication No. WO 00/03683. The particles of the technology described herein typically have a mean diameter of about 50 nm to about 150 nm, more typically about 60 nm to about 130 nm, more typically about 70 nm to about 110 nm, and most typically about 70 nm to about 90 nm, and are substantially nontoxic. In addition, in some embodiments, nucleic acids when present in the nucleic acid-lipid particles are resistant in aqueous solution to degradation with a nuclease. Nucleic acid-lipid particles and related methods of preparation are disclosed in, e.g., U.S. Pat. Nos. 5,976,567; 5,981,501; 6,534,484; 6,586,410; 6,815,432; and International Application Publication No. WO 96/40964.

In some embodiments, the RNAi agent is delivered via a liposome or other lipid formulation, wherein the lipid to drug ratio (mass/mass ratio) (e.g., lipid to siRNA ratio) is in the range of from about 1:1 to about 50:1, from about 1:1 to about 25:1, from about 3:1 to about 15:1, from about 4:1 to about 10:1, from about 5:1 to about 9:1, or about 6:1 to about 9:1.

III. Anti-HBV Antibodies

The present disclosure provides anti-HBV antibodies for use in a combination therapy for treating HBV.

a. Antibodies that Bind to HBV Proteins

In some embodiments, the anti-HBV antibody of the combination therapy, or the antigen binding fragment thereof, binds to the antigenic loop region of HBsAg. The envelope of the hepatitis B virus contains three "HBV envelope proteins" (also known as "HBsAg", "hepatitis B surface antigen"): S protein (for "small", also referred to as S-HBsAg), M protein (for "middle", also referred to as M-HBsAg), and L protein (for "large", also referred to as L-HBsAg). S-HBsAg, M-HBsAg, and L-HBsAg share the same C-terminal extremity (also referred to as "S domain", 226 amino acids), which corresponds to the S protein (S-HBsAg) and which is involved in virus assembly and infectivity. S-HBsAg, M-HBsAg, and L-HBsAg are synthesized in the endoplasmic reticulum (ER), assembled, and secreted as particles through the Golgi apparatus. The S domain comprises four predicted transmembrane (TM) domains, whereby both the N-terminus and the C-terminus of the S domain are exposed to the lumen. The transmembrane domains TM1 and TM2 are both necessary for cotranslational protein integration into the ER membrane and the transmembrane domains TM3 and TM4 are located in the C-terminal third of the S domain. The "antigenic loop region" of HBsAg is located between the predicted TM3 and TM4 transmembrane domains of the S domain of HBsAg, whereby the antigenic loop region comprises amino acids 101-172 of the S domain (Salisse J., and Sureau C. Journal of Virology 83:9321-8 (2009)). An important determinant of infectivity resides in the antigenic loop region of HBV envelope proteins. In particular, residues between 119 and 125 of the HBsAg contain a CXXC motif, which has been demonstrated to be the most important sequence required for the infectivity of HBV (Jaoude, G. A., and Sureau, C., Journal of Virology 79:10460-6 (2005)).

As used herein, the S domain of HBsAg refers to an amino acid sequence as set forth in SEQ ID NO:13 (shown below) or to natural or artificial sequence variants therof.

```
MENITSGFLGPLLVLQAGFFLLTRILTIPQSLDSWWTSLNFLGGTTVCL

GQNSQSPTSNHSPTSCPPTCPGYRWMCLRRFIIFLFILLLCLIFLLVLL

DYQGMLPVCPLIPGSSTTSTGPCRTCMTTAQGTSMYPSCCCTKPSDGNC

TCIPIPSSWAFGKFLWEWASARFSWLSLLVPFVQWFVGLSPTVWLSVIW

MMWYWGPSLYSILSPFLPLLPIFFCLWVYI (SEQ ID NO: 13; amino acids 101-172 are shown
underlined)
```

For example, the expression "amino acids 101-172 of the S domain" refers to the amino acid residues from positions 101-172 of the polypeptide according to SEQ ID NO:13. However, a person skilled in the art will understand that mutations or variations (including, but not limited to, substitution, deletion and/or addition, for example, HBsAg of a different genotype or a different HBsAg mutant as described herein) may occur naturally in the amino acid sequence of the S domain of HBsAg or be introduced artificially into the amino acid sequence of the S domain of HBsAg without affecting its biological properties. Therefore, the term "S domain of HBsAg" comprises all such polypeptides, for example, including the polypeptide according to SEQ ID NO:13 and its natural or artificial mutants. In addition, when sequence fragments of the S domain of HBsAg are described herein (e.g., amino acids 101-172 or amino acids 120-130 of the S domain of HBsAg), they include not only the corresponding sequence fragments of SEQ ID NO:13, but also the corresponding sequence fragments of its natural or artificial mutants. For example, the expression "amino acid residues from positions 101-172 of the S domain of HBsAg" includes amino acid residues from positions 101-172 of SEQ ID NO:13 and the corresponding fragments of its mutants (natural or artificial mutants).

As used herein, the expression "corresponding sequence fragments" or "corresponding fragments" refers to fragments that are located in equal positions of sequences when the sequences are subjected to optimized alignment, namely, the sequences are aligned to obtain a highest percentage of identity. The M protein (M-HBsAg) corresponds to the S protein extended by an N-terminal domain of 55 amino acids called "pre-S2". The L protein (L-HBsAg) corresponds to the M protein extended by an N-terminal domain of 108 amino acids called "pre-S1" (genotype D). The pre-S1 and pre-S2 domains of the L protein can be present either at the inner face of viral particles (on the cytoplasmic side of the ER), playing a crucial role in virus assembly, or on the outer face (on the luminal side of the ER), available for the interaction with target cells and necessary for viral infectivity. Moreover, HBV surface proteins (HBsAgs) are not only incorporated into virion envelopes but also spontaneously bud from ER-Golgi intermediate compartment membranes to form empty "subviral particles" (SVPs) that are released from the cell by secretion.

Since all three HBV envelope proteins S-HBsAg, M-HBsAg, and L-HBsAg comprise the S domain, all three HBV envelope proteins S-HBsAg, M-HBsAg, and L-HBsAg also comprise the "antigenic loop region". Accordingly, an antibody or an antigen binding fragment thereof that binds to the antigenic loop region of HBsAg binds to all three HBV envelope proteins: S-HBsAg, M-HBsAg, and L-HBsAg.

Moreover, in some embodiments, the anti-HBV antibody of the combination therapy, or an antigen binding fragment thereof, neutralizes infection with hepatitis B virus. In other words, the antibody, or the antigen binding fragment thereof, may reduce viral infectivity of hepatitis B virus.

To study and quantitate virus infectivity (or "neutralization") in the laboratory the person skilled in the art knows various standard "neutralization assays." For a neutralization assay, animal viruses are typically propagated in cells and/or cell lines. In the context of the present disclosure, for a neutralization assay, cultured cells may be incubated with a fixed amount of HBV in the presence (or absence) of the antibody to be tested. As a readout, the levels of hepatitis B surface antigen (HBsAg) or hepatitis B e antigen (HBeAg) secreted into the cell culture supernatant may be used and/or HBcAg staining may be assessed. In one embodiment of a HBV neutralization assay, cultured cells, for example HepaRG cells, in particular differentiated HepaRG cells, are incubated with a fixed amount of HBV in the presence or absence of the antibody to be tested, for example for 16 hours at 37° C. The incubation may be performed in a medium (e.g., supplemented with 4% PEG 8000). After incubation, cells may be washed and further cultivated. To measure virus infectivity, the levels of hepatitis B surface antigen (HBsAg) and hepatitis B e antigen (HBeAg) secreted into the culture supernatant, e.g., from day 7 to day 11 post-infection, may be determined by enzyme-linked immunosorbent assay (ELISA). Additionally, HBcAg staining may be assessed in an immunofluorescence assay.

In some embodiments, the antibody and antigen binding fragment have high neutralizing potency. The concentration of an antibody of the present disclosure required for 50% neutralization of hepatitis B virus (HBV) is, for example, about 10 pg/ml or less. In certain embodiments, the concentration of an antibody of the present disclosure required for 50% neutralization of HBV is about 5 pg/ml, about 1 pg/ml, or about 750 ng/ml. In certain embodiments, the concentration of an antibody of the present disclosure required for 50% neutralization of HBV is 500 ng/ml or less, e.g., 450, 400, 350, 300, 250, 200, 175, 150, 125, 100, 90, 80, 70, 60, or about 50 ng/ml or less. This means that only low concentrations of the antibody are required for 50% neutralization of HBV. Specificity and potency can be measured using standard assays as known to one of skill in the art.

In some embodiments, the anti-HBV antibody, as a component of the combination therapy, is useful in the prevention and/or treatment of hepatitis B.

In some embodiments, an antibody according to the present disclosure, or an antigen binding fragment thereof, promotes clearance of HBsAg and HBV. In particular, an antibody according to the present disclosure, or an antigen binding fragment thereof, may promote clearance of both HBV and subviral particles of hepatitis B virus (SVPs). Clearance of HBsAg or of subviral particles may be assessed by measuring the level of HBsAg for example in a blood sample, e.g., from a hepatitis B patient. Similarly, clearance of HBV may be assessed by measuring the level of HBV for example in a blood sample, e.g., from a hepatitis B patient.

In the sera of patients infected with HBV, in addition to infectious particles (HBV), there is typically an excess (typically 1,000- to 100,000-fold) of empty subviral particles (SVP) composed solely of HBV envelope proteins (HBsAg) in the form of relatively smaller spheres and filaments of variable length. Subviral particles were shown to strongly enhance intracellular viral replication and gene expression of HBV (Bruns, M., et al., J Virol 72(2):1462-8 (1998)). This is also important in the context of infectivity of sera containing HBV, since the infectivity depends not only on the number of viruses but also on the number of SVPs (Bruns, M., et al., J Virol 72(2):1462-8 (1998)). Moreover, an excess of subviral particles can serve as a decoy by absorbing neutralizing antibodies and therefore delay the clearance of infection. Typically, achievement of hepatitis B surface antigen (HBsAg) loss is thus considered to be an ideal endpoint of treatment and the closest outcome to cure chronic hepatitis B (CHB). Accordingly, in some embodiments, an antibody according to the present disclosure, or an antigen binding fragment thereof, which promotes clearance of HBsAg, and in particular, clearance of subviral particles of hepatitis B virus and HBV, enables improved treatment of hepatitis B, in particular in the context of chronic hepatitis B. Thereby, an antibody according to the present disclosure, or an antigen binding fragment thereof, may potently neutralize HBV since less of the antibody is absorbed by SVPs acting as a decoy. In addition, in certain embodiments, an antibody according to the present disclosure, or an antigen binding fragment thereof, promotes clearance of subviral particles of hepatitis B virus, and decreases infectivity of HBV in sera.

HBV is differentiated into many genotypes, according to genome sequence. To date, eight well-known genotypes (A-H) of the HBV genome have been defined. Moreover, two new genotypes, I and J, have also been identified (Sunbul, M., World J Gastroenterol 20(18):5427-34 (2014)). The genotype is known to affect the progression of the disease, and differences between genotypes in response to antiviral treatment have been determined. For example, genotype A has a tendency for chronicity, whereas viral mutations are frequently encountered in genotype C. Both chronicity and mutation frequency are common in genotype D. Moreover, the genotypes of HBV are differentially distributed over the world (Sunbul, M., 2014, supra). In certain embodiments, an antibody according to the present disclosure, or an antigen binding fragment thereof, binds to at least 6, to at least 8, or to all 10 of the HBsAg genotypes A, B, C, D, E, F, G, H, I, and J. In certain embodiments, an antibody according to the present disclosure, or an antigen binding fragment thereof, binds to 1, 2, 3, 4, 5, 6, 7, 8, 9, or 10 of the HBsAg genotypes A, B, C, D, E, F, G, H, I, and J. Examples for the different genotypes of HBsAg include the following: GenBank accession number J02203 (HBV-D, ayw3), GenBank accession number FJ899792.1 (HBV-D, adw2), GenBank accession number AM282986 (HBV-A), GenBank accession number D23678 (HBV-B1 Japan), GenBank accession number AB1 1 7758 (HBV-C1 Cambodia), GenBank accession number AB205192 (HBV-E Ghana), GenBank accession number X69798 (HBV-F4 Brazil), GenBank accession number AF160501 (HBV-G USA), GenBank accession number AY090454 (HBV-H Nicaragua), GenBank accession number AF241409 (HBV-I Vietnam), and GenBank accession number AB486012 (HBV-J Borneo). The amino acid sequences of the antigenic loop region of the S domain of HBsAg of the different genotypes are shown in Table 2 (SEQ ID NOs:14-42).

TABLE 2

Antigenic Loop Sequences from various HBV genotypes

| HBsAg Antigenic Loop Sequence | Strain | SEQ ID NO: |
|---|---|---|
| QGMLPVCPLIPGSSTTSTGPCRTCMTTAQGTS MYPSCCCTKPSDGNCTCIPIPSSWAFGKFLWE WASARFSW | J02203 (D, ayw3) | 14 |
| QGMLPVCPLIPGSSTTGTGPCRTCTTPAQGTS MYPSCCCTKPSDGNCTCIPIPSSWAFGKFLWE WASARFSW | FJ899792 (D, adw2) | 15 |
| QGMLPVCPLIPGTTTTSTGPCKTCTTPAQGNS MFPSCCCTKPSDGNCTCIPIPSSWAFAKYLWE WASVRFSW | AM282986 (A) | 16 |
| QGMLPVCPLIPGSSTTSTGPCKTCTTPAQGTS MFPSCCCTKPTDGNCTCIPIPSSWAFAKYLWE WASVRFSW | D23678 (B1) | 17 |
| QGMLPVCPLLPGTSTTSTGPCKTCTIPAQGTS MFPSCCCTKPSDGNCTCIPIPSSWAFARFLWE WASVRFSW | AB117758 (C1) | 18 |
| QGMLPVCPLIPGSSTTSTGPCRTCTTLAQGTS MFPSCCCSKPSDGNCTCIPIPSSWAFGKFLWE WASARFSWLS | AB205192(E) | 19 |
| QGMLPVCPLLPGTTTSTGPCTCTTLAQGTSM FPSCCCSKPSDGNCTCIPIPSSWALGKYLWEW ASARFSW | X69798 (F4) | 20 |
| QGMLPVCPLIPGSSTTSTGPCTCTTPAQGNSM YPSCCCTPSDGNCTCIPIPSSWAFAKYLWEWA SVRFSW | AF1 60501 (G) | 21 |
| QGMLPVCPLLPGTTTSTGPCKTCTTLAQGTS MFPSCCCTKPSDGNCTCIPIPSSWAFGKYLWE WASARFSW | AY090454 (H) | 22 |
| QGMLPVCPLIPGSSTTSTGPCKTCTTPAQGNS MYPSCCCTKPSDGNCTCIPIPSSWAFAKYLWE WASARFSW | AF241409 (I) | 23 |
| QGMLPVCPLLPGSTTTSTGPCRTCTITAQGTS MFPSCCCTKPSDGNCTCIPIPSSWAFAKFLWE WASVRFSW | AB486012 (J) | 24 |
| CQGMLPVCPLIPGSSTTGTGTCRTCTTPAQGT SMYPSCCCTKPSDGNCTCIPIPSSWAFG FLWEWASARFSW | HBsAg Y100C/P120T | 25 |
| QGMLPVCPLIPGSSTTGTGTCRTCTTPAQGTS MYPSCCCTKPSDGNCTCIPIPSSWAFGKFLWE WASARFSW | HBsAg P120T | 26 |

TABLE 2-continued

Antigenic Loop Sequences from various HBV genotypes

| HBsAg Antigenic Loop Sequence | Strain | SEQ ID NO: |
|---|---|---|
| QGMLPVCPLIPGSSTTGTGTCRTCTTPAQGTS MYPSCCCTKPLDGNCTCIPIPSSWAFGKFLWE WASARFSW | HBsAg P120T/S143L | 27 |
| QGMLPVCPLIPGSSTTGTGTGPSRTCTTPAQGTS MYPSCCCTKPSDGNCTCIPIPSSWAFGKFLWE WASARFSW | HBsAg C121 S | 28 |
| QGMLPVCPLIPGSSTTGTGPCDTCTTPAQGTS MYPSCCCTKPSDGNCTCIPIPSSWAFG KFLWEWASARFSW | HBsAg R122D | 29 |
| QGMLPVCPLIPGSSTTGTGPCITCTTPAQGTSM YPSCCCTPSDGNCTCIPIPSSWAFGKFLWEWA SARFSW | HBsAg R122I | 30 |
| QGMLPVCPLIPGSSTTGTGPCRNCTTPAQGTS MYPSCCCTKPSDGNCTCIPIPSSWAFGKFLWE WASARFSW | HBsAg TI23N | 31 |
| QGMLPVCPLIPGSSTTGTGPCRTCTTPAHGTS MYPSCCCTKPSDGNCTCIPIPSSWAFGKF LWEWASARFSW | HBsAg Q129H | 32 |
| QGMLPVCPLIPGSSTTGTGPCRTCTTPALGTS MYPSCCCTKPSDGNCTCIPIPSSWAFGKFLWE WASARFSW | HBsAg Q129L | 33 |
| QGMLPVCPLIPGSSTTGTGPCRTCTTPAQGTS HYPSCCCTKPSDGNCTCIPIPSSWAFGKFLWE WASARFSW | HBsAg MI33H | 34 |
| QGMLPVCPLIPGSSTTGTGPCRTCTTPAQGTS LYPSCCCTKPSDGNCTCIPIPSSWAFGKFLWE WASARFSW | HBsAg MI33L | 35 |
| QGMLPVCPLIPGSSTTGTGPCRTCTTPAQGTS TYPSCCCTKPSDGNCTCIPIPSSWAFGKFLWE WASARFSW | HBsAg MI33T | 36 |
| QGMLPVCPLIPGSSTTGTGPCRTCTTPAQGTS MYPSCCCTEPSDGNCTCIPIPSSWAFGKFLWE WASARFSW | HBsAg K141 E | 37 |
| QGMLPVCPLIPGSSTTGTGPCRTCTTPAQGTS MYPSCCCTKSSDGNCTCIPIPSSWAFGKFLWE WASARFSW | HBsAg P142S | 38 |
| QGMLPVCPLIPGSSTTGTGPCRTCTTPAQGTS MYPSCCCTKPKDGNCTCIPIPSSWAFGKFLWE WASARFSW | HBsAg S143K | 39 |
| QGMLPVCPLIPGSSTTGTGPCRTCTTPAQGTS MYPSCCCTPSAGNCTCIPIPSSWAFGKFLWEW ASARFSW | HBsAg D144A | 40 |
| QGMLPVCPLIPGSSTTGTGPCRTCTTPAQGTS MYPSCCCTKPSDRNCTCIPIPSSWAFGKFLWE WASARFSW | HBsAg G145R | 41 |
| QGMLPVCPLIPGSSTTGTGPCRTCTTPAQGTS MYPSCCCTKPSDGACTCIPIPSSWAFGKFLWE WASARFSW | HBsAg N146A | 42 |

In certain embodiments, an antibody according to the present disclosure, or an antigen binding fragment thereof, binds to 1, 2, 3, 4, 5, 6, 7, 8, 9, 10, 11, 12, 13, 14, 15, 16, 17 or 18 of the HBsAg mutants having mutations in the antigenic loop region: HBsAg Y100C/P120T, HBsAg P120T, HBsAg P120T/S143L, HBsAg C121 S, HBsAg R122D, HBsAg R122I, HBsAg T123N, HBsAg Q129H, HBsAg Q129L, HBsAg M133H, HBsAg M133L, HBsAg M133T, HBsAg K141 E, HBsAg P142S, HBsAg S143K, HBsAg D144A, HBsAg G145R, and HBsAg $N_{146}$A. These mutants are naturally occurring mutants based on the S domain of HBsAg Genotype D (SEQ ID NO:43), Genbank accession no. FJ899792 (whereby the mutated amino acid residue(s) are indicated in the name).

(SEQ ID NO: 43)
MENVTSGFLGPLLVLQAGFFLLTRILTIPQSLDSWWTSLNFLGGTTVCL

GQNSQSPTSNHSPTSCPPTCPGYRWMCLRRFIIFLFILLLCLIFLLVLL

DYQGMLPVCPLIPGSSTTGTGPCRTCTTPAQGTSMYPSCCCTKPSDGNC

TCIPIPSSWAFGKFLWEWASARFSWLSLLVPFVQWFVGLSPTVWLSVIW

MMWYWGPSLYSTLSPFLPLLPIFFCLWVYI (the antigenic loop region, i.e., amino acids 101-172, is shown underlined).

In particular embodiments, an antibody according to the present disclosure, or an antigen binding fragment thereof, binds to at least 12, to at least 15, or to all 18 of the infectious HBsAg mutants having mutations in the antigenic loop region: HBsAg Y100C/P120T, HBsAg P120T, HBsAg P120T/S143L, HBsAg C121 S, HBsAg R122D, HBsAg R122I, HBsAg T123N, HBsAg Q129H, HBsAg Q129L, HBsAg M1 33H, HBsAg M133L, HBsAg M1 33T, HBsAg K141 E, HBsAg P142S, HBsAg S143K, HBsAg D144A, HBsAg G145R, and HBsAg N146A.

In certain embodiments, an antibody according to the present disclosure, or an antigen binding fragment thereof, binds to an epitope comprising at least one, at least two, at least three amino acids, or e at least four amino acids of the antigenic loop region of HBsAg, wherein the at least two, at least three, or at least four amino acids are selected from amino acids 115-133 of the S domain of HBsAg, amino acids 120-133 of the S domain of HBsAg, or amino acids 120-130 of the S domain of HBsAg. Of note, the position of the amino acids (e.g., 115-133, 120-133, 120-130) refers to the S domain of HBsAg as described above, which is present in all three HBV envelope proteins S-HBsAg, M-HBsAg, and L-HBsAg.

In particular embodiments, an antibody according to the present disclosure, or an antigen binding fragment thereof, binds to an epitope in the antigenic loop region of HBsAg, whereby the epitope is formed by one or more amino acids located at positions selected from amino acid positions 115-133, amino acid positions 120-133, or amino acid positions 120-130 of the S domain of HBsAg.

The term "formed by" as used herein in the context of an epitope means, that the epitope to which an antibody of the present disclosure, or an antigen binding fragment thereof, binds to may be linear (continuous) or conformational (discontinuous). A linear or a sequential epitope is an epitope that is recognized by antibodies by its linear sequence of amino acids, or primary structure. In contrast, a conformational epitope has a specific three-dimensional shape and protein structure. Accordingly, if the epitope is a linear epitope and comprises more than one amino acid located at positions selected from amino acid positions 115-133, or amino acid positions 120-133 of the S domain of HBsAg, the amino acids comprised by the epitope may be located in adjacent positions of the primary structure (i.e., consecutive amino acids in the amino acid sequence). In the case of a conformational epitope (3D structure), in contrast, the amino acid sequence typically forms a 3D structure as epitope and, thus, the amino acids forming the epitope (or the amino acids "comprised by" the epitope) may be or may be not located in adjacent positions of the primary structure (i.e., may or may not be consecutive amino acids in the amino acid sequence). In certain embodiments, the epitope to which an antibody of the present disclosure, or an antigen binding fragment thereof, binds is only formed by amino acid(s) selected from amino acid positions 115-133, amino acid positions 120-133, or amino acid positions 120-130 of the S domain of HBsAg. In particular embodiments, no (further) amino acids—which are located outside the positions 115-133, positions 120-133, or positions 120-130—are required to form the epitope to which an antibody of the present disclosure, or an antigen binding fragment thereof, binds.

In certain embodiments, the epitope in the antigenic loop region of HBsAg to which an antibody of the present disclosure, or an antigen binding fragment thereof, binds is formed by two or more amino acids located at positions selected from amino acid positions 115-133, amino acid positions 120-133, or amino acid positions 120-130 of the S domain of HBsAg. In certain embodiments, the epitope in the antigenic loop region of HBsAg to which an antibody of the present disclosure, or an antigen binding fragment thereof, binds is formed by three or more amino acids located at positions selected from amino acid positions 115-133, amino acid positions 120-133, and amino acid positions 120-130 of the S domain of HBsAg. In some embodiments, the epitope in the antigenic loop region of HBsAg to which an antibody of the present disclosure, or an antigen binding fragment thereof, binds is formed by four or more amino acids located at positions selected from amino acid positions 115-133, amino acid positions 120-133, or amino acid positions 120-130 of the S domain of HBsAg. As such, an antibody according to the present disclosure, or an antigen binding fragment thereof, may bind to at least one, at least two, at least three, or at least four amino acids of the antigenic loop region of HBsAg selected from amino acids 115-133 of the S domain of HBsAg, amino acids 120-133 of the S domain of HBsAg, or amino acids 120-130 of the S domain of HBsAg. In particular embodiments, an antibody according to the present disclosure, or the antigen binding fragment thereof, binds to an epitope comprising at least two, at least three, or at least four amino acids of the antigenic loop region of HBsAg, wherein the at least two, at least three, or at least four amino acids are selected from amino acids 120-133, or amino acids 120-130 of the S domain of HBsAg and wherein the at least two, at least three, or at least four amino acids are located in adjacent positions (i.e., are consecutive amino acids in the amino acid sequence/primary structure).

In certain embodiments, the epitope to which an antibody according to the present disclosure, or an antigen binding fragment thereof, binds to, is a conformational epitope. Accordingly, an antibody according to the present disclosure, or an antigen binding fragment thereof, may bind to an epitope comprising at least two, at least three, or at least four amino acids of the antigenic loop region of HBsAg, wherein the at least two, at least three, or at least four amino acids are selected from amino acids 120-133, or amino acids 120-130, of the S domain of HBsAg and wherein at least two, or at least three, or at least four amino acids are not located in adjacent positions (of the primary structure).

In certain specific embodiments, an antibody of the present disclosure is a bispecific antibody, with a first specificity for HBsAg, and a second specificity that stimulates an immune effector cell (e.g., by targeting a T cell surface protein such as, for example, a CD3 protein extracellular portion). The second specificity may cause, for example, a cytotoxic effect or a vaccinal effect.

b. Fc Moieties

In some embodiments, a binding protein (e.g., antibody or an antigen binding fragment thereof) comprises an Fc moiety. In certain embodiments, the Fc moiety may be derived from human origin, e.g., from human IgG1, IgG2, IgG3, and/or IgG4. In specific embodiments, an antibody or antigen binding fragments can comprise an Fc moiety derived from human IgG1.

As used herein, the term "Fc moiety" refers to a sequence comprising or derived from a portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. In certain embodiments, a complete Fc moiety comprises a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Amino acid positions within an Fc moiety have been numbered according to the EU numbering system of Kabat (see, e.g., Kabat, et al., "Sequences of Proteins of Immunological Interest", U.S. Dept. Health and Human Services, 1983 and 1987). Amino acid positions of an Fc moiety can also be numbered according to the IMGT numbering system (including unique numbering for the C-domain and exon numbering) and the Kabat numbering system.

In some embodiments, an Fc moiety comprises at least one of: a hinge (e.g., upper, middle, and/or lower hinge region) domain, a CH2 domain, a CH3 domain, or a variant, portion, or fragment thereof. In some embodiments, an Fc moiety comprises at least a hinge domain, a CH2 domain, or a CH3 domain. In further embodiments, the Fc moiety is a complete Fc moiety. The amino acid sequence of an exemplary Fc moiety of human IgG1 isotype is provided in SEQ ID NO:96. The Fc moiety may also comprise one or more amino acid insertions, deletions, or substitutions relative to a naturally occurring Fc moiety. For example, at least one of a hinge domain, CH2 domain, or CH3 domain, or a portion thereof, may be deleted. For example, an Fc moiety may comprise or consist of: (i) hinge domain (or a portion thereof) fused to a CH2 domain (or a portion thereof), (ii) a hinge domain (or a portion thereof) fused to a CH3 domain (or a portion thereof), (iii) a CH2 domain (or a portion thereof) fused to a CH3 domain (or a portion thereof), (iv) a hinge domain (or a portion thereof), (v) a CH2 domain (or a portion thereof), or (vi) a CH3 domain or a portion thereof.

An Fc moiety of the present disclosure may be modified such that it varies in amino acid sequence from the complete Fc moiety of a naturally occurring immunoglobulin molecule, while retaining (or enhancing) at least one desirable function conferred by the naturally occurring Fc moiety. Such functions include, for example, Fc receptor (FcR) binding, antibody half-life modulation (e.g., by binding to FcRn), ADCC function, protein A binding, protein G binding, and complement binding. Portions of naturally occurring Fc moieties which are involved with such functions have been described in the art.

For example, to activate the complement cascade, the C1q protein complex can bind to at least two molecules of IgG1 or one molecule of IgM when the immunoglobulin molecule(s) is attached to the antigenic target (Ward, E. S., and Ghetie, V., Ther. Immunol. 277-94 (1995)). The heavy chain region comprising amino acid residues 318 to 337 is involved in complement fixation (Burton, D. R., Mol. Immunol. 22:161-206 (1985)). Duncan, A. R., and Winter, G. (Nature 332:738-40 (1988)), using site directed mutagenesis, reported that Glu318, Lys320, and Lys322 form the binding site to C1q. The role of Glu318, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on cells including hematopoietic cells. Fc receptors belong to the immunoglobulin superfamily, and shown to mediate both the removal of antibody-coated pathogens by phagocytosis of immune complexes, and the lysis of erythrocytes and various other cellular targets (e.g., tumor cells) coated with the corresponding antibody, via antibody dependent cell mediated cytotoxicity (ADCC; Van de Winkel, J. G., and Anderson, C. L., J. Leukoc. Biol. 49:511-24 (1991)). FcRs are defined by their specificity for immunoglobulin classes; Fc receptors for IgG antibodies are referred to as FcγR, for IgE as FcR, for IgA as FcαR, and so on, and neonatal Fc receptors are referred to as FcRn. Fc receptor binding is described in, for example, Ravetch, J. V., and Kinet, J. P., Annu. Rev. Immunol. 9:457-92 (1991); Capel, P. J., et al., Immunomethods 4:25-34 (1994); de Haas, M., et al., J Lab. Clin. Med. 126:330-41 (1995); and Gessner, J. E., et al., Ann. Hematol. 76:231-48 (1998).

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Fc moieties providing cross-linking of receptors (e.g., FcγR) are contemplated herein. In humans, three classes of FcγR have been characterized: (i) FcγRI (CD64), which binds monomeric IgG with high affinity and is expressed on macrophages, monocytes, neutrophils, and eosinophils; (ii) FcγRII (CD32), which binds complexed IgG with medium to low affinity, is widely expressed, in particular on leukocytes, is believed to be a central player in antibody-mediated immunity, and which can be divided into FcγRIIA, FcγRIIB, and FcγRIIC, which perform different functions in the immune system, but bind with similar low affinity to the IgG-Fc, and the ectodomains of these receptors are highly homologuous; and (iii) FcγRIII (CD16), which binds IgG with medium to low affinity and has been found in two forms: FcγRIIIA, which has been found on NK cells, macrophages, eosinophils, and some monocytes and T cells, and is believed to mediate ADCC; and FcγRIIIB, which is highly expressed on neutrophils.

FcγRIIA is found on many cells involved in killing (e.g., macrophages, monocytes, neutrophils) and seems able to activate the killing process. FcγRIIB seems to play a role in inhibitory processes and is found on B-cells, macrophages and on mast cells and eosinophils. It has been shown that 75% of all FcγRIIB is found in the liver (Ganesan, L. P., et al., Journal of Immunology 189:4981-8 (2012)). FcγRIIB is abundantly expressed on Liver Sinusoidal Endothelium, called LSEC, and in Kupffer cells in the liver, and LSEC are the major site of small immune complexes clearance (Ganesan, L. P. et al., 2012, supra).

In some embodiments the antibodies disclosed herein and the antigen binding fragments thereof comprise an Fc moiety for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al. (Molecular Immunology 45:3926-33 (2008)). Thereby, the clearance of immune complexes can be enhanced (Chu, S., et al., Am J Respir Crit, American Thoracic Society International Conference Abstracts (2014)). In some embodiments, the antibodies of the present disclosure, or the antigen binding fragments thereof, comprise an engineered Fc moiety with the mutations S267E and L328F, in particular as described by Chu, S. Y. et al. (2008, supra).

On B cells, FcγRIIB seems to function to suppress further immunoglobulin production and isotype switching to, for example, the IgE class. On macrophages, FcγRIIB is thought to inhibit phagocytosis as mediated through FcγRIIA. On eosinophils and mast cells, the b form may help to suppress activation of these cells through IgE binding to its separate receptor.

Regarding FcγRI binding, modification in native IgG of at least one of E233-G236, P238, D265, $N_{297}$, A327, and P329 reduces binding to FcγRI. IgG2 residues at positions 233-236, substituted into corresponding positions IgG1 and IgG4, reduces binding of IgG1 and IgG4 to FcγRI by $10^3$-fold and eliminated the human monocyte response to antibody-sensitized red blood cells (Armour, K. L., et al., Eur. J. Immunol. 29:2613-2624 (1999)).

Regarding FcγRII binding, reduced binding for FcγRIIA is found, e.g., for IgG mutation of at least one of E233-G236, P238, D265, $N_{297}$, A327, P329, D270, Q295, A327, R292, and K414.

Regarding FcγRIII binding, reduced binding to FcγRIIIA is found, e.g., for mutation of at least one of E233-G236, P238, D265, $N_{297}$, A327, P329, D270, Q295, A327, S239, E269, E293, Y296, V303, A327, K338, and D376.

Mapping of the binding sites on human IgG1 for Fc receptors, the above mentioned mutation sites, and methods for measuring binding to FcγRI and FcγRIIA, are described in Shields, R. L., et al. (J. Biol. Chem. 276:6591-6604 (2001)).

Regarding binding to FcγRII, two regions of native IgG Fc appear to be involved in interactions between FcγRIIs and IgGs, namely (i) the lower hinge site of IgG Fc, in particular amino acid residues L, L, G, and G (234-237, EU numbering), and (ii) the adjacent region of the CH2 domain of IgG Fc, in particular a loop and strands in the upper CH2 domain adjacent to the lower hinge region, e.g., in a region of P331 (Wines, B. D., et al., J. Immunol. 164:5313-8 (2000)). Moreover, FcγRI appears to bind to the same site on IgG Fc, whereas FcRn and Protein A bind to a different site on IgG Fc, which appears to be at the CH2-CH3 interface (Wines, B. D., et al., 2000, supra).

Also contemplated are mutations that increase binding affinity of an Fc moiety of the present disclosure to a (i.e., one or more) Fcγ receptor (e.g., as compared to a reference Fc moiety or antibody that does not comprise the mutation(s)). See, e.g., Delillo and Ravetch, Cell 161(5): 1035-45 (2015) and Ahmed et al., J. Struc. Biol. 194(1):78 (2016), the Fc mutations and techniques of which are incorporated herein by reference. In any of the herein disclosed embodiments, a binding protein can comprise a Fc moiety comprising a mutation selected from G236A; S239D; A330L; and I332E; or a combination comprising the same; e.g., S239D/I332E; S239D/A330L/I332E; G236A/S239D/I332E; G236A/A330L/I332E; and G236A/S239D/A330L/I332E.

In certain embodiments, the Fc moiety may comprise or consist of at least a portion of an Fc moiety that is involved in binding to FcRn binding. In certain embodiments, the Fc moiety comprises one or more amino acid modifications that improve binding affinity for FcRn and, in some embodiments, thereby extend in vivo half-life of a molecule comprising the Fc moiety (e.g., as compared to a reference Fc moiety or antibody that does not comprise the modification(s)). In certain embodiments, Fc moiety comprises or is derived from a IgG Fc and a half-life-extending mutation comprises any one or more of: M428L; N434S; N434H; N434A; N434S; M252Y; S254T; T256E; T250Q; P257I; Q311I; D376V; T307A; and E380A (EU numbering). In certain embodiments, a half-life-extending mutation comprises M428L/N434S. In certain embodiments, a half-life-extending mutation comprises M252Y/S254T/T256E. In certain embodiments, a half-life-extending mutation comprises T250Q/M428L. In certain embodiments, a half-life-extending mutation comprises P257I/Q311I. In certain embodiments, a half-life-extending mutation comprises P257I/N434H. In certain embodiments, a half-life-extending mutation comprises D376V/N434H. In certain embodiments, a half-life-extending mutation comprises T307A/E380A/N434A.

In particular embodiments, a binding protein includes an Fc moiety that comprises the substitution mutations: M428L/N434S and G236A/A330L/I332E. In certain embodiments, an antibody or antigen binding fragment includes a Fc moiety that comprises the substitution mutations: M428L/N434S and G236A/S239D/A330L/I332E.

In particular embodiments, a binding protein includes an Fc moiety that comprises the substitution mutations: G236A/A330L/I332E. In certain embodiments, an antibody or antigen binding fragment includes a Fc moiety that comprises the substitution mutations: G236A/S239D/A330L/I332E.

Alternatively or additionally, the Fc moiety of a binding protein of the disclosure can comprise at least a portion known in the art to be required for Protein A binding; and/or the Fc moiety of an antibody of the disclosure comprises at least the portion of an Fc molecule known in the art to be required for protein G binding. In some embodiments, a retained function comprises the clearance of HBsAg and HBVg. Accordingly, in certain embodiments, an Fc moiety comprises at least a portion known in the art to be required for FcγR binding. As outlined above, an Fc moiety may thus at least comprise (i) the lower hinge site of native IgG Fc, in particular amino acid residues L, L, G, and G (234-237, EU numbering), and (ii) the adjacent region of the CH2 domain of native IgG Fc, in particular a loop and strands in the upper CH2 domain adjacent to the lower hinge region, e.g., in a region of P331, for example a region of at least 3, 4, 5, 6, 7, 8, 9, or 10 consecutive amino acids in the upper CH2 domain of native IgG Fc around P331, e.g., between amino acids 320 and 340 (EU numbering) of native IgG Fc.

In some embodiments, a binding protein according to the present disclosure comprises an Fc region. As used herein, the term "Fc region" refers to the portion of an immunoglobulin formed by two or more Fc moieties of antibody heavy chains. For example, an Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2, and are incorporated herein by reference. The Fc region can be or comprise a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties (e.g., one Fc monomer of the dimeric Fc region comprises at least one amino acid modification (e.g., substitution, deletion, insertion, or chemical modification) that is not present in the other Fc monomer, or one Fc monomer may be truncated as compared to the other).

Presently disclosed Fc moieties may comprise Fc sequences or regions of the same or different class and/or subclass. For example, Fc moieties may be derived from an immunoglobulin (e.g., a human immunoglobulin) of an IgG1, IgG2, IgG3, or IgG4 subclass, or from any combination thereof. In certain embodiments, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. In certain embodiments, a dimeric Fc region can comprise sequences from two or more different isotypes or subclasses; e.g., a SEEDbody ("strand-exchange engineered domains") (see Davis, et al., Protein Eng. Des. Sel. 23(4):195 (2010)).

Additionally or alternatively, chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2, or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2, or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or moiety may (additionally or alternatively) for example comprise a chimeric hinge region. For example, the chimeric hinge may be derived, e.g., in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In some other embodiments, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKY-GPPCPPCPAPPVAGP (SEQ ID NO:105)). Further chimeric hinges, which may be used in the Fc moiety of an antibody according to the present disclosure, are described in US 2005/0163783 A1.

In some embodiments, an Fc moiety or Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

c. HBC34 and HBC24 Antibodies

In certain embodiments, the anti-HBV antibody is HBC34 or an engineered variant thereof, or is HBC24 or an engineered variant thereof. HBC34 and HBC24 are human antibodies against HBsAg with high neutralizing activity. HBC34 binds to the antigenic loop of THBsAg with high affinity (in the pM range), recognizes all 10 HBV genotypes and 18 mutants, and binds to spherical SVPs with low stoichiometry. The activity of HBC34, as measured diagnostically with an immunoassay, is 5000 IU/mg. As a comparison, the activity of HBIG is ~1 IU/mg.

As referred to herein, the terms "an HBC34 antibody" and "HBC antibodies" can include the wild-type HBC34 antibody or an engineered variant thereof (e.g., HBC34 and HBC34 variants described in Table 3), unless stated otherwise.

Table 3 shows the amino acid sequences of the CDRs, heavy chain variable regions ($V_H$), and light chain variable regions($V_L$) of HBC34 and engineered variants thereof ("HBC34v7," HBC34v23," "HBC34v31," "HBC34v32," "HBC34v33," "HBC34v34," and "HBC34v35"), as well as of "HBC24". Also shown are full-length heavy chain (HC) and light chain (LC) amino acid sequences of exemplary antibodies of the present disclosure.

TABLE 3

Sequences for HBC34 and HBC24 antibodies.

| Antibodies | Antibody Region | Amino Acid Sequence | SEQ ID NO |
|---|---|---|---|
| HBC34, HBC34v7, HBC34v23, HBC34v31, | CDRH1 | GRIFRSFY | 44 |

TABLE 3-continued

Sequences for HBC34 and HBC24 antibodies.

| Antibodies | Antibody Region | Amino Acid Sequence | SEQ ID NO |
|---|---|---|---|
| HBC34v32, HBC34v33, HBC34v34, HBC34v35, HBC34_LC40S, HBC34_LC40A, HBC34v23_LC40S, HBC34v23_LC40A, HBC34v31_LC40S, HBC34v31_LC40A, HBC34v32_LC40S, HBC34v32_LC40A, HBC34v33_LC40S, HBC34v33_LC40A | | | |
| HBC34, HBC34v7, HBC34v23, HBC34v31, HBC34v32, HBC34v33, HBC34v34, HBC34v35, HBC34_LC40S, HBC34_LC40A, HBC34v23_LC40S, HBC34v23_LC40A, HBC34v31_LC40S, HBC34v31_LC40A, HBC34v32_LC40S, HBC34v32_LC40A, HBC34v33_LC40S, HBC34v33_LC40A | (short) CDRH2 | NQDGSEK | 45 |
| HBC34, HBC34v7, HBC34v23, HBC34v31, HBC34v32, HBC34v33, HBC34v34, HBC34v35, HBC34_LC40S, HBC34_LC40A, HBC34v23_LC40S, HBC34v23_LC40A, HBC34v31_LC40S, HBC34v31_LC40A, HBC34v32_LC40S, HBC34v32_LC40A, HBC34v33_LC40S, HBC34v33_LC40A | (long) CDRH2 | INQDGSEK | 46 |
| HBC34, HBC34v7, HBC34v23, HBC34v31, HBC34v32, HBC34v33, HBC34v34, HBC34v35, HBC34_LC40S, HBC34_LC40A, HBC34v23_LC40S, HBC34v23_LC40A, HBC34v31_LC40S, HBC34v31_LC40A, HBC34v32_LC40S, HBC34v32_LC40A, HBC34v33_LC40S, HBC34v33_LC40A | CDRH3 | AAWSGNSGGMDV | 47 |

TABLE 3-continued

Sequences for HBC34 and HBC24 antibodies.

| Antibodies | Antibody Region | Amino Acid Sequence | SEQ ID NO |
|---|---|---|---|
| HBC34,<br>HBC34v7,<br>HBC34v23,<br>HBC34v31,<br>HBC34v32,<br>HBC34v33,<br>HBC34v34,<br>HBC34v35,<br>HBC34_LC40S,<br>HBC34_LC40A,<br>HBC34v23_LC40S,<br>HBC34v23_LC40A,<br>HBC34v31_LC40S,<br>HBC34v31_LC40A,<br>HBC34v32_LC40S,<br>HBC34v32_LC40A,<br>HBC34v33_LC40S,<br>HBC34v33_LC40A | CDRL1 | KLGNKN | 48 |
| HBC34,<br>HBC34v7,<br>HBC34v23,<br>HBC34v31,<br>HBC34v32,<br>HBC34v33,<br>HBC34v34,<br>HBC34v35,<br>HBC34_LC40S,<br>HBC34_LC40A,<br>HBC34-v23_LC40S,<br>HBC34-v23_LC40A,<br>HBC34-v31_LC40S,<br>HBC34-v31_LC40A,<br>HBC34-v32_LC40S,<br>HBC34-v32_LC40A,<br>HBC34-v33_LC40S,<br>HBC34-v33_LC40A | (short) CDRL2 | EVK | 49 |
| HBC34,<br>HBC34v7,<br>HBC34v23,<br>HBC34v31,<br>HBC34v32,<br>HBC34v33,<br>HBC34v34,<br>HBC34v35,<br>HBC34_LC40S,<br>HBC34_LC40A,<br>HBC34-v23_LC40S,<br>HBC34-v23_LC40A,<br>HBC34-v31_LC40S,<br>HBC34-v31_LC40A,<br>HBC34-v32_LC40S,<br>HBC34-v32_LC40A,<br>HBC34-v33_LC40S,<br>HBC34-v33_LC40A | (long) CDRL2 | VIYEVKYRP | 50 |
| HCB34,<br>HBC34v31,<br>HBC34_LC40S,<br>HBC34_LC40A,<br>HBC34-v31_LC40S,<br>HBC34-v31_LC40A | CDRL3 | QTWDSTTVV | 51 |
| HBC34v7,<br>HBC34v23,<br>HBC34v32,<br>HBC34v33,<br>HBC34v34,<br>HBC34v35,<br>HBC34v23_C40S,<br>HBC34v23_C40A,<br>HBC34v32_C40S,<br>HBC34v32_C40A, | CDRL3 | QTFDSTTVV | 52 |

TABLE 3-continued

Sequences for HBC34 and HBC24 antibodies.

| Antibodies | Antibody Region | Amino Acid Sequence | SEQ ID NO |
|---|---|---|---|
| HBC34v33_C40S, HBC34v33_C40A | | | |
| HBC34, HBC34v7, HBC34v23, HBC34v34, HBC34v35, HBC34_C40S, HBC34_C40A, HBC34v23_C40S, HBC34v23_C40A | $V_H$ | ELQLVESGGGWVQP GGSQRLSCAASGRIF RSFYMSWVRQAPGK GLEWVATINQDGSE KLYVDSVKGRFTISR DNAKNSLFLQMNNL RVEDTAVYYCAAWS GNSGGMDVWGQGT TVSVSS | 53 |
| HBC34v31, HBC34v32, HBC34v33, HBC34v31_LC40A, HBC34v31_LC40S, HBC34v32_LC40A, HBC34v32_LC40S, HBC34v33_LC40A, HBC34v32_LC40S | $V_H$ | EVQLVESGGGLVQP GGSLRLSCAASGRIF RSFYMSWVRQAPGK GLEWVANINQDGSE KLYVDSVKGRFTISR DNAKNSLFLQMNNL RVEDTAVYYCAAWS GNSGGMDVWGQGT TVTVSS | 54 |
| HBC34, HBC34v31 | $V_L$ | SYELTQPPSVSVSPG QTVSIPCSGDKLGNK NVCWFQHKPGQSPV LVIYEVKYRPSGIPER FSGSNSGNTATLTISG TQAMDEAAYFCQT WDSTTVVFGGGTRL TVL | 55 |
| HBC34v7, HBC34v32 | $V_L$ | SYELTQPPSVSVSPG QTVSIPCSGDKLGNK NVCWFQHKPGQSPV LVIYEVKYRPSGIPER FSGSNSGNTATLTISG TQAMDEAAYFCQTF DSTTVVFGGGTRLTV L | 56 |
| HBC34v23, HBC34v33 | $V_L$ | SYELTQPPSVSVSPG QTASITCSGDKLGNK NACWYQQKPGQSPV LVIYEVKYRPSGIPER FSGSNSGNTATLTISG TQAMDEADYYCQTF DSTTVVFGGGTKLT VL | 57 |
| HBC34v34 | $V_L$ | SYELTQPPSVSVSPG QTVSIPCSGDKLGNK NVSWFQHKPGQSPV LVIYEVKYRPSGIPER FSGSNSGNTATLTISG TQAMDEAAYFCQTF DSTTVVFGGGTRLTV L | 58 |
| HBC34v35 | $V_L$ | SYELTQPPSVSVSPG QTVSIPCSGDKLGNK NVAWFQHKPGQSPV LVIYEVKYRPSGIPER FSGSNSGNTATLTISG TQAMDEAAYFCQTF DSTTVVFGGGTRLTV L | 59 |
| HBC34_LC40S | $V_L$ | SYELTQPPSVSVSPG QTVSIPCSGDKLGNK NVSWFQHKPGQSPV LVIYEVKYRPSGIPER | 60 |

TABLE 3-continued

Sequences for HBC34 and HBC24 antibodies.

| Antibodies | Antibody Region | Amino Acid Sequence | SEQ ID NO |
|---|---|---|---|
| | | FSGSNSGNTATLTISG TQAMDEAAYFCQT WDSTTVVFGGGTRL TVL | |
| HBC34_LC40A | V_L | SYELTQPPSVSVSPG QTVSIPCSGDKLGNK NVAWFQHKPGQSPV LVIYEVKYRPSGIPER FSGSNSGNTATLTISG TQAMDEAAYFCQT WDSTTVVFGGGTRL TVL | 61 |
| HBC34v23_LC40S | V_L | SYELTQPPSVSVSPG QTASITCSGDKLGNK NASWYQQKPGQSPV LVIYEVKYRPSGIPER FSGSNSGNTATLTISG TQAMDEADYYCQTF DSTTVVFGGGTKLT VL | 62 |
| HBC34v23_LC40A | V_L | SYELTQPPSVSVSPG QTASITCSGDKLGNK NAAWYQQKPGQSPV LVIYEVKYRPSGIPER FSGSNSGNTATLTISG TQAMDEADYYCQTF DSTTVVFGGGTKLT VL | 63 |
| HBC34v31_LC40S | V_L | SYELTQPPSVSVSPG QTVSIPCSGDKLGNK NVSWFQHKPGQSPV LVIYEVKYRPSGIPER FSGSNSGNTATLTISG TQAMDEAAYFCQT WDSTTVVFGGGTRL TVL | 64 |
| HBC34v31_LC40A | V_L | SYELTQPPSVSVSPG QTVSIPCSGDKLGNK NVAWFQHKPGQSPV LVIYEVKYRPSGIPER FSGSNSGNTATLTISG TQAMDEAAYFCQT WDSTTVVFGGGTRL TVL | 65 |
| HBC34v32_LC40S | V_L | SYELTQPPSVSVSPG QTVSIPCSGDKLGNK NVSWFQHKPGQSPV LVIYEVKYRPSGIPER FSGSNSGNTATLTISG TQAMDEAAYFCQTF DSTTVVFGGGTRLTV L | 66 |
| HBC34v32_LC40A | V_L | SYELTQPPSVSVSPG QTVSIPCSGDKLGNK NVAWFQHKPGQSPV LVIYEVKYRPSGIPER FSGSNSGNTATLTISG TQAMDEAAYFCQTF DSTTVVFGGGTRLTV L | 67 |
| HBC34v33_LC40S | V_L | SYELTQPPSVSVSPG QTASITCSGDKLGNK NASWYQQKPGQSPV LVIYEVKYRPSGIPER | 68 |

TABLE 3-continued

Sequences for HBC34 and HBC24 antibodies.

| Antibodies | Antibody Region | Amino Acid Sequence | SEQ ID NO |
|---|---|---|---|
| | | FSGSNSGNTATLTISG TQAMDEADYYCQTF DSTTVVFGGGTKLT VL | |
| HBC34v33_LC40A | V<sub>L</sub> | SYELTQPPSVSVSPG QTASITCSGDKLGNK NAAWYQQKPGQSPV LVIYEVKYRPSGIPER FSGSNSGNTATLTISG TQAMDEADYYCQTF DSTTVVFGGGTKLT VL | 69 |
| HBC34v34, HBC34v35, HBC34, HBC34v7, HBC34v23, HBC34_LC40S, HBC34_LC40A, HBC34v23_LC40S, HBC34v23_LC40A | HC | ELQLVESGGGWVQP GGSQRLSCAASGRIF RSFYMSWVRQAPGK GLEWVATINQDGSE KLYVDSVKGRFTISR DNAKNSLFLQMNNL RVEDTAVYYCAAWS GNSGGMDVWGQGT TVSVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKV EPKSCDKTHTCPPCP APELLGGPSVFLFPP KPKDTLMISRTPEVT CVVVDVSHEDPEVK FNWYVDGVEVHNA KTKPREEQYNSTYR VVSVLTVLHQDWLN GKEYKCKVSNKALP APIEKTISKAKGQPRE PQVYTLPPSRDELTK NQVSLTCLVKGFYPS DIAVEWESNGQPEN NYKTTPPVLDSDGSF FLYSKLTVDKSRWQ QGNVFSCSVMHEAL HNHYTQKSLSLSPGK | 70 |
| HBC34v34-MLNS-GAALIE, HBC34v35-MLNS-GAALIE_(g1M17, 1) | HC | ELQLVESGGGWVQP GGSQRLSCAASGRIF RSFYMSWVRQAPGK GLEWVATINQDGSE KLYVDSVKGRFTISR DNAKNSLFLQMNNL RVEDTAVYYCAAWS GNSGGMDVWGQGT TVSVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKV EPKSCDKTHTCPPCP APELLAGPSVFLFPP KPKDTLMISRTPEVT CVVVDVSHEDPEVK FNWYVDGVEVHNA KTKPREEQYNSTYR VVSVLTVLHQDWLN GKEYKCKVSNKALP LPEEKTISKAKGQPR EPQVYTLPPSRDELT KNQVSLTCLVKGFY PSDIAVEWESNGQPE NNYKTTPPVLDSDGS | 71 |

TABLE 3-continued

Sequences for HBC34 and HBC24 antibodies.

| Antibodies | Antibody Region | Amino Acid Sequence | SEQ ID NO |
|---|---|---|---|
| | | FFLYSKLTVDKSRW QQGNVFSCSVLHEA LHSHYTQKSLSLSPG K | |
| HBC34v34-MLNS, HBC34v35-MLNS | HC | ELQLVESGGGWVQP GGSQRLSCAASGRIF RSFYMSWVRQAPGK GLEWVATINQDGSE KLYVDSVKGRFTISR DNAKNSLFLQMNNL RVEDTAVYYCAAWS GNSGGMDVWGQGT TVSVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKV EPKSCDKTHTCPPCP APELLGGPSVFLFPP KPKDTLMISRTPEVT CVVVDVSHEDPEVK FNWYVDGVEVHNA KTKPREEQYNSTYR VVSVLTVLHQDWLN GKEYKCKVSNKALP APIEKTISKAKGQPRE PQVYTLPPSRDELTK NQVSLTCLVKGFYPS DIAVEWESNGQPEN NYKTTPPVLDSDGSF FLYSKLTVDKSRWQ QGNVFSCSVLHEAL HSHYTQKSLSLSPGK | 72 |
| HBC34v35, HBC34v35-MLNS, HBC34v35-MLNS-GAALIE | LC | SYELTQPPSVSVSPG QTVSIPCSGDKLGNK NVAWFQHKPGQSPV LVIYEVKYRPSGIPER FSGSNSGNTATLTISG TQAMDEAAYFCQTF DSTTVVFGGGTRLTV LGQPKAAPSVTLFPP SSEELQANKATLVCL ISDFYPGAVTVAWK ADSSPVKAGVETTTP SKQSNNKYAASSYLS LTPEQWKSHRSYSC QVTHEGSTVEKTVA PTECS | 73 |
| HBC34v34, HBC34v34-MLNS, HBC34v34-MLNS-GAALIE | LC | SYELTQPPSVSVSPG QTVSIPCSGDKLGNK NVSWFQHKPGQSPV LVIYEVKYRPSGIPER FSGSNSGNTATLTISG TQAMDEAAYFCQTF DSTTVVFGGGTRLTV LGQPKAAPSVTLFPP SSEELQANKATLVCL ISDFYPGAVTVAWK ADSSPVKAGVETTTP SKQSNNKYAASSYLS LTPEQWKSHRSYSC QVTHEGSTVEKTVA PTECS | 74 |
| HBC24 | $V_H$ | EVQLLESGGGLVQP GGSLRLSCAASGSTF TKYAMSWVRQAPG KGLEWVASISGSVPG FGIDTYYADSVKGRF | 75 |

TABLE 3-continued

Sequences for HBC34 and HBC24 antibodies.

| Antibodies | Antibody Region | Amino Acid Sequence | SEQ ID NO |
|---|---|---|---|
| | | TISRDTSKNTLYLQM NSLRAEDTALYYCA KDVGVIGSYYYYAM DVWGQGTAVTVSS | |
| HBC24 | $V_L$ | EIVLTQSPGTLSLSPG ERATLSCRASQGLSS SYLAWYQQKPGQAP RLLIYSASTRATGIPD RFSGSGSGTDFTLTIS RLEPEDFAVYYCQQ YAYSPRWTFGQGTK VEIK | 76 |
| HBC24 | CDRH1 | GSTFTKYA | 77 |
| HBC24 | CDRH2 | ISGSVPGF | 78 |
| HBC24 | CDRH3 | LYYCAKDVGVIGSY YYYAMDV | 79 |
| HBC24 | CDRL1 | QGLSSSY | 80 |
| HBC24 | CDRL2 | SAS | 81 |
| HBC24 | CDRL3 | QQYAYSPRWT | 82 |
| HBC34, HBC34v31 | LC | SYELTQPPSVSVSPG QTVSIPCSGDKLGNK NVCWFQHKPGQSPV LVIYEVKYRPSGIPER FSGSNSGNTATLTISG TQAMDEAAYFCQT WDSTTVVFGGGTRL TVL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 83 |
| HBC34v7, HBC34v32 | LC | SYELTQPPSVSVSPG QTVSIPCSGDKLGNK NVCWFQHKPGQSPV LVIYEVKYRPSGIPER FSGSNSGNTATLTISG TQAMDEAAYFCQTF DSTTVVFGGGTRLTV L GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 84 |
| HBC34v23, HBC34v33 | LC | SYELTQPPSVSVSPG QTASITCSGDKLGNK NACWYQQKPGQSPV LVIYEVKYRPSGIPER FSGSNSGNTATLTISG TQAMDEADYYCQTF DSTTVVFGGGTKLT VL GQPKAAPSVTLFPPS SEELQANKATLVCLI SDFYPGAVTVAWKA DSSPVKAGVETTTPS KQSNNKYAASSYLS | 85 |

TABLE 3-continued

Sequences for HBC34 and HBC24 antibodies.

| Antibodies | Antibody Region | Amino Acid Sequence | SEQ ID NO |
|---|---|---|---|
| | | LTPEQWKSHRSYSC QVTHEGSTVEKTVA PTECS | |
| HBC34_LC40S | LC | SYELTQPPSVSVSPG QTVSIPCSGDKLGNK NVSWFQHKPGQSPV LVIYEVKYRPSGIPER FSGSNSGNTATLTISG TQAMDEAAYFCQT WDSTTVVFGGGTRL TVL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 86 |
| HBC34_LC40A | LC | SYELTQPPSVSVSPG QTVSIPCSGDKLGNK NVAWFQHKPGQSPV LVIYEVKYRPSGIPER FSGSNSGNTATLTISG TQAMDEAAYFCQT WDSTTVVFGGGTRL TVL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 87 |
| HBC34v23_LC40S | LC | SYELTQPPSVSVSPG QTASITCSGDKLGNK NASWYQQKPGQSPV LVIYEVKYRPSGIPER FSGSNSGNTATLTISG TQAMDEADYYCQTF DSTTVVFGGGTKLT VL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 88 |
| HBC34v23_LC40A | LC | SYELTQPPSVSVSPG QTASITCSGDKLGNK NAAWYQQKPGQSPV LVIYEVKYRPSGIPER FSGSNSGNTATLTISG TQAMDEADYYCQTF DSTTVVFGGGTKLT VL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 89 |

TABLE 3-continued

Sequences for HBC34 and HBC24 antibodies.

| Antibodies | Antibody Region | Amino Acid Sequence | SEQ ID NO |
|---|---|---|---|
| HBC34v31_LC40S | LC | SYELTQPPSVSVSPG QTVSIPCSGDKLGNK NVSWFQHKPGQSPV LVIYEVKYRPSGIPER FSGSNSGNTATLTISG TQAMDEAAYFCQT WDSTTVVFGGGTRL TVL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 90 |
| HBC34v31_LC40A | LC | SYELTQPPSVSVSPG QTVSIPCSGDKLGNK NVAWFQHKPGQSPV LVIYEVKYRPSGIPER FSGSNSGNTATLTISG TQAMDEAAYFCQT WDSTTVVFGGGTRL TVL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 91 |
| HBC34v32_LC40S | LC | SYELTQPPSVSVSPG QTVSIPCSGDKLGNK NVSWFQHKPGQSPV LVIYEVKYRPSGIPER FSGSNSGNTATLTISG TQAMDEAAYFCQTF DSTTVVFGGGTRLTV L GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 92 |
| HBC34v32_LC40A | LC | SYELTQPPSVSVSPG QTVSIPCSGDKLGNK NVAWFQHKPGQSPV LVIYEVKYRPSGIPER FSGSNSGNTATLTISG TQAMDEAAYFCQTF DSTTVVFGGGTRLTV L GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 93 |
| HBC34v33_LC40S | LC | SYELTQPPSVSVSPG QTASITCSGDKLGNK NASWYQQKPGQSPV LVIYEVKYRPSGIPER FSGSNSGNTATLTISG TQAMDEADYYCQTF | 94 |

TABLE 3-continued

Sequences for HBC34 and HBC24 antibodies.

| Antibodies | Antibody Region | Amino Acid Sequence | SEQ ID NO |
|---|---|---|---|
| | | DSTTVVFGGGTKLT VL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | |
| HBC34v33_LC40A | LC | SYELTQPPSVSVSPG QTASITCSGDKLGNK NAAWYQQKPGQSPV LVIYEVKYRPSGIPER FSGSNSGNTATLTISG TQAMDEADYYCQTF DSTTVVFGGGTKLT VL GQPKAAPSVTLFPPS SEELQANKATLVCLI SDFYPGAVTVAWKA DSSPVKAGVETTTPS KQSNNKYAASSYLS LTPEQWKSHRSYSC QVTHEGSTVEKTVA PTECS | 95 |
| WT hIgG1 Fc | Fc | APELLGGPSVFLFPP KPKDTLMISRTPEVT CVVVDVSHEDPEVK FNWYVDGVEVHNA KTKPREEQYNSTYR VVSVLTVLHQDWLN GKEYKCKVSNKALP APIEKTISKAKGQPRE PQVYTLPPSRDELTK NQVSLTCLVKGFYPS DIAVEWESNGQPEN NYKTTPPVLDSDGSF FLYSKLTVDKSRWQ QGNVFSCSVMHEAL HNHYTQKSLSLSPGK | 96 |
| HBC34, HBC34v7, HBC34v23, HBC34v34, HBC34v35, HBC34_C40S, HBC34_C40A, HBC34v23_C40S, HBC34v23_C40A HC with GAALIE mutation in hIgG1 Fc | HC | ELQLVESGGGWVQP GGSQRLSCAASGRIF RSFYMSWVRQAPGK GLEWVATINQDGSE KLYVDSVKGRFTISR DNAKNSLFLQMNNL RVEDTAVYYCAAWS GNSGGMDVWGQGT TVSVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKV EPKSCDKTHTCPPCP APELLAGPSVFLFPP KPKDTLMISRTPEVT CVVVDVSHEDPEVK FNWYVDGVEVHNA KTKPREEQYNSTYR VVSVLTVLHQDWLN GKEYKCKVSNKALP LPEEKTISKAKGQPR EPQVYTLPPSRDELT KNQVSLTCLVKGFY PSDIAVEWESNGQPE NNYKTTPPVLDSDGS FFLYSKLTVDKSRW | 97 |

TABLE 3-continued

Sequences for HBC34 and HBC24 antibodies.

| Antibodies | Antibody Region | Amino Acid Sequence | SEQ ID NO |
|---|---|---|---|
| | | QQGNVFSCSVMHEA LHNHYTQKSLSLSPG K | |
| HBC34v31, HBC34v32, HBC34v33, HBC34v31_LC40A, HBC34v31_LC40S, HBC34v32_LC40A, HBC34v32_LC40S, HBC34v33_LC40A, HBC34v32_LC40S HC with GAALIE mutation in hIgG1 Fc | HC | EVQLVESGGGLVQP GGSLRLSCAASGRIF RSFYMSWVRQAPGK GLEWVANINQDGSE KLYVDSVKGRFTISR DNAKNSLFLQMNNL RVEDTAVYYCAAWS GNSGGMDVWGQGT TVTVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKV EPKSCDKTHTCPPCP APELLAGPSVFLFPP KPKDTLMISRTPEVT CVVVDVSHEDPEVK FNWYVDGVEVHNA KTKPREEQYNSTYR VVSVLTVLHQDWLN GKEYKCKVSNKALP LPEEKTISKAKGQPR EPQVYTLPPSRDELT KNQVSLTCLVKGFY PSDIAVEWESNGQPE NNYKTTPPVLDSDGS FFLYSKLTVDKSRW QQGNVFSCSVMHEA LHNHYTQKSLSLSPG K | 98 |

In certain embodiments, an antibody of the present disclosure is HBC34, or a non-natural variant of an HBC34 antibody. Examples of non-natural variants of HBC34 include, for example, "HBC34v7," "HBC34v23," "HBC34v31," "HBC34v32," "HBC34v33," "HBC34v34," and "HBC34v35."

In certain embodiments, the anti-HBV antibody comprises one or more amino acid sequences as set forth in Table 3. In certain embodiments, the antibody, or the antigen-binding fragment thereof, according to the present disclosure comprises an amino acid sequence having at least 70%, at least 75%, at least 80%, at least 85%, at least 88%, at least 90%, at least 92%, at least 95%, at least 96%, at least 97%, at least 98%, or at least 99% identity to a CDR sequence, a $V_H$ sequence, a $V_L$ sequence, an HC sequence, and/or an LC sequence as shown in Table 3. In any of the presently disclosed embodiments, an antibody or antigen-binding fragment can comprise a CDR, $V_H$, $V_L$, HC, and/or LC sequence as set forth in Table 3.

In some embodiments, an antibody or antigen-binding fragment of the present disclosure comprises: (i) CDRH1, CDRH2, and CDRH3 amino acid sequences according to SEQ ID NOs:44, 45 or 46, and 47, respectively; and (ii) CDRL1, CDRL2, and CDRL3 amino acid sequences according to SEQ ID NOs:48, 49 or 50, and 51 or 52, respectively.

Accordingly, in some embodiments, CDRH1, CDRH2, and CDRH3 are according to SEQ ID NOs:44, 45, and 47, respectively. In some embodiments, CDRH1, CDRH2, and CDRH3 are according to SEQ ID NOs:44, 46, and 47, respectively. In some embodiments, CDRL1, CDRL2, and CDRL3 are according to SEQ ID NOs:48, 49, and 51, respectively. In some embodiments, CDRL1, CDRL2, and CDRL3 are according to SEQ ID NOs:48, 49, and 52, respectively. In some embodiments, CDRL1, CDRL2, and CDRL3 are according to SEQ ID NOs:48, 50, and 51, respectively. In some embodiments, CDRL1, CDRL2, and CDRL3 are according to SEQ ID NOs:48, 50, and 52, respectively.

It will be understood that an antibody or antigen-binding fragment of the present disclosure can comprise any combination of the CDRH1, CDRH2, CDRH3, CDRL1, CDRL2, and CDRL3 amino acid sequences according to SEQ ID NOs:44-52.

In particular embodiments, an antibody or antigen-binding fragment of the present disclosure, comprises: CDRH1, CDRH2, and CDRH3 amino acid sequences according to SEQ ID NOs:44, 45, and 47, respectively; and CDRL1, CDRL2, and CDRL3 amino acid sequences according to SEQ ID NOs:48, 49, and 51, respectively. In other embodiments, an antibody or antigen-binding fragment of the present disclosure comprises: CDRH1, CDRH2, and CDRH3 amino acid sequences according to SEQ ID NOs: 44, 45, and 47, respectively; and CDRL1, CDRL2, and CDRL3 amino acid sequences according to SEQ ID NOs: 48, 49, and 52, respectively.

In certain embodiments, an antibody or antigen-binding fragment of the present disclosure comprises: (a) a light chain variable domain (V$_L$) comprising or consisting of an amino acid sequence that is at least 90%, at least 95%, or 100% identical to the amino acid sequence set forth in any one of SEQ ID NOs:55-69; and (b) a heavy chain variable domain (V$_H$) comprising or consisting of an amino acid sequence that is at least 90%, at least 95%, or 100% identical to the amino acid sequence set forth in SEQ ID NO:53 or 54.

In certain embodiments, an antibody or antigen-binding fragment of the present disclosure comprises:
(a) a light chain variable domain (V$_L$) comprising or consisting of an amino acid sequence that is at least 90%, at least 95%, or 100% identical to the amino acid sequence set forth in any one of SEQ ID NOs:55-63; and (b) a heavy chain variable domain (V$_H$) comprising or consisting of an amino acid sequence that is at least 90%, at least 95%, or 100% identical to the amino acid sequence set forth in SEQ ID NO:53.

In certain embodiments, an antibody or antigen-binding fragment of the present disclosure comprises:
(a) a light chain variable domain (V$_L$) comprising or consisting of an amino acid sequence that is at least 90%, at least 95%, or 100% identical to the amino acid sequence as set forth in any one of SEQ ID NOs:55-57 or 64-69; and (b) a heavy chain variable domain (V$_H$) comprising or consisting of an amino acid sequence that is at least 90%, at least 95%, or 100% identical to the amino acid sequence set forth in SEQ ID NO:54.

In certain embodiments, an antibody or antigen-binding fragment of the present disclosure comprises:
(i) (a) a light chain variable domain (V$_L$) comprising or consisting of an amino acid sequence that is at least 90%, at least 95%, or 100% identical to the amino acid sequence set forth in SEQ ID NO:55, and (b) a heavy chain variable domain (V$_H$) comprising or consisting of an amino acid sequence that is at least 90%, at least 95%, or 100% identical to the amino acid sequence set forth in SEQ ID NO:53;
(ii) (a) a light chain variable domain (V$_L$) comprising or consisting of an amino acid sequence that is at least 90%, at least 95%, or 100% identical to the amino acid sequence set forth in SEQ ID NO:55, and (b) a heavy chain variable domain (V$_H$) comprising or consisting of an amino acid sequence that is at least 90%, at least 95%, or 100% identical to the amino acid sequence set forth in SEQ ID NO:54;
(iii) (a) a light chain variable domain (V$_L$) comprising or consisting of an amino acid sequence that is at least 90%, at least 95%, or 100% identical to the amino acid sequence set forth in SEQ ID NO:56, and (b) a heavy chain variable domain (V$_H$) comprising or consisting of an amino acid sequence that is at least 90%, at least 95%, or 100% identical to the amino acid sequence set forth in SEQ ID NO:53;
(iv) (a) a light chain variable domain (V$_L$) comprising or consisting of an amino acid sequence that is at least 90%, at least 95%, or 100% identical to the amino acid sequence set forth in SEQ ID NO:56, and (b) a heavy chain variable domain (V$_H$) comprising or consisting of an amino acid sequence that is at least 90%, at least 95%, or 100% identical to the amino acid sequence set forth in SEQ ID NO:54;
(v) (a) a light chain variable domain (V$_L$) comprising or consisting of an amino acid sequence that is at least 90%, at least 95%, or 100% identical to the amino acid sequence set forth in SEQ ID NO:57, and (b) a heavy chain variable domain (V$_H$) comprising or consisting of an amino acid sequence that is at least 90%, at least 95%, or 100% identical to the amino acid sequence set forth in SEQ ID NO:53;
(vi) (a) a light chain variable domain (V$_L$) comprising or consisting of an amino acid sequence that is at least 90%, at least 95%, or 100% identical to the amino acid sequence set forth in SEQ ID NO:57, and (b) a heavy chain variable domain (V$_H$) comprising or consisting of an amino acid sequence that is at least 90%, at least 95%, or 100% identical to the amino acid sequence set forth in SEQ ID NO:54;
(vii) (a) a light chain variable domain (V$_L$) comprising or consisting of an amino acid sequence that is at least 90%, at least 95%, or 100% identical to the amino acid sequence set forth in SEQ ID NO:58, and (b) a heavy chain variable domain (V$_H$) comprising or consisting of an amino acid sequence that is at least 90%, at least 95%, or 100% identical to the amino acid sequence set forth in SEQ ID NO:53;
(viii) (a) a light chain variable domain (V$_L$) comprising or consisting of an amino acid sequence that is at least 90%, at least 95%, or 100% identical to the amino acid sequence set forth in SEQ ID NO:59, and (b) a heavy chain variable domain (V$_H$) comprising or consisting of an amino acid sequence that is at least 90%, at least 95%, or 100% identical to the amino acid sequence set forth in SEQ ID NO:53;
(ix) (a) a light chain variable domain (V$_L$) comprising or consisting of an amino acid sequence that is at least 90%, at least 95%, or 100% identical to the amino acid sequence set forth in SEQ ID NO:60, and (b) a heavy chain variable domain (V$_H$) comprising or consisting of an amino acid sequence that is at least 90%, at least 95%, or 100% identical to the amino acid sequence set forth in SEQ ID NO:53;
(x) (a) a light chain variable domain (V$_L$) comprising or consisting of an amino acid sequence that is at least 90%, at least 95%, or 100% identical to the amino acid sequence set forth in SEQ ID NO:61, and (b) a heavy chain variable domain (V$_H$) comprising or consisting of an amino acid sequence that is at least 90%, at least 95%, or 100% identical to the amino acid sequence set forth in SEQ ID NO:53;
(xi) (a) a light chain variable domain (V$_L$) comprising or consisting of an amino acid sequence that is at least 90%, at least 95%, or 100% identical to the amino acid sequence set forth in SEQ ID NO:62, and (b) a heavy chain variable domain (V$_H$) comprising or consisting of an amino acid sequence that is at least 90%, at least 95%, or 100% identical to the amino acid sequence set forth in SEQ ID NO:53;
(xii) (a) a light chain variable domain (V$_L$) comprising or consisting of an amino acid sequence that is at least 90%, at least 95%, or 100% identical to the amino acid sequence set forth in SEQ ID NO:63, and (b) a heavy chain variable domain (V$_H$) comprising or consisting of an amino acid sequence that is at least 90%, at least 95%, or 100% identical to the amino acid sequence set forth in SEQ ID NO:53;
(xiii) (a) a light chain variable domain (V$_L$) comprising or consisting of an amino acid sequence that is at least 90%, at least 95%, or 100% identical to the amino acid sequence set forth in SEQ ID NO:64, and (b) a heavy chain variable domain (V$_H$) comprising or consisting of an amino acid sequence that is at least 90%, at least 95%, or 100% identical to the amino acid sequence set forth in SEQ ID NO:54;

(xiv) (a) a light chain variable domain (V$_L$) comprising or consisting of an amino acid sequence that is at least 90%, at least 95%, or 100% identical to the amino acid sequence set forth in SEQ ID NO:65, and (b) a heavy chain variable domain (V$_H$) comprising or consisting of an amino acid sequence that is at least 90%, at least 95%, or 100% identical to the amino acid sequence set forth in SEQ ID NO:54;

(xv) (a) a light chain variable domain (V$_L$) comprising or consisting of an amino acid sequence that is at least 90%, at least 95%, or 100% identical to the amino acid sequence set forth in SEQ ID NO:66, and (b) a heavy chain variable domain (V$_H$) comprising or consisting of an amino acid sequence that is at least 90%, at least 95%, or 100% identical to the amino acid sequence set forth in SEQ ID NO:54;

(xvi) (a) a light chain variable domain (V$_L$) comprising or consisting of an amino acid sequence that is at least 90%, at least 95%, or 100% identical to the amino acid sequence set forth in SEQ ID NO:67, and (b) a heavy chain variable domain (V$_H$) comprising or consisting of an amino acid sequence that is at least 90%, at least 95%, or 100% identical to the amino acid sequence set forth in SEQ ID NO:54;

(xvii) (a) a light chain variable domain (V$_L$) comprising or consisting of an amino acid sequence that is at least 90%, at least 95%, or 100% identical to the amino acid sequence set forth in SEQ ID NO:68, and (b) a heavy chain variable domain (V$_H$) comprising or consisting of an amino acid sequence that is at least 90%, at least 95%, or 100% identical to the amino acid sequence set forth in SEQ ID NO:54; or (xviii) (a) a light chain variable domain (V$_L$) comprising or consisting of an amino acid sequence that is at least 90%, at least 95%, or 100% identical to the amino acid sequence set forth in SEQ ID NO:69, and (b) a heavy chain variable domain (V$_H$) comprising or consisting of an amino acid sequence that is at least 90%, at least 95%, or 100% identical to the amino acid sequence set forth in SEQ ID NO:54.

In certain embodiments, an antibody or antigen-binding fragment of the present disclosure comprises:

(a) a light chain comprising or consisting of an amino acid sequence that is at least 90%, at least 95%, or 100% identical to an amino acid sequence as set forth in SEQ ID NO:73, and (b) a heavy chain comprising or consisting of an amino acid sequence that is at least 90%, at least 95%, or 100% identical to the amino acid sequence set forth in any one of SEQ ID NOs:70-72 and 97; or (a) a light chain comprising or consisting of an amino acid sequence that is at least 90%, at least 95%, or 100% identical to the amino acid sequence set forth in SEQ ID NO:74, and (b) a heavy chain comprising or consisting of an amino acid sequence that is at least 90%, at least 95%, or 100% identical to the amino acid sequence set forth in any one of SEQ ID NOs:70-72 and 97; or (a) a light chain comprising or consisting of an amino acid sequence that is at least 90%, at least 95%, or 100% identical to the amino acid sequence set forth in any one of SEQ ID NOs:83-95, and (b) a heavy chain comprising or consisting of an amino acid sequence that is at least 90%, at least 95%, or 100% identical to the amino acid sequence set forth in any one of SEQ ID NOs:70-72, 97, and 98.

In particular embodiments, an antibody or antigen-binding fragment of the present disclosure comprises (a) a light chain comprising or consisting of the amino acid sequence set forth in SEQ ID NO:73, and (b) a heavy chain comprising or consisting of the amino acid sequence set forth in SEQ ID NO:70.

In particular embodiments, an antibody or antigen-binding fragment of the present disclosure comprises (a) a light chain comprising or consisting of the amino acid sequence set forth in SEQ ID NO:73, and (b) a heavy chain comprising or consisting of the amino acid sequence set forth in SEQ ID NO:71.

In other embodiments, an antibody or antigen-binding fragment of the present disclosure comprises (a) a light chain comprising or consisting of the amino acid sequence set forth in SEQ ID NO:73, and (b) a heavy chain comprising or consisting of the amino acid sequence set forth in SEQ ID NO:72.

In other embodiments, an antibody or antigen-binding fragment of the present disclosure comprises (a) a light chain comprising or consisting of the amino acid sequence set forth in SEQ ID NO:73, and (b) a heavy chain comprising or consisting of the amino acid sequence set forth in SEQ ID NO:97.

In still other embodiments, an antibody or antigen-binding fragment of the present disclosure comprises (a) a light chain comprising or consisting of the amino acid sequence set forth in SEQ ID NO:74, and (b) a heavy chain comprising or consisting of the amino acid sequence set forth in SEQ ID NO:70.

In still other embodiments, an antibody or antigen-binding fragment of the present disclosure comprises (a) a light chain comprising or consisting of the amino acid sequence set forth in SEQ ID NO:74, and (b) a heavy chain comprising or consisting of the amino acid sequence set forth in SEQ ID NO:71.

In yet other embodiments, an antibody or antigen-binding fragment of the present disclosure comprises (a) a light chain comprising or consisting of the amino acid sequence set forth in SEQ ID NO:74, and (b) a heavy chain comprising or consisting of the amino acid sequence set forth in SEQ ID NO:72.

In still other embodiments, an antibody or antigen-binding fragment of the present disclosure comprises (a) a light chain comprising or consisting of the amino acid sequence set forth in SEQ ID NO:74, and (b) a heavy chain comprising or consisting of the amino acid sequence set forth in SEQ ID NO:97.

In certain embodiments, an antibody or antigen-binding fragment of the present disclosure comprises a CDRH1, a CDRH2, a CDRH3, a CDRL1, a CDRL2, and a CDRL3 having the amino acid sequences according to SEQ ID NOs:77-82, respectively. In certain embodiments, an antibody or antigen-binding fragment of the present disclosure comprises (a) a light chain variable domain (VL) amino acid sequence according to SEQ ID NO:76; and (b) a heavy chain variable domain (VH) amino acid sequence according to SEQ ID NO:75.

In certain embodiments, an antibody or antigen-binding fragment of the present disclosure comprises (a) a light chain variable domain (V$_L$) that is at least 90%, at least 95%, or 100% identical to the amino acid sequence set forth in SEQ ID NO:76, and (b) a heavy chain variable domain (V$_H$) that is at least 90%, at least 95%, or 100% identical to the amino acid sequence set forth in SEQ ID NO:75.

d. Pharmaceutical Compositions

In some embodiments, an antibody or antigen binding fragment thereof of the combination therapy is provided as a pharmaceutical composition, which includes the anti-HBV antibody and optionally, a pharmaceutically acceptable carrier. In some embodiments, a composition may include an anti-HBV antibody, wherein the antibody may make up at least 50% by weight (e.g., 60%, 70%, 75%, 80%, 85%, 90%, 95%, 96%, 97%, 98%, 99%, or more) of the total protein in the composition. In such a composition, the antibody may be in purified form.

Pharmaceutical compositions of the anti-HBV antibody may include an antimicrobial, particularly if packaged in a multiple dose format. They may comprise detergent, e.g., a Tween (polysorbate), such as Tween 80. When present, detergents are typically present at low levels, e.g., less than 0.01%. Compositions may also include sodium salts (e.g., sodium chloride) for tonicity. For example, in some embodiments, a pharmaceutical composition comprises NaCl at a concentration of 10±2 mg/ml.

Further, pharmaceutical compositions may comprise a sugar alcohol (e.g., mannitol) or a disaccharide (e.g., sucrose or trehalose), e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

An antibody composition of the present disclosure may also comprise one or more immunoregulatory agents. In some embodiments, one or more of the immunoregulatory agents include(s) an adjuvant.

Methods of preparing a pharmaceutical composition of the anti-HBV antibody may include the steps: (i) preparing the antibody; and (ii) admixing the purified antibody with one or more pharmaceutically acceptable carriers.

IV. Methods of Treatment Using the Combination Therapy

In some embodiments the present disclosure provides methods for treating an HBV infection or a Hepatitis B virus-associated disease.

As used herein, a "subject" is an animal, such as a mammal, including any mammal that can be infected with HBV, e.g., a primate (such as a human, a non-human primate, e.g., a monkey, or a chimpanzee), or an animal that is considered an acceptable clinical model of HBV infection, HBV-AAV mouse model (see, e.g., Yang, et al., Cell and Mol Immunol 11:71 (2014)) or the HBV 1.3×fs transgenic mouse model (Guidotti, et al., J. Virol. 69:6158 (1995)). In some embodiments, the subject has a hepatitis B virus (HBV) infection. In some other embodiments, the subject has both a hepatitis B virus (HBV) infection and a hepatitis D virus (HDV) infection. In some other embodiments, the subject is a human, such as a human being having an HBV infection, especially a chronic hepatitis B virus (CHBV) infection.

As used herein, the terms "treating" or "treatment" refer to a beneficial or desired result including, but not limited to, alleviation or amelioration of one or more signs or symptoms associated with unwanted HBV gene expression or HBV replication, e.g., the presence of serum or liver HBV cccDNA, the presence of serum HBV DNA, the presence of serum or liver HBV antigen, e.g., HBsAg or HBeAg, elevated ALT, elevated AST (normal range is typically considered about 10 to 34 U/L), the absence of or low level of anti-HBV antibodies; a liver injury; cirrhosis; delta hepatitis; acute hepatitis B; acute fulminant hepatitis B; chronic hepatitis B; liver fibrosis; end-stage liver disease; hepatocellular carcinoma; serum sickness-like syndrome; anorexia; nausea; vomiting, low-grade fever; myalgia; fatigability; disordered gustatory acuity and smell sensations (aversion to food and cigarettes); or right upper quadrant and epigastric pain (intermittent, mild to moderate); hepatic encephalopathy; somnolence; disturbances in sleep pattern; mental confusion; coma; ascites; gastrointestinal bleeding; coagulopathy; jaundice; hepatomegaly (mildly enlarged, soft liver); splenomegaly; palmar erythema; spider nevi; muscle wasting; spider angiomas; vasculitis; variceal bleeding; peripheral edema; gynecomastia; testicular atrophy; abdominal collateral veins (caput medusa); ALT levels higher than AST levels; elevated gamma-glutamyl transpeptidase (GGT) (normal range is typically considered about 8 to 65 U/L) and alkaline phosphatase (ALP) levels (normal range is typically considered about 44 to 147 IU/L (international units per liter), not more than 3 times the ULN); slightly low albumin levels; elevated serum iron levels; leukopenia (i.e., granulocytopenia); lymphocytosis; increased erythrocyte sedimentation rate (ESR); shortened red blood cell survival; hemolysis; thrombocytopenia; a prolongation of the international normalized ratio (INR); presence of serum or liver HBsAg, HBeAg, Hepatitis B core antibody (anti-HBc) immunoglobulin M (IgM); hepatitis B surface antibody (anti-HBs), hepatitis B e antibody (anti-HBe), or HBV DNA; increased bilirubin levels; hyperglobulinemia; the presence of tissue-nonspecific antibodies, such as anti-smooth muscle antibodies (ASMAs) or antinuclear antibodies (ANAs) (10-20%); the presence of tissue-specific antibodies, such as antibodies against the thyroid gland (10-20%); elevated levels of rheumatoid factor (RF); low platelet and white blood cell counts; lobular, with degenerative and regenerative hepatocellular changes, and accompanying inflammation; and predominantly centrilobular necrosis, whether detectable or undetectable. The likelihood of developing, e.g., liver fibrosis, is reduced, for example, when an individual having one or more risk factors for liver fibrosis, e.g., chronic hepatitis B infection, either fails to develop liver fibrosis or develops liver fibrosis with less severity relative to a population having the same risk factors and not receiving treatment as described herein. "Treatment" can also mean prolonging survival as compared to expected survival in the absence of treatment.

As used herein, the terms "preventing" or "prevention" refer to the failure to develop a disease, disorder, or condition, or the reduction in the development of a sign or symptom associated with such a disease, disorder, or condition (e.g., by a clinically relevant amount), or the exhibition of delayed signs or symptoms delayed (e.g., by days, weeks, months, or years). Prevention may require the administration of more than one dose.

In some embodiments, treatment of HBV infection results in a "functional cure" of hepatitis B. As used herein, functional cure is understood as clearance of circulating HBsAg and is may be accompanied by conversion to a status in which HBsAg antibodies become detectable using a clinically relevant assay. For example, detectable antibodies can include a signal higher than 10 mIU/ml as measured by Chemiluminescent Microparticle Immunoassay (CMIA) or any other immunoassay. Functional cure does not require clearance of all replicative forms of HBV (e.g., cccDNA from the liver). Anti-HBs seroconversion occurs spontaneously in about 0.2-1% of chronically infected patients per year. However, even after anti-HBs seroconversion, low level persistence of HBV is often observed for decades indicating that a functional rather than a complete cure occurs. Without being bound to a particular mechanism, the immune system may be able to keep HBV in check under conditions in which a functional cure has been achieved. A functional cure permits discontinuation of any treatment for the HBV infection. However, it is understood that a "functional cure" for HBV infection may not be sufficient to prevent or treat diseases or conditions that result from HBV infection, e.g., liver fibrosis, HCC, or cirrhosis. In some specific embodiments, a "functional cure" can refer to a sustained reduction in serum HBsAg, such as <1 IU/mL, for at least 3 months, at least 6 months, or at least one year following the initiation of a treatment regimen or the completion of a treatment regimen.

As used herein, the term "Hepatitis B virus-associated disease" or "HBV-associated disease," is a disease or disorder that is caused by, or associated with HBV infection or replication. The term "HBV-associated disease" includes a disease, disorder or condition that would benefit from reduction in HBV gene expression or replication. Non-limiting examples of HBV-associated diseases include, for example, hepatitis D virus infection, delta hepatitis, acute hepatitis B; acute fulminant hepatitis B; chronic hepatitis B; liver fibrosis; end-stage liver disease; and hepatocellular carcinoma.

In some embodiments, an HBV-associated disease is hepatitis D virus infection. Hepatitis D virus or hepatitis delta virus (HDV) is a human pathogen. However, the virus is defective and depends on obligatory helper functions provided by hepatitis B virus (HBV) for transmission; indeed, HDV requires an associated or pre-existing HBV infection to become infectious and thrive, in particular, the viral envelope containing the surface antigen of hepatitis B. HDV can lead to severe acute and chronic forms of liver disease in association with HBV. Hepatitis D infection or delta hepatitis is highly endemic to several African countries, the Amazonian region, and the Middle East, while its prevalence is low in industrialized countries, except in the Mediterranean.

Transmission of HDV can occur either via simultaneous infection with HBV (coinfection) or superimposed on chronic hepatitis B or hepatitis B carrier state (superinfection). Both superinfection and coinfection with HDV typically result in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B virus, hepatitis D has the highest fatality rate of all the hepatitis infections, at 20%.

In some embodiments, an HBV-associated disease is acute hepatitis B. Acute hepatitis B includes inflammation of the liver that lasts less than six months. Typical symptoms of acute hepatitis B are fatigue, anorexia, nausea, and vomiting. Very high aminotransferase values (>1000 U/L) and hyperbilirubinemia are often observed. Severe cases of acute hepatitis B may progress rapidly to acute liver failure, marked by poor hepatic synthetic function. This is often defined as a prothrombin time (PT) of 16 seconds or an international normalized ratio (INR) of 1.5 in the absence of previous liver disease. Acute hepatitis B may evolve into chronic hepatitis B.

In some embodiments, an HBV-associated disease is chronic hepatitis. Chronic hepatitis B (CHB) includes inflammation of the liver that lasts more than six months. Subjects having CHB are HBsAg positive and have either high viremia ($\geq 10^4$ HBV-DNA copies/ml blood) or low viremia ($<10^3$ HBV-DNA copies/ml blood). In certain embodiments, subjects have been infected with HBV for at least five years. In certain embodiments, subjects have been infected with HBV for at least ten years. In certain embodiments, subjects became infected with HBV at birth. Subjects having chronic hepatitis B disease can be immune tolerant or have an inactive chronic infection without any evidence of active disease, and they are also asymptomatic. Patients with chronic active hepatitis, especially during the replicative state, may have symptoms similar to those of acute hepatitis. Subjects having chronic hepatitis B disease may have an active chronic infection accompanied by necroinflammatory liver disease, have increased hepatocyte turn-over in the absence of detectable necroinflammation, or have an inactive chronic infection without any evidence of active disease, and they are also asymptomatic. The persistence of HBV infection in CHB subjects is the result of cccHBV DNA. In some embodiments, a subject having CHB is HBeAg positive. In some other embodiments, a subject having CHB is HBeAg negative. Subjects having CHB have a level of serum HBV DNA of less than $10^5$ and a persistent elevation in transaminases, for examples ALT, AST, and gamma-glutamyl transferase. A subject having CHB may have a liver biopsy score of less than 4 (e.g., a necroinflammatory score).

In some embodiments, an HBV-associated disease is acute fulminant hepatitis B. A subject having acute fulminant hepatitis B has symptoms of acute hepatitis and the additional symptoms of confusion or coma (due to the liver's failure to detoxify chemicals) and bruising or bleeding (due to a lack of blood clotting factors).

Subjects having an HBV infection, e.g., CHB, may develop liver fibrosis. Accordingly, in some embodiments, an HBV-associated disease is liver fibrosis. Liver fibrosis, or cirrhosis, is defined histologically as a diffuse hepatic process characterized by fibrosis (excess fibrous connective tissue) and the conversion of normal liver architecture into structurally abnormal nodules.

Subjects having an HBV infection, e.g., CHB, may develop end-stage liver disease. Accordingly, in some embodiments, an HBV-associated disease is end-stage liver disease. For example, liver fibrosis may progress to a point where the body may no longer be able to compensate for, e.g., reduced liver function, as a result of liver fibrosis (i.e., decompensated liver), and result in, e.g., mental and neurological symptoms and liver failure.

Subjects having an HBV infection, e.g., CHB, may develop hepatocellular carcinoma (HCC), also referred to as malignant hepatoma. Accordingly, in some embodiments, an HBV-associated disease is HCC. HCC commonly develops in subjects having CHB and may be fibrolamellar, pseudoglandular (adenoid), pleomorphic (giant cell), or clear cell.

An "HDV-associated disorder" or a Hepatitis D-virus-associated disorder" is a disease or disorder associated with expression of an HDV. Exemplary HDV-associated disorders include hepatitis B virus infection, acute hepatits B, acute hepatitis D; acute fulminant hepatitis D; chronic hepatitis D; liver fibrosis; end-stage liver disease; and hepatocellular carcinoma.

"Therapeutically effective amount," as used herein, is intended to include the amount of an RNAi agent or anti-HBV antibody, that, when administered to a patient for treating a subject having an HBV infection or HBV-associated disease, is sufficient to effect treatment of the disease (e.g., by diminishing or maintaining the existing disease or one or more symptoms of disease). The "therapeutically effective amount" may vary depending on the RNAi agent and/or anti-HBV antibody, how they are administered, the disease and its severity, and the history, age, weight, family history, genetic makeup, stage of pathological processes mediated by HBV gene expression, the types of preceding or concomitant treatments, if any, and other individual characteristics of the patient to be treated. A therapeutically effective amount may require the administration of more than one dose.

A "therapeutically-effective amount" also includes an amount of an RNAi agent or anti-HBV antibody that produces some desired effect at a reasonable benefit/risk ratio applicable to any treatment. Therapeutic agents (e.g. RNAi agents, anti-HBV antibodies) used in the methods of the present disclosure may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum, and serosal fluids, plasma, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In certain embodiments, a "sample derived from a subject" refers to blood, or plasma or serum obtained from blood drawn from the subject. In further embodiments, a "sample derived from a subject" refers to liver tissue (or subcomponents thereof) or blood tissue (or subcomponents thereof, e.g., serum) derived from the subject.

Some embodiments of the present disclosure provide methods of treating chronic HBV infection or an HBV-associated disease in a subject in need thereof, comprising: (i) administering to the subject an agent that reduces HBV antigenic load; and (ii) administering to the subject an anti-HBV antibody. In certain embodiments, the agent that reduces HBV antigenic load is administered before the anti-HBV antibody. In certain embodiments, administering the agent that reduces HBV antigenic load before the anti-HBV antibody causes the viral load to be reduced when the anti-HBV antibody is administered. In certain embodiments, the therapeutically effective amount of the anti-HBV antibody of the combination therapy is less than a therapeutically effective amount of the anti-HBV antibody delivered when the agent that reduces HBV antigenic load has not been administered to the subject (e.g., when the anti-HBV antibody is administered alone as a monotherapy). In some embodiments, the agent that reduces HBV antigenic load is an RNAi agent (e.g., an siRNA) that inhibits expression of an HBV transcript.

In certain embodiments, the present disclosure provides a method of treating a chronic HBV infection or HBV-associated disease in a subject in need thereof, comprising: administering to the subject an agent that reduces HBV antigenic load; and administering to the subject an anti-HBV antibody; and further comprising measuring the amount of HBsAg present in a blood sample from the subject before and after administering the agent that reduces HBV antigenic load, wherein a decrease in HBsAg indicates reduced expression of the at least one HBV gene.

In certain embodiments, the present disclosure provides an agent that reduces HBV antigenic load for use in the treatment of a chronic HBV infection or an HBV-associated disease in a subject, wherein the subject is subsequently administered an anti-HBV antibody. In certain other embodiments, the present disclosure provides an anti-HBV antibody for use in the treatment of a chronic HBV infection or an HBV-associated disease in a subject, and the subject has been previously administered an agent that reduces HBV antigenic load. In further embodiments, expression of at least one HBV gene is reduced after administration of the agent that reduces HBV antigenic load, and the anti-HBV antibody is administered to the subject when expression of the at least one HBV gene is reduced.

In certain embodiments, the present disclosure provides the use of an agent that reduces HBV antigenic load and/or an anti-HBV antibody in the manufacture of a medicament for the treatment of a chronic HBV infection or an HBV-associated disease.

Some embodiments of the present disclosure provide methods of treating chronic HBV infection or an HBV-associated disease in a subject in need thereof, comprising: (i) administering to the subject an inhibitor of HBV gene expression; and (ii) administering to the subject an anti-HBV antibody. In certain embodiments, the inhibitor of HBV gene expression is administered before the anti-HBV antibody. In certain embodiments, administering the inhibitor of HBV gene expression before the anti-HBV antibody causes the viral load to be reduced when the anti-HBV antibody is administered. In certain embodiments, the therapeutically effective amount of the anti-HBV antibody of the combination therapy is less than a therapeutically effective amount of the anti-HBV antibody delivered when the inhibitor of HBV gene expression has not been administered to the subject (e.g., when the anti-HBV antibody is administered alone as a monotherapy).

In certain embodiments, expression of at least one HBV gene is reduced after administering the inhibitor of HBV gene expression, and the anti-HBV antibody is administered to the subject when expression of the at least one HBV gene is reduced. In particular embodiments, the at least one HBV gene is HBV X gene and/or HBsAg.

In certain embodiments, the present disclosure provides a method of treating a chronic HBV infection or HBV-associated disease in a subject in need thereof, comprising: administering to the subject an inhibitor of HBV gene expression; and administering to the subject an anti-HBV antibody; and further comprising measuring the amount of HBsAg present in a blood sample from the subject before and after administering the inhibitor of HBV expression, wherein a decrease in HBsAg indicates reduced expression of the at least one HBV gene.

In certain embodiments, the present disclosure provides an inhibitor of HBV gene expression for use in the treatment of a chronic HBV infection or an HBV-associated disease in a subject, wherein the subject is subsequently administered an anti-HBV antibody. In certain other embodiments, the present disclosure provides an anti-HBV antibody for use in the treatment of a chronic HBV infection or an HBV-associated disease in a subject, and the subject has been previously administered an inhibitor of gene expression. In further embodiments, expression of at least one HBV gene is reduced after administration of the inhibitor of HBV gene expression, and the anti-HBV antibody is administered to the subject when expression of the at least one HBV gene is reduced.

In certain embodiments, the present disclosure provides the use of an inhibitor of HBV gene expression and/or an anti-HBV antibody in the manufacture of a medicament for the treatment of a chronic HBV infection or an HBV-associated disease.

In any of the above methods, compositions for use, or uses in manufacture, the methods and compositions may be used for treating a chronic HBV infection.

In certain embodiments, the inhibitor of HBV gene expression is administered in a single dose, two doses, three doses, four doses, or five doses. In certain particular embodiments, at least the first dose of the inhibitor of HBV gene expression is administered prior to administering the anti-HBV antibody.

In certain embodiments, the inhibitor of HBV gene expression is administered in a single dose, two doses, three doses, four doses, or five doses, six doses, seven doses, or eight doses. The dose or doses may be administered, for example, twice daily, once daily, every two days, every three days, twice per week, once per week, every other week, every four weeks, or once per month.

In certain embodiments, administering the anti-HBV antibody comprises administering the anti-HBV antibody twice per week, once per week, every other week, every two weeks, or once a month.

In certain embodiments, administering the anti-HBV antibody comprises administering at least two doses of a therapeutically effective amount of the anti-HBV antibody. In certain further embodiments, the at least two doses are administered twice per week, once per week, every other week, every two weeks, or once a month.

In certain embodiments, administering the anti-HBV antibody begins at least 1 week after administering the inhibitor of HBV gene expression. In certain embodiments, administering the anti-HBV antibody begins 2 weeks after administering the inhibitor of HBV gene expression. In certain embodiments, administering the anti-HBV antibody begins 8 weeks after administering the inhibitor of HBV gene expression.

In certain embodiments, the anti-HBV antibody and the inhibitor of HBV gene expression are each administered subcutaneously.

In particular embodiments of the above methods, compositions for use, or uses in manufacture, the anti-HBV antibody may recognize HBV genotypes A, B, C, D, E, F, G, H, I, and J.

In particular embodiments of the above methods, compositions for use, or uses in manufacture, the anti-HBV antibody may be a human antibody; a monoclonal antibody; or a bispecific antibody, with a first specificity for HBsAg and a second specificity that stimulates an immune effector (e.g., a second specificity that stimulates cytotoxicity or a vaccinal effect). In certain other embodiments of the above methods, compositions for use, or uses in manufacture disclosed herein, the anti-HBV antibody is a monoclonal antibody.

In particular embodiments of the above methods, compositions for use, or uses in manufacture, the anti-HBV antibody may be HBC34 or a non-natural variant of HBC34 as disclosed herein. For example, in certain embodiments, the anti-HBV antibody comprises CDRs having the amino acid sequences (i) according to SEQ ID NOs:44, 45, 47-49, and 51; or (ii) according to SEQ ID NOs:44, 45, 47-49, and 52. In certain embodiments, the anti-HBV antibody comprises CDRs having the amino acid sequences according to SEQ ID NOs:44, 45, 47, 48, 49, and 51. In certain embodiments, the anti-HBV antibody comprises CDRs having the amino acid sequences according to SEQ ID NOs:44, 45, 47, 48, 49, and 52. In certain embodiments, the anti-HBV antibody comprises: (1) (a) a light chain variable domain ($V_L$) that is at least 90%, at least 95%, or 100% identical to an amino acid sequence as set forth in any one of SEQ ID NOs:55-63; and (b) a heavy chain variable domain ($V_H$) that is at least 90%, at least 95%, or 100% identical to an amino acid sequence as set forth in SEQ ID NO:53: or (2) (a) a light chain variable domain ($V_L$) that is at least 90%, at least 95%, or 100% identical to an amino acid sequence as set forth in any one of SEQ ID NOs:55-57 and 64-69; and (b) a heavy chain variable domain ($V_H$) that is at least 90%, at least 95%, or 100% identical to an amino acid sequence as set forth in SEQ ID NO:54.

In certain embodiments, the anti-HBV antibody comprises: (1) (a) a light chain variable domain ($V_L$) that is at least 90%, at least 95%, or 100% identical to an amino acid sequence as set forth in any one of SEQ ID NOs:55-69; and (b) a heavy chain variable domain ($V_H$) that is at least 90%, at least 95%, or 100% identical to an amino acid sequence as set forth in SEQ ID NO:53: or (2) (a) a light chain variable domain ($V_L$) that is at least 90%, at least 95%, or 100% identical to an amino acid sequence as set forth in any one of SEQ ID NOs:55-69; and (b) a heavy chain variable domain ($V_H$) that is at least 90%, at least 95%, or 100% identical to an amino acid sequence as set forth in SEQ ID NO:54.

In certain embodiments, the anti-HBV antibody comprises: (a) a light chain variable domain ($V_L$) sequence according to SEQ ID NO:59; and (b) a heavy chain variable domain ($V_H$) sequence according to SEQ ID NO: 53.

In certain embodiments, the anti-HBV antibody comprises: (a) a light chain variable domain ($V_L$) sequence according to SEQ ID NO:58; and (b) a heavy chain variable domain ($V_H$) sequence according to SEQ ID NO:53.

In particular embodiments of the methods, compositions for use, or uses in manufacture, the anti-HBV antibody comprises: (a) a light chain that is at least 90%, at least 95%, or 100% identical to an amino acid sequence as set forth in SEQ ID NO:73, and (b) a heavy chain that is at least 90%, at least 95%, or 100% identical to an amino acid sequence as set forth in any one of SEQ ID NOs:70-72 and 97.

In particular embodiments of the methods, compositions for use, or uses in manufacture, the anti-HBV antibody comprises: (a) a light chain that is at least 90%, at least 95%, or 100% identical to an amino acid sequence as set forth in SEQ ID NO:74, and (b) a heavy chain that is at least 90%, at least 95%, or 100% identical to an amino acid sequence as set forth in any one of SEQ ID NOs:70-72 and 97.

In particular embodiments of the methods, compositions for use, or uses in manufacture, the anti-HBV antibody comprises: (a) a light chain that is at least 90%, at least 95%, or 100% identical to an amino acid sequence as set forth in any one of SEQ ID NOs:83-95, and (b) a heavy chain that is at least 90%, at least 95%, or 100% identical to an amino acid sequence as set forth in any one of SEQ ID NOs:70-72, 97 and 98.

In particular embodiments of the methods, compositions for use, or uses in manufacture, the anti-HBV antibody comprises: (a) a light chain amino acid sequence according to SEQ ID NO:73, and (b) a heavy chain amino acid sequence according to SEQ ID NO:70.

In particular embodiments of the methods, compositions for use, or uses in manufacture, the anti-HBV antibody comprises: (a) a light chain amino acid sequence according to SEQ ID NO:73, and (b) a heavy chain amino acid sequence according to SEQ ID NO:71.

In particular embodiments of the methods, compositions for use, or uses in manufacture, the anti-HBV antibody comprises: (a) a light chain amino acid sequence according to SEQ ID NO:74, and (b) a heavy chain amino acid sequence according to SEQ ID NO:70.

In certain other embodiments of the above methods, compositions for use, or uses in manufacture, the anti-HBV antibody comprises CDRs having the amino acid sequences according to SEQ ID NOs:77-82. In certain embodiments of the above methods, compositions for use, or uses in manufacture, the anti-HBV antibody comprises (a) a light chain variable domain (VL) amino acid sequence according to SEQ ID NO:76; and (b) a heavy chain variable domain (VH) amino acid sequence according to SEQ ID NO:75.

In certain embodiments of the above methods, compositions for use, or uses in manufacture, the anti-HBV antibody comprises (a) a light chain variable domain ($V_L$) that is at least 90%, at least 95%, or 100% identical to an amino acid sequence as set forth in SEQ ID NO:76, and (b) a heavy chain variable domain ($V_H$) that is at least 90%, at least 95%, or 100% identical to an amino acid sequence as set forth in SEQ ID NO:75.

In certain embodiments, a therapeutically effective amount of the anti-HBV antibody is less than a therapeutically effective amount of the anti-HBV antibody delivered when the inhibitor of HBV gene expression has not been administered to the subject. For example, the combination therapy may lower the effective dose of the anti-HBV antibody, as compared to administration of the anti-HBV antibody alone.

In certain embodiments, the anti-HBV antibody is administered in at least two separate doses. In particular embodiments, the at least two doses are administered twice per week, once per week, every other week, every two weeks, or once a month.

In certain embodiments, the subject is a human and a therapeutically effective amount of the anti-HBV antibody is administered; wherein the therapeutically effective amount is from about 3 mg/kg to about 30 mg/kg.

In particular embodiments of the above methods, compositions for use, or uses in manufacture, the inhibitor is an RNAi agent that inhibits expression of an HBV transcript. In some embodiments, inhibition of expression of an HBV transcript is measured by rtPCR. In some embodiments, inhibition of expression of an HBV transcript is measured by a reduction in protein levels as measured by ELISA.

In certain embodiments, the RNAi agent comprises a sense strand and an antisense strand forming a double-stranded region, wherein the sense strand comprises at least 15 contiguous nucleotides differing by no more than 3 nucleotides from nucleotides 1579-1597 of SEQ ID NO:1. In certain embodiments, the RNAi agent comprises a sense strand and an antisense strand, wherein the sense strand comprises nucleotides 1579-1597 of SEQ ID NO:1.

In particular embodiments of the above methods, compositions for use, or uses in manufacture, at least one strand of the RNAi agent may comprise a 3' overhang of at least 1 nucleotide or at least 2 nucleotides.

In particular embodiments of the above methods, compositions for use, or uses in manufacture, the double-stranded region of the RNAi agent may be 15-30 nucleotide pairs in length; 17-23 nucleotide pairs in length; 17-25 nucleotide pairs in length; 23-27 nucleotide pairs in length; 19-21 nucleotide pairs in length; or 21-23 nucleotide pairs in length.

In particular embodiments of the above methods, compositions for use, or uses in manufacture, each strand of the RNAi agent may be 15-30 nucleotides or 19-30 nucleotides.

In particular embodiments of the above methods, compositions for use, or uses in manufacture, the RNAi agent is an siRNA. In particular embodiments, the siRNA inhibits expression of an HBV transcript that encodes an HBsAg protein, an HBcAg protein, and HBx protein, or an HBV DNA polymerase protein. In certain embodiments, the siRNA binds to at least 15 contiguous nucleotides of a target encoded by: P gene, nucleotides 2309-3182 and 1-1625 of NC_003977.2; S gene (encoding L, M, and S proteins), nucleotides 2850-3182 and 1-837 of NC_003977.2; HBx, nucleotides 1376-1840 of NC_003977.2; or C gene, nucleotides 1816-2454 of NC_003977.2.

In particular embodiments of the above methods, compositions for use, or uses in manufacture, the RNAi agent is an siRNA, and the antisense strand of the siRNA comprises at least 15 contiguous nucleotides or 19 contiguous nucleotides of the nucleotide sequence of 5'-UGUGAAGCGAAGUGCACACUU-3' (SEQ ID NO:4). In some embodiments, the antisense strand of the siRNA comprises the nucleotide sequence of 5'-UGUGAAGCGAAGUGCACACUU-3' (SEQ ID NO:4). In some embodiments, the antisense strand consists of the nucleotide sequence of 5'-UGUGAAGCGAAGUGCACACUU-3' (SEQ ID NO:4). In some embodiments, the sense strand of the siRNA comprises the nucleotide sequence of 5'-GUGUGCACUUCGCUUCACA-3' (SEQ ID NO:3). In some embodiment, the sense strand of the siRNA consists of the nucleotide sequence of 5'-GUGUGCACUUCGCUUCACA-3' (SEQ ID NO:3).

In particular embodiments of the above methods, compositions for use, or uses in manufacture, the RNAi agent is an siRNA, and the antisense strand of the siRNA comprises at least 15 contiguous nucleotides or 19 contiguous nucleotides of the nucleotide sequence of 5'-UAAAAUUGAGAGAAGUCCACCAC-3' (SEQ ID NO:107). In some embodiments, the antisense strand of the siRNA comprises the nucleotide sequence of 5'-UAAAAUUGAGAGAAGUCCACCAC-3' (SEQ ID NO:107). In some embodiments, the antisense strand consists of the nucleotide sequence of 5'-UAAAAUUGAGAGAAGUCCACCAC-3' (SEQ ID NO:107). In some embodiments, the sense strand of the siRNA comprises the nucleotide sequence of 5'-GGUGGACUUCUCUCAAUUUUA-3' (SEQ ID NO:106). In some embodiment, the sense strand of the siRNA consists of the nucleotide sequence of 5'-GGUGGACUUCUCUCAAUUUUA-3' (SEQ ID NO:106).

In particular embodiments of the above methods, compositions for use, or uses in manufacture, the RNAi agent is an siRNA, wherein substantially all of the nucleotides of said sense strand and substantially all of the nucleotides of said antisense strand are modified nucleotides, and wherein said sense strand is conjugated to a ligand attached at the 3'-terminus. In particular embodiments, the ligand is one or more GalNAc derivatives attached through a monovalent linker, bivalent branched linker, or trivalent branched linker. In certain embodiments, the GalNAc derivative attached through a linker is or comprises:

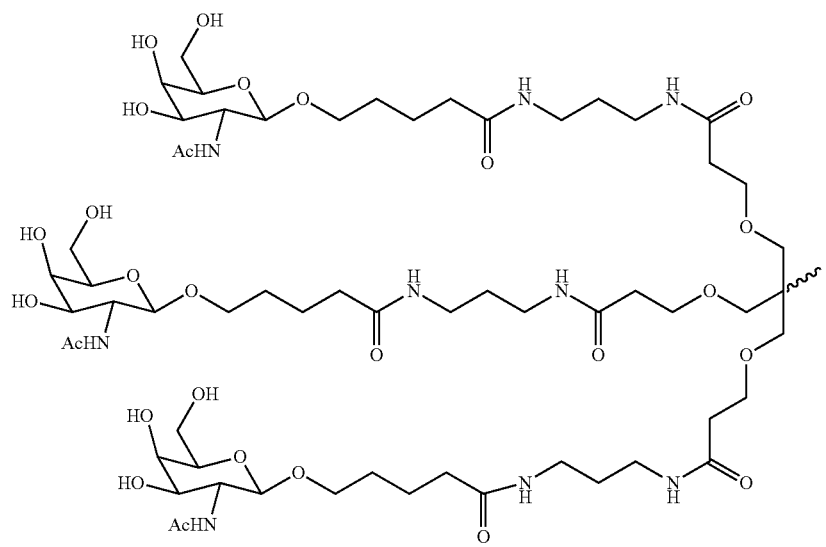 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In particular embodiments, the siRNA is conjugated to the ligand as shown in the following schematic (i.e., the GalNAc derivative attached through a linker is):

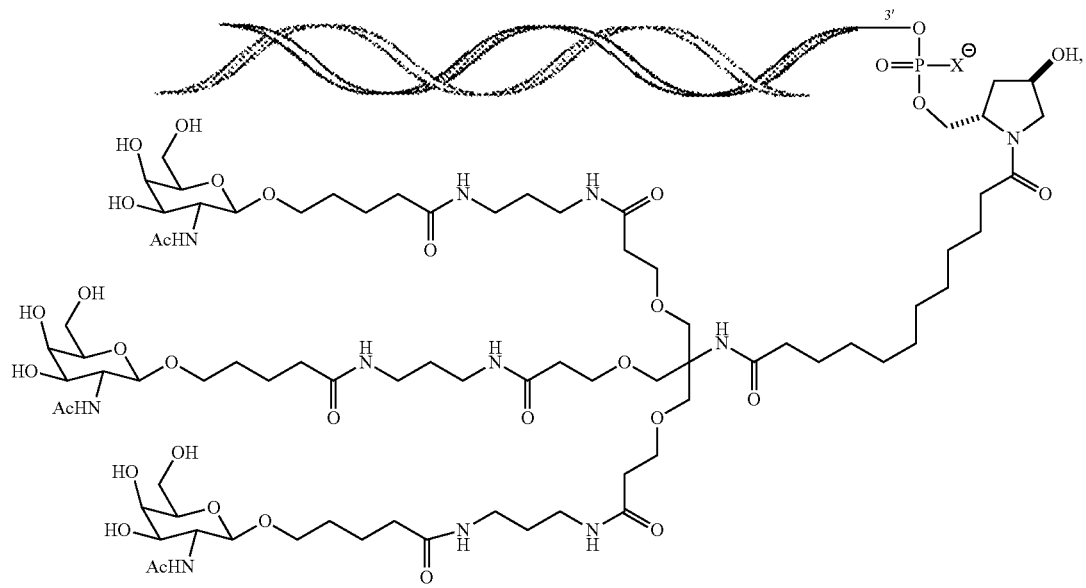

wherein X is O or S.

In particular embodiments of the above methods, compositions for use, or uses in manufacture, the RNAi agent is an siRNA, wherein at least one nucleotide of the siRNA is a modified nucleotide comprising a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, an adenosine-glycol nucleic acid, or a nucleotide comprising a 5'-phosphate mimic. In certain embodiments, the siRNA comprises a phosphate backbone modification, a 2' ribose modification, 5' triphosphate modification, or a GalNAc conjugation modification. In certain embodiments, the phosphate backbone modification comprises a phosphorothioate bond. In certain embodiments, the 2' ribose modification comprises a fluoro or —O-methyl substitution.

In particular embodiments of the above methods, compositions for use, or uses in manufacture, the RNAi agent is an siRNA having a sense strand comprising 5'-gsusguGfcAfCfUfucgcuucacaL96-3' (SEQ ID NO:5) and an antisense strand comprising 5'-usGfsugaAf-gCfGfaaguGfcAfcacsusu-3' (SEQ ID NO:6),
  wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;
  Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;
  s is a phosphorothioate linkage; and
  L96 is N-[tris(GalNAc-alkyl)-amidodecanoyl)]-4-hydroxyprolinol.

In particular embodiments of the above methods, compositions for use, or uses in manufacture, the RNAi agent is an siRNA having a sense strand comprising 5'-gsusguGfcAfCfUfucgcuucacaL96-3' (SEQ ID NO:7) and an antisense strand comprising 5'-usGfsuga(Agn)gCfGfaaguGfcAfcacsusu-3' (SEQ ID NO:8)
  wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;
  Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;
  (Agn) is adenosine-glycol nucleic acid (GNA);
  s is a phosphorothioate linkage; and
  L96 is N-[tris(GalNAc-alkyl)-amidodecanoyl)]-4-hydroxyprolinol.

In particular embodiments of the above methods, compositions for use, or uses in manufacture, the RNAi agent is an siRNA having a sense strand comprising 5'-gsgsuggaCfuUfCfUfcucaAfUfuuuaL96-3' (SEQ ID NO:108) and an antisense strand comprising 5'-usAfsaaaU-fuGfAfgagaAfgUfccaccsasc-3' (SEQ ID NO:109),
  wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;
  Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;
  s is a phosphorothioate linkage; and
  L96 is N-[tris(GalNAc-alkyl)-amidodecanoyl)]-4-hydroxyprolinol.

In particular embodiments of the above methods, compositions for use, or uses in manufacture, the subject is a human and a therapeutically effective amount of RNAi or siRNA is administered to the subject; and wherein the effective amount of the RNAi or siRNA is from about 1 mg/kg to about 8 mg/kg.

In some embodiments of the methods, compositions for use, or uses disclosed herein, the siRNA is administered to the subject twice daily, once daily, every two days, every three days, twice per week, once per week, every other week, every four weeks, or once per month. In some embodiments, wherein the siRNA is administered to the subject every four weeks.

In certain embodiments, the methods include administering two inhibitors of HBV gene expression with an anti-HBV antibody. The two inhibitors of HBV gene expression may be two siRNAs, such as two siRNAs that target different HBV genes. The two different HBV genes may, for example, be HBsAg, and HBV X. The two inhibitors of HBV gene expression may be administered simultaneously. In certain embodiments, two siRNAs each directed to an HBV gene are administered, and the first siRNA has an antisense strand comprising SEQ ID NO:4, SEQ ID NO:6, or SEQ ID NO:8; and the second siRNA comprises an siRNA having a sense strand that comprises at least 15 contiguous nucleotides of nucleotides 2850-3182 of SEQ ID NO:1. In certain embodiments, two siRNAs each directed to an HBV gene are administered, and the first siRNA has an antisense strand comprising SEQ ID NO:107 or SEQ ID NO:109; and the second siRNA comprises an siRNA having a sense strand that comprises at least 15 contiguous nucleotides of nucleotides 2850-3182 of SEQ ID NO:1. In certain embodiments, two siRNAs each directed to an HBV gene are administered, and the first siRNA has an antisense strand comprising SEQ ID NO:4, SEQ ID NO:6, or SEQ ID NO:8; and the second siRNA has an antisense strand comprising SEQ ID NO: 107 or SEQ ID NO:109. In certain embodiments, the first siRNA has a sense strand comprising SEQ ID NO:3, SEQ ID NO:5, or SEQ ID NO:7; and the second siRNA has a sense strand comprising SEQ ID NO:106 or SEQ ID NO:108.

In certain embodiments, the anti-HBV antibody and the inhibitor of HBV gene expression exhibit a synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

In some embodiments, an RNAi agent targeting an HBV mRNA is administered to a subject having an HBV infection, and/or an HBV-associated disease, such that the expression of one or more HBV genes, HBV ccc DNA levels, HBV antigen levels, HBV viral load levels, ALT, and/or AST, e.g., in a cell, tissue, blood, or fluid of the subject are reduced by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more.

In some embodiments, an RNAi agent targeting an HBV mRNA is administered to a subject having an HBV infection, and/or an HBV-associated disease, and inhibits HBV gene expression by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or about 100%, i.e., to below the level of detection of the assay.

In some embodiments, the combination therapy according to the present disclosure comprises administering a nucleot(s)ide analog as a third component. As used herein, the term "nucelot(s)ide analog" (or "polymerase inhibitor" or "reverse transcriptase inhibitor") is an inhibitor of DNA replication that is structurally similar to a nucleotide or nucleoside and specifically inhibits replication of the HBV cccDNA and does not significantly inhibit the replication of the host (e.g., human) DNA. Such inhibitors include tenofovir disoproxil fumarate (TDF), tenofovir alafenamide (TAF), lamivudine, adefovir dipivoxil, entecavir (ETV), telbivudine, AGX-1009, emtricitabine (FTC), clevudine, ritonavir, dipivoxil, lobucavir, famvir, N-Acetyl-Cysteine (NAC), PC1323, theradigm-HBV, thymosin-alpha, ganciclovir, besifovir (ANA-380/LB-80380), and tenofvir-exaliades (TLX/CMX157). In certain embodiments, the nucelot(s)ide analog is entecavir (ETV). Nucleot(s)ide analogs are commercially available from a number of sources and are used in the methods provided herein according to their label indication (e.g., typically orally administered at a specific dose) or as determined by a skilled practitioner in the treatment of HBV.

The anti-HBV antibody or the inhibitor of HBV gene expression can be present either in the same pharmaceutical composition as the third active component or, the anti-HBV antibody, the inhibitor of HBV gene expression, and the third active component are present in three different pharmaceutical compositions. Such different pharmaceutical compositions may be administered either combined/simultaneously or at separate times or at separate locations (e.g., separate parts of the body).

V. Kits for HBV Combination Therapy

Provided herein are kits including components of the HBV therapy. In some embodiments, the kit includes one or more anti-HBV antibodies, one or more inhibitors of HBV gene expression, and optionally a third component of HBV combination therapy (e.g., an nucelot(s)ide analog). Kits may additionally include instructions for preparing and/or administering the components of the HBV combination therapy.

EXAMPLES

Example 1

Combination Therapy with an Antibody and an HBV-Targeting siRNA Decreases Markers of HBV Infection in AAV-HBV-Mice To determine whether an siRNA-antibody combination therapy may be effective in treating HBV infections, AAV/HBV-infected C57BL/6 mice were administered one of fourteen different treatments: (1) an HBV-specific siRNA (HBV02, having an antisense strand of SEQ ID NO:8); (2)-(5) an anti-HBV antibody (a mouse-chimeric version of the HBC34 antibody HBC34v7, HBC34-v7-mu-IgG2a) at one of four doses; (6-7) the HBV02 siRNA and the HBC34-v7-mu-IgG2a antibody, at one of two antibody doses; (8-11) the HBV02 siRNA, the HBC34-v7-mu-IgG2a antibody, and entecavir (ETV), at one of four antibody doses; (12) a control siRNA and a control antibody; (13) entecavir only; or (14) saline only (see Table 4).

TABLE 4

Treatment levels and dosages.

| Treatment | HBV02 (mg/kg) | HBC34v7 (mg/kg) | Control siRNA (mg/kg) | Control mAb (mg/kg) | ETV (mg/kg) | saline |
|---|---|---|---|---|---|---|
| 1 | 3 | — | — | — | — | — |
| 2 | — | 15 | — | — | — | — |
| 3 | — | 5 | — | — | — | — |
| 4 | — | 1 | — | — | — | — |
| 5 | — | 0.1 | — | — | — | — |
| 6 | 3 | 15 | — | — | — | — |
| 7 | 3 | 1 | — | — | — | — |
| 8 | 3 | 15 | — | — | 0.001 | — |
| 9 | 3 | 5 | — | — | 0.001 | — |
| 10 | 3 | 1 | — | — | 0.001 | — |
| 11 | 3 | 0.1 | — | — | 0.001 | — |
| 12 | — | — | 3 | 15 | — | — |
| 13 | — | — | — | — | 0.001 | — |
| 14 | — | — | — | — | — | X |

HBV02 is a chemically synthesized double-stranded oligonucleotide covalently linked to a ligand containing three GalNAc residues. All nucleosides are 2'-OMe or 2'-F modified and one nucleoside of the antisense strand is replaced with (S)-1-(2,3-dihydroxypropyl)adenosine (Agn). The nucleosides of the sense and antisense strand are connected through 3'-5' phosphodiester linkages or 3'-5' phosphorothioate linkages, that form the sugar-phosphate backbone of the oligonucleotide.

HBC34 is a highly neutralizing monoclonal antibody against HBV surface antigen (PreS1, PreS2, and S). The HBC34 antibody used in this experiment was a fully murinized HBC34v7, with the exception of the part of the Fab fragment that binds the HBV surface antigen. The human HBC34v7 has the $V_H$ sequence as set forth in SEQ ID NO:53 and a $V_L$ sequence as set forth in SEQ ID NO:56. The mouse-chimeric version of HBC34v7 sequences used in the HBC34-v7-mu-IgG2a antibody for this experiment had heavy chain and light chain amino acid sequences as set forth in SEQ ID NOs:99 and 100, respectively.

An siRNA targeting the human transthyretin gene was used as a control siRNA, as it is not expected to cause a decrease in HBV markers of infection in serum.

The control monoclonal antibody (mAb) used in this example was an antibody specific for respiratory syncytial virus, and is not expected to cause a decrease in HBV markers of infection in serum.

The mice (C57BL/6 strain) were inoculated with the following amount of rAAV8-1.3HBV strain ayw, D type: $1.0 \times 10^{11}$ viral genomes per mouse in 200 µl volume via tail veins injection. Four weeks after viral inoculation, treatment with test compounds was initiated.

The dosing schedule is shown in FIG. 1. Entecavir was administered orally once per day. The HBV-specific siRNA was administered subcutaneously once at the start of the study, and the anti-HBV antibody was administered intraperitoneally twice per week, during weeks three and four of the study. A subset of the mice were sacrificed at week four, and the other subset was sacrificed at week six of the study.

Twice per week, viral load, HBsAg, and free HBC34 antibody were measured from serum samples. Measurements were also taken for serum HBeAg, serum alanine transferase (ALT), liver HBcAg, liver HBsAg, total HBV DNA in liver (by qPCR), and serum anti-HBV antibodies. Liver lymphocytes, splenocytes, and lymph nodes (portal/celiac versus inguinal) were assayed to determine the proportion of HBV-specific IFNg$^+$CD4$^+$ cells and IFNg$^+$CD8$^+$ cells.

The average HBsAg values for the treatment groups are shown in Table 5.

TABLE 5

HBsAg levels[a] from mouse serum following treatment with an HBV-specific siRNA, an anti-HBV antibody, and/or entecavir (EVT), or with controls.

| | \multicolumn{13}{c|}{Day Post-Dose} | | | | | | | | | | | | |
|---|---|---|---|---|---|---|---|---|---|---|---|---|---|
| | 0 | 3 | 7 | 10 | 14 | 17 | 21 | 24 | 28 | 31 | 35 | 38 | 42 |
| 1 | 4.55 | 3.99 | 3.67 | 3.59 | 3.71 | 3.69 | 3.60 | 3.57 | 3.57 | 3.81 | 3.72 | 3.72 | 3.55 |
|  | (0.06) | (0.11) | (0.08) | (0.05) | (0.08) | (0.11) | (0.18) | (0.21) | (0.25) | (0.15) | (0.30) | (0.33) | (0.35) |
| 2 | 4.64 | 4.58 | 4.46 | 4.42 | 4.34 | 3.87 | 4.09 | 3.65 | 4.15 | 4.29 | 4.25 | 4.26 | 4.28 |
|  | (0.04) | (0.09) | (0.21) | (0.22) | (0.25) | (0.15) | (0.13) | (0.16) | (0.11) | (0.32) | (0.31) | (0.28) | (0.20) |
| 3 | 4.49 | 4.37 | 4.44 | 4.35 | 4.30 | 4.28 | 4.32 | 4.26 | 4.23 | 3.99 | 3.99 | 4.08 | 4.05 |
|  | (0.03) | (0.16) | (0.11) | (0.09) | (0.12) | (0.08) | (0.11) | (0.08) | (0.14) | (0.30) | (0.29) | (0.23) | (0.24) |
| 4 | 4.50 | 4.46 | 4.42 | 4.37 | 4.40 | 4.31 | 4.31 | 4.38 | 4.29 | 4.15 | 4.16 | 4.09 | 4.08 |
|  | (0.04) | (0.07) | (0.06) | (0.05) | (0.04) | (0.04) | (0.06) | (0.06) | (0.06) | (0.24) | (0.27) | (0.38) | (0.38) |
| 5 | 4.51 | 4.36 | 4.31 | 4.17 | 4.26 | 4.17 | 4.23 | 4.25 | 4.20 | 4.26 | 4.38 | 4.38 | 4.30 |
|  | (0.08) | (0.13) | (0.21) | (0.26) | (0.22) | (0.20) | (0.18) | (0.12) | (0.11) | (0.12) | (0.07) | (0.08) | (0.01) |
| 6 | 4.56 | 3.94 | 3.54 | 3.45 | 3.50 | 2.01 | 1.85 | 1.95 | 1.95 | 1.69 | 2.99 | 3.80 | 3.99 |
|  | (0.06) | (0.09) | (0.18) | (0.21) | (0.19) | (0.12) | (0.08) | (0.11) | (0.12) | (0.13) | (0.67) | (0.19) | (0.24) |
| 7 | 4.53 | 3.96 | 3.56 | 3.51 | 3.47 | 3.36 | 3.45 | 3.49 | 3.46 | 3.80 | 3.82 | 3.98 | 3.96 |
|  | (0.07) | (0.15) | (0.18) | (0.18) | (0.22) | (0.25) | (0.30) | (0.29) | (0.36) | (0.27) | (0.36) | (0.32) | (0.31) |
| 8 | 4.57 | 3.99 | 3.44 | 3.38 | 3.34 | 2.03 | 1.86 | 1.82 | 1.81 | 2.26 | 3.57 | 3.87 | 3.85 |
|  | (0.06) | (0.15) | (0.26) | (0.27) | (0.29) | (0.18) | (0.13) | (0.12) | (0.13) | (0.18) | (0.40) | (0.43) | (0.44) |
| 9 | 4.51 | 3.94 | 3.52 | 3.51 | 3.58 | 2.43 | 2.91 | 3.27 | 3.73 | 3.87 | 3.93 | 3.94 | 3.94 |
|  | (0.10) | (0.19) | (0.19) | (0.20) | (0.21) | (0.30) | (0.34) | (0.16) | (0.15) | (0.22) | (0.18) | (0.17) | (0.19) |
| 10 | 4.68 | 4.10 | 3.72 | 3.57 | 3.61 | 3.80 | 3.92 | 3.95 | 4.03 | 3.79 | 3.73 | 3.77 | 3.87 |
|  | (0.06) | (0.13) | (0.21) | (0.25) | (0.21) | (0.05) | (0.06) | (0.05) | (0.07) | (0.30) | (0.45) | (0.35) | (0.31) |
| 11 | 4.60 | 4.01 | 3.65 | 3.62 | 3.65 | 3.68 | 3.75 | 3.71 | 3.54 | 3.27 | 3.32 | 3.24 | 3.26 |
|  | (0.03) | (0.09) | (0.10) | (0.06) | (0.08) | (0.07) | (0.07) | (0.09) | (0.16) | (0.44) | (0.47) | (0.53) | (0.51) |
| 12 | 4.46 | 4.40 | 4.41 | 4.35 | 4.22 | 4.03 | 3.89 | 3.87 | 3.85 | 3.76 | 3.96 | 3.87 | 3.83 |
|  | (0.07) | (0.09) | (0.11) | (0.10) | (0.15) | (0.22) | (0.24) | (0.25) | (0.20) | (0.31) | (0.21) | (0.12) | (0.15) |
| 13 | 4.54 | 4.54 | 4.39 | 4.29 | 4.28 | 4.24 | 4.13 | 4.21 | 3.98 | 4.02 | 3.88 | 3.92 | 3.84 |
|  | (0.06) | (0.04) | (0.08) | (0.15) | (0.21) | (0.20) | 0.19 | (0.14) | (0.24) | (0.24) | (0.29) | (0.25) | (0.29) |
| 14 | 4.54 | 4.54 | 4.51 | 4.47 | 4.40 | 4.37 | 4.39 | 4.44 | 4.32 | 4.50 | 4.52 | 4.56 | 4.51 |
|  | (0.05) | (0.05) | (0.07) | (0.05) | (0.12) | (0.16) | 0.15 | (0.13) | (0.16) | (0.13) | (0.10) | (0.07) | (0.07) |

[a] Average log [HBsAg content (IU/ml)] (standard error).

Figure 2A:
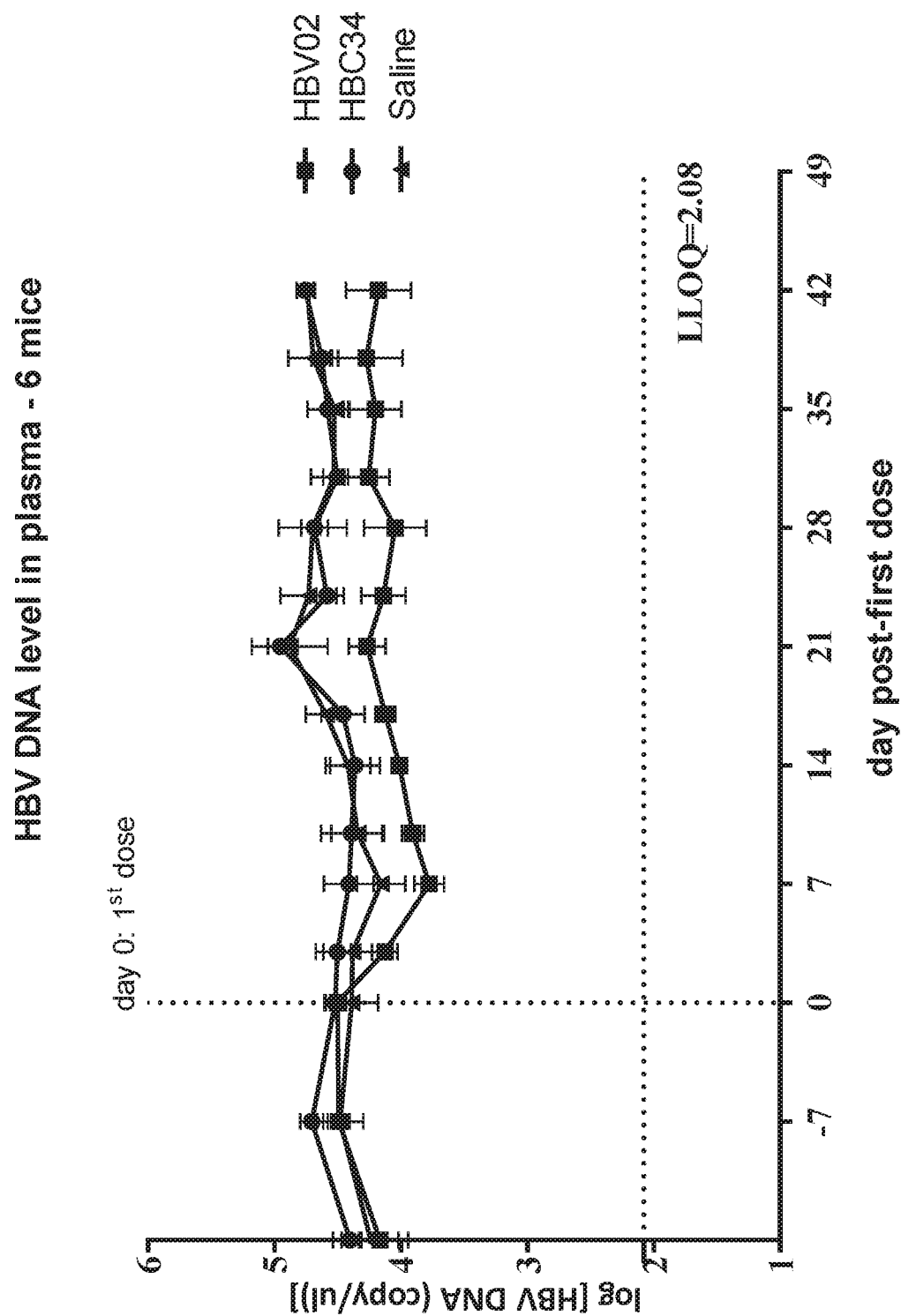
Figure 2B:
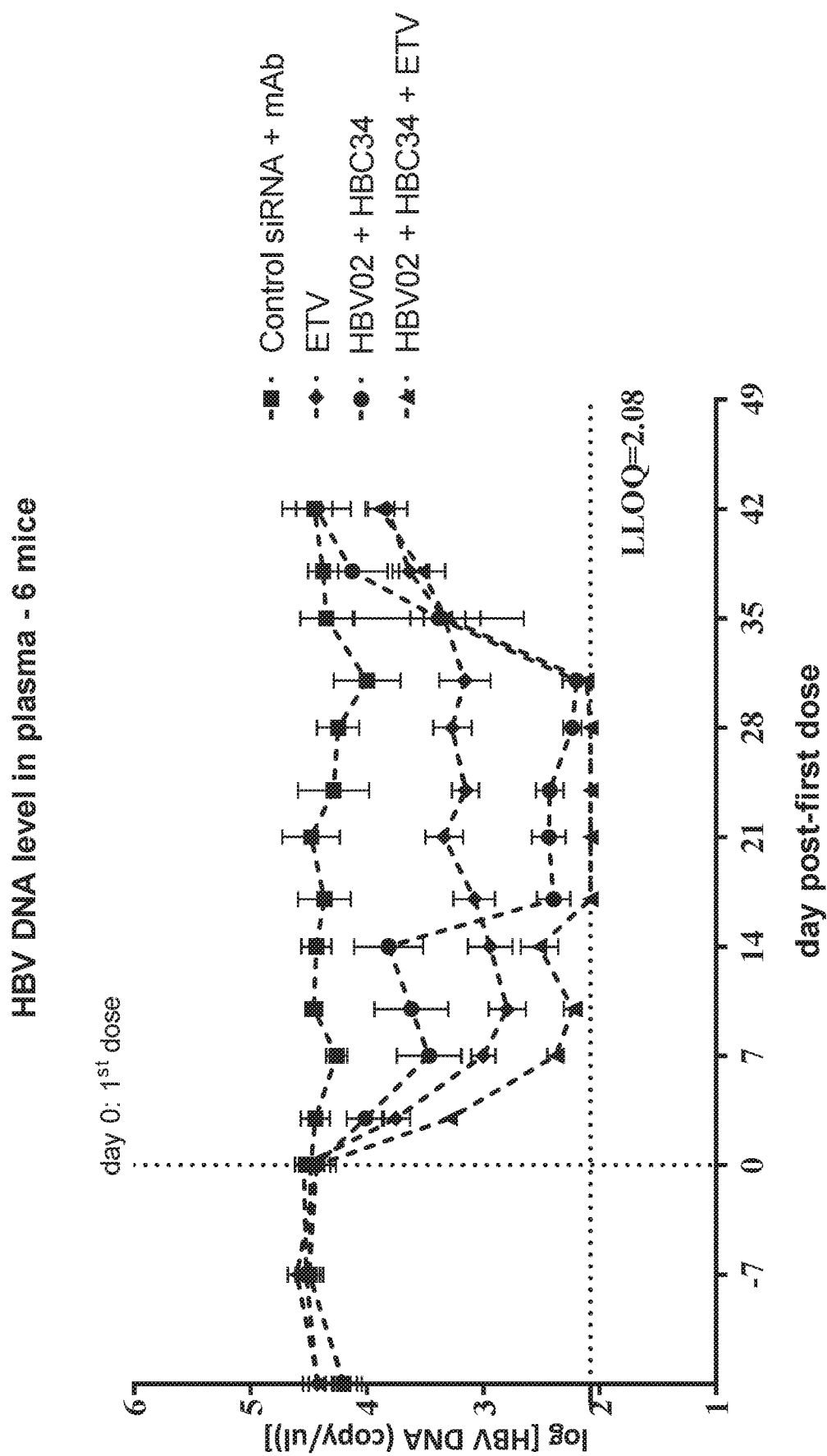
Figure 3A:
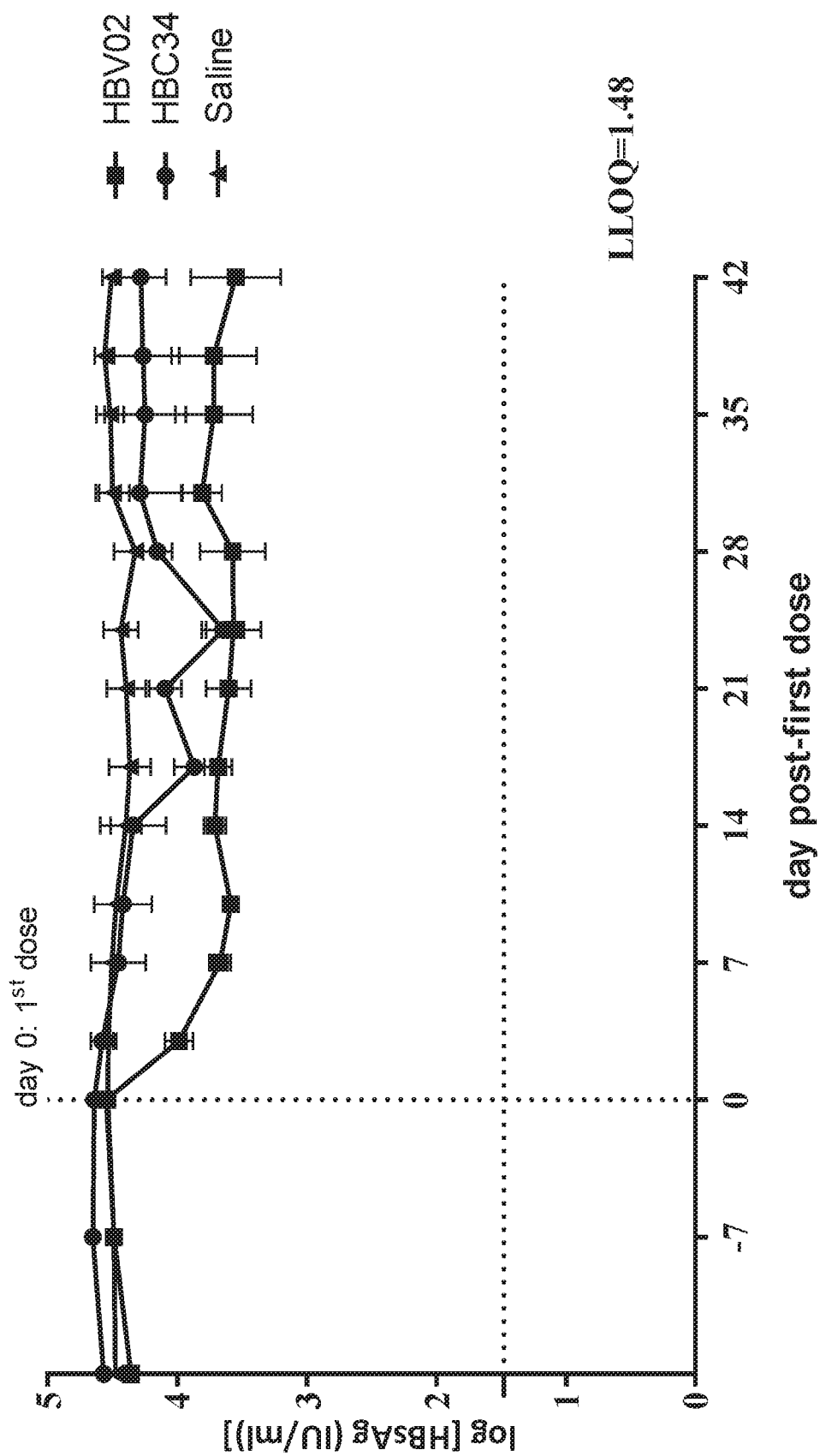
Figure 3B:
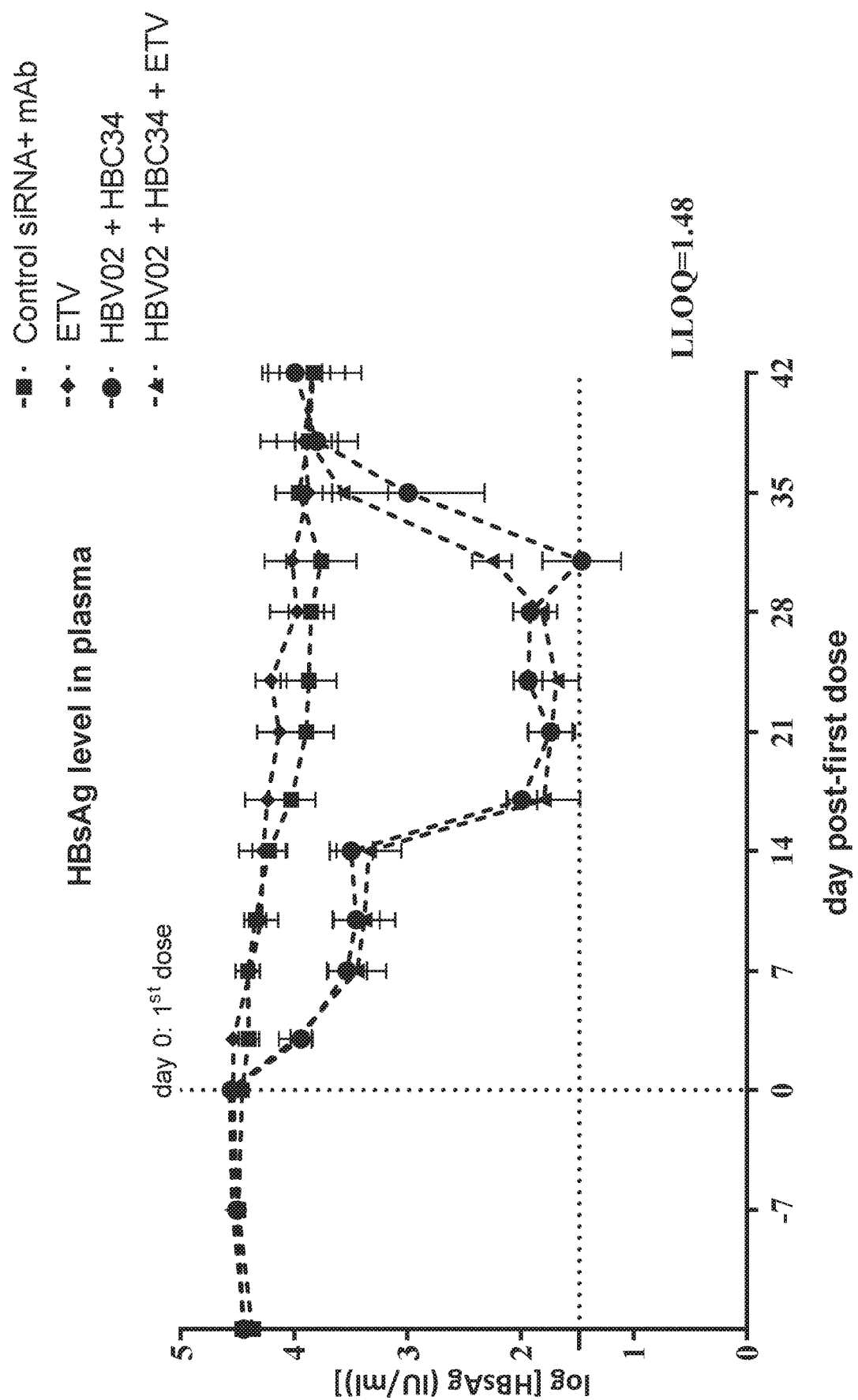

FIGS. 2A and 2B show the viral load as measured by HBV DNA copy number, and FIGS. 3A and 3B show serum HBsAg levels. FIGS. 2A and 3A, respectively, show viral load and HBsAg levels when the HBV02 siRNA or the HBC34 antibody (at 15 mg/kg) were each administered alone. The HBV02 siRNA reduced serum HBV DNA and HBsAg by ~0.5-$\log_{10}$ and 1-$\log_{10}$, respectively, relative to the saline control. The HBC34 antibody alone had no effect on HBV DNA and reduced serum HBsAg by <1-$\log_{10}$ relative to the saline control. FIGS. 2B and 3B demonstrate that treatment with both the HBV02 siRNA and the HBC34 antibody (at 15 mg/kg) reduced viral load and HBsAg levels by ~3-$\log_{10}$, relative to the saline control. The reduction of serum HBV DNA and HBsAg were significantly stronger when the HBV02 siRNA and the HBC34 antibody were used in combination relative to treatment with either molecule individually, and the combinatorial effect exceeded the sum of the effects of the monotherapies. The combination therapy also reduced viral load and HbsAg levels more than treatment with entecavir alone. The effects of the combination of the HBV02 siRNA and the HBC34 antibody were observed regardless of whether entecavir was also administered. These results demonstrate that the HBV02 siRNA and the HBC34 antibody have the potential to act synergistically in reducing viral load and HBsAg, and this effect is independent of entecavir treatment.

Figure 4:
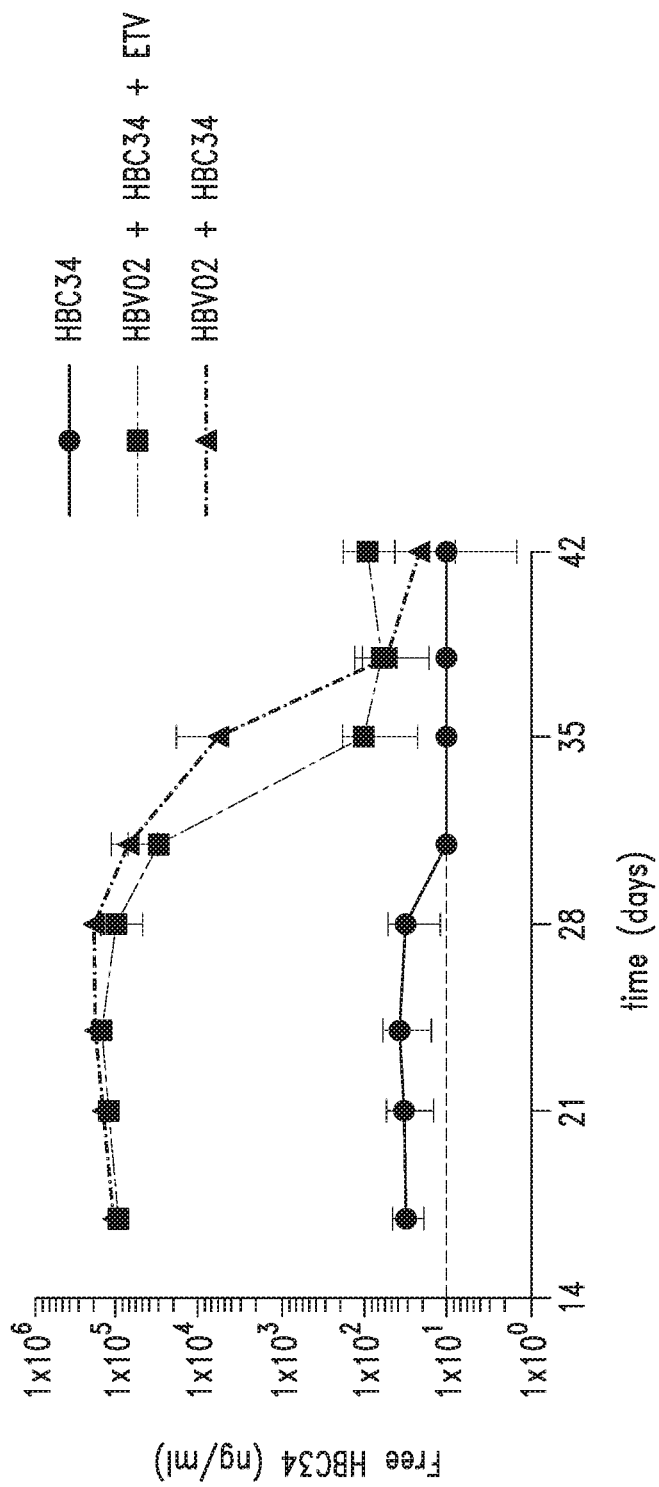

FIG. 4 depicts the free HBC34 antibody levels measured between 14 days and 42 days following initiation of the study on Day 1 (Day 1=siRNA administration to select treatment groups). Relative to treatment with HBC34 alone, treatment with the HBV02 siRNA and the HBC34 antibody combination resulted in much higher initial free antibody levels, which were maintained for more than 28 days, regardless of whether the treatment included entecavir. The results shown in FIG. 4, taken together with the viral load and serum HBsAg levels, indicate that the effects of treatment are dependent on the amount of free circulating HBC34 antibody, and that lower doses the antibody may become effective as HBsAg load decreases. For example, a combination therapy may allow for effective treatments with: fewer doses of antibody, lower doses of antibody, and/or less invasive administration routes (e.g., subcutaneous instead of intravenous), based at least in part on the reduction of HBsAg load prior to antibody treatment.

In summary, this study demonstrates that administering an siRNA targeting HBV and then administering an antibody targeting HBV effectively decreases serum HBV DNA and HBsAg. Moreover, the individual components appear to interact synergistically, such that the effect of this combination therapy is greater than for each component alone and greater than that which would be expected if the effects were merely additive. Finally, the results suggest that administration of the siRNA reduces serum HBsAg, allowing the antibody to be more effective.

Example 2

Combination Therapy with One of Two Anti-HBV Antibodies and an HBV-Targeting siRNA To determine whether an siRNA-antibody combination therapy using an siRNA and the anti-HBV antibody HBC24 is effective in treating HBV infections, AAV/HBV-infected C57BL/6 mice were administered one of eleven different treatments: (1) an HBV-specific siRNA (HBV02, having an antisense strand of SEQ ID NO:8; see description in Example 1); (2)-(3) an anti-HBV antibody (a fully murinized HBC24), at one of two doses; (4)-(5) the HBV02 siRNA at one dose, and the fully murinized HBC24 at one of two doses; (6-9) the HBV02 siRNA at one of two doses, and a fully murinized anti-HBV antibody HBC34 (HBC34-v35-mu-IgG2a), at one of three antibody doses; (10) a control siRNA and a control antibody; or (11) PBS only, administered intraperitoneally (see Table 6).

TABLE 6

Treatment levels and dosages for Example 2.

| Treatment | HBV02 (mg/kg) | HBC24 (mg/kg) | HBC34v35 (mg/kg) | Control siRNA (mg/kg) | Control mAb (mg/kg) | PBS |
|---|---|---|---|---|---|---|
| 1 | 3 | — | — | — | — | — |
| 2 | — | 15 | — | — | — | — |
| 3 | — | 5 | — | — | — | — |
| 4 | 3 | 15 | — | — | — | — |
| 5 | 3 | 5 | — | — | — | — |
| 6 | 3 | — | 15 | — | — | — |
| 7 | 9 | — | 15 | — | — | — |
| 8 | 9 | — | 5 | — | — | — |
| 9 | 9 | — | 1 | — | — | — |
| 10 | — | — | — | 3 | 15 | — |
| 11 | — | — | — | — | — | X |

The HBC24 and HBC34 antibodies used in this experiment are fully murinized with the exception of the part of the Fab fragment that binds the HBV surface antigen. The human HBC24 has a $V_H$ amino acid sequence as set forth in SEQ ID NO:75 and a $V_L$ amino acid sequence as set forth in SEQ ID NO:76. The murinized version of HBC24 sequences used in the antibody for this experiment had heavy chain and light chains comprising the amino acid sequences set forth in SEQ ID NOs:103 and 104, respectively. The HBC34 antibody was a murinized HBC34v35 variant, HBC34-v35-mu-IgG2a. The human HBC34v35 has a heavy chain amino acid sequence as set forth in SEQ ID NO:70 and a light chain amino acid sequence as set forth in SEQ ID NO:73. The murinized version of HBC34v35 sequences used in the HBC34-v35-mu-IgG2a antibody for this experiment had heavy chain and light chains comprising the amino acid sequences set forth in SEQ ID NOs:101 and 102, respectively.

The control siRNA targets the human transthyretin gene, and is not expected to cause a decrease in HBV markers of infection in serum.

The control monoclonal antibody (mAb) was an antibody specific for respiratory syncytial virus, which is not expected to cause a decrease in HBV markers of infection in serum.

Treatments were administered to a WuXi immunocompromised HBV mouse. This murine model is generated by transduction of hepatocytes in immunocompetent mice with adeno-associated virus containing HBV genome. Using this model, HBV protein production is under the control of endogenous HBV promoters, and the mice develop HBV-specific cellular and humoral T cell responses. However, no HBV infection occurs, no cccDNA is produced, replication is transient, and the immune response is hampered by vector-driven interference.

The mice (C57BL/6 strain) were inoculated with rAAV8-1.3HBV strain ayw, D type, by injecting the tail vein with a 200 µl volume containing $1.0 \times 10^{11}$ viral genomes per mouse.

Each treatment group included five mice. The HBV-specific siRNA were administered subcutaneously once at the start of the study, and the anti-HBV antibodies were administered intraperitoneally twice per week, during weeks two and three of the study. The mice were sacrificed at week six of the study.

Serum samples were collected periodically throughout the study, and viral load, HBsAg, and free HBC34 antibody were measured. Measurements were also taken for serum HBeAg, serum alanine transferase (ALT), liver HBcAg, liver HBsAg, total HBV DNA in liver (by qPCR), and serum anti-HBV antibodies. Liver lymphocytes, splenocytes, and lymph nodes (portal/celiac versus inguinal) were assayed to determine the proportion of HBV-specific IFNg$^+$CD4$^+$ cells and IFNg$^+$CD8$^+$ cells.

Figure 5A:
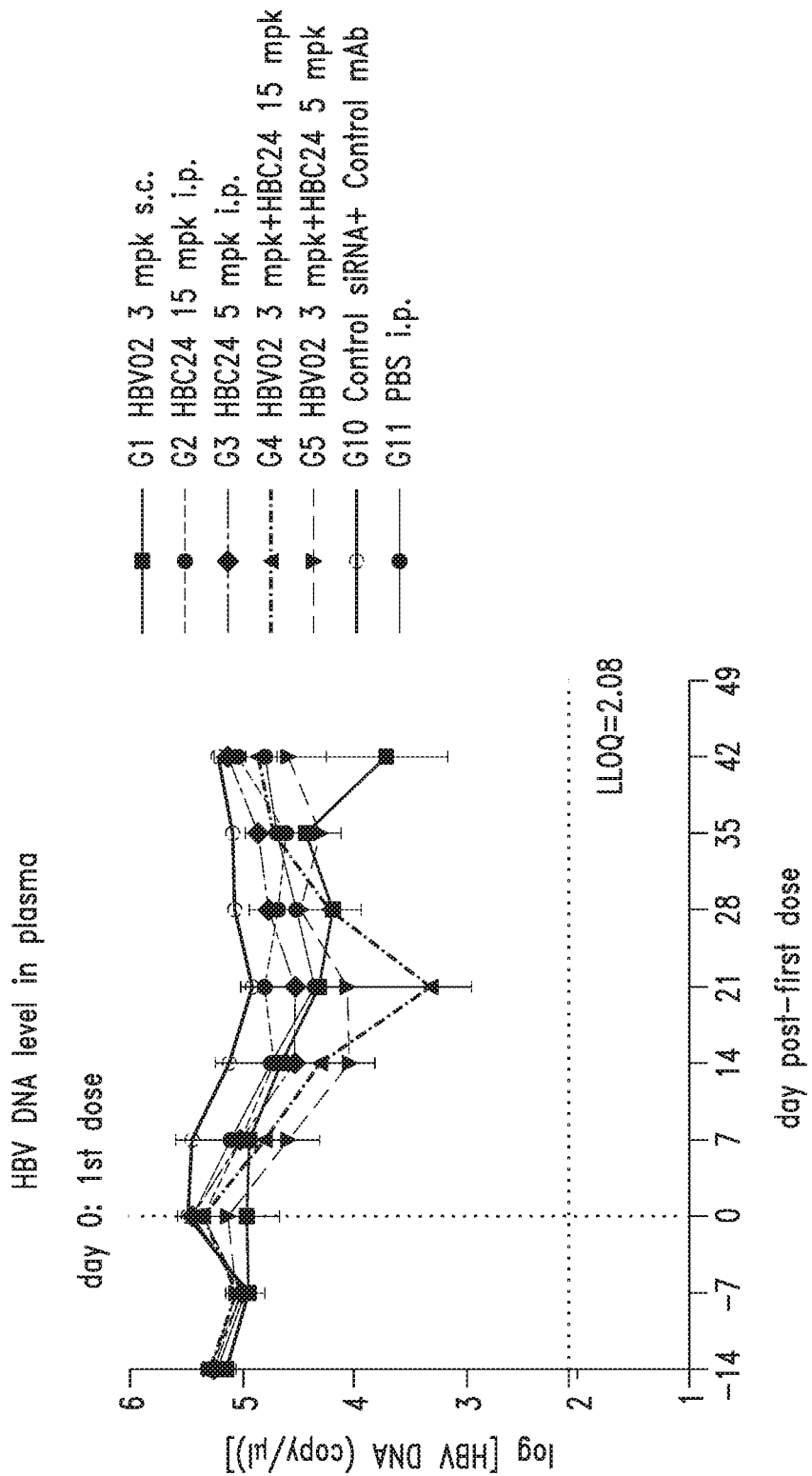
Figure 5B:
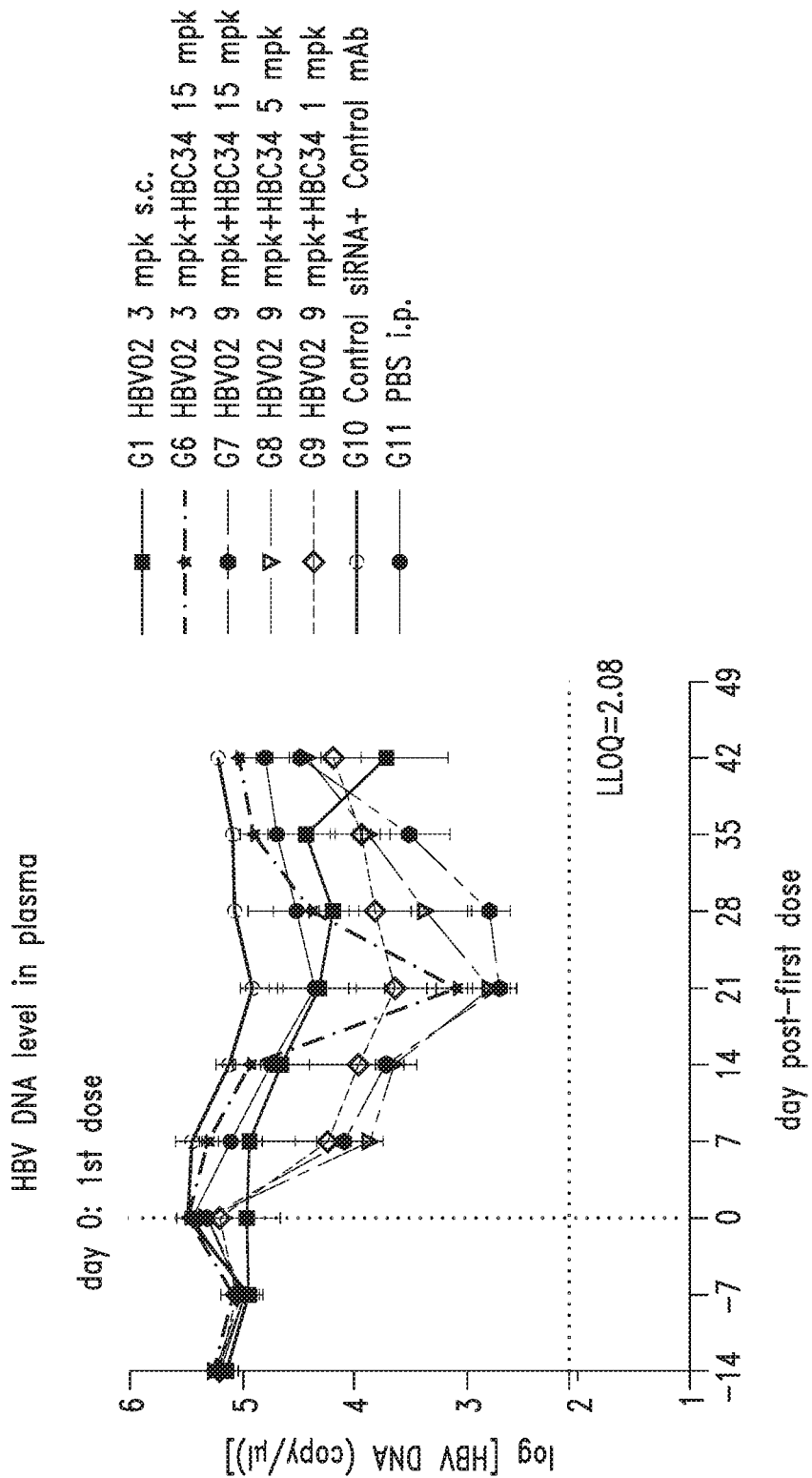
Figure 6A:
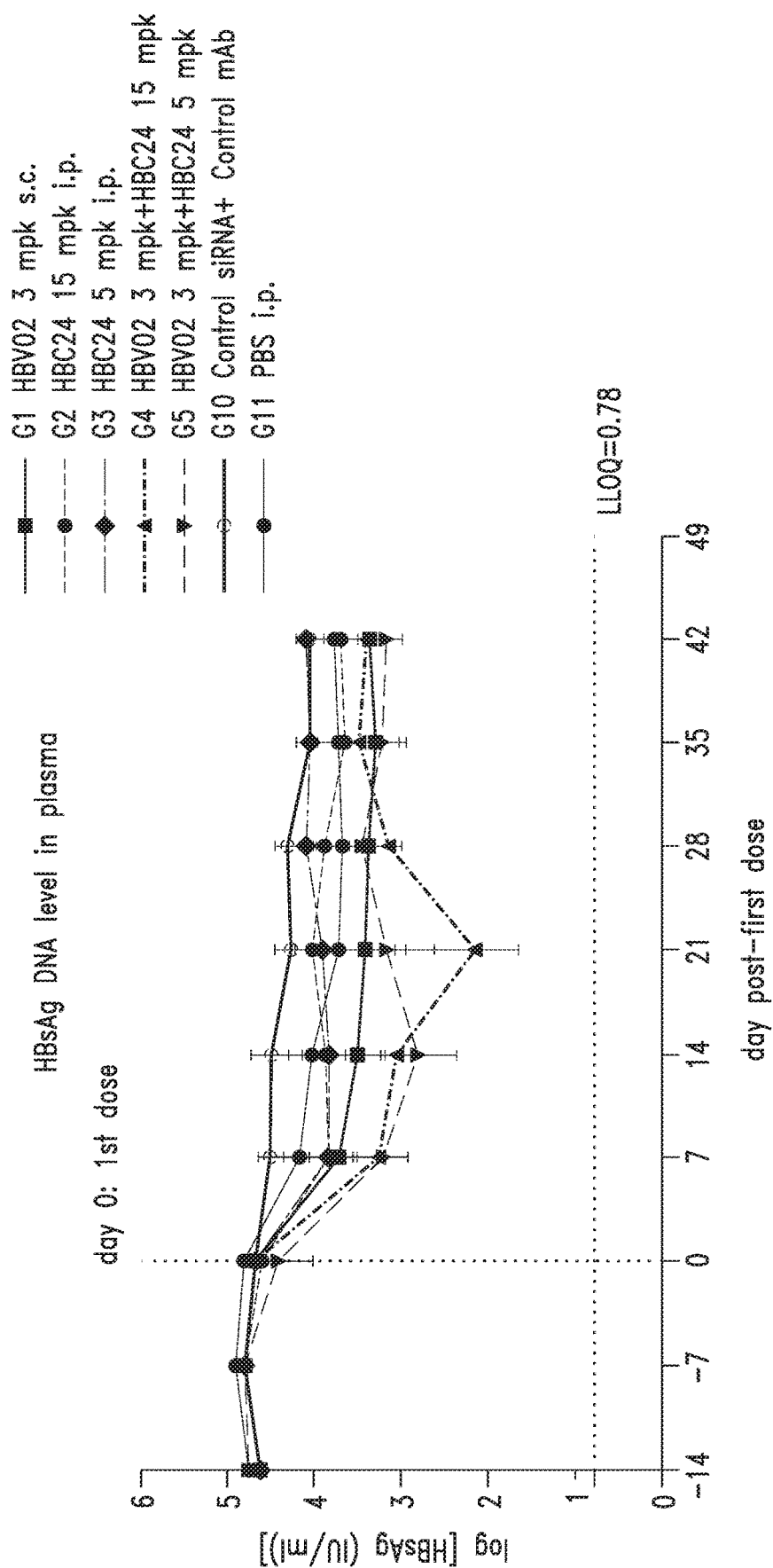
Figure 6B:
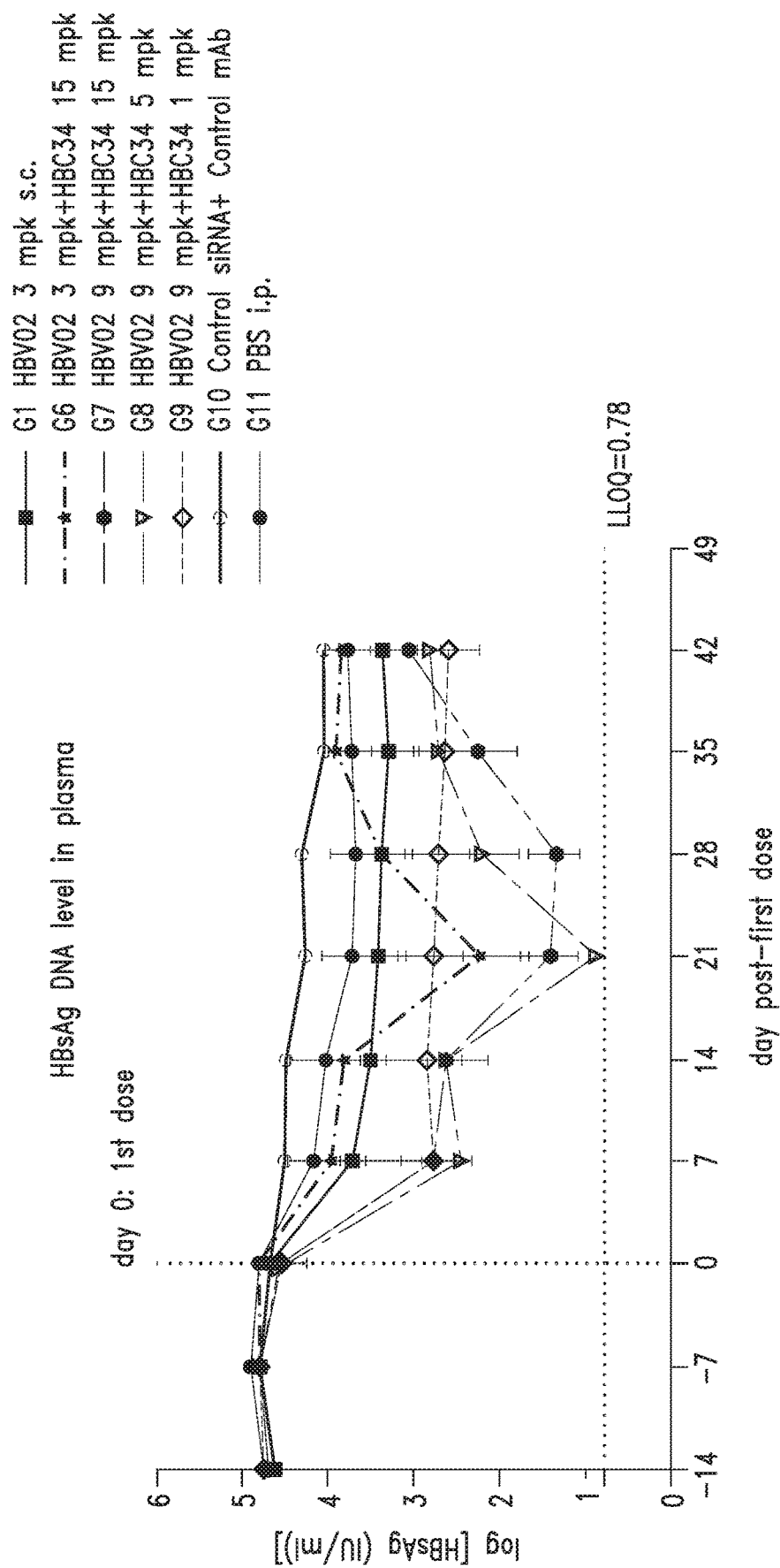
Figure 7A:
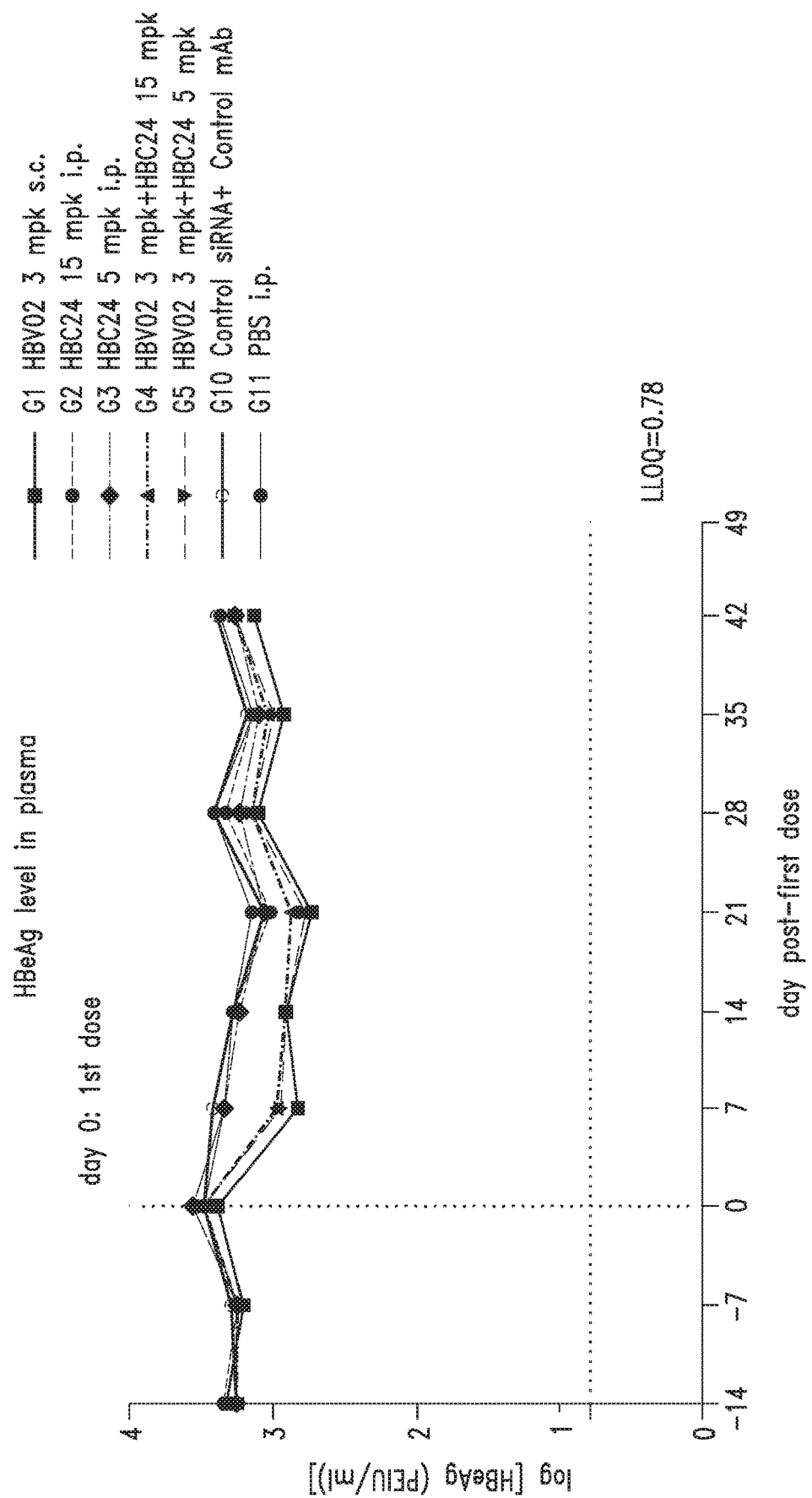
Figure 7B:
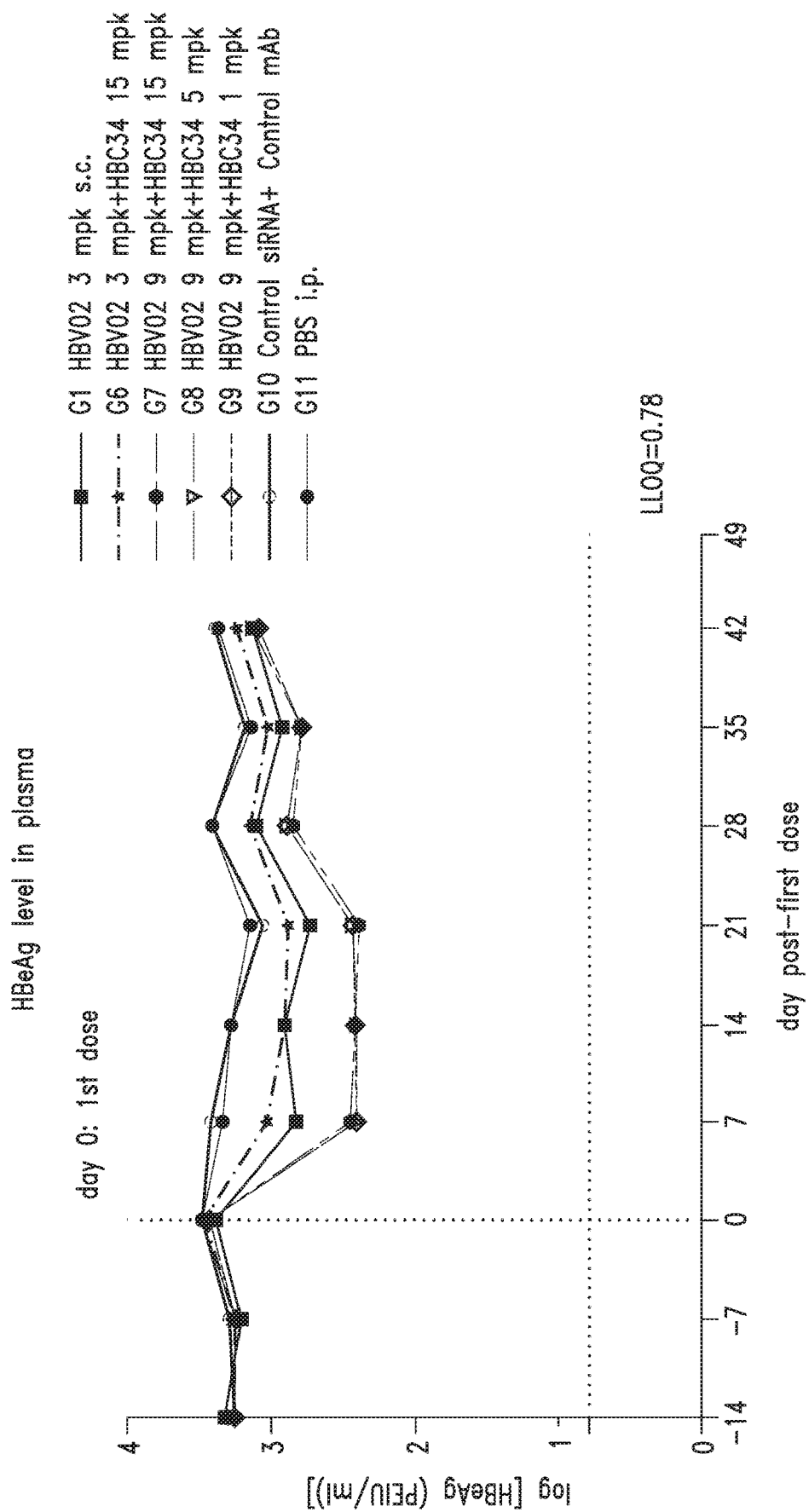

The results of the experiment are shown in FIGS. 5A and 5B (serum HBV DNA concentration), FIGS. 6A and 6B (serum HBsAg concentration), and FIGS. 7A and 7B (serum HBeAg concentration). Serum HBV DNA concentration, HBsAg concentration, and HBeAg concentration were lower for mice treated with HBV02 and one of the anti-HBV antibodies relative to mice treated with the siRNA alone or with controls. This effect was observed for both the HBC34 and HBC24 antibodies. Additionally, the effect was greater at higher doses of HBV02, and when higher doses of HBV02 were used, a reduction in HBsAg was achieved at lower antibody doses. These results provide further evidence that combination treatment using HBV02 and a monoclonal antibody targeting HBV reduces HBsAg, and HBeAg more than HBV02 monotherapy. These results also indicate that higher doses of siRNA prior to administration of the antibody can provide a similar decrease in HBsAg at lower doses of antibody.

Example 3

Serum Clearance of HBsAG and Viral Entry Inhibition in a Mouse Model

An immune-deficient mouse having transplanted human hepatocytes was used to test the effectiveness of a combination therapy with an HBV-specific siRNA and an anti-HBV antibody in clearing HBsAg. The PXB-Mouse® model (PhoenixBio, Japan) uses the uPA/SCID mouse to generate mice with ≥70% repopulation of the mouse liver with human hepatocytes (Ohshita H and Tateno C, Methods Mol Biol. 1506:91-100, (2017)). Unlike the AAV-HBV model, cccDNA is established and intrahepatic spread of HBV can occur.

Primary human hepatocytes were transplanted into SCID mice for which mouse hepatocytes had previously been destroyed enzymatically. The mice were T- and B-cell deficient. This model is useful for studying HBV infection including entry, spreading, cccDNA regulation, hepatocyte-intrinsic immune responses, and viral integration into host genome. This model can also be used to study the effect of human IFNa on infection. However, this model does not include the induction of an adaptive immune response. Mice were inoculated via tail vein injection with HBV genotype C at $1.0 \times 10^7$ viral genomes per mouse. Treatments began eight weeks post-infection.

Figure 8:
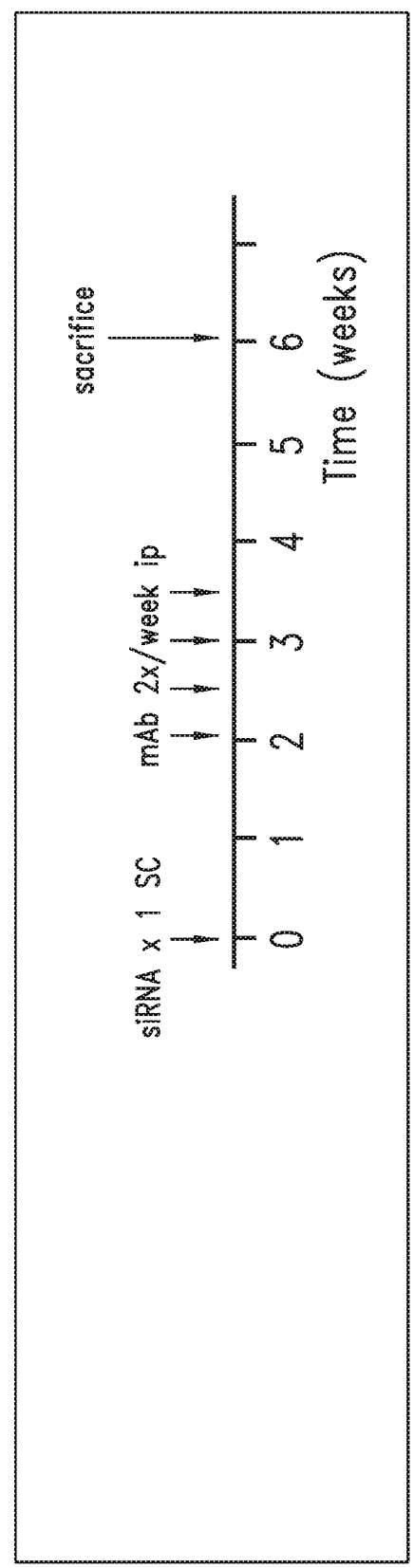

HBV-infected mice (n=4 per treatment group) were administered one of seven different treatments: (1) PBS only; (2-4) an anti-HBV antibody (a fully murinized HBC34v35 antibody, HBC34-v35-mu-IgG2a), at one of three doses, administered intraperitoneally twice per week during weeks two and three; or (5-7) an HBV-specific siRNA (HBV02, having an antisense strand of SEQ ID NO:8; see description in Example 1) administered subcutaneously once at the beginning of the study, and the fully murinized HBC34v35, at one of three antibody doses, administered intraperitoneally twice per week during weeks two and three (see Table 7). Mice were sacrificed at week 6. The study design is also shown in FIG. 8.

TABLE 7

Treatment levels and dosages.

| Treatment | n | HBV02 (mg/kg) | HBC34 v35 mg/kg | PBS |
|---|---|---|---|---|
| 1 | 4 | — | — | X |
| 2 | 4 | — | 1 | — |
| 3 | 4 | — | 5 | — |
| 4 | 4 | — | 15 | — |
| 5 | 4 | 3 | 1 | — |
| 6 | 4 | 3 | 5 | — |
| 7 | 4 | 3 | 15 | — |

The HBC34 antibody used in this experiment, HBC34v35, was fully murinized with the exception of the part of the Fab fragment that binds the HBV surface antigen. The human HBC34v35 has a heavy chain amino acid sequence as set forth in SEQ ID NO:70 and a light chain amino acid sequence as set forth in SEQ ID NO:73. The murinized version of HBC34v35 sequences used in the HBC34-v35-mu-IgG2a antibody for this experiment had heavy chain and light chains comprising the amino acid sequences set forth in SEQ ID NOs:101 and 102, respectively.

Serum samples were collected periodically throughout the study, and viral load, HBsAg, and free HBC34 antibody were measured. Measurements were also taken for serum HBeAg, serum alanine transferase (ALT), liver HBcAg, liver HBsAg, total HBV DNA in liver (by qPCR), and serum anti-HBV antibodies. Liver lymphocytes, splenocytes, and lymph nodes (portal/celiac versus inguinal) were assayed to determine the proportion of HBV-specific IFNg$^+$CD4$^+$ cells and IFNg$^+$CD8$^+$ cells.

Figure 9:
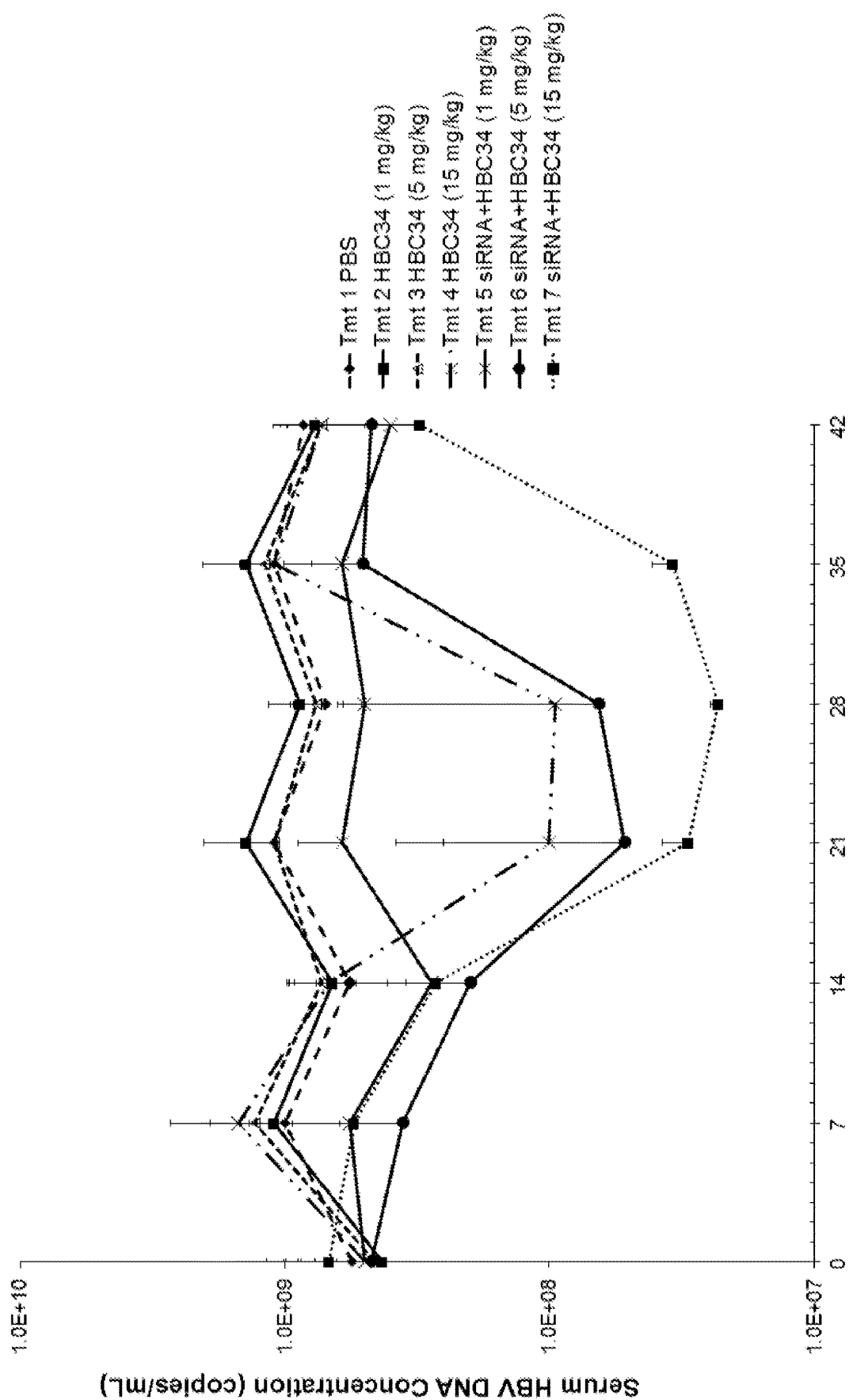
FIG. 9 shows serum HBV DNA concentration in mice in SCID mice with transplanted primary human hepatocytes after treatment with PBS (control); HBC34v35 antibody; or HBV34v35 antibody and HBV02 siRNA.
Figure 10:
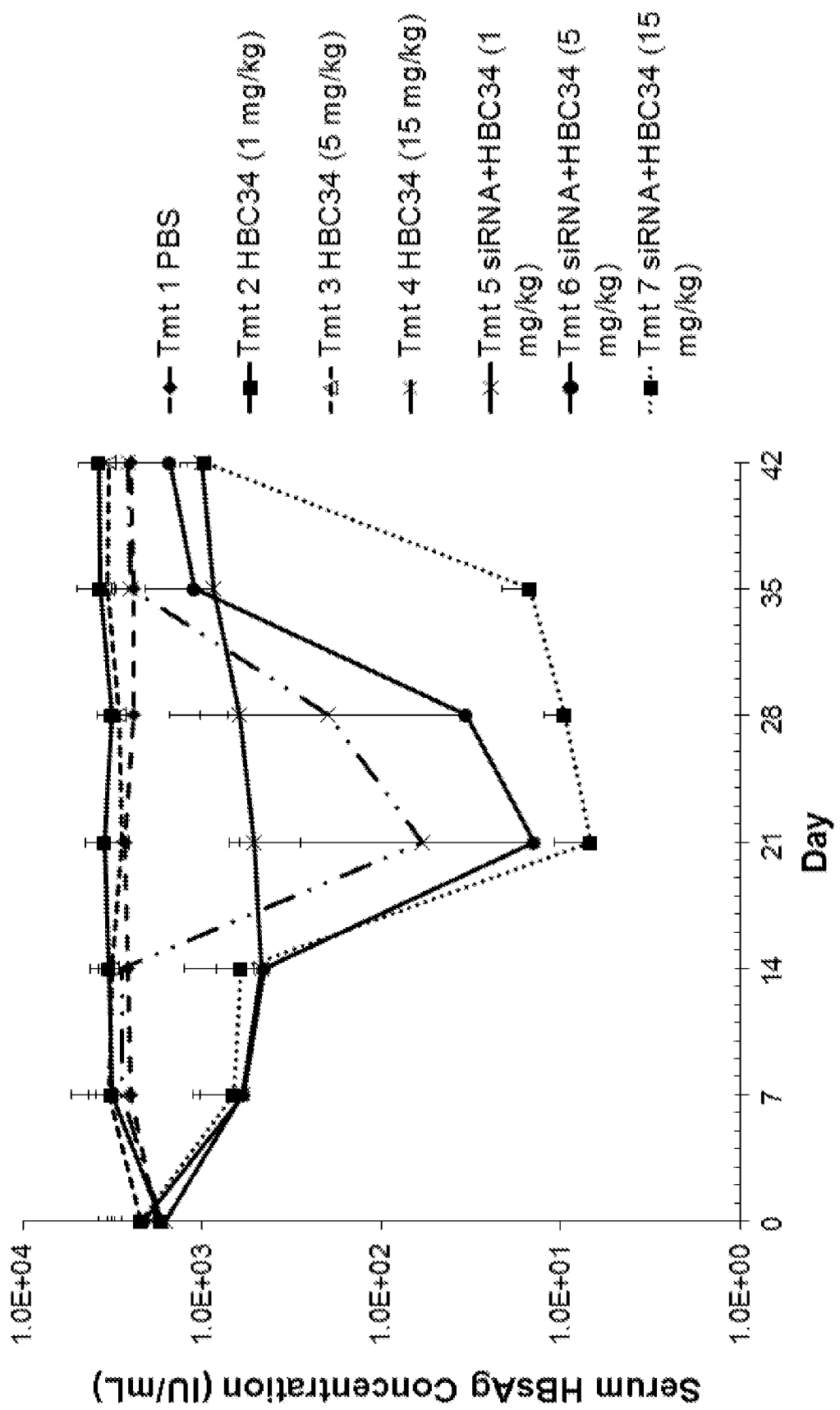
FIG. 10 shows serum HBsAg concentration in mice in SCID mice with transplanted primary human hepatocytes after treatment with PBS (control); HBC34v35 antibody; or HBV34v35 antibody and HBV02 siRNA.
Figure 11:
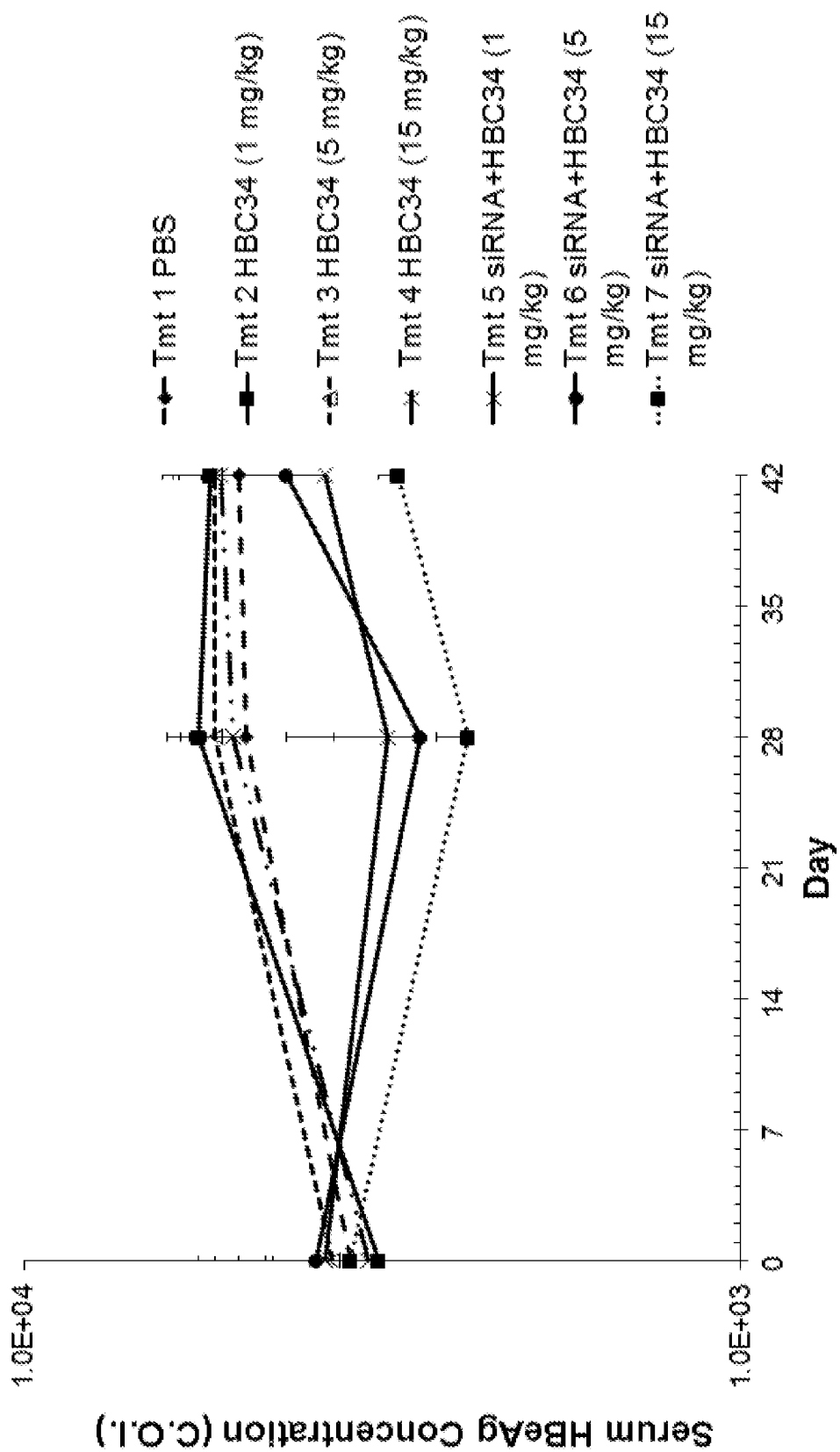
FIG. 11 shows serum HBeAg concentration in mice in SCID mice with transplanted primary human hepatocytes after treatment with PBS (control); HBC34v35 antibody; or HBV34v35 antibody and HBV02 siRNA.
Figure 12:
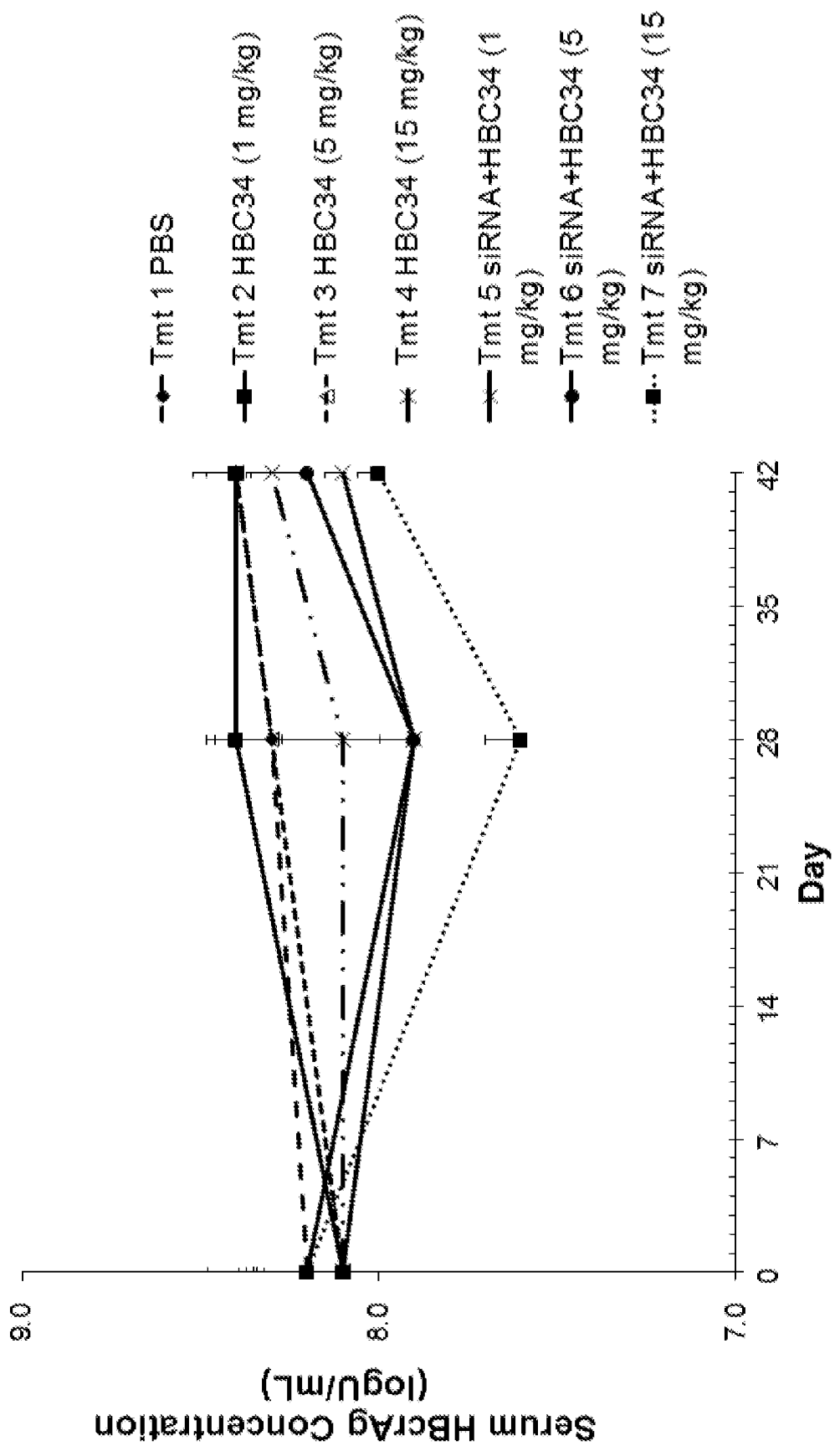
FIG. 12 shows serum HBcrAg concentration in mice in SCID mice with transplanted primary human hepatocytes after treatment with PBS (control); HBC34v35 antibody; or HBV34v35 antibody and HBV02 siRNA.

Administering the combination of siRNA and anti-HBV antibody reduced serum HBV DNA concentration (FIG. 9) and serum HBsAg concentration (FIG. 10) relative to administration of the antibody at the same dose. Similar trends were observed for serum HBeAg concentration (FIG. 11) and serum HBcrAg concentration (FIG. 12). Additionally, in this model system, the antibody also functions as an inhibitor for viral entry into hepatocytes; serum HBV DNA concentration (FIG. 9) and serum HBsAg concentration (FIG. 10) were also lower when the HBC34 antibody was administered as a monotherapy (i.e., not in combination with the siRNA) at 15 mg/kg.

This study provides experimental support in an authentic infection model that the HBV02 siRNA and an HBC34 antibody, when administered in combination, decrease HBV DNA and HBsAg levels to a greater extent than HBC34 monotherapy.

Example 4

Clinical Evaluation of an siRNA-Antibody Combination Therapy to Treat Chronic HBV Infection A Phase 2 clinical study of an siRNA-antibody combination therapy is conducted to evaluate the efficacy of the combination therapy in human patients with chronic HBV infection. Table 8 shows the treatment regimens for the study. The study may include additional cohorts to test the effects of additional therapeutics on the combination therapy (e.g., nine cohorts, if two additional therapeutics are tested). Each group/cohort includes fifteen patients.

TABLE 8

Treatment levels and dosages for clinical trial.

| Group/Cohort (n) | NUCs | HBV02 | HBC34 | Additional therapeutic | Additional therapeutic |
|---|---|---|---|---|---|
| 1 (n = 15) | yes | yes | — | yes | |
| 2 (n = 15) | yes | yes | low | yes | |
| 3 (n = 15) | yes | yes | high | yes | |
| 4 (n = 15) | yes | yes | low | — | |
| 5 (n = 15) | yes | yes | high | — | |
| 6 (n = 15) | yes | yes | low | — | yes |
| 7 (n = 15) | yes | yes | high | — | yes |

Figure 13:
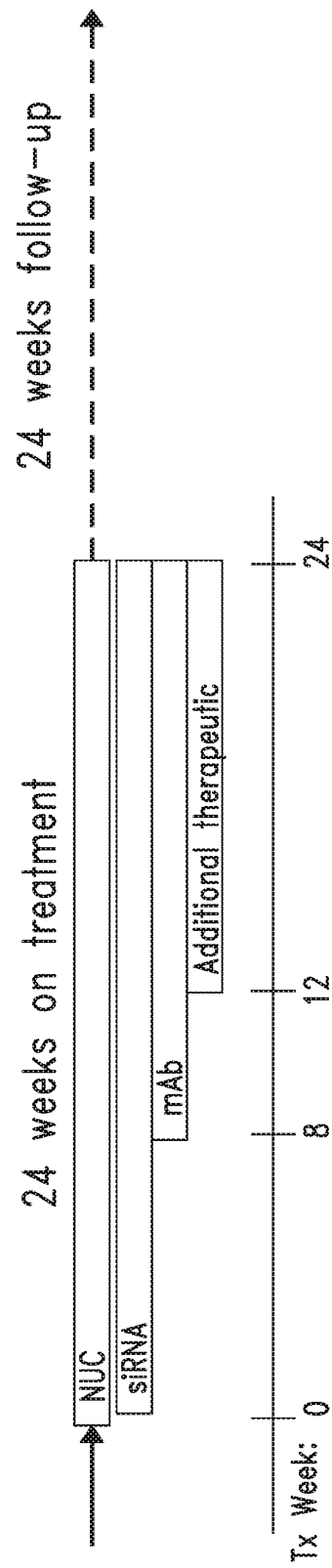
FIG. 13 depicts a treatment schedule designed for a Phase 2 study for evaluating the efficacy of an siRNA-antibody combination therapy in treating HBV.

FIG. 13 shows a treatment schedule designed for the Phase 2 study. The study includes twenty-four weeks of treatment, and twenty-four weeks of follow-up. All patients are non-cirrhotic and NUC suppressed (treated with a nucleot(s)ide analog) upon entering the study. All patient cohorts may receive NUC therapy throughout the study (e.g., tenofivir or entecavir administered orally, daily). The study begins with all cohorts receiving an eight-week lead-in treatment with the HBV02 siRNA. The doses of HBV02 may be, for example, two doses of 400 mg administered subcutaneously, every four weeks. However, an appropriate dose can be determined by a monotherapy trial prior to the Phase 2 trial. After eight weeks of the study, all cohorts continue treatment with HBV02; cohorts 2, 4, and 6 begin treatment with a low dose of an HBC34 antibody (HBC34v35); cohorts 3, 5, and 7 begin treatment with a higher dose of HBC34 antibody; and cohort 1 does not receive the HBC34 antibody treatment. The low dose of HBC34v35 may be, for example, 0.5 grams administered intravenously, every two weeks; and the higher dose may be, for example, 2 grams administered intravenously, every two weeks. Appropriate doses can be verified with a monotherapy trial prior to the Phase 2 trial. During week twelve of the study, cohorts 1-3 may receive an additional therapeutic, once per week. Additionally, some cohorts (e.g., cohorts 6 and 7) may receive yet another therapeutic. After 24 weeks of treatment, patients are monitored and evaluated to determine if a functional cure was achieved, indicated by a loss of detectable serum HBsAg and/or anti-HBs seroconversion.

While specific embodiments have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications, and non-patent publications referred to in this specification, or listed in the Application Data Sheet, including U.S. Provisional Patent Application No. 62/782, 896 filed Dec. 20, 2018 and International Application No. PCT/US2019/067643 filed Dec. 19, 2019, are incorporated herein by reference, in their entirety, unless otherwise stated. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

That which is claimed is:

1. A method of treating chronic hepatitis B virus (HBV) infection or a HBV-associated disease in a subject in need thereof, comprising:

administering to the subject an agent that reduces HBV antigenic load or inhibits HBV gene expression, wherein the agent that reduces HBV antigenic load or inhibits HBV gene expression is an siRNA that inhibits expression of an HBV transcript, the siRNA having a sense strand comprising 5'-gsusguGfcAfCfUfucgcuu-cacaL96-3' (SEQ ID NO:7) and an antisense strand comprising 5'-usGfsuga(Agn) gCfGfaaguGfcAfcacsusu-3' (SEQ ID NO:8), wherein:

(i) a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

(ii) Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

(iii) (Agn) is adenosine-glycol nucleic acid (GNA);

(iv) s is a phosphorothioate linkage; and (v) L96 is

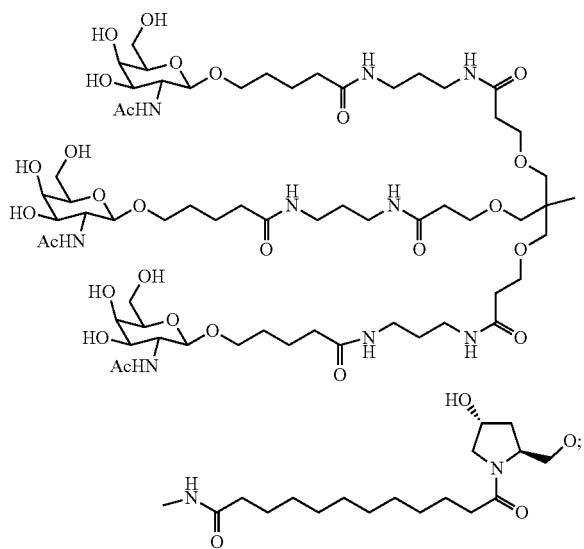

and administering to the subject an anti-HBV antibody, wherein the anti-HBV antibody comprises (i) CDRH1, CDRH2, and CDRH3 amino acid sequences according to SEQ ID NOs:44, 45, and 47, respectively; and (ii) CDRL1, CDRL2, and CDRL3 amino acid sequences according to SEQ ID NOs:48, 49, and 52, respectively.

2. The method of claim 1, wherein (a) expression of at least one HBV gene is reduced after administering the agent that reduces HBV antigenic load or the inhibitor of HBV gene expression, and the anti-HBV antibody is administered to the subject when expression of the at least one HBV gene is reduced; or (b) administering the anti-HBV antibody begins at least 1 week after administering the inhibitor of HBV gene expression or the agent that reduces HBV antigenic load.

3. The method according to claim 1, wherein administering the anti-HBV antibody comprises administering at least two doses of a therapeutically effective amount of the anti-HBV antibody.

4. The method according to claim 1, wherein the at least two doses are administered twice per week, once per week, every other week, every two weeks, every four weeks, or once a month.

5. The method according to claim 1, wherein the anti-HBV antibody is administered subcutaneously.

6. The method according to claim 1, wherein the anti-HBV antibody comprises:

(i) (a) a light chain variable domain ($V_L$) that is at least 90%, at least 95%, or 100% identical to the amino acid sequence set forth in SEQ ID NO:59; and (b) a heavy chain variable domain ($V_H$) that is at least 90%, at least 95%, or 100% identical to the amino acid sequence set forth in SEQ ID NO:53; or (ii) (a) a light chain that is at least 90%, at least 95%, or 100% identical to the amino acid sequence set forth in SEQ ID NO:73, and (b) a heavy chain that is at least 90%, at least 95%, or 100% identical to the amino acid sequence set forth in any one of SEQ ID NOs:70-72 and 97.

7. The method according to claim 1, wherein the subject is a human and a therapeutically effective amount of the anti-HBV antibody is administered; wherein the therapeutically effective amount is from about 3 mg/kg to about 30 mg/kg.

8. The method according to claim 1, wherein the siRNA is conjugated to the L96 as shown in the following structure:

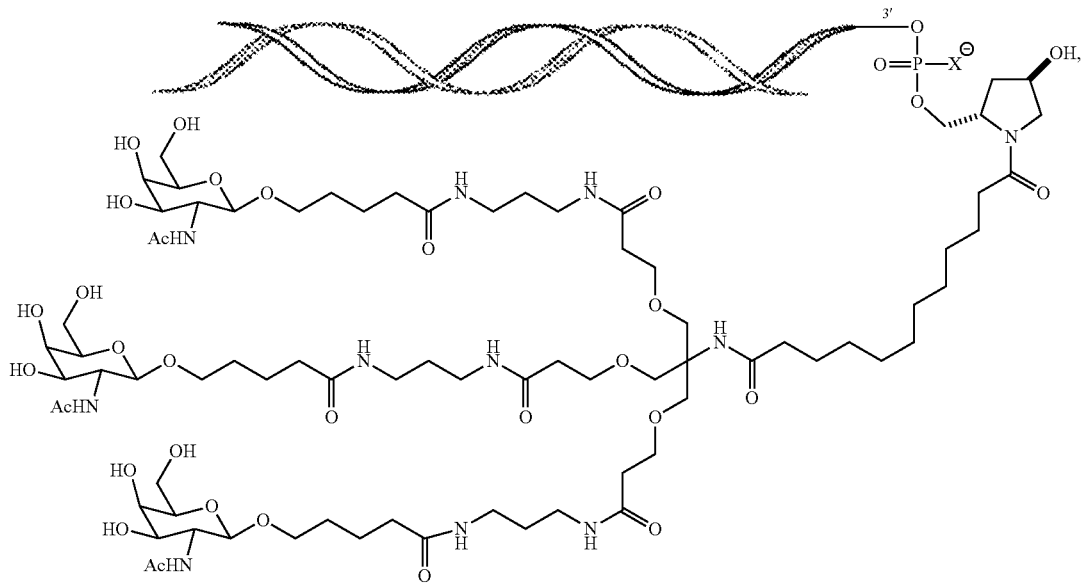

wherein X is O.

9. The method according to claim 1, wherein (a) the subject is a human and a therapeutically effective amount of RNAi agent is administered to the subject; and wherein the effective amount of the RNAi agent is from about 1 mg/kg to about 8 mg/kg; or (b) the RNAi agent is administered to the subject twice daily, once daily, every two days, every three days, twice per week, once per week, every other week, every four weeks, or once per month.

10. The method according to claim 1, further comprising administering a second siRNA to the subject, wherein the second siRNA has an antisense strand that comprises SEQ ID NO:107 or SEQ ID NO:109.

11. The method according to claim 1, further comprising administering a nucleot(s)ide analog to the subject, or wherein the subject is also administered a nucleot(s)ide analog.

12. A kit comprising:
a pharmaceutical composition comprising an RNAi agent that targets an mRNA encoded by an HBV gene, and a pharmaceutically acceptable excipient, wherein the RNAi agent has a sense strand comprising 5'-gsusguGfcAfCfUfucgcuucacaL96-3' (SEQ ID NO:7) and an antisense strand comprising 5'-usGfsuga(Agn)gCfGfaaguGfcAfcacsusu-3' (SEQ ID NO:8), wherein:
(i) a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;
(ii) Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;
(iii) (Agn) is adenosine-glycol nucleic acid (GNA);
(iv) s is a phosphorothioate linkage; and
(v) L96 is

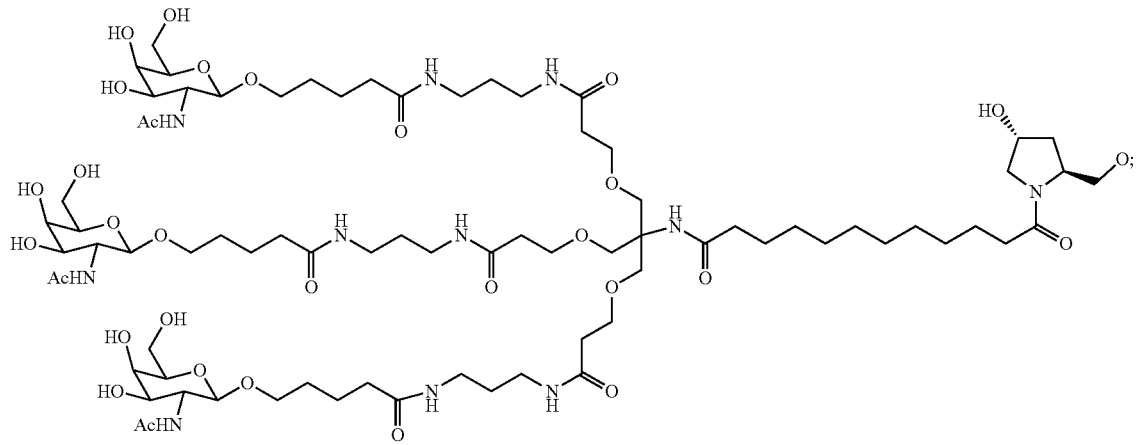

and
a pharmaceutical composition comprising an anti-HBV antibody, and a pharmaceutically acceptable excipient, wherein the anti-HBV antibody comprises (i) CDRH1, CDRH2, and CDRH3 amino acid sequences according to SEQ ID NOs:44, 45, and 47, respectively; and (ii) CDRL1, CDRL2, and CDRL3 amino acid sequences according to SEQ ID NOs:48, 49, and 52, respectively.

13. The method according to claim 1, wherein the HBV-associated disease is a Hepatitis D virus (HDV) infection.

14. The method according to claim 10, wherein the second siRNA has a sense strand comprising 5'-gsgsugga CfuUfCfUfcucaAfUfuuuaL96-3' (SEQ ID NO:108) and an antisense strand comprising 5'-usAfsaaaUfuGfAfgagaAf-gUfccaccsasc-3' (SEQ ID NO:109), wherein:
  (i) a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;
  (ii) Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;
  (iii) s is a phosphorothioate linkage; and
  (iv) L96 is

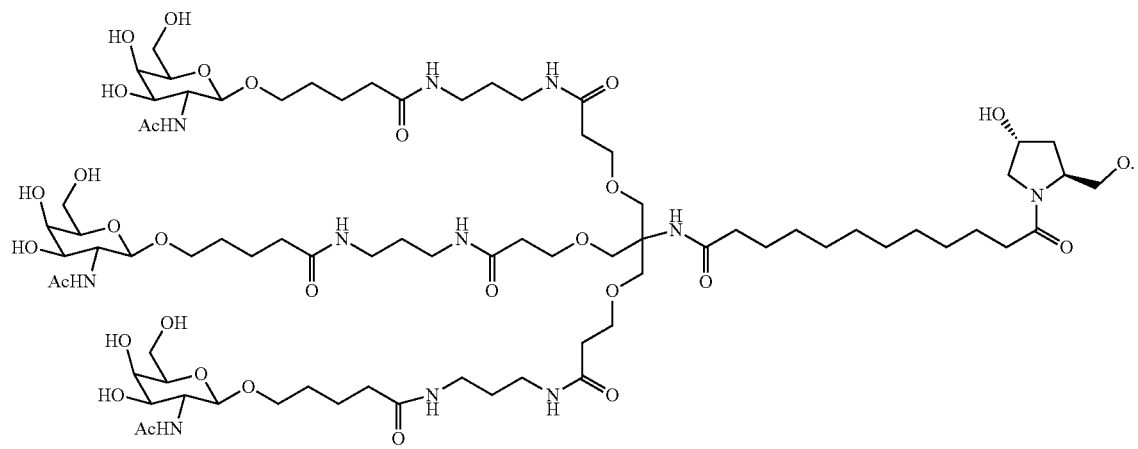

15. The method according to claim 1, wherein the siRNA is administered subcutaneously.

16. A method of treating chronic HBV hepatitis B virus (HBV) infection or a HDV infection in a subject in need thereof, comprising:
  administering an anti-HBV antibody to the subject, the anti-HBV antibody comprises a light chain amino acid sequence according to SEQ ID NO:73, and a heavy chain amino acid sequence according to SEQ ID NO:71; and
  administering an siRNA to the subject, wherein the siRNA has a sense strand comprising 5'-gsusguGfcAfCfUfucgcuucacaL96-3' (SEQ ID NO:7) and an antisense strand comprising 5'-usGfsuga(Agn)gCfGfaaguGfcAfcacsusu-3' (SEQ ID NO:8), and
  (a) a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;
  (b) Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;
  (c) (Agn) is adenosine-glycol nucleic acid (GNA);
  (d) s is a phosphorothioate linkage; and (e) L96 is
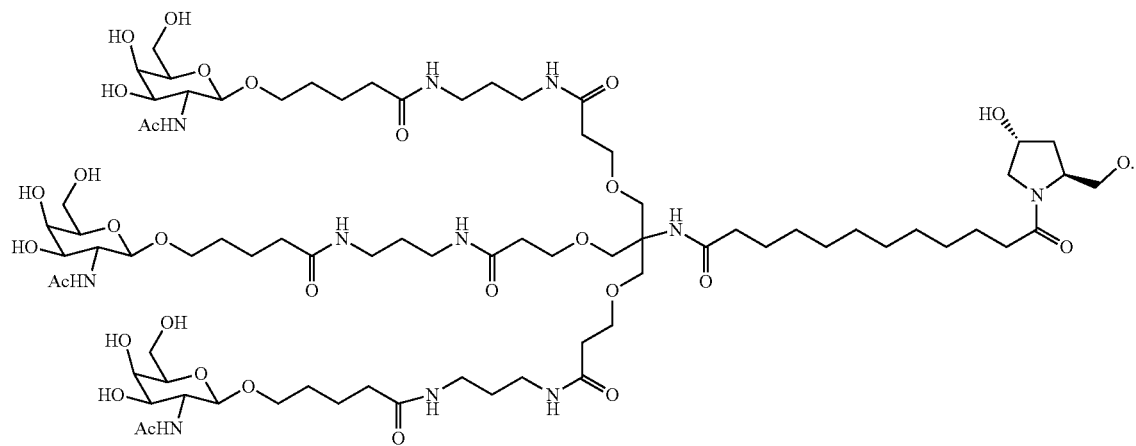
* * * * *

SEQUENCE LISTING

<160> NUMBER OF SEQ ID NOS: 109

<210> SEQ ID NO 1
<211> LENGTH: 3182
<212> TYPE: DNA
<213> ORGANISM: Hepatitis B Virus
<220> FEATURE:
<223> OTHER INFORMATION: Hepatitis B Virus genome, NC_003977.2

<400> SEQUENCE: 1

| | | | | | |
|---|---|---|---|---|---|
| aattccacaa | ccttccacca | aactctgcaa | gatcccagag | tgagaggcct | gtatttccct | 60 |
| gctggtggct | ccagttcagg | aacagtaaac | cctgttctga | ctactgcctc | tcccttatcg | 120 |
| tcaatcttct | cgaggattgg | ggaccctgcg | ctgaacatgg | agaacatcac | atcaggattc | 180 |
| ctaggacccc | ttctcgtgtt | acaggcgggg | tttttcttgt | tgacaagaat | cctcacaata | 240 |
| ccgcagagtc | tagactcgtg | gtggacttct | ctcaattttc | taggggggaac | taccgtgtgt | 300 |
| cttggccaaa | attcgcagtc | cccaacctcc | aatcactcac | caacctcttg | tcctccaact | 360 |
| tgtcctggtt | atcgctggat | gtgtctgcgg | cgttttatca | tcttcctctt | catcctgctg | 420 |
| ctatgcctca | tcttcttgtt | ggttcttctg | gactatcaag | gtatgttgcc | cgtttgtcct | 480 |
| ctaattccag | gatcctcaac | aaccagcacg | ggaccatgcc | ggacctgcat | gactactgct | 540 |
| caaggaacct | ctatgtatcc | ctcctgttgc | tgtaccaaac | cttcggacgg | aaattgcacc | 600 |
| tgtattccca | tcccatcatc | ctgggctttc | ggaaaattcc | tatgggagtg | ggcctcagcc | 660 |
| cgtttctcct | ggctcagttt | actagtgcca | tttgttcagt | ggttcgtagg | gctttccccc | 720 |
| actgtttggc | tttcagttat | atggatgatg | tggtattggg | ggccaagtct | gtacagcatc | 780 |
| ttgagtccct | ttttaccgct | gttaccaatt | ttcttttgtc | tttgggtata | catttaaacc | 840 |
| ctaacaaaac | aaagagatgg | ggttactctc | taaattttat | gggttatgtc | attggatgtt | 900 |
| atgggtcctt | gccacaagaa | cacatcatac | aaaaaatcaa | agaatgtttt | agaaaacttc | 960 |
| ctattaacag | gcctattgat | tggaaagtat | gtcaacgaat | tgtgggtctt | ttgggttttg | 1020 |
| ctgcccccttt | tacacaatgt | ggttatcctg | cgttgatgcc | tttgtatgca | tgtattcaat | 1080 |
| ctaagcaggc | tttcactttc | tcgccaactt | acaaggcctt | tctgtgtaaa | caatacctga | 1140 |
| acctttaccc | cgttgcccgg | caacggccag | gtctgtgcca | agtgtttgct | gacgcaaccc | 1200 |
| ccactggctg | gggcttggtc | atgggccatc | agcgcatgcg | tggaaccttt | tcggctcctc | 1260 |
| tgccgatcca | tactgcggaa | ctcctagccg | cttgttttgc | tcgcagcagg | tctggagcaa | 1320 |
| acattatcgg | gactgataac | tctgttgtcc | tatcccgcaa | atatacatcg | tttccatggc | 1380 |
| tgctaggctg | tgctgccaac | tggatcctgc | gcgggacgtc | ctttgtttac | gtcccgtcgg | 1440 |
| cgctgaatcc | tgcggacgac | ccttctcggg | gtcgcttggg | actctctcgt | cccctcctcc | 1500 |
| gtctgccgtt | ccgaccgacc | acggggcgca | cctctcttta | cgcggactcc | ccgtctgtgc | 1560 |
| cttctcatct | gccggaccgt | gtgcacttcg | cttcacctct | gcacgtcgca | tggagaccac | 1620 |
| cgtgaacgcc | caccaaatat | tgcccaaggt | cttacataag | aggactcttg | gactctcagc | 1680 |
| aatgtcaacg | accgaccttg | aggcatactt | caaagactgt | ttgtttaaag | actgggagga | 1740 |
| gttgggggag | gagattaggt | taaaggtctt | tgtactagga | ggctgtaggc | ataaattggt | 1800 |
| ctgcgcacca | gcaccatgca | acttttttcac | ctctgcctaa | tcatctcttg | ttcatgtcct | 1860 |
| actgttcaag | cctccaagct | gtgccttggg | tggctttggg | gcatggacat | cgaccccttat | 1920 |
| aaagaatttg | gagctactgt | ggagttactc | tcgtttttgc | cttctgactt | ctttccttca | 1980 |
| gtacgagatc | ttctagatac | cgcctcagct | ctgtatcggg | aagccttaga | gtctcctgag | 2040 |

```
cattgttcac ctcaccatac tgcactcagg caagcaattc tttgctgggg ggaactaatg   2100
actctagcta cctgggtggg tgttaatttg gaagatccag cgtctagaga cctagtagtc   2160
agttatgtca acactaatat gggcctaaag ttcaggcaac tcttgtggtt tcacatttct   2220
tgtctcactt ttggaagaga aacagttata gagtatttgg tgtctttcgg agtgtggatt   2280
cgcactcctc cagcttatag accaccaaat gcccctatcc tatcaacact tccggagact   2340
actgttgtta gacgacgagg caggtcccct agaagaagaa ctccctcgcc tcgcagacga   2400
aggtctcaat cgccgcgtcg cagaagatct caatctcggg aatctcaatg ttagtattcc   2460
ttggactcat aaggtgggga actttactgg gctttattct tctactgtac ctgtctttaa   2520
tcctcattgg aaaacaccat ctttttcctaa tatacattta caccaagaca ttatcaaaaa   2580
atgtgaacag tttgtaggcc cactcacagt taatgagaaa agaagattgc aattgattat   2640
gcctgccagg ttttatccaa aggttaccaa atatttacca ttggataagg gtattaaacc   2700
ttattatcca gaacatctag ttaatcatta cttccaaact agacactatt tacacactct   2760
atggaaggcg ggtatattat ataagagaga acaacacat agcgcctcat tttgtgggtc   2820
accatattct tgggaacaag atctacagca tggggcagaa tctttccacc agcaatcctc   2880
tgggattctt tcccgaccac cagttggatc cagccttcag agcaaacacc gcaaatccag   2940
attgggactt caatcccaac aaggacacct ggccagacgc caacaaggta ggagctggag   3000
cattcgggct gggttttcacc ccaccgcacg gaggcctttt ggggtggagc cctcaggctc   3060
agggcatact acaaactttg ccagcaaatc cgcctcctgc ctccaccaat cgccagtcag   3120
gaaggcagcc taccccgctg tctccacctt tgagaaacac tcatcctcag gccatgcagt   3180
gg                                                                 3182

<210> SEQ ID NO 2
<211> LENGTH: 18
<212> TYPE: DNA
<213> ORGANISM: Hepatitis B Virus
<220> FEATURE:
<223> OTHER INFORMATION: Hepatitis B Virus genome, nucleotides 1579-1597
      of NC_003977.2

<400> SEQUENCE: 2
gtgtgcactt cgcttcac                                                  18

<210> SEQ ID NO 3
<211> LENGTH: 19
<212> TYPE: RNA
<213> ORGANISM: Artificial Sequence
<220> FEATURE:
<223> OTHER INFORMATION: Synthetic sequence HBV02, sense strand

<400> SEQUENCE: 3
gugugcacuu cgcuucaca                                                 19

<210> SEQ ID NO 4
<211> LENGTH: 21
<212> TYPE: RNA
<213> ORGANISM: Artificial Sequence
<220> FEATURE:
<223> OTHER INFORMATION: Synthetic sequence HBV02, antisense strand

<400> SEQUENCE: 4
ugugaagcga agugcacacu u                                              21
```

```
<210> SEQ ID NO 5
<211> LENGTH: 19
<212> TYPE: RNA
<213> ORGANISM: Artificial Sequence
<220> FEATURE:
<223> OTHER INFORMATION: Synthetic oligonucleotide (HBV01, sense strand)

<400> SEQUENCE: 5
gugugcacuu cgcuucaca                                                19

<210> SEQ ID NO 6
<211> LENGTH: 21
<212> TYPE: RNA
<213> ORGANISM: Artificial Sequence
<220> FEATURE:
<223> OTHER INFORMATION: Synthetic oligonucleotide (HBV01, antisense
      strand)

<400> SEQUENCE: 6
ugugaagcga agugcacacu u                                             21

<210> SEQ ID NO 7
<211> LENGTH: 19
<212> TYPE: RNA
<213> ORGANISM: Artificial Sequence
<220> FEATURE:
<223> OTHER INFORMATION: Synthetic oligonucleotide (HBV02, sense strand)

<400> SEQUENCE: 7
gugugcacuu cgcuucaca                                                19

<210> SEQ ID NO 8
<211> LENGTH: 21
<212> TYPE: RNA
<213> ORGANISM: Artificial Sequence
<220> FEATURE:
<223> OTHER INFORMATION: Synthetic oligonucleotide (HBV02, antisense
      strand)

<400> SEQUENCE: 8
ugugaagcga agugcacacu u                                             21

<210> SEQ ID NO 9
<211> LENGTH: 16
<212> TYPE: PRT
<213> ORGANISM: Artificial Sequence
<220> FEATURE:
<223> OTHER INFORMATION: Membrane translocation sequence-containing
      peptide RFGF

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: Membrane translocation sequence-containing
      peptide RFGF analogue

<400> SEQUENCE: 10

Ala Ala Leu Leu Pro Val Leu Leu Ala Ala Pro
1               5                   10

<210> SEQ ID NO 11
```

```
<211> LENGTH: 13
<212> TYPE: PRT
<213> ORGANISM: Artificial Sequence
<220> FEATURE:
<223> OTHER INFORMATION: HIV Tat protein

<400> SEQUENCE: 11

Gly Arg Lys Lys Arg Arg Gln Arg Arg Arg Pro Pro Gln
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Drosophila Antennapedia protein

<400> SEQUENCE: 12

Arg Gln Ile Lys Ile Trp Phe Gln Asn Arg Arg Met Lys Trp Lys
1               5                   10                  15

<210> SEQ ID NO 13
<211> LENGTH: 226
<212> TYPE: PRT
<213> ORGANISM: Hepatitis B Virus
<220> FEATURE:
<223> OTHER INFORMATION: HBsAg S domain

<400> SEQUENCE: 13

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Thr Thr Val Cys
            35                  40                  45

Leu Gly Gln Asn Ser Gln Ser Pro Thr Ser Asn His Ser Pro Thr Ser
        50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225
```

<210> SEQ ID NO 14
<211> LENGTH: 72
<212> TYPE: PRT
<213> ORGANISM: Hepatitis B Virus
<220> FEATURE:
<223> OTHER INFORMATION: J02203 (D, ayw3) HBsAg Antigenic Loop Sequence

<400> SEQUENCE: 14

```
Gln Gly Met Leu Pro Val Cys Pro Leu Ile Pro Gly Ser Ser Thr Thr
1               5                   10                  15

Ser Thr Gly Pro Cys Arg Thr Cys Met Thr Thr Ala Gln Gly Thr Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70
```

<210> SEQ ID NO 15
<211> LENGTH: 72
<212> TYPE: PRT
<213> ORGANISM: Hepatitis B Virus
<220> FEATURE:
<223> OTHER INFORMATION: FJ899792 (D, adw2) HBsAg Antigenic Loop
      Sequence

<400> SEQUENCE: 15

```
Gln Gly Met Leu Pro Val Cys Pro Leu Ile Pro Gly Ser Ser Thr Thr
1               5                   10                  15

Gly Thr Gly Pro Cys Arg Thr Cys Thr Thr Pro Ala Gln Gly Thr Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70
```

<210> SEQ ID NO 16
<211> LENGTH: 72
<212> TYPE: PRT
<213> ORGANISM: Hepatitis B Virus
<220> FEATURE:
<223> OTHER INFORMATION: AM282986 (A) HBsAg Antigenic Loop Sequence

<400> SEQUENCE: 16

```
Gln Gly Met Leu Pro Val Cys Pro Leu Ile Pro Gly Thr Thr Thr Thr
1               5                   10                  15

Ser Thr Gly Pro Cys Lys Thr Cys Thr Thr Pro Ala Gln Gly Asn Ser
            20                  25                  30

Met Phe Pro Ser Cys Cys Cys Thr Lys Pro Ser Asp Gly Asn Cys Thr
        35                  40                  45

Cys Ile Pro Ile Pro Ser Ser Trp Ala Phe Ala Lys Tyr Leu Trp Glu
    50                  55                  60

Trp Ala Ser Val Arg Phe Ser Trp
65                  70
```

<210> SEQ ID NO 17
<211> LENGTH: 72

<212> TYPE: PRT
<213> ORGANISM: Hepatitis B Virus
<220> FEATURE:
<223> OTHER INFORMATION: D23678 (B1) HBsAg Antigenic Loop Sequence

<400> SEQUENCE: 17

Gln Gly Met Leu Pro Val Cys Pro Leu Ile Pro Gly

<400> SEQUENCE: 20

Gln Gly Met Leu Pro Val Cys Pro Leu Leu Pro Gly Ser Thr Thr Thr
1               5                   10                  15

Ser Thr Gly Pro Cys Thr Cys Thr Thr Leu Ala Gln Gly Thr Ser Met
            20                  25                  30

Phe Pro Ser Cys Cys Cys Ser Lys Pro Ser Asp Gly Asn Cys Thr Cys
        35                  40                  45

Ile Pro Ile Pro Ser Ser Trp Ala Leu Gly Lys Tyr Leu Trp Glu Trp
50                  55                  60

Ala Ser Ala Arg Phe Ser Trp
65                  70

<210> SEQ ID NO 21
<211> LENGTH: 70
<212> TYPE: PRT
<213> ORGANISM: Hepatitis B Virus
<220> FEATURE:
<223> OTHER INFORMATION: AF1 60501 (G) HBsAg Antigenic Loop Sequence

<400> SEQUENCE: 21

Gln Gly Met Leu Pro Val Cys Pro Leu Ile Pro Gly Ser Ser Thr Thr
1               5                   10                  15

Ser Thr Gly Pro Cys Thr Cys Thr Thr Pro Ala Gln Gly Asn Ser Met
            20                  25                  30

Tyr Pro Ser Cys Cys Cys Thr Pro Ser Asp Gly Asn Cys Thr Cys Ile
        35                  40                  45

Pro Ile Pro Ser Ser Trp Ala Phe Ala Lys Tyr Leu Trp Glu Trp Ala
50                  55                  60

Ser Val Arg Phe Ser Trp
65                  70

<210> SEQ ID NO 22
<211> LENGTH: 72
<212> TYPE: PRT
<213> ORGANISM: Hepatitis B Virus
<220> FEATURE:
<223> OTHER INFORMATION: AY090454 (H) HBsAg Antigenic Loop Sequence

<400> SEQUENCE: 22

Gln Gly Met Leu Pro Val Cys Pro Leu Leu Pro Gly Ser Thr Thr Thr
1               5                   10                  15

Ser Thr Gly Pro Cys Lys Thr Cys Thr Thr Leu Ala Gln Gly Thr Ser
            20                  25                  30

Met Phe Pro Ser Cys Cys Cys Thr Lys Pro Ser Asp Gly Asn Cys Thr
        35                  40                  45

Cys Ile Pro Ile Pro Ser Ser Trp Ala Phe Gly Lys Tyr Leu Trp Glu
    50                  55                  60

Trp Ala Ser Ala Arg Phe Ser Trp
65                  70

<210> SEQ ID NO 23
<211> LENGTH: 72
<212> TYPE: PRT
<213> ORGANISM: Hepatitis B Virus
<220> FEATURE:
<223> OTHER INFORMATION: AF241409 (I) HBsAg Antigenic Loop Sequence

<400> SEQUENCE: 23

Gln Gly Met Leu Pro Val Cys Pro Leu Ile Pro Gly Ser Ser Thr Thr

```
                1               5                  10                 15
Ser Thr Gly Pro Cys Lys Thr Cys Thr Thr Pro Ala Gln Gly Asn Ser
            20                  25                 30

Met Tyr Pro Ser Cys Cys Cys Thr Lys Pro Ser Asp Gly Asn Cys Thr
            35                  40                 45

Cys Ile Pro Ile Pro Ser Ser Trp Ala Phe Ala Lys Tyr Leu Trp Glu
50                      55                  60

Trp Ala Ser Ala Arg Phe Ser Trp
65                  70

<210> SEQ ID NO 24
<211> LENGTH: 72
<212> TYPE: PRT
<213> ORGANISM: Hepatitis B Virus
<220> FEATURE:
<223> OTHER INFORMATION: AB486012 (J) HBsAg Antigenic Loop Sequence

<400> SEQUENCE: 24

Gln Gly Met Leu Pro Val Cys Pro Leu Leu Pro Gly Ser Thr Thr Thr
1               5                   10                  15

Ser Thr Gly Pro Cys Arg Thr Cys Thr Ile Thr Ala Gln Gly Thr Ser
            20                  25                  30

Met Phe Pro Ser Cys Cys Cys Thr Lys Pro Ser Asp Gly Asn Cys Thr
            35                  40                  45

Cys Ile

```
Met Tyr Pro Ser Cys Cys Cys Thr Lys Pro Ser Asp Gly Asn Cys Thr
            35                  40                  45

Cys Ile Pro Ile Pro Ser Ser Trp Ala Phe Gly Lys Phe Leu Trp Glu
     50                  55                  60

Trp Ala Ser Ala Arg Phe Ser Trp
65                  70

<210> SEQ ID NO 27
<211> LENGTH: 72
<212> TYPE: PRT
<213> ORGANISM: Hepatitis B Virus
<220> FEATURE:
<223> OTHER INFORMATION: HBsAg P120T/S143L HBsAg Antigenic Loop Sequence

<400> SEQUENCE: 27

Gln Gly Met Leu Pro Val Cys Pro Leu Ile Pro Gly Ser Ser Thr Thr
1               5                   10                  15

Gly Thr Gly Thr Cys Arg Thr Cys Thr Thr Pro Ala Gln Gly Thr Ser
            20                  25                  30

Met Tyr Pro Ser Cys Cys Cys Thr Lys Pro Leu

Cys Ile Pro Ile Pro Ser Ser Trp Ala Phe Gly Lys Phe Leu Trp Glu
        50                  55                  60

Trp Ala Ser Ala Arg Phe Ser Trp
65                  70

<210> SEQ ID NO 30
<211> LENGTH: 71
<212> TYPE: PRT
<213> ORGANISM: Hepatitis B Virus
<220> FEATURE:
<223> OTHER INFORMATION: HBsAg R122I HBsAg Antigenic Loop Sequence

<400> SEQUENCE: 30

Gln Gly Met Leu Pro Val Cys Pro Leu 65                  70

<210> SEQ ID NO 33
<211> LENGTH: 72
<212> TYPE: PRT
<213> ORGANISM: Hepatitis B Virus
<220> FEATURE:
<223> OTHER INFORMATION: HBsAg Q129L HBsAg Antigenic Loop Sequence

<400> SEQUENCE: 33

Gln Gly Met Leu Pro Val Cys Pro Leu Ile Pro Gly Ser Ser Thr Thr
1               5                   10                  15

Gly Thr Gly Pro Cys Arg Thr Cys Thr Thr Pro Ala Leu Gly Thr Ser
20 25 30

Met Tyr Pro Ser Cys Cys Cys Thr Lys Pro Ser Asp Gly Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 34
<211> LENGTH: 72
<212> TYPE: PRT
<213> ORGANISM: Hepatitis B Virus
<220> FEATURE:
<223> OTHER INFORMATION: HBsAg M1 33H HBsAg Antigenic Loop Sequence

<400> SEQUENCE: 34

Gln Gly Met Leu Pro Val Cys Pro Leu Ile Pro Gly Ser Ser Thr Thr
1 5 10 15

Gly Thr Gly Pro Cys Arg Thr Cys Thr Thr Pro Ala Gln Gly Thr Ser
20 25 30

His Tyr Pro Ser Cys Cys Cys Thr Lys Pro Ser Asp Gly Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 35
<211> LENGTH: 72
<212> TYPE: PRT
<213> ORGANISM: Hepatitis B Virus
<220> FEATURE:
<223> OTHER INFORMATION: HBsAg M1 33L HBsAg Antigenic Loop Sequence

<400> SEQUENCE: 35

Gln Gly Met Leu Pro Val Cys Pro Leu Ile Pro Gly Ser Ser Thr Thr
1 5 10 15

Gly Thr Gly Pro Cys Arg Thr Cys Thr Thr Pro Ala Gln Gly Thr Ser
20 25 30

Leu Tyr Pro Ser Cys Cys Cys Thr Lys Pro Ser Asp Gly Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 36

```
<211> LENGTH: 72
<212> TYPE: PRT
<213> ORGANISM: Hepatitis B Virus
<220> FEATURE:
<223> OTHER INFORMATION: HBsAg M133T HBsAg Antigenic Loop Sequence

<400> SEQUENCE: 36

Gln Gly Met Leu Pro Val Cys Pro Leu Ile Pro Gly Ser Ser Thr Thr
 1               5                  10                  15

Gly Thr Gly Pro Cys Arg Thr Cys Thr Thr Pro Ala Gln Gly Thr

-continued

<223> OTHER INFORMATION: HBsAg S143K HBsAg Antigenic Loop Sequence

<400> SEQUENCE: 39

Gln Gly Met Leu Pro Val Cys Pro Leu Ile Pro Gly Ser Ser Thr Thr
1 5 10 15

Gly Thr Gly Pro Cys Arg Thr Cys Thr Thr Pro Ala Gln Gly Thr Ser
20 25 30

Met Tyr Pro Ser Cys Cys Cys Thr Lys Pro Lys Asp Gly Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 40
<211> LENGTH: 71
<212> TYPE: PRT
<213> ORGANISM: Hepatitis B Virus
<220> FEATURE:
<223> OTHER INFORMATION: HBsAg D144A HBsAg Antigenic Loop Sequence

<400> SEQUENCE: 40

Gln Gly Met Leu Pro Val Cys Pro Leu Ile Pro Gly Ser Ser Thr Thr
1 5 10 15

Gly Thr Gly Pro Cys Arg Thr Cys Thr Thr Pro Ala Gln Gly Thr Ser
20 25 30

Met Tyr Pro Ser Cys Cys Cys Thr Pro Ser Ala Gly Asn Cys Thr Cys
35 40 45

Ile Pro Ile Pro Ser Ser Trp Ala Phe Gly Lys Phe Leu Trp Glu Trp
50 55 60

Ala Ser Ala Arg Phe Ser Trp
65 70

<210> SEQ ID NO 41
<211> LENGTH: 72
<212> TYPE: PRT
<213> ORGANISM: Hepatitis B Virus
<220> FEATURE:
<223> OTHER INFORMATION: HBsAg G145R HBsAg Antigenic Loop Sequence

<400> SEQUENCE: 41

Gln Gly Met Leu Pro Val Cys Pro Leu Ile Pro Gly Ser Ser Thr Thr
1 5 10 15

Gly Thr Gly Pro Cys Arg Thr Cys Thr Thr Pro Ala Gln Gly Thr Ser
20 25 30

Met Tyr Pro Ser Cys Cys Cys Thr Lys Pro Ser Asp Arg Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 42
<211> LENGTH: 72
<212> TYPE: PRT
<213> ORGANISM: Hepatitis B Virus
<220> FEATURE:
<223> OTHER INFORMATION: HBsAg N146A HBsAg Antigenic Loop Sequence

<400> SEQUENCE: 42

```
Gln Gly Met Leu Pro Val Cys Pro Leu Ile Pro Gly Ser Ser Thr Thr
1               5                   10                  15

Gly Thr Gly Pro Cys Arg Thr Cys Thr Thr Pro Ala Gln Gly Thr Ser
            20                  25                  30

Met Tyr Pro Ser Cys Cys Cys Thr Lys Pro Ser Asp Gly Ala Cys Thr
            35                  40                  45

Cys Ile Pro Ile Pro Ser Ser Trp Ala Phe Gly Lys Phe Leu Trp Glu
50              55                  60

Trp Ala Ser Ala Arg Phe Ser Trp
65              70
```

<210> SEQ ID NO 43
<211> LENGTH: 226
<212> TYPE: PRT
<213> ORGANISM: Hepatitis B Virus
<220> FEATURE:
<223> OTHER INFORMATION: HBsAg Genotype D S domain (Genbank accession no. FJ899792)

<400> SEQUENCE: 43

```
Met Glu Asn Val Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
            35                  40                  45

Leu Gly Gln Asn Ser Gln Ser Pro Thr Ser Asn His Ser Pro Thr Ser
50              55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
            85                  90                  95

Leu Leu Asp Tyr Gln Gly Met Leu Pro Val Cys Pro Leu Ile Pro Gly
            100                 105                 110

Ser Ser Thr Thr Gly Thr Gly Pro Cys Arg Thr Cys Thr Thr Pro Ala
            115                 120                 125

Gln Gly Thr Ser Met Tyr Pro Ser Cys Cys Cys Thr Lys Pro Ser Asp
            130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
            165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Thr
            195                 200                 205

Leu Ser Pro Phe Leu Pro Leu Leu Pro Ile Phe Phe Cys Leu Trp Val
        210                 215                 220

Tyr Ile
225
```

<210> SEQ ID NO 44
<211> LENGTH: 8
<212> TYPE: PRT
<213> ORGANISM: Artificial Sequence
<220> FEATURE:
<223> OTHER INFORMATION: Synthetic sequence HBC34 CDRH1

```
<400> SEQUENCE: 44

Gly Arg Ile Phe Arg Ser Phe Tyr
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic sequence HBC34 short CDRH2

<400> SEQUENCE: 45

Asn Gln Asp Gly Ser Glu Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic sequence HBC34 long CDRH2

<400> SEQUENCE: 46

Ile Asn Gln Asp Gly Ser Glu Lys
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic sequence HBC34 CDRH3

<400> SEQUENCE: 47

Ala Ala Trp Ser Gly Asn Ser Gly Gly Met Asp Val
1               5                   10

<210> SEQ ID NO 48
<211> LENGTH: 6
<212> TYPE: PRT
<213> ORGANISM: Artificial Sequence
<220> FEATURE:
<223> OTHER INFORMATION: Synthetic sequence HBC34 CDRL1

<400> SEQUENCE: 48

Lys Leu Gly Asn Lys Asn
1               5

<210> SEQ ID NO 49
<211> LENGTH: 3
<212> TYPE: PRT
<213> ORGANISM: Artificial Sequence
<220> FEATURE:
<223> OTHER INFORMATION: Synthetic sequence HBC34 short CDRL2

<400> SEQUENCE: 49

Glu Val Lys
1

<210> SEQ ID NO 50
<211> LENGTH: 9
<212> TYPE: PRT
<213> ORGANISM: Artificial Sequence
<220> FEATURE:
<223> OTHER INFORMATION: Synthetic sequence HBC34 long CDRL2

<400> SEQUENCE: 50
```

```
Val Ile Tyr Glu Val Lys Tyr Arg Pro
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence HBC34 CDRL3

<400> SEQUENCE: 51

Gln Thr Trp Asp Ser Thr Thr Val Val
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic sequence HBC34v35 CDRL3

<400> SEQUENCE: 52

Gln Thr Phe Asp Ser Thr Thr Val Val
1               5

<210> SEQ ID NO 53
<211> LENGTH: 119
<212> TYPE: PRT
<213> ORGANISM: Artificial Sequence
<220> FEATURE:
<223> OTHER INFORMATION: Synthetic sequence HBC34 VH

<400> SEQUENCE: 53

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Ser Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Synthetic sequence HBC34v31 VH

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Arg Ser Phe
            20                  25                  30
```

```
Tyr Met Ser Trp Val Arg Gln Ala Pro Gly Lys Gly Leu Glu Trp Val
        35                  40                  45

Ala Asn Ile Asn Gln Asp Gly Ser Glu Lys Leu Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Val Glu Asp Thr Ala Val Tyr Tyr Cys
                 85                  90                  95

Ala Ala Trp Ser Gly Asn Ser Gly Met Asp Val Trp Gly Gln Gly
            100                 105                 110

Thr Thr Val Thr Val Ser Ser
        115
```

<210> SEQ ID NO 55
<211> LENGTH: 106
<212> TYPE: PRT
<213> ORGANISM: Artificial Sequence
<220> FEATURE:
<223> OTHER INFORMATION: Synthetic sequence HBC34 VL

<400> SEQUENCE: 55

```
Ser Tyr Glu Leu Thr Gln Pro Pro Ser Val Ser Val Ser Pro Gly Gln
 1               5                  10                  15

Thr Val Ser Ile Pro Cys Ser Gly Asp Lys Leu Gly Asn Lys Asn Val
             20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Ala Tyr Phe Cys Gln Thr Trp Asp Ser Thr Thr Val Val
                 85                  90                  95

Phe Gly Gly Gly Thr Arg Leu Thr Val Leu
            100                 105
```

<210> SEQ ID NO 56
<211> LENGTH: 106
<212> TYPE: PRT
<213> ORGANISM: Artificial Sequence
<220> FEATURE:
<223> OTHER INFORMATION: Synthetic sequence HBC34v7 VL

<400> SEQUENCE: 56

```
Ser Tyr Glu Leu Thr Gln Pro Pro Ser Val Ser Val Ser Pro Gly Gln
 1               5                  10                  15

Thr Val Ser Ile Pro Cys Ser Gly Asp Lys Leu Gly Asn Lys Asn Val
             20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Ala Tyr Phe Cys Gln Thr Phe Asp Ser Thr Thr Val Val
                 85                  90                  95

Phe Gly Gly Gly Thr Arg Leu Thr Val Leu
```

<210> SEQ ID NO 57
<211> LENGTH: 106
<212> TYPE: PRT
<213> ORGANISM: Artificial Sequence
<220> FEATURE:
<223> OTHER INFORMATION: Synthetic sequence HBC34v23 VL

<400> SEQUENCE: 57

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Cys Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105

<210> SEQ ID NO 58
<211> LENGTH: 106
<212> TYPE: PRT
<213> ORGANISM: Artificial Sequence
<220> FEATURE:
<223> OTHER INFORMATION: Synthetic sequence HBC34v34 VL

<400> SEQUENCE: 58

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu
            100                 105

<210> SEQ ID NO 59
<211> LENGTH: 106
<212> TYPE: PRT
<213> ORGANISM: Artificial Sequence
<220> FEATURE:
<223> OTHER INFORMATION: Synthetic sequence HBC34v35 VL

<400> SEQUENCE: 59

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
            35                  40                  45

Glu Val Lys Tyr Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Ala Tyr Phe Cys Gln Thr Phe Asp Ser Thr Thr Val Val
                 85                  90                  95

Phe Gly Gly Gly Thr Arg Leu Thr Val Leu
            100                 105

<210> SEQ ID NO 60
<211> LENGTH: 106
<212> TYPE: PRT
<213> ORGANISM: Artificial Sequence
<220> FEATURE:
<223> OTHER INFORMATION: Synthetic sequence HBC34_LC40S VL

<400> SEQUENCE: 60

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
            35                  40                  45

Glu Val Lys Tyr Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Ala Tyr Phe Cys Gln Thr Trp Asp Ser Thr Thr Val Val
                 85                  90                  95

Phe Gly Gly Gly Thr Arg Leu Thr Val Leu
            100                 105

<210> SEQ ID NO 61
<211> LENGTH: 106
<212> TYPE: PRT
<213> ORGANISM: Artificial Sequence
<220> FEATURE:
<223> OTHER INFORMATION: Synthetic sequence HBC34_LC40A VL

<400> SEQUENCE: 61

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
            35                  40                  45

Glu Val Lys Tyr Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Ala Tyr Phe Cys Gln Thr Trp Asp Ser Thr Thr Val Val
                 85                  90                  95

Phe Gly Gly Gly Thr Arg Leu Thr Val Leu
            100                 105

-continued

<210> SEQ ID NO 62
<211> LENGTH: 106
<212> TYPE: PRT
<213> ORGANISM: Artificial Sequence
<220> FEATURE:
<223> OTHER INFORMATION: Synthetic sequence HBC34v23_LC40S VL

<400> SEQUENCE: 62

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ser Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105
```

<210> SEQ ID NO 63
<211> LENGTH: 106
<212> TYPE: PRT
<213> ORGANISM: Artificial Sequence
<220> FEATURE:
<223> OTHER INFORMATION: Synthetic sequence HBC34v23_LC40A VL

<400> SEQUENCE: 63

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ala Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105
```

<210> SEQ ID NO 64
<211> LENGTH: 106
<212> TYPE: PRT
<213> ORGANISM: Artificial Sequence
<220> FEATURE:
<223> OTHER INFORMATION: Synthetic sequence HBC34v31_LC40S VL

<400> SEQUENCE: 64

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45
```

Glu Val Lys Tyr Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu
            100                 105

<210> SEQ ID NO 65
<211> LENGTH: 106
<212> TYPE: PRT
<213> ORGANISM: Artificial Sequence
<220> FEATURE:
<223> OTHER INFORMATION: Synthetic sequence HBC34v31_L C40A VL

<400> SEQUENCE: 65

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu
            100                 105

<210> SEQ ID NO 66
<211> LENGTH: 106
<212> TYPE: PRT
<213> ORGANISM: Artificial Sequence
<220> FEATURE:
<223> OTHER INFORMATION: Synthetic sequence HBC34v32_LC40S VL

<400> SEQUENCE: 66

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu
            100                 105

<210> SEQ ID NO 67
<211> LENGTH: 106
<212> TYPE: PRT

<213> ORGANISM: Artificial Sequence
<220> FEATURE:
<223> OTHER INFORMATION: Synthetic sequence HBC34v32_LC40A VL

<400> SEQUENCE: 67

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu
            100                 105
```

<210> SEQ ID NO 68
<211> LENGTH: 106
<212> TYPE: PRT
<213> ORGANISM: Artificial Sequence
<220> FEATURE:
<223> OTHER INFORMATION: Synthetic sequence HBC34v33_LC40S VL

<400> SEQUENCE: 68

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ser Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105
```

<210> SEQ ID NO 69
<211> LENGTH: 106
<212> TYPE: PRT
<213> ORGANISM: Artificial Sequence
<220> FEATURE:
<223> OTHER INFORMATION: Synthetic sequence HBC34v33_LC40A VL

<400> SEQUENCE: 69

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ala Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60
```

```
Asn Ser Gly Asn Thr Ala Thr Leu Thr Ile Ser Gly Thr Gln Ala Met
 65                  70                  75                  80

Asp Glu Ala Asp Tyr Tyr Cys Gln Thr Phe Asp Ser Thr Val Val
             85                  90                  95

Phe Gly Gly Gly Thr Lys Leu Thr Val Leu
            100                 105

<210> SEQ ID NO 70
<211> LENGTH: 449
<212> TYPE: PRT
<213> ORGANISM: Artificial Sequence
<220> FEATURE:
<223> OTHER INFORMATION: Synthetic sequence HBC34v35 HC

<400> SEQUENCE: 70

Glu Leu Gln Leu Val Glu Ser Gly Gly Gly Trp Val Gln Pro Gly Gly
  1               5                  10                  15

Ser Gln Arg Leu Ser Cys Ala Ala Ser Gly Arg Ile Phe Arg Ser Phe
             20                  25                  30

Tyr Met Ser Trp Val Arg Gln Ala Pro Gly Lys Gly Leu Glu Trp Val
         35                  40                  45

Ala Thr Ile Asn Gln Asp Gly Ser Glu Lys Leu Tyr Val Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Val Glu Asp Thr Ala Val Tyr Tyr Cys
                 85                  90                  95

Ala Ala Trp Ser Gly Asn Ser Gly Gly Met Asp Val Trp Gly Gln Gly
            100                 105                 110

Thr Thr Val Ser Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 71
<211> LENGTH: 449
<212> TYPE: PRT
<213> ORGANISM: Artificial Sequence
<220> FEATURE:
<223> OTHER INFORMATION: Synthetic sequence HBC34v35-MLNS-GAALIE (g1M17,
      1) HC

<400> SEQUENCE: 71

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Ser Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

```
Thr His Thr Cys Pro Pro Cys Pro Ala Pro Glu Leu Leu Ala Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro Gly
            435                 440                 445

Lys

<210> SEQ ID NO 72
<211> LENGTH: 449
<212> TYPE: PRT
<213> ORGANISM: Artificial Sequence
<220> FEATURE:
<223> OTHER INFORMATION: Synthetic sequence HBC34v35-MLNS HC

<400> SEQUENCE: 72

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Ser Val Ser Ser Ala Ser Thr Lys Gly Pro Ser Val Phe
            115                 120                 125
```

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro Gly
        435                 440                 445

Lys

<210> SEQ ID NO 73
<211> LENGTH: 212
<212> TYPE: PRT
<213> ORGANISM: Artificial Sequence
<220> FEATURE:
<223> OTHER INFORMATION: Synthetic sequence HBC34v35 LC

<400> SEQUENCE: 73

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr

```
            35                  40                  45
Glu Val Lys Tyr Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Met
 65                  70                  75                  80
Asp Glu Ala Ala Tyr Phe Cys Gln Thr Phe Asp Ser Thr Thr Val Val
                 85                  90                  95
Phe Gly Gly Gly Thr Arg Leu Thr Val Leu Gly Gln Pro Lys Ala Ala
                100                 105                 110
Pro Ser Val Thr Leu Phe Pro Pro Ser Ser Glu Glu Leu Gln Ala Asn
                115                 120                 125
Lys Ala Thr Leu Val Cys Leu Ile Ser Asp Phe Tyr Pro Gly Ala Val
                130                 135                 140
Thr Val Ala Trp Lys Ala Asp Ser Ser Pro Val Lys Ala Gly Val Glu
145                 150                 155                 160
Thr Thr Thr Pro Ser Lys Gln Ser Asn Asn Lys Tyr Ala Ala Ser Ser
                165                 170                 175
Tyr Leu Ser Leu Thr Pro Glu Gln Trp Lys Ser His Arg Ser Tyr Ser
                180                 185                 190
Cys Gln Val Thr His Glu Gly Ser Thr Val Glu Lys Thr Val Ala Pro
                195                 200                 205
Thr Glu Cys Ser
    210

<210> SEQ ID NO 74
<211> LENGTH: 212
<212> TYPE: PRT
<213> ORGANISM: Artificial Sequence
<220> FEATURE:
<223> OTHER INFORMATION: Synthetic sequence HBC34v34 LC

<400> SEQUENCE: 74

Ser Tyr Glu Leu Thr Gln Pro Pro Ser Val Ser Val Ser Pro Gly Gln
  1               5                  10                  15
Thr Val Ser Ile Pro Cys Ser Gly Asp Lys Leu Gly Asn Lys Asn Val
                 20                  25                  30
Ser Trp Phe Gln His Lys Pro Gly Gln Ser Pro Val Leu Val Ile Tyr
             35                  40                  45
Glu Val Lys Tyr Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Met
 65                  70                  75                  80
Asp Glu Ala Ala Tyr Phe Cys Gln Thr Phe Asp Ser Thr Thr Val Val
                 85                  90                  95
Phe Gly Gly Gly Thr Arg Leu Thr Val Leu Gly Gln Pro Lys Ala Ala
                100                 105                 110
Pro Ser Val Thr Leu Phe Pro Pro Ser Ser Glu Glu Leu Gln Ala Asn
                115                 120                 125
Lys Ala Thr Leu Val Cys Leu Ile Ser Asp Phe Tyr Pro Gly Ala Val
                130                 135                 140
Thr Val Ala Trp Lys Ala Asp Ser Ser Pro Val Lys Ala Gly Val Glu
145                 150                 155                 160
Thr Thr Thr Pro Ser Lys Gln Ser Asn Asn Lys Tyr Ala Ala Ser Ser
                165                 170                 175
Tyr Leu Ser Leu Thr Pro Glu Gln Trp Lys Ser His Arg Ser Tyr Ser
```

```
            180                 185                 190
Cys Gln Val Thr His Glu Gly Ser Thr Val Glu Lys Thr Val Ala Pro
        195                 200                 205

Thr Glu Cys Ser
        210

<210> SEQ ID NO 75
<211> LENGTH: 128
<212> TYPE: PRT
<213> ORGANISM: Artificial Sequence
<220> FEATURE:
<223> OTHER INFORMATION: Synthetic sequence HBC24 VH

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Lys Tyr
            20                  25                  30

Ala Met Ser Trp Val Arg Gln Ala Pro Gly Lys Gly Leu Glu Trp Val
        35                  40                  45

Ala Ser Ile Ser Gly Ser Val Pro Gly Phe Gly Ile Asp Thr Tyr Tyr
    50                  55                  60

Ala Asp Ser Val Lys Gly Arg Phe Thr Ile Ser Arg Asp Thr Ser Lys
65                  70                  75                  80

Asn Thr Leu Tyr Leu Gln Met Asn Ser Leu Arg Ala Glu Asp Thr Ala
                85                  90                  95

Leu Tyr Tyr Cys Ala Lys Asp Val Gly Val Ile Gly Ser Tyr Tyr Tyr
            100                 105                 110

Tyr Ala Met Asp Val Trp Gly Gln Gly Thr Ala Val Thr Val Ser Ser
        115                 120                 125

<210> SEQ ID NO 76
<211> LENGTH: 109
<212> TYPE: PRT
<213> ORGANISM: Artificial Sequence
<220> FEATURE:
<223> OTHER INFORMATION: Synthetic sequence HBC24 VL

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Leu Ser Ser Ser
            20                  25                  30

Tyr Leu Ala Trp Tyr Gln Gln Lys Pro Gly Gln Ala Pro Arg Leu Leu
        35                  40                  45

Ile Tyr Ser Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95

Arg Trp Thr Phe Gly Gln Gly Thr Lys Val Glu Ile Lys
            100                 105

<210> SEQ ID NO 77
<211> LENGTH: 8
<212> TYPE: PRT
<213> ORGANISM: Artificial Sequence
<220> FEATURE:
```

-continued

```
<223> OTHER INFORMATION: Synthetic sequence HBC24 CDRH1

<400> SEQUENCE: 77

Gly Ser Thr Phe Thr Lys Tyr Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic sequence HBC24 CDRH2

<400> SEQUENCE: 78

Ile Ser Gly Ser Val Pro Gly Phe
1               5

<210> SEQ ID NO 79
<211> LENGTH: 21
<212> TYPE: PRT
<213> ORGANISM: Artificial Sequence
<220> FEATURE:
<223> OTHER INFORMATION: Synthetic sequence HBC24 CDRH3

<400> SEQUENCE: 79

Leu Tyr Tyr Cys Ala Lys Asp Val Gly Val Ile Gly Ser Tyr Tyr
1               5                   10                  15

Tyr Ala Met Asp Val
            20

<210> SEQ ID NO 80
<211> LENGTH: 7
<212> TYPE: PRT
<213> ORGANISM: Artificial Sequence
<220> FEATURE:
<223> OTHER INFORMATION: Synthetic sequence HBC24 CDRL1

<400> SEQUENCE: 80

Gln Gly Leu Ser Ser Ser Tyr
1               5

<210> SEQ ID NO 81
<211> LENGTH: 3
<212> TYPE: PRT
<213> ORGANISM: Artificial Sequence
<220> FEATURE:
<223> OTHER INFORMATION: Synthetic sequence HBC24 CDRL2

<400> SEQUENCE: 81

Ser Ala Ser
1

<210> SEQ ID NO 82
<211> LENGTH: 10
<212> TYPE: PRT
<213> ORGANISM: Artificial Sequence
<220> FEATURE:
<223> OTHER INFORMATION: Synthetic sequence HBC24 CDRL3

<400> SEQUENCE: 82

Gln Gln Tyr Ala Tyr Ser Pro Arg Trp Thr
1               5                   10

<210> SEQ ID NO 83
<211> LENGTH: 212
<212> TYPE: PRT
```

<213> ORGANISM: Artificial Sequence
<220> FEATURE:
<223> OTHER INFORMATION: Synthetic sequence HBC34 LC

<400> SEQUENCE: 83

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Val Val
                85                  90                  95

Phe Gly Gly Gly Thr Arg Leu Thr Val Leu Gly Gln Pro Lys Ala Ala
                100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 84
<211> LENGTH: 212
<212> TYPE: PRT
<213> ORGANISM: Artificial Sequence
<220> FEATURE:
<223> OTHER INFORMATION: Synthetic sequence HBC34v7 LC

<400> SEQUENCE: 84

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Val Val
                85                  90                  95

Phe Gly Gly Gly Thr Arg Leu Thr Val Leu Gly Gln Pro Lys Ala Ala
                100                 105                 110
```

```
Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210
```

<210> SEQ ID NO 85
<211> LENGTH: 212
<212> TYPE: PRT
<213> ORGANISM: Artificial Sequence
<220> FEATURE:
<223> OTHER INFORMATION: Synthetic sequence HBC34v23 LC

<400> SEQUENCE: 85

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Cys Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
            85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210
```

<210> SEQ ID NO 86
<211> LENGTH: 212
<212> TYPE: PRT
<213> ORGANISM: Artificial Sequence
<220> FEATURE:

<223> OTHER INFORMATION: Synthetic sequence HBC34_LC40S LC

<400> SEQUENCE: 86

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 87
<211> LENGTH: 212
<212> TYPE: PRT
<213> ORGANISM: Artificial Sequence
<220> FEATURE:
<223> OTHER INFORMATION: Synthetic sequence HBC34_LC40A LC

<400> SEQUENCE: 87

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 88
<211> LENGTH: 212
<212> TYPE: PRT
<213> ORGANISM: Artificial Sequence
<220> FEATURE:
<223> OTHER INFORMATION: Synthetic sequence HBC34v23_LC40S LC

<400> SEQUENCE: 88

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ser Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
            85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 89
<211> LENGTH: 212
<212> TYPE: PRT
<213> ORGANISM: Artificial Sequence
<220> FEATURE:
<223> OTHER INFORMATION: Synthetic sequence HBC34v23_LC40A LC -continued

```
<400> SEQUENCE: 89

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ala Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 90
<211> LENGTH: 212
<212> TYPE: PRT
<213> ORGANISM: Artificial Sequence
<220> FEATURE:
<223> OTHER INFORMATION: Synthetic sequence HBC34v31_LC40S

<400> SEQUENCE: 90

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
```

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 91
<211> LENGTH: 212
<212> TYPE: PRT
<213> ORGANISM: Artificial Sequence
<220> FEATURE:
<223> OTHER INFORMATION: Synthetic sequence HBC34v31_LC40A LC

<400> SEQUENCE: 91

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 92
<211> LENGTH: 212
<212> TYPE: PRT
<213> ORGANISM: Artificial Sequence
<220> FEATURE:
<223> OTHER INFORMATION: Synthetic sequence HBC34v32_LC40S LC

<400> SEQUENCE: 92

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
                195                 200                 205

Thr Glu Cys Ser
            210

<210> SEQ ID NO 93
<211> LENGTH: 212
<212> TYPE: PRT
<213> ORGANISM: Artificial Sequence
<220> FEATURE:
<223> OTHER INFORMATION: Synthetic sequence HBC34v32_LC40A LC

<400> SEQUENCE: 93

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
130                 135                 140
```

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 94
<211> LENGTH: 212
<212> TYPE: PRT
<213> ORGANISM: Artificial Sequence
<220> FEATURE:
<223> OTHER INFORMATION: Synthetic sequence HBC34v33_LC40S LC

<400> SEQUENCE: 94

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ser Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 95
<211> LENGTH: 212
<212> TYPE: PRT
<213> ORGANISM: Artificial Sequence
<220> FEATURE:
<223> OTHER INFORMATION: Synthetic sequence HBC34v33_LC40A LC

<400> SEQUENCE: 95

Ser Tyr Glu Leu Thr Gln Pro Pro Ser Val Ser Val Ser Pro Gly Gln
1               5                   10                  15

```
Thr Ala Ser Ile Thr Cys Ser Gly Asp Lys Leu Gly Asn Lys Asn Ala
            20                  25                  30

Ala Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 96
<211> LENGTH: 217
<212> TYPE: PRT
<213> ORGANISM: Homo sapiens
<220> FEATURE:
<223> OTHER INFORMATION: WT hIgG1 Fc

<400> SEQUENCE: 96

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160
```

```
Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 97
<211> LENGTH: 449
<212> TYPE: PRT
<213> ORGANISM: Artificial Sequence
<220> FEATURE:
<223> OTHER INFORMATION: Synthetic sequence HBC34+GAALIE HC

<400> SEQUENCE: 97

```
Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Ser Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 98
<211> LENGTH: 449
<212> TYPE: PRT
<213> ORGANISM: Artificial Sequence
<220> FEATURE:
<223> OTHER INFORMATION: Synthetic sequence HBC34v31+GAALIE HC

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Arg Ser Phe
                20                  25                  30

Tyr Met Ser Trp Val Arg Gln Ala Pro Gly Lys Gly Leu Glu Trp Val
            35                  40                  45

Ala Asn Ile Asn Gln Asp Gly Ser Glu Lys Leu Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

-continued

```
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Ala Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
    275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Leu Pro Glu Glu Lys
            325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Thr Lys Asn Gln Val Ser Leu Thr
    355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
    435                 440                 445
Lys

<210> SEQ ID NO 99
<211> LENGTH: 449
<212> TYPE: PRT
<213> ORGANISM: Artificial Sequence
<220> FEATURE:
<223> OTHER INFORMATION: Synthetic sequence murinized HBC34v7,
      BC34-v7-mu-IgG2a - HC

<400> SEQUENCE: 99

Glu Leu Gln Leu Val Glu Ser Gly Gly Gly Trp Val Gln Pro Gly Gly
1               5                   10                  15
Ser Gln Arg Leu Ser Cys Ala Ala Ser Gly Arg Ile Phe Arg Ser Phe
            20                  25                  30
Tyr Met Ser Trp Val Arg Gln Ala Pro Gly Lys Gly Leu Glu Trp Val
        35                  40                  45
Ala Thr Ile Asn Gln Asp Gly Ser Glu Lys Leu Tyr Val Asp Ser Val
    50                  55                  60
Lys Gly Arg Phe Thr Ile Ser Arg Asp Asn Ala Lys Asn Ser Leu Phe
65                  70                  75                  80
Leu Gln Met Asn Asn Leu Arg Val Glu Asp Thr Ala Val Tyr Tyr Cys
                85                  90                  95
Ala Ala Trp Ser Gly Asn Ser Gly Gly Met Asp Val Trp Gly Gln Gly
            100                 105                 110
```

```
Thr Thr Val Ser Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
            130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
            210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
            290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
            435                 440                 445

Lys
```

<210> SEQ ID NO 100
<211> LENGTH: 212
<212> TYPE: PRT
<213> ORGANISM: Artificial Sequence
<220> FEATURE:
<223> OTHER INFORMATION: Synthetic sequence murinized HBC34v7,
      BC34-v7-mu-IgG2a - LC

<400> SEQUENCE: 100

```
Ser Tyr Glu Leu Thr Gln Pro Pro Ser Val Ser Val Pro Gly Gln
1               5                   10                  15
```

-continued

```
Thr Val Ser Ile Pro Cys Ser Gly Asp Lys Leu Gly Asn Lys Asn Val
             20                  25                  30

Cys Trp Phe Gln His Lys Pro Gly Gln Ser Pro Val Leu Val Ile Tyr
         35                  40                  45

Glu Val Lys Tyr Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Ala Tyr Phe Cys Gln Thr Phe Asp Ser Thr Thr Val Val
                 85                  90                  95

Phe Gly Gly Gly Thr Arg Leu Thr Val Leu Gly Gln Pro Lys Ser Ser
             100                 105                 110

Pro Ser Val Thr Leu Phe Pro Pro Ser Ser Glu Glu Leu Glu Thr Asn
         115                 120                 125

Lys Ala Thr Leu Val Cys Thr Ile Thr Asp Phe Tyr Pro Gly Val Val
     130                 135                 140

Thr Val Asp Trp Lys Val Asp Gly Thr Pro Val Thr Gln Gly Met Glu
145                 150                 155                 160

Thr Thr Gln Pro Ser Lys Gln Ser Asn Asn Lys Tyr Met Ala Ser Ser
                 165                 170                 175

Tyr Leu Thr Leu Thr Ala Arg Ala Trp Glu Arg His Ser Ser Tyr Ser
             180                 185                 190

Cys Gln Val Thr His Glu Gly His Thr Val Glu Lys Ser Leu Ser Arg
         195                 200                 205

Ala Asp Cys Ser
    210
```

<210> SEQ ID NO 101
<211> LENGTH: 449
<212> TYPE: PRT
<213> ORGANISM: Artificial Sequence
<220> FEATURE:
<223> OTHER INFORMATION: Synthetic sequence murinized HBC34v35,
      HBC34-v35-mu-IgG2a - HC

<400> SEQUENCE: 101

```
Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
             20                  25                  30

Tyr Met Ser Trp Val Arg Gln Ala Pro Gly Lys Gly Leu Glu Trp Val
         35                  40                  45

Ala Thr Ile Asn Gln Asp Gly Ser Glu Lys Leu Tyr Val Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Val Glu Asp Thr Ala Val Tyr Tyr Cys
                 85                  90                  95

Ala Ala Trp Ser Gly Asn Ser Gly Gly Met Asp Val Trp Gly Gln Gly
             100                 105                 110

Thr Thr Val Ser Val Ser Ser Ala Lys Thr Thr Ala Pro Ser Val Tyr
         115                 120                 125

Pro Leu Ala Pro Val Cys Gly Asp Thr Thr Gly Ser Ser Val Thr Leu
     130                 135                 140

Gly Cys Leu Val Lys Gly Tyr Phe Pro Glu Pro Val Thr Leu Thr Trp
145                 150                 155                 160
```

Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Thr Ser Ser
        180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 102
<211> LENGTH: 212
<212> TYPE: PRT
<213> ORGANISM: Artificial Sequence
<220> FEATURE:
<223> OTHER INFORMATION: Synthetic sequence murinized HBC34v35,
      HBC34-v35-mu-IgG2a - LC

<400> SEQUENCE: 102

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ser Ser
            100                 105                 110

Pro Ser Val Thr Leu Phe Pro Pro Ser Ser Glu Glu Leu Glu Thr Asn
            115                 120                 125

Lys Ala Thr Leu Val Cys Thr Ile Thr Asp Phe Tyr Pro Gly Val Val
130                 135                 140

Thr Val Asp Trp Lys Val Asp Gly Thr Pro Val Thr Gln Gly Met Glu
145                 150                 155                 160

Thr Thr Gln Pro Ser Lys Gln Ser Asn Asn Lys Tyr Met Ala Ser Ser
                165                 170                 175

Tyr Leu Thr Leu Thr Ala Arg Ala Trp Glu Arg His Ser Ser Tyr Ser
            180                 185                 190

Cys Gln Val Thr His Glu Gly His Thr Val Glu Lys Ser Leu Ser Arg
        195                 200                 205

Ala Asp Cys Ser
    210

<210> SEQ ID NO 103
<211> LENGTH: 458
<212> TYPE: PRT
<213> ORGANISM: Artificial Sequence
<220> FEATURE:
<223> OTHER INFORMATION: Synthetic sequence murinized HBC24, HBC24-mu-
      IgG2a - HC

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Lys Tyr
            20                  25                  30

Ala Met Ser Trp Val Arg Gln Ala Pro Gly Lys Gly Leu Glu Trp Val
        35                  40                  45

Ala Ser Ile Ser Gly Ser Val Pro Gly Phe Gly Ile Asp Thr Tyr Tyr
    50                  55                  60

Ala Asp Ser Val Lys Gly Arg Phe Thr Ile Ser Arg Asp Thr Ser Lys
65                  70                  75                  80

Asn Thr Leu Tyr Leu Gln Met Asn Ser Leu Arg Ala Glu Asp Thr Ala
                85                  90                  95

Leu Tyr Tyr Cys Ala Lys Asp Val Gly Val Ile Gly Ser Tyr Tyr Tyr
            100                 105                 110

Tyr Ala Met Asp Val Trp Gly Gln Gly Thr Ala Val Thr Val Ser Ser
        115                 120                 125

Ala Lys Thr Thr Ala Pro Ser Val Tyr Pro Leu Ala Pro Val Cys Gly
    130                 135                 140

Asp Thr Thr Gly Ser Ser Val Thr Leu Gly Cys Leu Val Lys Gly Tyr
145                 150                 155                 160

Phe Pro Glu Pro Val Thr Leu Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Thr Ser Ser Thr Trp Pro Ser Gln Ser Ile

```
                  195                 200                 205
Thr Cys Asn Val Ala His Pro Ala Ser Ser Thr Lys Val Asp Lys Lys
    210                 215                 220

Ile Glu Pro Arg Gly Pro Thr Ile Lys Pro Cys Pro Pro Cys Lys Cys
225                 230                 235                 240

Pro Ala Pro Asn Leu Leu Gly Gly Pro Ser Val Phe Ile Phe Pro Pro
                245                 250                 255

Lys Ile Lys Asp Val Leu Met Ile Ser Leu Ser Pro Ile Val Thr Cys
            260                 265                 270

Val Val Val Asp Val Ser Glu Asp Asp Pro Asp Val Gln Ile Ser Trp
        275                 280                 285

Phe Val Asn Asn Val Glu Val His Thr Ala Gln Thr Gln Thr His Arg
    290                 295                 300

Glu Asp Tyr Asn Ser Thr Leu Arg Val Val Ser Ala Leu Pro Ile Gln
305                 310                 315                 320

His Gln Asp Trp Met Ser Gly Lys Glu Phe Lys Cys Lys Val Asn Asn
                325                 330                 335

Lys Asp Leu Pro Ala Pro Ile Glu Arg Thr Ile Ser Lys Pro Lys Gly
            340                 345                 350

Ser Val Arg Ala Pro Gln Val Tyr Val Leu Pro Pro Glu Glu Glu
        355                 360                 365

Met Thr Lys Lys Gln Val Thr Leu Thr Cys Met Val Thr Asp Phe Met
370                 375                 380

Pro Glu Asp Ile Tyr Val Glu Trp Thr Asn Asn Gly Lys Thr Glu Leu
385                 390                 395                 400

Asn Tyr Lys Asn Thr Glu Pro Val Leu Asp Ser Asp Gly Ser Tyr Phe
                405                 410                 415

Met Tyr Ser Lys Leu Arg Val Glu Lys Lys Asn Trp Val Glu Arg Asn
            420                 425                 430

Ser Tyr Ser Cys Ser Val Val His Glu Gly Leu His Asn His His Thr
        435                 440                 445

Thr Lys Ser Phe Ser Arg Thr Pro Gly Lys
    450                 455

<210> SEQ ID NO 104
<211> LENGTH: 215
<212> TYPE: PRT
<213> ORGANISM: Artificial Sequence
<220> FEATURE:
<223> OTHER INFORMATION: Synthetic sequence murinized HBC24, HBC24-mu-
      IgG2a - LC

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Leu Ser Ser Ser
            20                  25                  30

Tyr Leu Ala Trp Tyr Gln Gln Lys Pro Gly Gln Ala Pro Arg Leu Leu
        35                  40                  45

Ile Tyr Ser Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95
```

```
Arg Trp Thr Phe Gly Gln Gly Thr Lys Val Glu Ile Lys Ala Asp Ala
            100                 105                 110
Ala Pro Thr Val Ser Ile Phe Pro Pro Ser Ser Glu Gln Leu Thr Ser
        115                 120                 125
Gly Gly Ala Ser Val Val Cys Phe Leu Asn Asn Phe Tyr Pro Lys Asp
    130                 135                 140
Ile Asn Val Lys Trp Lys Ile Asp Gly Ser Glu Arg Gln Asn Gly Val
145                 150                 155                 160
Leu Asn Ser Trp Thr Asp Gln Asp Ser Lys Asp Ser Thr Tyr Ser Met
                165                 170                 175
Ser Ser Thr Leu Thr Leu Thr Lys Asp Glu Tyr Glu Arg His Asn Ser
            180                 185                 190
Tyr Thr Cys Glu Ala Thr His Lys Thr Ser Thr Ser Pro Ile Val Lys
        195                 200                 205
Ser Phe Asn Arg Asn Glu Cys
    210                 215

<210> SEQ ID NO 105
<211> LENGTH: 19
<212> TYPE: PRT
<213> ORGANISM: Artificial Sequence
<220> FEATURE:
<223> OTHER INFORMATION: Synthetic sequence chimeric hinge

<400> SEQUENCE: 105

Glu Ser Lys Tyr Gly Pro Pro Cys Pro Pro Cys Pro Ala Pro Pro Val
1               5                   10                  15
Ala Gly Pro

<210> SEQ ID NO 106
<211> LENGTH: 21
<212> TYPE: RNA
<213> ORGANISM: Artificial Sequence
<220> FEATURE:
<223> OTHER INFORMATION: Synthetic sequence siRNA3 sense strand

<400> SEQUENCE: 106
gguggacuuc ucucaauuuu a                                            21

<210> SEQ ID NO 107
<211> LENGTH: 23
<212> TYPE: RNA
<213> ORGANISM: Artificial Sequence
<220> FEATURE:
<223> OTHER INFORMATION: Synthetic sequence siRNA3 antisense strand

<400> SEQUENCE: 107
uaaaauugag agaguccac cac                                           23

<210> SEQ ID NO 108
<211> LENGTH: 21
<212> TYPE: RNA
<213> ORGANISM: Artificial Sequence
<220> FEATURE:
<223> OTHER INFORMATION: Synthetic oligonucleotide (siRNA3 sense strand)

<400> SEQUENCE: 108
gguggacuuc ucucaauuuu a                                            21

<210> SEQ ID NO 109
<211> LENGTH: 23
<212> TYPE: RNA
```

-continued

```
<213> ORGANISM: Artificial Sequence
<220> FEATURE:
<223> OTHER INFORMATION: Synthetic oligonucleotide (siRNA3 antisense
      strand)

<400> SEQUENCE: 109
uaaaauugag agaaguccac cac                                              23
```